United States Patent
Luithle et al.

(10) Patent No.: US 9,067,931 B2
(45) Date of Patent: Jun. 30, 2015

(54) 2-HETEROARYL CARBOXAMIDES

(71) Applicant: BAYER INTELLECTUAL PROPERTY GMBH, Monheim (DE)

(72) Inventors: Joachim Luithle, Wulfrath (DE); Frank-Gerhard Boess, Basel (CH); Christina Erb, Wiesbaden (DE); Frank-Thorsten Hafner, Wuppertal (DE); Katrin Schnizler, Rodenbach (DE); Timo Flessner, Wuppertal (DE); Marja Van Kampen, Neu-Isenburg (DE); Franz-Josef Van Der Staay, Dronten (NL)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 0 days.

(21) Appl. No.: 14/261,616

(22) Filed: Apr. 25, 2014

(65) Prior Publication Data

US 2014/0350008 A1    Nov. 27, 2014

Related U.S. Application Data

(60) Continuation of application No. 13/412,946, filed on Mar. 6, 2012, now abandoned, which is a continuation of application No. 13/179,957, filed on Jul. 11, 2011, now abandoned, which is a division of application No. 10/516,777, filed as application No. PCT/EP03/05735 on Jun. 2, 2003, now Pat. No. 7,977,485.

(30) Foreign Application Priority Data

Jun. 10, 2002 (DE) .................. 102 25 536
Dec. 6, 2002 (DE) .................. 102 57 078
Dec. 10, 2002 (DE) .................. 102 57 537
Feb. 13, 2003 (DE) .................. 103 05 922

(51) Int. Cl.
*A61K 31/40* (2006.01)
*C07D 453/02* (2006.01)

(52) U.S. Cl.
CPC .................. *C07D 453/02* (2013.01)

(58) Field of Classification Search
CPC .................. C07D 209/52
USPC .................. 514/412
See application file for complete search history.

(56) References Cited

U.S. PATENT DOCUMENTS

| 7,732,477 | B2 | 6/2010 | Hendrix et al. |
| 8,076,355 | B2 | 12/2011 | Hendrix et al. |
| 2010/0222378 | A1 | 9/2010 | Hendrix et al. |
| 2010/0324085 | A1 | 12/2010 | Flessner et al. |
| 2012/0202842 | A1 | 8/2012 | Hendrix et al. |

FOREIGN PATENT DOCUMENTS

| WO | WO-02100857 A1 | 12/2002 |
| WO | WO-03029252 A1 | 4/2003 |
| WO | WO-03055878 A1 | 7/2003 |

OTHER PUBLICATIONS

Thomsen et al PLoS One, Nov. 2011, vol. 6, issue 1, pp. 1-9.*
F. Zaragoza Dorwald "Side Reactions in Organic Synthesis" 2005, Wiley-VCH.
Romanelli, M.N. et al. Arzneimittel-Forschung 1993, 43, 913-918, abstract.
Georgi, Sean, The Journal of Young Investigators, Nicotinic Acetylcholine Receptors and Alzheimer's Disease Therapeutics: A Review of Current Literature, Feb. 1, 2005, vol. 12, issue 2.
Swerdlow and Wright, Institute for Neurological Disorder—University of Kansas Medical Center, 2011—www.indkc.orgneurodegerative.html.

* cited by examiner

*Primary Examiner* — John Mabry
(74) *Attorney, Agent, or Firm* — Locke Lord LLP; Ralph A. Loren; Nicholas J. DiCeglie, Jr.

(57) ABSTRACT

The invention relates to novel 2-heteroaryl carboxamides and to the use thereof for producing medicaments for the treatment and/or prophylaxis of diseases and for improving perception, concentration, learning and/or memory.

12 Claims, No Drawings

2-HETEROARYL CARBOXAMIDES

CROSS REFERENCE TO RELATED APPLICATIONS

This application is a Continuation of U.S. patent application Ser. No. 13/412,946, filed Mar. 6, 2012, which application is a Continuation of U.S. patent application Ser. No. 13/179,957, filed Jul. 7, 2011, now abandoned, which application is a divisional of U.S. patent application Ser. No. 10/516,777 filed Jan. 13, 2006, now U.S. Pat. No. 7,977,485, which is a 371 US National Phase Application of PCT/EP03/05735 filed Jun. 2, 2003, which claims priority to German Patent Application No. 10225536.9, filed Jun. 10, 2002; German Patent Application No. 10257078.7, filed Dec. 6, 2002; German Patent Application No. 10257537.1, filed Dec. 10, 2002; and German Patent Application No. 10305922.9, filed Feb. 13, 2003, the disclosures of each of which are expressly incorporated herein by reference in their entireties.

The invention relates to novel 2-heteroaryl carboxamides, processes for their preparation, and their use for producing medicaments for the treatment and/or prophylaxis of diseases and for improving perception, concentration, learning and/or memory.

Nicotinic acetylcholine receptors (nAChR) form a large family of ion channels which are activated by the messenger acetylcholine which is produced in the body (Galzi et al., *Neuropharmacol.* 1995, 34, 563-582). A functional nAChR consists of five subunits which may be different (certain combinations of α1-9 and β1-4,γ,δ,ε subunits) or identical (α7-9). This leads to the formation of a diversity of subtypes which differ in the distribution in the muscles, the nervous system and other organs (McGehee et al., *Annu. Rev. Physiol.* 1995, 57, 521-546). Activation of nAChR leads to influx of cations into the cell and to stimulation of nerve cells or muscle cells. Selective activation of individual nAChR subtypes restricts this stimulation to the cell types which have a corresponding subtype and is thus able to avoid unwanted side effects such as, for example, stimulation of nAChR in the muscles. Clinical experiments with nicotine and experiments in various animal models indicate that central nicotinic acetylcholine receptors are involved in learning and memory processes (e.g. Rezvani et al., *Biol. Psychiatry* 2001, 49, 258-267). Nicotinic acetylcholine receptors of the alpha7 subtype (α7 nAChR) have a particularly high concentration in regions of the brain which are important for learning and memory, such as the hippocampus and the cerebral cortex (Séguéla et al., *J. Neurosci.* 1993, 13, 596-604). The α7 nAChR has a particularly high permeability for calcium ions, increases glutamatergic neurotransmission, influences the growth of axons and, in this way, modulates neuronal plasticity (Broide et al., *Mol. Neurobiol.* 1999, 20, 1-16).

Certain N-(1-azabicyclo[2.2.2]oct-3-yl)heteroaryl carboxamides for the treatment of, inter alia, psychoses are described in DE-A 37 24 059.

N-(Azabicycloalkyl)heteroaryl carboxamides, in particular N-(1-azabicyclo-[2.2.2]oct-4-yl)benzothiophene-3-carboxamides, are disclosed in WO 93/15073 and in EP-A 485 962 as intermediates for the synthesis of pharmaceutically active compounds.

U.S. Pat. No. 4,605,652 and EP-A 372 335 disclose, for example, N-(1-azabicyclo[2.2.2]oct-3-yl)thiophene-2-carboxamide and its memory-improving effect.

JP-A 14 030 084 describes 1-azabicycloalkanes for the treatment of, inter alia, dementia, attention deficit hyperactivity disorder and impairments of learning and memory.

WO 02/44176, WO 02/085901, WO 01/60821, EP-A 1 231 212 and EP-A 1 219 622 disclose further α7 nicotinic acetylcholine receptor agonists for the treatment of central nervous system diseases.

The present invention relates to compounds of the formula

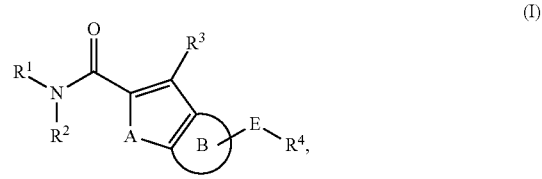

in which
$R^1$ is 1-azabicyclo[2.2.2]oct-3-yl, which is optionally substituted via the nitrogen atom by a radical selected from the group of $C_1$-$C_4$-alkyl, benzyl and oxy,
$R^2$ is hydrogen or $C_1$-$C_6$-alkyl,
$R^3$ is hydrogen, halogen or $C_1$-$C_6$-alkyl,
$R^4$ is hydrogen, halogen, cyano, amino, trifluoromethyl, trifluoromethoxy, $C_1$-$C_6$-alkyl, $C_1$-$C_6$-alkylcarbonyl, $C_1$-$C_6$-alkylamino, formyl, hydroxycarbonyl, $C_1$-$C_6$-alkoxy, $C_1$-$C_6$-alkoxycarbonyl, $C_1$-$C_1$-alkylthio, $C_1$-$C_1$-alkylcarbonylamino, $C_1$-$C_6$-alkylaminocarbonyl, $C_1$-$C_4$-alkylsulphonylamino, $C_3$-$C_8$-cycloalkylcarbonylamino, $C_3$-$C_6$-cycloalkylaminocarbonyl, pyrrolyl, $C_1$-$C_6$-alkylaminocarbonylamino, heterocyclylcarbonyl, heterocyclylcarbonylamino, heteroarylcarbonylamino, hydroxyl, phenyl or heterocyclyl,
where
$C_1$-$C_6$-alkyl may optionally be substituted by hydroxyl, cyano, amino, $C_1$-$C_6$-alkylaminocarbonylamino, $C_1$-$C_6$-alkylaminocarboxyl, heterocyclyl or aryl,
$C_1$-$C_6$-alkylaminocarbonyl may optionally be substituted by $C_1$-$C_6$-alkoxy or $C_1$-$C_6$-alkylamino,
$C_1$-$C_1$-alkylcarbonylamino may optionally be substituted by $C_1$-$C_1$-alkoxy, and heterocyclyl may optionally be substituted by oxo,
A is oxygen or sulphur,
the ring B is benzo or pyrido, each of which are optionally substituted by radicals from the series halogen, cyano, formyl, trifluoromethyl, trifluoromethoxy, nitro, amino, $C_1$-$C_6$-alkyl and $C_1$-$C_6$-alkoxy,
and
E is C≡C, arylene and heteroarylene, where arylene and heteroarylene may be substituted by radicals from the series halogen, cyano, trifluoromethyl, trifluoromethoxy, nitro, amino, $C_1$-$C_6$-alkoxy and $C_1$-$C_6$-alkyl,
and the solvates, salts or solvates of the salts of these compounds.

Solvates is the term used for the purposes of the invention for those forms of the compounds which form a complex with solvent molecules by coordination in the solid or liquid state. Hydrates are a special form of solvates in which the coordination takes place with water.

Salts which are preferred for the purposes of the invention are physiologically acceptable salts of the compounds of the invention.

Physiologically acceptable salts of the compounds (I) may be acid addition salts of the compounds with mineral acids, carboxylic acids or sulphonic acids. Particularly preferred examples are salts with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, oxalic acid, lactic acid, tartaric acid, citric acid, fumaric acid, maleic acid or benzoic acid.

However, salts which may be mentioned are also salts with conventional bases, such as, for example, alkali metal salts (e.g. sodium or potassium salts), alkaline earth metal salts (e.g. calcium or magnesium salts) or ammonium salts derived from ammonia or organic amines such as, for example, monoethanolamine, diethanolamine; triethanolamine, arginine, lysine, dimethylaminoethanol, diethylamine, triethylamine, ethyldiisopropylamine, procaine, dibenzylamine, N-methylmorpholine, dihydroabietylamine, 1-ephenamine or methylpiperidine.

The compounds of the invention may exist in stereoisomeric forms (enantiomers, diastereomers). The invention therefore relates both to the enantiomers or diastereomers and to respective mixtures thereof. These enantiomer and diastereomer mixtures can be separated in a known manner into the stereoisomerically pure constituents.

For the purposes of the present invention, the substituents generally have the following meaning:

$C_1$-$C_6$- and $C_1$-$C_4$-alkoxy are a straight-chain or branched alkoxy radical having 1 to 6, preferably 1 to 4, particularly preferably 1 to 3, carbon atoms. Nonlimiting examples include methoxy, ethoxy, n-propoxy, isopropoxy, tert-butoxy, n-pentoxy and n-hexoxy.

$C_1$-$C_6$- and $C_1$-$C_4$-alkyl are a straight-chain or branched alkyl radical having 1 to 6, preferably 1 to 4, particularly preferably 1 to 3, carbon atoms. Nonlimiting examples include methyl, ethyl, n-propyl, isopropyl, tert-butyl, n-pentyl and n-hexyl.

$C_1$-$C_6$- and $C_1$-$C_4$-alkylamino is a straight-chain or branched mono- or dialkylamino radical having 1 to 6, preferably having 1 to 4, carbon atoms per alkyl radical. Nonlimiting examples include methylamino, dimethylamino, ethylamino, diethylamino, n-propylamino, di-n-propylamino, isopropylamino, diisopropylamino, tert-butylamino, di-tert-butylamino, n-pentylamino, di-n-pentylamino, n-hexylamino, di-n-hexylamino, ethylmethylamino, isopropylmethylamino, n-butylethylamino, n-hexyl-1-pentylamino.

$C_1$-$C_6$- and $C_1$-$C_4$-alkylcarbonylamino is a straight-chain or branched alkylcarbonylamino radical having 1 to 6, preferably 1 to 4, and particularly preferably having 1 to 3, carbon atoms. Nonlimiting examples include methylcarbonyl-amino, ethylcarbonylamino, n-propylcarbonylamino, isopropylcarbonylamino, tert-butylcarbonylamino, n-pentylcarbonylamino and n-hexylcarbonylamino.

$C_1$-$C_6$- and $C_1$-$C_4$-alkylaminocarboxyl is a straight-chain or branched mono- or dialkylaminocarboxyl radical having 1 to 6, preferably having 1 to 4, particularly preferably having 1 to 3, carbon atoms per alkyl radical. Nonlimiting examples include methylaminocarboxyl, dimethylaminocarboxyl, ethylaminocarboxyl, diethylaminocarboxyl, n-propylaminocarboxyl, di-n-propylaminocarboxyl, isopropyl-aminocarboxyl, diisopropylaminocarboxyl, tert-butylaminocarboxyl, di-tert-butyl-aminocarboxyl, n-pentylaminocarboxyl, di-n-pentylaminocarboxyl, n-hexyl-aminocarboxyl, di-n-hexylaminocarboxyl, ethylmethylaminocarboxyl, isopropyl-methylaminocarboxyl, n-butylethylaminocarboxyl, n-hexyl-i-pentylaminocarboxyl.

$C_1$-$C_6$- and $C_1$-$C_4$-alkylaminocarbonyl is a straight-chain or branched mono- or dialkylaminocarbonyl radical having 1 to 6, preferably having 1 to 4, particularly preferably having 1 to 3, carbon atoms per alkyl radical. Nonlimiting examples include methylaminocarbonyl, dimethylaminocarbonyl, ethylaminocarbonyl, diethylaminocarbonyl, n-propylaminocarbonyl, di-n-propylaminocarbonyl, isopropyl-aminocarbonyl, diisopropylaminocarbonyl, tert-butylaminocarbonyl, di-tert-butylaminocarbonyl, n-pentylaminocarbonyl, di-n-pentylaminocarbonyl, n-hexylamino-carbonyl, di-n-hexylaminocarbonyl, ethylmethylaminocarbonyl, isopropylmethyl-aminocarbonyl, n-butylethylaminocarbonyl, n-hexyl-i-pentylaminocarbonyl.

$C_1$-$C_6$- and $C_1$-$C_4$-alkylaminocarbonylamino is a straight-chain or branched mono- or dialkylaminocarbonylamino radical having 1 to 6, preferably having 1 to 4, particularly preferably having 1 to 3, carbon atoms per alkyl radical. Nonlimiting examples include methylaminocarbonylamino, dimethylaminocarbonylamino, ethylaminocarbonyl-amino, diethylaminocarbonylamino, n-propylaminocarbonylamino, di-n-propylaminocarbonylamino, isopropylaminocarbonylamino, diisopropylamino-carbonylamino, tert-butylaminocarbonylamino, di-tert-butylaminocarbonylamino, n-pentylaminocarbonylamino, di-n-pentylaminocarbonylamino, n-hexylamino-carbonylamino, di-n-hexylaminocarbonylamino, ethylmethylaminocarbonylamino, isopropylmethylaminocarbonylamino, n-butylethylaminocarbonylamino, n-hexyl-i-pentylaminocarbonylamino.

$C_1$-$C_6$-Alkylcarbonyl is a straight-chain or branched alkylcarbonyl radical having 1 to 6, preferably having 1 to 4, carbon atoms. Nonlimiting examples include: acetyl, ethylcarbonyl, propylcarbonyl, isopropylcarbonyl, butylcarbonyl, isobutylcarbonyl, tert-butylcarbonyl, pentylcarbonyl and hexylcarbonyl.

$C_1$-$C_4$-Alkylsulphonylamino is a straight-chain or branched alkylsulphonylamino radical having 1 to 4, preferably having 1 to 3, carbon atoms. Mention may be made by way of example and preferably of: methanesulphonylamino, ethanesulphonylamino, n-propanesulphonylamino, isopropanesulphonylamino, tert-butanesulphonylamino.

$C_1$-$C_6$- and $C_1$-$C_4$-alkoxycarbonyl is a straight-chain or branched alkoxycarbonyl radical having 1 to 6, preferably having 1 to 4 and particularly preferably having 1 to 3, carbon atoms. Nonlimiting examples include methoxycarbonyl, ethoxycarbonyl, n-propoxycarbonyl, isopropoxycarbonyl and tert-butoxycarbonyl.

$C_1$-$C_6$- and $C_1$-$C_4$-alkoxycarbonylamino is a straight-chain or branched alkoxycarbonylamino radical having 1 to 6, preferably having 1 to 4 and particularly preferably having 1 to 3, carbon atoms. Nonlimiting examples include methoxycarbonylamino, ethoxycarbonylamino, n-propoxycarbonylamino, isopropoxy-carbonylamino, tert-butoxycarbonylamino, n-pentoxycarbonylamino and n-hexoxycarbonylamino.

$C_3$-$C_6$-Cycloalkylaminocarbonyl is a 3- to 6-membered, preferably 5- to 6-membered cycloalkylaminocarbonyl radical. Nonlimiting examples include cyclopropylaminocarbonyl, cyclobutylaminocarbonyl, cyclopentylaminocarbonyl, cyclohexylaminocarbonyl, cycloheptylaminocarbonyl and cyclooctylaminocarbonyl.

$C_3$-$C_8$- and $C_5$-$C_6$-cycloalkylcarbonylamino is a 3- to 8-membered, preferably 5- to 6-membered, cycloalkylcarbonylamino radical. Nonlimiting examples include cyclopropylcarbonylamino, cyclobutylcarbonylamino, cyclopentylcarbonylamino, cyclohexylcarbonylamino, cycloheptylcarbonylamino and cyclooctylcarbonylamino.

Heterocyclyl is a mono- or polycyclic, preferably mono- or bicyclic, nonaromatic radical having, as a rule, 4 to 10, preferably 5 to 8, ring atoms and up to 3, preferably up to 2, hetero ring members from the series N, O, S, SO, $SO_2$. The heterocyclyl radicals may be saturated or partially unsaturated. Nonlimiting examples include 5- to 8-membered monocyclic saturated heterocyclyl radicals having up to two hetero ring atoms from the series O, N and S such as tetrahydrofuran-2- yl, piperazinyl, N-methylpiperazinyl, pyrrolidin-2-yl, pyrrolidin-3-yl, pyrrolinyl, piperidinyl, morpholinyl and perhydroazepinyl.

Heteroaryl is an aromatic, mono- or bicyclic radical having 5 to 10 ring atoms and up to 5 heteroatoms from the series S, O and/or N. Preference is given to 5- to 6-membered heteroaryls having up to 4 heteroatoms. The heteroaryl radical may be bonded via a carbon atom or heteroatom. Nonlimiting examples include: thienyl, furyl, pyrrolyl, thiazolyl, oxadiazolyl, oxazolyl, isoxazolyl, imidazolyl, tetrazolyl, pyridyl, pyrimidinyl, pyridazinyl, indolyl, indazolyl, benzofuranyl, benzothiophenyl, quinolinyl, isoquinolinyl.

Heterocyclylcarbonylamino is a carbonylamino group which is linked to a mono- or polycyclic, preferably mono- or bicyclic, nonaromatic radical having, as a rule, 4 to 10, preferably 5 to 8, ring atoms and up to 3, preferably up to 2, hetero ring members from the series N, O, S, SO, $SO_2$. The heterocyclyl radicals may be saturated or partially unsaturated. Nonlimiting examples include carbonylamino groups linked to 5- to 8-membered monocyclic saturated heterocyclyl radicals having up to two hetero ring atoms from the series O, N and S such as tetrahydrofuran-2-ylcarbonylamino, piperazinylcarbonylamino, N-methylpiperazinylcarbonylamino, pyrrolidin-2-ylcarbonylamino, pyrrolidin-3-ylcarbonylamino, pyrrolinylcarbonylamino, piperidinyl-carbonylamino, morpholinylcarbonylamino and perhydroazepinylcarbonylamino.

Heteroarylcarbonylamino is a carbonylamino group which is linked to a mono- or bicyclic aromatic radical having 5 to 10 ring atoms and up to 5 heteroatoms from the series S, O and/or N. Preference is given to 5- to 6-membered heteroaryls having up to 4 heteroatoms. The heteroaryl radical may be bonded to the carbonylamino group via a carbon atom or heteroatom. Nonlimiting examples include: thienylcarbonylamino, furylcarbonylamino, pyrrolylcarbonylamino, thiazolylcarbonylamino, isoxazolylcarbonylamino, oxadiazolylcarbonylamino, oxazolylcarbonylamino, imidazolylcarbonylamino, tetrazolylcarbonylamino, pyridylcarbonylamino, pyrimidinylcarbonylamino, pyridazinylcarbonylamino, indolylcarbonylamino, indazolylcarbonylamino, benzofuranylcarbonylamino, benzothiophenylcarbonylamino, quinolinylcarbonylamino, isoquinolinylcarbonylamino.

Heterocyclylcarbonyl is a carbonyl group which is linked to a mono- or polycyclic, preferably mono- or bicyclic, nonaromatic radical having, as a rule, 4 to 10, preferably 5 to 8, ring atoms and up to 3, preferably up to 2, hetero ring members from the series N, O, S, SO, $SO_2$. The heterocyclyl radicals may be saturated or partially unsaturated. Nonlimiting examples include carbonyl groups linked to 5- to 8-membered monocyclic saturated heterocyclyl radicals having up to two hetero ring atoms from the series O, N and S such as tetrahydrofuran-2-ylcarbonyl, piperazinylcarbonyl, N-methylpiperazinylcarbonyl, pyrrolidin-2-ylcarbonyl, pyrrolidin-3-ylcarbonyl, pyrrolinylcarbonyl, piperidinylcarbonyl, morpholinyl-carbonyl and perhydroazepinylcarbonyl.

Aryl is a mono- to tricyclic aromatic, carbocyclic radical having, as a rule, 6 to 10 carbon ring atoms. Nonlimiting examples include phenyl and naphthyl.

Halogen is fluorine, chlorine, bromine and iodine. Preference is given to fluorine, chlorine and bromine, and particular preference to fluorine and chlorine.

$C_1$-$C_6$- and $C_1$-$C_4$-alkylthio are a straight-chain or branched alkylthio radical having 1 to 6, preferably 1 to 4, particularly preferably 1 to 3, carbon atoms. Nonlimiting examples include methylthio, ethylthio, n-propylthio, isopropylthio, tert-butylthio, n-pentylthio and n-hexylthio.

When radicals in the compounds of the invention are optionally substituted, unless indicated otherwise the radicals may have one or more identical or different substituents.

Preference is given to compounds of the formula (I) in which $R^1$ is (3R)-1-azabicyclo[2.2.2]oct-3-yl, and $R^2$, $R^3$, $R^4$, A, E and the ring B have the meanings indicated above, and the solvates, salts or solvates of the salts of these compounds.

Preference is likewise given to compounds of the formula (I) in which $R^2$ is hydrogen or methyl, and $R^1$, $R^3$, $R^4$, A, E and the ring B have the meanings indicated above, and the solvates, salts or solvates of the salts of these compounds.

Particular preference is given to compounds of the formula (I) in which $R^2$ is hydrogen, and $R^1$, $R^3$, $R^4$, A, E and the ring B have the meanings indicated above, and the solvates, salts or solvates of the salts of these compounds.

Preference is likewise given to compounds of the formula (I) in which $R^3$ is hydrogen or methyl, and $R^1$, $R^2$, $R^4$, A, E and the ring B have the meanings indicated above, and the solvates, salts or solvates of the salts of these compounds.

Particular preference is given to compounds of the formula (I) in which $R^3$ is hydrogen, and $R^1$, $R^2$, $R^4$, A, E and the ring B have the meanings indicated above, and the solvates, salts or solvates of the salts of these compounds.

Preference is likewise given to compounds of the formula (I) in which $R^4$ is hydrogen, fluorine, chlorine, bromine, trifluoromethoxy, hydroxymethyl, methoxy or 6-membered heterocyclyl, and $R^1$, $R^2$, $R^3$, A, E and the ring B have the meanings indicated above, and the solvates, salts or solvates of the salts of these compounds.

Preference is likewise given to compounds of the formula (I) in which A is a sulphur atom, and $R^1$, $R^2$, $R^3$, $R^4$, E and the ring B have the meanings indicated above, and the solvates, salts or solvates of the salts of these compounds.

Preference is likewise given to compounds of the formula (I) in which A is an oxygen atom, and $R^1$, $R^2$, $R^3$, $R^4$, E and the ring B have the meanings indicated above, and the solvates, salts or solvates of the salts of these compounds.

Preference is likewise given to compounds of the formula (I) in which the ring B is benzo which is optionally substituted by 1 to 3 radicals from the series halogen, cyano, trifluoromethyl, trifluoromethoxy and $C_1$-$C_4$-alkyl, and $R^1$, $R^2$, $R^3$, $R^4$, A and E have the meanings indicated above, and the solvates, salts or solvates of the salts of these compounds.

Preference is likewise given to compounds of the formula (I) in which E is phenylene which is optionally substituted by radicals from the series fluorine, chlorine, bromine, cyano, trifluoromethoxy, $C_1$-$C_6$-alkyl and $C_1$-$C_6$-alkoxy, and $R^1$, $R^2$, $R^3$, $R^4$, A and the ring B have the meanings indicated above, and the solvates, salts or solvates of the salts of these compounds.

Preference is likewise given to compounds of the formula (I) in which
$R^1$ is 1-azabicyclo[2.2.2]oct-3-yl,
$R^2$ is hydrogen or $C_1$-$C_4$-alkyl,
$R^3$ is hydrogen, fluorine, chlorine, bromine or $C_1$-$C_4$-alkyl,
$R^4$ is hydrogen, fluorine, chlorine, bromine, cyano, amino, trifluoromethyl, trifluoromethoxy, $C_1$-$C_4$-alkyl, $C_1$-$C_4$-alkylcarbonyl, $C_1$-$C_4$-alkylamino, formyl, hydroxycarbonyl, $C_1$-$C_4$-alkoxy, $C_1$-$C_4$-alkoxycarbonyl, $C_1$-$C_4$-alkylthio, $C_1$-$C_4$-alkylcarbonylamino, $C_1$-$C_4$-alkylaminocarbonyl, $C_1$-$C_4$-alkylsulphonylamino, $C_3$-$C_6$-cycloalkylcarbonylamino, $C_3$-$C_6$-cycloalkylaminocarbonyl, pyrrolyl, $C_1$-$C_4$-alkylaminocarbonylamino, heterocyclylcarbonyl, heterocyclylcarbonylamino, heteroarylcarbonylamino, hydroxyl, phenyl or heterocyclyl, where $C_1$-$C_4$-alkyl may optionally be substituted by hydroxyl, cyano, amino, $C_1$-$C_4$-alkylaminocarbonylamino, $C_1$-$C_4$-alkylaminocarboxyl, heterocyclyl or aryl, $C_1$-$C_4$-alkylaminocarbonyl may optionally be substituted by $C_1$-$C_4$-alkoxy or $C_1$-$C_4$-alkylamino, $C_1$-$C_4$-alkylcarbonylamino may optionally be substituted by $C_1$-$C_4$-alkoxy, and heterocyclyl may optionally be substituted by oxo, A is oxygen or sulphur, the ring B is benzo or pyrido, each of which are optionally substituted by radicals from the series halogen, cyano, trifluoromethyl, trifluoromethoxy and $C_1$-$C_4$-alkyl, and E is C≡C, arylene and heteroarylene, where arylene and heteroarylene may be substituted by radicals from the series halogen, cyano, trifluoromethyl, trifluoromethoxy, nitro, amino, $C_1$-$C_4$-alkoxy and $C_1$-$C_4$-alkyl, and the solvates, salts or solvates of the salts of these compounds.

Preference is likewise given to compounds of the formula (I) in which $R^1$ is 1-azabicyclo[2.2.2]oct-3-yl, $R^2$ and $R^3$ are hydrogen, $R^4$ is hydrogen, fluorine, chlorine, bromine, cyano, amino, trifluoromethyl, trifluoromethoxy, $C_1$-$C_4$-alkyl, $C_1$-$C_4$-alkylcarbonyl, $C_1$-$C_4$-alkylamino, formyl, hydroxycarbonyl, $C_1$-$C_4$-alkoxy, $C_1$-$C_4$-alkoxycarbonyl, $C_1$-$C_6$-alkylthio, $C_1$-$C_4$-alkylcarbonylamino, $C_1$-$C_4$-alkylaminocarbonyl, $C_1$-$C_4$-alkylsulphonylamino, $C_3$-$C_6$-cycloalkylcarbonylamino, $C_3$-$C_6$-cycloalkylaminocarbonyl, pyrrolyl, $C_1$-$C_4$-alkylaminocarbonylamino, heterocyclylcarbonyl, heterocyclylcarbonylamino, heteroarylcarbonylamino, hydroxyl, phenyl or heterocyclyl, where $C_1$-$C_4$-alkyl may optionally be substituted by hydroxyl, cyano, amino, $C_1$-$C_4$-alkylaminocarbonylamino, $C_1$-$C_4$-alkylaminocarboxyl, heterocyclyl or aryl, $C_1$-$C_4$-alkylaminocarbonyl may optionally be substituted by $C_1$-$C_4$-alkoxy or $C_1$-$C_4$-alkylamino, $C_1$-$C_4$-alkylcarbonylamino may optionally be substituted by $C_1$-$C_4$-alkoxy, and heterocyclyl may optionally be substituted by oxo, A is oxygen, the ring B is benzo or pyrido, each of which are optionally substituted by radicals from the series halogen, cyano, trifluoromethyl, trifluoromethoxy and $C_1$-$C_4$-alkyl, and E is C≡C, arylene and heteroarylene, where arylene and heteroarylene may be substituted by radicals from the series halogen, cyano, trifluoromethyl, trifluoromethoxy, nitro, amino, $C_1$-$C_4$-alkoxy and $C_1$-$C_4$-alkyl, and the solvates, salts or solvates of the salts of these compounds.

Preference is likewise given to compounds of the formula (I) in which $R^1$ is 1-azabicyclo[2.2.2]oct-3-yl, $R^2$ is hydrogen or $C_1$-$C_6$-alkyl, $R^3$ is hydrogen, halogen or $C_1$-$C_6$-alkyl, $R^4$ is hydrogen, halogen, cyano, amino, trifluoromethyl, trifluoromethoxy, $C_1$-$C_6$-alkyl, $C_1$-$C_6$-alkylcarbonyl, $C_1$-$C_6$-alkylamino, formyl, hydroxycarbonyl, $C_1$-$C_6$-alkoxy, $C_1$-$C_6$-alkoxycarbonyl, $C_1$-$C_6$-alkylthio, $C_1$-$C_6$-alkylcarbonylamino, $C_1$-$C_4$-alkylsulphonylamino, $C_3$-$C_8$-cycloalkylcarbonylamino, pyrrolyl, $C_1$-$C_6$-alkylaminocarbonylamino, heterocyclylcarbonyl, phenyl or heterocyclyl, where $C_1$-$C_6$-alkyl may optionally be substituted by hydroxyl, amino, $C_1$-$C_6$-alkylaminocarbonylamino, $C_1$-$C_6$-alkylaminocarboxyl, heterocyclyl or aryl, $C_1$-$C_6$-alkylcarbonylamino may optionally be substituted by $C_1$-$C_6$-alkoxy, and heterocyclyl may optionally be substituted by oxo, A is oxygen or sulphur, the ring B is benzo or pyrido, each of which are optionally substituted by radicals from the series halogen, cyano, formyl, trifluoromethyl, trifluoromethoxy, nitro, amino, $C_1$-$C_6$-alkyl and $C_1$-$C_6$-alkoxy, and E is C≡C, arylene and heteroarylene, where arylene and heteroarylene may be substituted by radicals from the series halogen, cyano, trifluoromethyl, trifluoromethoxy, nitro, amino, $C_1$-$C_6$-alkoxy and $C_1$-$C_6$-alkyl, and the solvates, salts or solvates of the salts of these compounds.

Preference is likewise, given to compounds of the formula (I) in which $R^1$ is 1-azabicyclo[2.2.2]oct-3-yl, $R^2$ is hydrogen or $C_1$-$C_6$-alkyl, $R^3$ is hydrogen, halogen or $C_1$-$C_6$-alkyl, $R^4$ is hydrogen, halogen, cyano, trifluoromethyl, trifluoromethoxy, $C_1$-$C_6$-alkyl, $C_1$-$C_6$-alkoxy or heterocyclyl, where alkyl is optionally substituted by a hydroxyl radical, A is oxygen or sulphur, the ring B is benzo or pyrido, each of which are optionally substituted by radicals from the series halogen, cyano, trifluoromethyl, trifluoromethoxy, nitro; amino, $C_1$-$C_6$-alkyl and $C_1$-$C_6$-alkoxy, and E is C≡C, arylene or heteroarylene, where arylene and heteroarylene may be substituted by radicals from the series halogen, cyano, trifluoromethyl, trifluoromethoxy, nitro, amino, $C_1$-$C_6$-alkyl and $C_1$-$C_6$-alkoxy, and the solvates, salts or solvates of the salts of these compounds.

Preference is likewise given to compounds of the formula

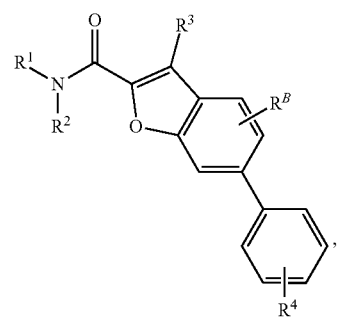

(Ia)

in which $R^1$ is (3R)-1-azabicyclo[2.2.2]oct-3-yl, $R^2$ and $R^3$ are, independently of one another, hydrogen or methyl, $R^4$ is hydrogen, halogen, cyano, trifluoromethyl, trifluoromethoxy, $C_1$-$C_6$-alkyl, $C_1$-$C_6$-alkoxy or heterocyclyl, where alkyl is optionally substituted by a hydroxyl radical, and $R^B$ is hydrogen, halogen, cyano, trifluoromethyl, trifluoromethoxy, nitro, amino, $C_1$-$C_6$-alkyl or $C_1$-$C_1$-alkoxy, and the solvates, salts or solvates of the salts of these compounds.

Very particular preference is likewise given to compouds of the formula (Ia) in which
$R^1$ is (3R)-1-azabicyclo[2.2.2]oct-3-yl,
$R^2$ and $R^3$ are hydrogen,
$R^4$ is hydrogen, fluorine, chlorine, bromine, trifluoromethoxy, hydroxymethyl, methoxy or 6-membered heterocyclyl and
$R^B$ is hydrogen, halogen, cyano, trifluoromethyl, trifluoromethoxy or $C_1$-$C_4$-alkyl,
and the solvates, salts or solvates of the salts of these compounds.

Preference is likewise given to compounds of the formula

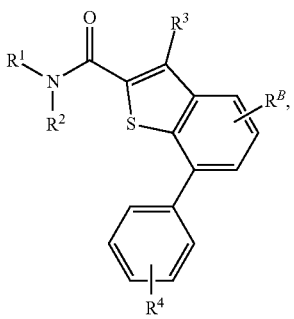

(Ib)

in which
$R^1$ is (3R)-1-azabicyclo[2.2.2]oct-3-yl,
$R^2$ and $R^3$ are, independently of one another, hydrogen or methyl,
$R^4$ is hydrogen, halogen, cyano, trifluoromethyl, trifluoromethoxy, $C_1$-$C_6$-alkyl, $C_1$-$C_6$-alkoxy or heterocyclyl, where alkyl is optionally substituted by a hydroxyl radical, and
$R^B$ is hydrogen, halogen, cyano, trifluoromethyl, trifluoromethoxy, nitro, amino, $C_1$-$C_6$-alkyl and $C_1$-$C_6$-alkoxy, and the solvates, salts or solvates of the salts of these compounds.

Preference is likewise given to compounds of the formula (Ib) in which
$R^1$ is (3R)-1-azabicyclo[2.2.2]oct-3-yl,
$R^2$ and $R^3$ are hydrogen,
$R^4$ is hydrogen, fluorine, chlorine, bromine, trifluoromethoxy, hydroxymethyl, methoxy or 6-membered heterocyclyl and
$R^B$ is hydrogen, halogen, cyano, trifluoromethyl, trifluoromethoxy or $C_1$-$C_4$-alkyl,
and the solvates, salts or solvates of the salts of these compounds.

Preference is likewise given to compounds of the formula

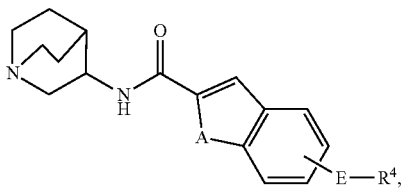

(Ic)

in which
E is phenylene,
$R^4$ is $C_1$-$C_6$-alkoxy, aminomethyl, hydroxycarbonyl, $C_3$-$C_8$-cycloalkylcarbonylamino, a group of the formula

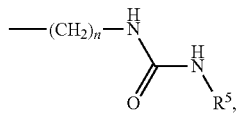

where
$R^5$ is $C_1$-$C_6$-alkyl,
n is zero, 1, 2, 3 or 4,
or
5- to 6-membered heterocyclyl which is optionally substituted by oxo,
A is sulphur or oxygen,
and the solvates, salts or solvates of the salts thereof.

The invention preferably relates to compounds of the formula (I) in which
E is phenylene,
$R^4$ is $C_1$-$C_4$-alkoxy, aminomethyl, hydroxycarbonyl, $C_3$-$C_6$-cycloalkylcarbonylamino, a group of the formula

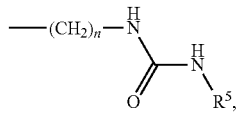

where
$R^5$ is $C_1$-$C_4$-alkyl,
n is zero, 1 or 2,
or
5- to 6-membered heterocyclyl which is optionally substituted by oxo,
A is sulphur or oxygen,
and the solvates, salts or solvates of the salts thereof.

The invention particularly preferably relates to compounds of the following formulae

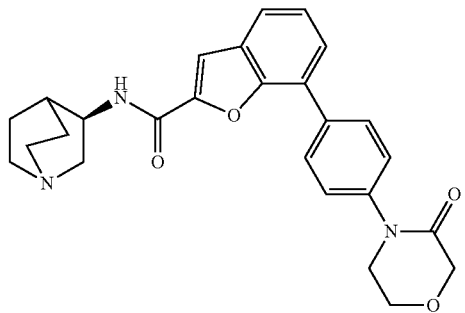

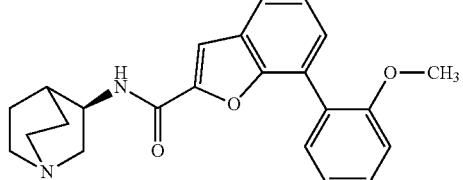

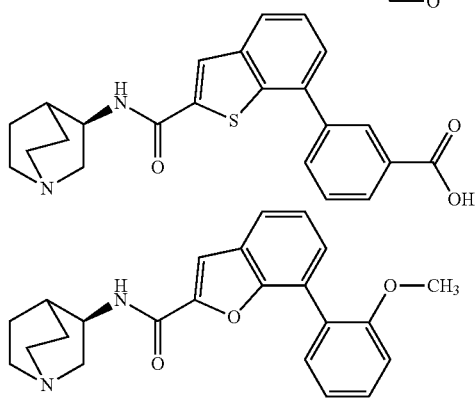

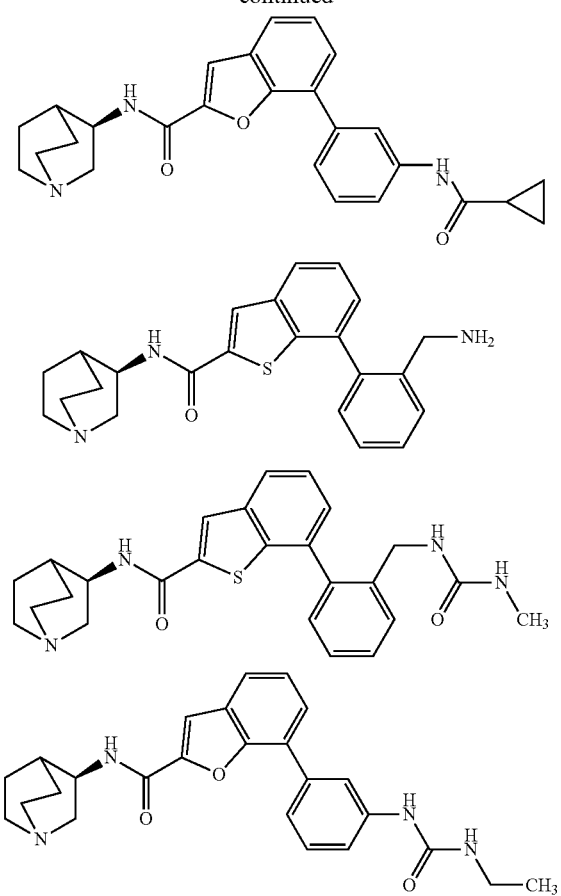

and the solvates, salts or solvates of the salts of these compounds.

Very particular preference is given to combinations of two or more of the preferred ranges mentioned above.

The invention further relates to processes for the preparation of the compounds of the invention, in which compounds of the formula $$X^1\text{-}E\text{-}R^4 \qquad (II),$$

in which
$R^4$ has the abovementioned meanings, and
$X^1$ is —B(OH)$_2$ or

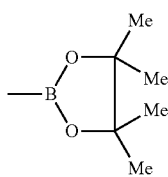

in the case where E is arylene or heteroarylene, and is hydrogen in the case where E is —C≡C—,
are reacted with a compound of the formula (III)

in which
$R^1$, $R^2$, $R^3$, A and the ring B have the abovementioned meanings, and
$X^2$ is triflate or halogen, preferably chlorine, bromine or iodine,
and where appropriate
[A] the resulting compounds (I) are alkylated on the quinuclidine nitrogen atom using appropriate alkylating reagents, or
[B] the resulting compounds (I) are oxidized on the quinuclidine nitrogen atom using suitable oxidizing agents,
and the resulting compounds (I) are converted into their solvates, salts or solvates of the salts where appropriate with the appropriate (i) solvents and/or (ii) bases or acids.

Reaction of the compounds (II) and (III) generally takes place in an inert solvent in the presence of a transition metal catalyst, in the presence of a base and, where appropriate, in the presence of copper(I) iodide.

The process of the invention is preferably carried out in a temperature range from 70° C. to 110° C. under atmospheric pressure.

Examples of inert solvents are ethers such as dioxane, tetrahydrofuran or 1,2-dimethoxyethane, hydrocarbons such as benzene, xylene or toluene, nitroaromatic compounds such as nitrobenzene, where appropriate N-alkylated carboxamides such as dimethylformamide, dimethylacetamide, alkyl sulphoxides such as dimethyl sulphoxide or cyclic lactams such as N-methylpyrrolidone. Preference is given to solvents from the series dimethylformamide, dimethylacetamide, dimethyl sulphoxide and 1,2-dimethoxyethane.

The transition metal catalysts preferably used are palladium(0) or palladium(II) compounds, in particular bis(diphenylphosphino)ferrocenepalladium(II) chloride, dichlorobis(triphenylphosphine)palladium or tetrakis(triphenylphosphine)-palladium(0).

Preferred bases are alkali metal hydroxides or salts such as potassium acetate, sodium hydroxide, sodium bicarbonate or sodium carbonate, where appropriate in the form of their aqueous solutions.

Process steps [A] and [B] can be carried out in inert solvents and at temperatures from −30 to 50° C. and under atmospheric pressure.

Bases which can be employed for process step [A] are alkali metal hydrides such as potassium or sodium hydride, alkali metal hydroxides such as sodium or potassium hydroxide or alkali metal carbonates such as sodium or potassium carbonate.

Alkylating reagents which can be employed for process step [A] are alkyl halides such as methyl iodide or benzyl halides such as benzyl bromide.

An oxidizing agent particularly suitable for process step [B] is hydrogen peroxide or metachloroperbenzoic acid.

The reactions metallized by transition metals can be carried out in analogy to processes known from the literature, e.g. reaction with alkynes: cf. N. Krause et al., *J. Org. Chem.* 1998, 63, 8551; with ketones, aromatic compounds and alkenes: cf. for example, A. Suzuki, *Acc. Chem. Res.* 1982, 15, 178ff; Miyaura et al. *J. Am. Chem. Soc.* 1989, 111, 314; J. K. Stille, *Angew. Chem.* 1986, 98, 504 and with substituted amines: cf. S. L. Buchwald et al., *J. Organomet. Chem.* 1999, 576, 125ff. (see also J. Tsuji, Palladium Reagents and Catalysts, Wiley, New York, 1995).

The compounds (II) are known or can be synthesized in analogy to known processes from the appropriate precursors.

The compounds (III) can be prepared by reacting compounds of the formula

in which $R^1$ and $R^2$ have the abovementioned meanings, with a compound of the formula

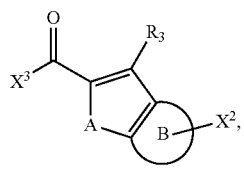

in which
$R^3$, $X^2$, A and the ring B have the abovementioned meanings, and
$X^3$ is hydroxyl or halogen, preferably bromine or chlorine.

Reaction of the compounds (IV) and (V) takes place, if $X^3$ is halogen, generally in inert, solvents, where appropriate in the presence of a base, preferably in a temperature range from 0° C. to 50° C. under atmospheric pressure.

Examples of inert solvents are halohydrocarbons such as methylene chloride, trichloromethane, tetrachloromethane, trichloroethane, tetrachloroethane, 1,2-dichloroethane or trichloroethylene, ethers such as diethyl ether, methyl tert-butyl ether, dioxane, tetrahydrofuran, glycol dimethyl ether or diethylene glycol dimethyl ether, hydrocarbons such as benzene, xylene, toluene, hexane, cyclohexane or petroleum fractions, nitroaromatic compounds such as nitromethane, carboxylic esters such as ethyl acetate, ketones such as acetone or 2-butanone, optionally N-alkylated carboxamides such as dimethylformamide or dimethylacetamide, alkyl sulphoxides such as dimethyl sulphoxide, carbonitriles such as acetonitrile or heteroaromatic compounds such as pyridine. Preference is given to dioxane, dimethylformamide or methylene chloride.

Examples of bases are alkali metal hydroxides such as sodium or potassium hydroxide, alkali metal carbonates and bicarbonates such as cesium carbonate, sodium bicarbonate, sodium or potassium carbonate, or amides such as lithium diisopropylamide, alkylamines such as triethylamine or diisopropylethylamine, preferably diisopropylethylamine or triethylamine, and other bases such as DBU.

The reaction takes place, if $X^3$ is hydroxyl, generally in inert solvents in the presence of condensing agents, where appropriate in the presence of a base, preferably in a temperature range from 20 to 50° C. under atmospheric pressure.

The term "inert solvents" includes for example halohydrocarbons such as methylene chloride, trichloromethane, tetrachloromethane, trichloroethane, tetrachloroethane, 1,2-dichloroethane or trichloroethylene, ethers such as diethyl ether, methyl tert-butyl ether, dioxane, tetrahydrofuran, glycol dimethyl ether or diethylene glycol dimethyl ether, hydrocarbons such as benzene, xylene, toluene, hexane, cyclohexane or petroleum fractions, nitroaromatic compounds such as nitromethane, carboxylic esters such as ethyl acetate, ketones such as acetone, optionally N-alkylated carboxamides such as dimethylformamide or dimethylacetamide, alkyl sulphoxides such as dimethyl sulphoxide, carbonitriles such as acetonitrile and heteroaromatic compounds such as pyridine. Preference, is given to tetrahydrofuran, dimethylformamide, 1,2-dichloroethane or methylene chloride.

Condensing agents for the purposes of the invention are, for example, carbodiimides such as, for example, N,N'-diethyl-, N,N'-dipropyl-, N,N'-diisopropyl-, N,N'-dicyclohexylcarbodiimide, N-(3-dimethylaminoisopropyl)-N'-ethylcarbodiimide hydrochloride (EDC), N-cyclohexylcarbodiimide-N-propyloxymethylpolystyrene (PS-carbodiimide); carbonyl compounds such as carbonyldiimidazole; 1,2-oxazolium compounds such as 2-ethyl-5-phenyl-1,2-oxazolium-3-sulphate or 2-tert-butyl-5-methylisoxazolium perchlorate; acylamino compounds such as 2-ethoxy-1-ethoxycarbonyl-1,2-dihydroquinoline; in addition propanephosphonic anhydride, isobutyl chloroformate, bis(2-oxo-3-oxazolidinyl)phosphoryl chloride, benzotriazolyloxy-tri(dimethylamino)phosphonium hexafluorophosphate, O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU), O-(7-azabenzotriazol-1-yl)-N,N,N',N'-tetramethyluronium hexafluorophosphate (HATU), benzotriazol-1-yloxytris(dimethylamino)phosphonium hexafluorophosphate (BOP), and mixtures thereof.

It may be advantageous where appropriate to use the condensing agent in the presence of an auxiliary nucleophile such as, for example, 1-hydroxybenzotriazole (HOBt).

Examples of bases are alkali metal carbonates and bicarbonates such as, for example, sodium or potassium carbonate or bicarbonate, organic bases such as alkylamines, e.g. triethylamine, or N-methylmorpholine, N-methylpiperidine, 4-dimethylaminopyridine or diisopropylethylamine.

Particular preference is given to the combination of N-(3-dimethylaminoisopropyl)-N'-ethylcarbodiimide hydrochloride (EDC), 1-hydroxybenzotriazole (HOBt) and triethylamine in dimethylformamide or of O-(7-azabenzotriazol-1-yl)-N,N,N',N'-tetramethyluronium hexafluorophosphate (HATU) and diisopropylethylamine in dimethylformamide.

The compounds (IV) and (V) are known or can be synthesized in analogy to known processes from the appropriate precursors (cf., for example, "Comprehensive Heterocyclic Chemistry", Katritzky et al., editors; Elsevier, 1996).

Thus, for example, substituted benzothiophene-2-carboxylic acids can be obtained from appropriately substituted 2-halobenzaldehydes by reaction with methyl mercaptoacetate (see, for example, A. J. Bridges et al., Tetrahedron Lett. 1992, 33, 7499) and subsequent hydrolysis of the ester:

Synthesis scheme 1:

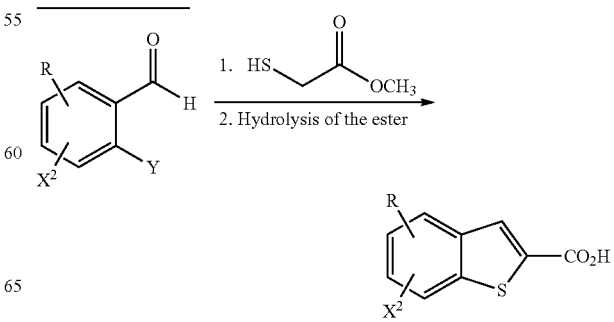

Y = F, Cl, Br
X² = halogen or triflate

The corresponding pyrido derivatives can be synthesized starting from 2-halobenzonitriles by reaction with methyl mercaptoacetate to give the 3-amino-benzothiophene-2-carboxylic esters:

Synthesis scheme 2:

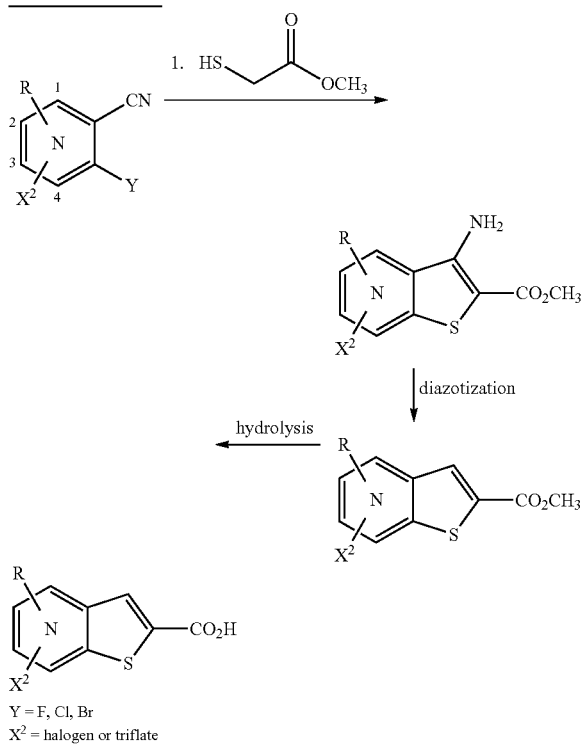

Y = F, Cl, Br
X² = halogen or triflate

The nitrogen atom shown in the ring may replace a CH group at one of positions 1 to 4 in the aromatic system.

The amino function can be removed by diazotization. Finally, the ester can be hydrolysed to give the target compound.

Substituted benzofuran-2-carboxylic acids can be obtained for example as described by D. Bogdal et al., *Tetrahedron* 2000, 56, 8769.

The compounds of the invention are suitable for use as medicaments for the treatment and/or prophylaxis of diseases in humans and animals.

They act as α7 nAChR agonists and show a valuable range of pharmacological effects which could not have been predicted.

The compounds of the invention can, because of their pharmacological properties, be employed alone or in combination with other active ingredients for the treatment and/or prevention of cognitive impairments, especially of Alzheimer's disease.

Because of their selective effect as α7 nAChR agonists, they are particularly suitable for improving perception, concentration, learning or memory, especially after cognitive impairments like those occurring for example in mild cognitive impairment, age-associated learning and memory impairments, age-associated memory loss, vascular dementia, craniocerebral trauma, stroke, dementia occurring after strokes (post-stroke dementia), post-traumatic brain syndrome, general concentration impairments, concentration impairments in children with learning and memory problems, attention deficit hyperactivity disorder, Alzheimer's disease, Lewy body dementia, dementia with degeneration of the frontal lobes, including Pick's syndrome, Parkinson's disease, progressive nuclear palsy, dementia with corticobasal degeneration, amyotrophic lateral sclerosis (ALS), Huntington's disease, multiple sclerosis, thalamic degeneration, Creutzfeld-Jakob dementia, HIV dementia, schizophrenia, schizophrenia with dementia or Korsakoffs psychosis.

The compounds of the invention can be employed alone or in combination with other active ingredients for the prophylaxis and treatment of acute and/or chronic pain (for a classification, see "Classification of Chronic Pain, Descriptions of Chronic Pain Syndromes and Definitions of Pain Terms", 2nd edition, Meskey and Begduk, editors; IASP Press, Seattle, 1994), especially for the treatment of cancer-induced pain and chronic neuropathic pain like, for example, that associated with diabetic neuropathy, postherpetic neuralgia, peripheral nerve damage, central pain (for example as a consequence of cerebral ischaemia) and trigeminal neuralgia, and other chronic pain such as, for example, lumbago, backache (low back pain) or rheumatic pain. In addition, these active ingredients are also suitable for the therapy of primary acute pain of any origin and of secondary states of pain resulting therefrom, and for the therapy of states of pain which were formerly acute and have become chronic.

The compounds of the invention can be employed alone or in combination with other active ingredients for the treatment of schizophrenia.

The in vitro effect of the compounds of the invention can be shown in the following assays:

1. Determination of the Affinity of Test Substaces for α7 nAChR by Inhibition of [³H]-Methyllycaconitine Binding to Rat Brain Membranes The [³H]-methyllycaconitine binding assay is a modification of the method described by Davies et al. in *Neurophar-macol.* 1999, 38, 679-690.

Rat brain tissue (hippocampus or whole brain) is homogenized in homogenization buffer (10% w/v, 0.32 M sucrose, 1 mM EDTA, 0.1 mM phenylmethylsulphonyl fluoride (PMSF), 0.01% (w/v) NaN₃, pH 7.4, 4° C.) at 600 rpm in a glass homogenizer. The homogenate is centrifuged (1000×g, 4° C., 10 min) and the supernatant is removed. The pellet is resuspended (20% w/v) and the suspension is centrifuged (1000×g, 4° C., 10 min). The two supernatants are combined and centrifuged (15 000×g, 4° C., 30 min). The pellet obtained in this way is referred to as the P2 fraction.

The P2 pellet is suspended in binding buffer (50 mM Tris-HCl, 1 mM MgCl₂, 120 mM NaCl, 5 mM KCl, 2 mM CaCl₂, pH 7.4), and the suspension is centrifuged (15 000×g, 4° C., 30 min), twice.

The residue is resuspended in binding buffer and incubated in a volume of 250 µl (amount of membrane protein 0.1-0.5 mg) in the presence of 1-5 nM [³H]-methyllycaconitine 0.1% (w/v) BSA (bovine serum albumin) and various concentrations of the test substance at 21° C. for 2.5 h. Incubation is then carried out in the presence of 1 µM α-bungarotoxin or 100 µM nicotine or 10 µM MLA (methyllycaconitine).

The incubation is stopped by adding 4 ml PBS (20 mM Na₂HPO₄, 5 mM KH₂PO₄, 150 mM NaCl, pH 7.4, 4° C.) and filtering through type A/E glass fibre filters (Gelman Sciences) which have previously been placed in 0.3% (v/v) polyethyleneimine (PEI) for 3 h. The filters are washed twice with 4 ml of PBS (4° C.), and the bound radioactivity is determined by scintillation measurement. All the assays are carried out in triplicate. The dissociation constant $K_i$ of the test substance was determined from the $IC_{50}$ of the compounds (concentration of the test substance at which 50% of the ligand bound to the receptor is displaced), the dissociation constant $K_D$ and the concentration L of [$^3$H]-methyllycaconitine using the equation $K_i=IC_{50}/(1+L/K_D)$.

In place of [$^3$H]-methyllycaconitine it is also possible to employ other α7 nAChR-selective radioligands such as, for example, [$^{125}$I]-α-bungarotoxin or nonselective nAChR radioligands together with inhibitors of other nAChRs.

Representative in vitro data for the effects of the compounds of the invention are shown in Table A:

TABLE A

| Example No. | $K_i$ (nM) |
|---|---|
| 3 | 60 |
| 4 | 24 |
| 17 | 17 |
| 19 | 20 |
| 20 | 1.6 |
| 73 | <1 |
| 75 | <0.1 |
| 76 | 3.3 |
| 90 | 14 |
| 102 | 62 |
| 108 | 17 |
| 116 | 17 |
| 130 | 26 |
| 149 | 97 |
| 150 | 35 |
| 151 | 88 |
| 154 | 3 |
| 163 | 14 |
| 175 | 8.3 |
| 186 | 120 |

The suitability of the compounds of the invention for the treatment of cognitive impairments can be shown in the following animal models:

2. Object Recognition Test

The object recognition test is a memory test. It measures the ability of rats (and mice) to distinguish between familiar and unfamiliar objects.

The test is described by Blokland et al., *NeuroReport* 1998, 9, 4205-4208; A. Ennaceur et al., *Behav. Brain Res.* 1988, 31, 47-59; A. Ennaceur et al., *Psychopharmacology* 1992, 109, 321-330; and Prickaerts et al., Eur. J. Pharmacol. 1997, 337, 125-136.

In a first run, a rat is confronted in an otherwise empty observation arena of relatively large size by two identical objects. The rat will investigate, i.e. sniff round and touch; both objects extensively. In a second run, after an interval of 24 hours, the rat is put in the observation arena again. One of the familiar objects has now been replaced by a new, unfamiliar object. If a rat recognizes the familiar object, it will concentrate on investigating the unfamiliar object. However, after 24 hours, a rat has normally forgotten which object it investigated in the first run, and it will therefore inspect both objects to the same extent. Administration of a substance with a learning- and memory-improving effect may lead to a rat recognizing the object seen in the first run 24 hours previously as familiar. It will investigate the new, unfamiliar object in more detail than the familiar one. This memory ability is expressed in a discrimination index. A discrimination index of zero means that the rat investigates both objects, the old and the new, for equal times; that is to say it has not recognized the old object and reacts to both objects as if they were new. A discrimination index greater than zero means that the rat inspects the new object longer than the old one; that is to say the rat has recognized the old object.

3. Social Recognition Test:

The social recognition test is a test to examine the learning- or memory-improving effect of test substances.

Adult rats housed in groups are placed singly in test cages 30 minutes before the start of the test. Four minutes before the start of the test, the test animal is put in an observation box. After this adaptation time, a juvenile animal is put in with the test animal and the time for which the adult animal investigates the juvenile animal is measured for 2 minutes (trial 1). All behaviours clearly directed at the young animal are measured, i.e. anogenital inspection, pursuit and fur care, during which the old animal is no further than 1 cm from the young animal. The juvenile animal is then taken out, and the adult is left in its test cage (for 24-hour retention, the animal is returned to its home cage). The adult test animal is treated with test substance before or after the first test. Depending on the timing of the treatment, the learning or the storage of the information about the young animal can be influenced by the substance. After a fixed period (retention), the test is repeated (trial 2). A larger difference between the investigation times measured in trials 1 and 2 means that the adult animal has remembered the young animal better.

The compounds of the invention are suitable for use as medicaments for humans and animals.

The present invention also includes pharmaceutical preparations which, besides inert, nontoxic, pharmaceutically suitable excipients and carriers, contain one or more compounds of the invention, or which consist of one or more compounds of the invention, and to processes for producing these preparations.

The compounds of the invention are to be present in these preparations in a concentration of from 0.1 to 99.5% by weight, preferably from 0.5 to 95% by weight, of the complete mixture.

Besides the compounds of the invention, the pharmaceutical preparations may also contain other active pharmaceutical ingredients.

The abovementioned pharmaceutical preparations can be produced by known methods in a conventional way.

The novel active ingredients can be converted in a known manner into conventional formulations such as tablets, coated tablets, pills, granules, aerosols, syrups, emulsions, suspensions and solutions, using inert, nontoxic, pharmaceutically suitable excipients or solvents. In these cases, the therapeutically active compound should in each case be present in a concentration of about 0.5 to 90% by weight of the formulation, i.e. in amounts which are sufficient to reach the stated dose range.

The formulations are produced for example by extending the active ingredients with solvents and/or excipients, where appropriate with use of emulsifiers and/or dispersants, it being possible for example when water is used as diluent where appropriate to use organic solvents as auxiliary solvents.

Administration can take place in a conventional way, preferably orally, transdermally or parenterally, especially perlingually or intravenously. However, it can also take place by inhalation through the mouth or nose, for example with the aid of a spray, or topically via the skin.

It has generally proved advantageous to administer amounts of about 0.001 to 10 mg/kg, on oral administration preferably about 0.005 to 3 mg/kg, of body weight to achieve effective results.

It may, nevertheless, be necessary where appropriate to deviate from the stated amounts, in particular as a function of the body weight or of the mode of administration, of the individual behaviour towards the medicament, the nature of its formulation and the time or interval over which administration takes place. Thus, it may be sufficient in some cases to make do with less than the aforementioned minimum amount, whereas in other cases the stated upper limit must be exceeded. Where larger amounts are administered, it may be advisable to divide these into a plurality of single doses over the day.

Unless indicated otherwise, all quantitative data relate to percentages by weight. Solvent ratios, dilution ratios and concentration data of liquid/liquid solutions are based in each case on volume. The statement "w/v" means "weight/volume". Thus, for example, "10% w/v" means: 100 ml of solution or suspension contain 10 g of substance.

ABBREVIATIONS conc. Concentrated
DAD Diode array detector.
DBU 1,5-Diazabicyclo[4.3.0]non-5-ene
DCI Desorption chemical ionization (in MS)
DMAP 4-N,N-Dimethylaminopyridine
DMF N,N-Dimethylformamide
DMSO Dimethyl sulphoxide
EDC N'—(3-Dimethylaminopropyl)-N-ethylcarbodiimide x HCl
eq. equivalent(s)
ESI Electrospray ionization (in MS)
HATU O-(7-Azabenzotriazol-1-yl)-N,N,N',N'-tetramethyluronium hexafluorophosphate
HOBt 1-Hydroxy-1H-benzotriazole x $H_2O$
HPLC High pressure/high performance liquid chromatography
LC-MS Liquid chromatography with coupled mass spectroscopy
MS Mass spectroscopy
NMR Nuclear magnetic resonance spectroscopy
PBS Phosphate-buffered saline
$PdCl_2$(dppf) Bis(diphenylphosphino)ferrocenepalladium(II) chloride
$PdCl_2(PPh_3)_2$ Dichlorobis(triphenylphosphine)palladium
$Pd(PPh_3)_4$ Tetrakis(triphenylphosphine)palladium(0)
Ph Phenyl
RT Room temperature
$R_t$ Retention time (in HPLC)
TBTU O-(Benzotriazol-1-yl)-N,N,N',N'-tetramethyluronium tetrafluoroborate
THF Tetrahydrofuran
TRIS Tris(hydroxymethyl)aminomethane

HPLC AND LC-MS METHODS

Method 1 (HPLC):
Instrument: HP 1100 with DAD; column: Kromasil RP-18, 60 mm×2 mm, 3.5 µm; eluent: A=5 ml $HClO_4$/L $H_2O$, eluent B=acetonitrile; gradient: 0 min 2% B, 0.5 min 2% B, 4.5 min 90% B, 6.5 min 90% B; flow rate: 0.75 mL/min; temperature: 30° C.; detection: UV 210 nm.
Method 2 (LC-MS):
MS apparatus type: Micromass ZQ; HPLC apparatus type: Waters Alliance 2790; column: symmetry C18, 50 mm×2.1 mm, 3.5 µm; eluent B: acetonitrile+0.05% formic acid, eluent A: water+0.05% formic acid; gradient: 0 min 5% B→4.5 min 90% B→5.5 min 90% B; oven: 50° C.; flow rate: 1.0 mL/min; UV detection: 210 nm.
Method 3 (LC-MS):
Instrument: Micromass Platform LCZ, HP1100; column: symmetry C18, 50 mm×2.1 mm, 3.5 µm; eluent A: water+0.05% formic acid, eluent B: acetonitrile+0.05% formic acid; gradient: 0 min 90% A→4.0 min 10% A→6.0 min 10% A; oven: 40° C.; flow rate: 0.5 mL/min; UV detection: 208-400 nm.
Method 4 (LC-MS):
MS apparatus type: Micromass ZQ; HPLC apparatus type: Waters Alliance 2790; column: Grom-Sil 1200DS-4 HE 50 mm×2 mm, 3.0 µm; eluent B: acetonitrile+0.05% formic acid, eluent A: water+0.05% formic acid; gradient: 0.0 min 5% B→2.0 min 40% B→4.5 min 90% B→5.5 min 90% B; oven: 45° C.; flow rate: 0.0 min 0.75 mL/min→4.5 min 0.75 mL/min→5.5 min 1.25 mL/min; UV detection: 210 nm.
Method 5 (LC-MS):
MS instrument: Micromass TOF (LCT); HPLC instrument: 2-column switching, Waters 2690; column: YMC-ODS-AQ, 50 mm×4.6 mm, 3.0 µm; eluent A: water+0.1% formic acid, eluent B: acetonitrile+0.1% formic acid; gradient: 0.0 min 100% A→0.2 min 95% A→1.8 min 25% A→1.9 min 10% A 3.2 min 10% A; oven: 40° C.; flow rate: 3.0 mL/min; UV detection: 210 nm.
Method 6 (LC-MS):
Flow injection, instrument: Micromass Platform LCZ+ Quattro LCZ; eluent A: water+0.05% formic acid, eluent B: acetonitrile+0.05% formic acid; gradient: 0.0 min 30% A→1.0 min 30% A; flow rate: 0.2-0.3 mL/min; HPLC: instrument HP 1100; UV detection: DAD.
Method 7 (HPLC):
Instrument: HP 1100 with DAD; column: Kromasil RP-18, 60 mm×2 mm, 3.5 µm; eluent A: 5 ml $HClO_4$/L $H_2O$, eluent B: acetonitrile; gradient: 0 min 2% B→0.5 min 2% B→4.5 min 90% B→9 min 90% B; flow rate: 0.75 mL/min; temperature: 30° C.; UV detection: 210 nm.

STARTING COMPOUNDS

General Method A

Synthesis of methyl 1-benzothiophene-2-carboxylates

Under an argon atmosphere, 1.5 equivalents of sodium hydride (60% in liquid paraffin) are introduced into absolute DMSO (0.60-1.26 M suspension). At room temperature, 1.1 equivalents of methyl mercaptoacetate are slowly added dropwise to the reaction mixture, and it is left to stir at room temperature until evolution of hydrogen ceases (about 15 min). 1.0 equivalent of the appropriate benzaldehyde are dissolved in absolute DMSO (1.60-3.36 M solution) and added at room temperature to the reaction mixture. The reaction mixture is stirred until the reaction is complete (about 5-10 min) and then poured into ice-water. The resulting precipitate is filtered off with suction, dried at 40° C. in vacuo overnight and reacted further as crude product.

General Method B

Synthesis of 1-benzothiophene-2-carboxylic acids

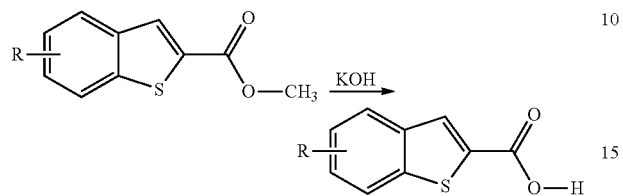

A mixture of equal parts of THF and 2 N aqueous potassium hydroxide solution (0.28-0.47 M solution) is added to the appropriate methyl 1-benzothiophene-2-carboxylate. The reaction mixture is left to stir at room temperature overnight. The THF is removed in vacuo, and the aqueous reaction mixture is acidified with concentrated hydrochloric acid. The resulting precipitate is filtered off with suction and dried in vacuo at 40° C.

General Method C

Amide linkage between 3-quinuclidinamine and 2-benzothiophene- or 2-benzo-furancarboxylic acids 1.0 eq. of the appropriate enantiomeric 3-quinuclidinamine hydrochloride is introduced together with 1 eq. of the carboxylic acid and 1.2 eq. of HATU into DMF at 0° C. After addition of 1.2 eq. of N,N-diisopropylethylamine, the mixture is stirred at RT. After 30 min., a further 2.4 eq. of N,N-diisopropylethylamine are added and the mixture is stirred at RT overnight.

EXAMPLE 1A

6-Bromo-1-benzofuran-2-carboxylic acid

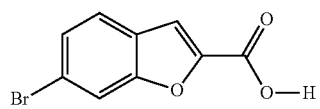

8.0 g (39.8 mmol) of 4-bromo-2-hydroxybenzaldehyde and 1.47 g (3.98 mmol) of tetra-n-butylammonium iodide are mixed with 22 g (159.19 mmol) of anhydrous potassium carbonate. 9.07 g (83.57 mmol) of methyl chloroacetate are added. The reaction mixture is heated at 130° C. for 4 h and then cooled to 0° C. in an ice bath. 100 ml of THF and a solution of 13.4 g (238.8 mmol) of potassium hydroxide in 50 ml of water are added, and the mixture is then stirred at RT overnight. The THF is removed under reduced pressure. The remaining aqueous phase is diluted with water and acidified with conc. hydrochloric acid. The precipitated product is filtered off and dried under high vacuum. Silica gel 60 (Merck, Darmstadt; eluent: toluene, toluene/acetic acid 50:1, toluene/acetic acid/methyl acetate 35:1:5) is used for final purification. The solvent is removed under reduced pressure. Finally, the last residues of solvent are removed under high vacuum. 3.8 g (40% of theory) of the title compound are isolated.

$^1$H-NMR (400 MHz, methanol-d$_4$): δ=7.91 (m, 1H), 7.61-7.51 (m, 3H).
HPLC (method 1): R$_1$=4.1 min:
MS (ESIpos): m/z=258 (M+NH$_4$).

EXAMPLE 2A

N-[(3R)-1-Azabicyclo[2.2.2]oct-3-yl]-6-bromo-1-benzofuran-2-carboxamide

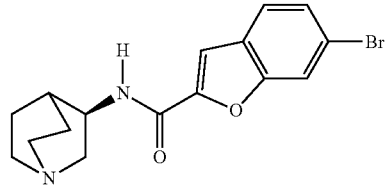 [SMILES: O=C(N[C@H]1CN2CCC1CC2)c1cc2ccc(Br)cc2o1]

3.8 g (15.77 mmol) of 6-bromobenzofuran-2-carboxylic acid (Example 1A), 3.14 g (15.77 mmol) of (R)-3-aminoquinuclidine dihydrochloride, 7.19 g (18.92 mmol) of HATU, 7.34 g (56.76 mmol) of N,N-diisopropylethylamine and 50 ml of DMF are reacted by general method C. The crude product is taken up in methanol and shaken together with acidic ion exchanger (Dowex® WX2-200) for about 20 min. The loaded ion exchanger is washed successively with methanol, dichloromethane and again with methanol. The product is eluted with methanol/triethylamine 90:10. The solvent is removed in a rotary evaporator under reduced pressure. Finally; the last residues of solvent are removed under high vacuum. 5.14 g (85% of theory) of the title compound are isolated. For analysis, a small amount is converted into the hydrochloride with 4N hydrogen chloride in dioxane.

$^1$H-NMR (200 MHz, DMSO-d$_6$): δ=10.55 (br. s, 1H), 9.22 (d, 1H), 8.05 (s, 1H), 7.75-7.55 (m, 3H), 4.43-4.29 (m, 1H), 3.70-3.55 (m, 1H), 3.45-3.10 (m, 5H), 2.25-2.00 (m, 2H), 1.98-1.82 (m, 2H), 1.80-1.60 (m, 1H).
HPLC (method 1): R$_1$=3.9 min.
MS (ESIpos): m/z=349 (M+H)$^+$.
LC-MS (method 2): R$_t$=1.49 min.
MS (ESIpos): m/z=349 (M+H)$^+$.

EXAMPLE 3A

N-[(3R)-1-Azabicyclo[2.2.2]oct-3-yl]-5-bromo-1-benzofuran-2-carboxamide hydrochloride

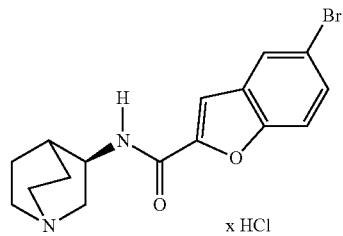 [SMILES: O=C(N[C@H]1CN2CCC1CC2)c1cc2cc(Br)ccc2o1]

240 mg (0.98 mmol) of 5-bromobenzofuran-2-carboxylic acid, 200 mg (0.98 mmol) of (R)-3-aminoquinuclidine dihydrochloride, 450 mg (1.18 mmol) of HATU, 460 mg (3.54 mmol) of N,N-diisopropylethylamine and 2.0 ml of DMF are reacted by general method C. The reaction mixture is purified by preparative HPLC. Finally, an excess of 1N hydrochloric acid is added to the product. The solvent is removed under reduced pressure. 202 mg (53% of theory) of the title compound are isolated.

$^1$H-NMR (200 MHz, DMSO-d$_6$): δ=9.38 (br. s, 1H), 8.88 (d, 1H), 7.60 (s, 1H), 7.38-7.20 (m, 2H), 7.09 (dd, 1H), 4.43-4.29 (m, 1H), 3.70-3.55 (m, 1H), 3.45-3.10 (m, 5H), 2.25-2.00 (m, 2H), 1.98-1.82 (m, 2H), 1.80-1.60 (m, 1H).

MS (ESIpos): m/z=349 (M+H)$^+$ (free base).

LC-MS (method 3): R$_f$=2.71 min.

MS (ESIpos): m/z=349 (M+H)$^+$ (free base).

EXAMPLE 4A

7-Bromo-5-fluoro-1-benzofuran-2-carboxylic acid

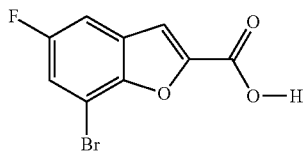 [SMILES: O=C(O)c1cc2cc(F)cc(Br)c2o1]

1.0 g (5.24 mmol) of 2-bromo-4-fluorophenol is introduced into 4.0 ml of trifluoroacetic acid. 1.47 g (10.47 mmol) of hexamethylenetetramine are added in portions over the course of 20 min. The mixture is then boiled under reflux for 28 h. At RT, 6 ml of water and 3 ml of 50% strength sulphuric acid are added. After 2 h, the mixture is extracted twice with a total of 60 ml of ethyl acetate. The combined organic phases are washed four times with 1N hydrochloric acid and once with water.

Drying over magnesium sulphate is followed by removal of the solvent under reduced pressure. Finally, the last residues of solvent are removed under high vacuum. The crude product (without further purification) and 0.19 g (0.52 mmol) of tetra-n-butylammonium iodide are mixed with 2.9 g (20.96 mmol) of anhydrous potassium carbonate. 1.19 g (11.0 mmol) of methyl chloroacetate are added. The reaction mixture is heated at 130° C. for 4 h and then cooled to 0° C. in an ice bath. 18 ml of THF and a solution of 1.76 g (31.44 mmol) of potassium hydroxide in 18 ml of water are added. The mixture is stirred at RT overnight. The solvent is removed under reduced pressure. Dilution with water is followed by acidification with concentrated hydrochloric acid. The mixture is extracted twice with ethyl acetate. The combined organic phases are dried over magnesium sulphate, and the solvent is removed in a rotary evaporator under reduced pressure, Silicagel 60 (Merck, Darmstadt; eluent: toluene/acetic acid 40:1) is used for purification. The solvent is removed under reduced pressure. Finally, the last residues of solvent are removed under high vacuum. 257 mg (19% of theory over the two stages) of the title compound are isolated.

$^1$H-NMR (400 MHz, methanol-d$_4$): δ=7.60 (m, 1H), 7.48-7.35 (m, H).

HPLC (method 1): R$_t$=4.1 min.

MS (ESIpos): m/z=276 (M+NH$_4$)$^+$.

EXAMPLE 5A

N-[(3R)-1-Azabicyclo[2.2.2]oct-3-yl]-5-fluoro-7-bromo-1-benzofuran-2-carboxamide

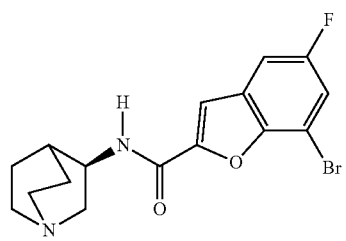 [SMILES: O=C(N[C@H]1CN2CCC1CC2)c1cc2cc(F)cc(Br)c2o1]

143 mg (0.55 mmol) of 5-fluoro-7-bromo-1-benzofuran-2-carboxylic acid (Example 4A), 100 mg (0.50 mmol) of (R)-3-aminoquinuclidine dihydrochloride, 229.14 mg (0.6 mmol) of HATU, 234 mg (1.81 mmol) of N,N-diisopropylethylamine and 2.0 ml of DMF are reacted by general method C. DMF is removed under reduced pressure, and the crude product is dissolved in 1N sodium hydroxide solution. The aqueous phase is extracted with ethyl acetate, and the organic phase is washed with saturated aqueous sodium chloride solution. The combined organic phases are dried over magnesium sulphate, and the solvent is removed in a rotary evaporator under reduced pressure. The crude product is taken up in methanol and shaken together with acidic ion exchanger (Dowex® WX2-200) for about 20 min. The loaded ion exchanger is washed three times with 30 ml of methanol each time, then with water, again with methanol, with dichloromethane and finally again with methanol. The product is eluted with methanol/triethylamine 95:5. The solvent is removed in a rotary evaporator under reduced pressure. 181 mg (98% of theory) of the title compound are isolated.

$^1$H-NMR (400 MHz, methanol-d$_4$): δ=7.59 (d, 1H), 7.53-7.46 (m, 2H), 4.24-4.18 (m, 1H), 3.34-3.29 (m, 1H), 3.07-2.97 (m, 1H), 2.93-2.77 (m, 4H), 2.13-2.05 (m, 1H), 1.98-1.86 (m, 1H), 1.84-1.75 (m, 2H), 1.63-1.53 (m, 1H).

MS (ESIpos): m/z=367 (M+H)$^+$.

LC-MS (method 3): R$_1$=2.92 min.

MS (ESIpos): m/z=367 (M+H)$^+$.

EXAMPLE 6A

Methyl 7-bromo-1-benzothiophene-2-carboxylate

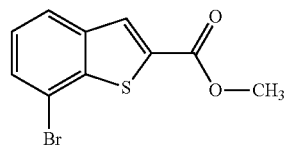

Starting from 27.8 g (137.1 mmol) of 3-bromo-2-fluorobenzaldehyde, by general method A with 8.2 g (205.7 mmol) of sodium hydride (60% in liquid paraffin) and 16.0 g (150.9 mmol) of methyl mercaptoacetate, 20.57 g of a mixture of the title compound and the corresponding acid (about 1:1) is obtained.

EXAMPLE 7A

7-Bromo-1-benzothiophene-2-carboxylic acid

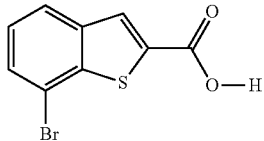 [SMILES: O=C(O)c1cc2cccc(Br)c2s1]

Starting from 10.0 g (36.9 mmol) of methyl 7-bromo-1-benzothiophene-2-carboxylate, by general method B 8.99 g (91.0% of theory) of the desired product are obtained.

$^1$H-NMR (200 MHz, DMSO-$d_6$): δ=13.76 (br. s, 1H), 8.28 (s, 1H), 8.07 (d, 1H), 7.78 (d, 1H), 7.46 (dd, 1H).

HPLC (method 1): $R_t$=4.4 min.

EXAMPLE 8A

N-(1-Azabicyclo[2.2.2]oct-3-yl)-7-bromo-1-benzothiophene-2-carboxamide hydrochloride

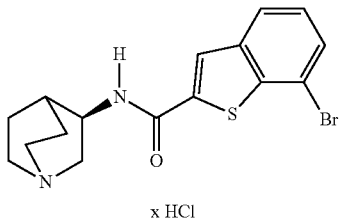 [SMILES: O=C(N[C@H]1CN2CCC1CC2)c1cc2cccc(Br)c2s1]

903.8 mg (3.52 mmol) of 7-bromo-1-benzothiophene-2-carboxylic acid (Example 7A), 700 mg (3.52 mmol) of (R)-3-aminoquinuclidine dihydrochloride, 1604.0 mg (4.22 mmol) of HATU, 1635.7 mg (12.66 mmol) of N,N-diisopropylethylamine and 7.0 ml of DMF are reacted by general method C. The reaction mixture is purified by preparative HPLC. The product is dissolved in a 1:1 mixture of 4 M hydrogen chloride in dioxane and 1N hydrochloric acid and then concentrated and dried under high vacuum. 1087 mg (77% of theory) of the title compound are obtained.

$^1$H-NMR (200 MHz, DMSO-$d_6$): δ=10.01 (br. s, 1H), 9.15 (d, 1H), 8.47 (s, 1H), 8.02 (m, 1H), 7.74 (m, 1H), 7.43 (dd, 1H), 4.34 (m, 1H), 3.80-3.10 (m, 6H), 2.22 (m, 1H), 2.14 (m, 1H), 1.93 (m, 2H), 1.78 (m, 1H).

HPLC (method 1): $R_t$=4.1 min.

MS (ESIpos): m/z=365 (M+H)$^+$ (free base).

EXAMPLE 9A

Methyl 6-bromo-1-benzothiophene-2-carboxylate

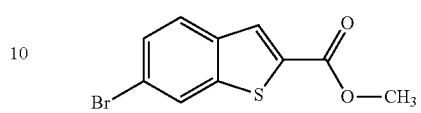

Starting from 6.54 g (32.2 mmol) of 4-bromo-2-fluorobenzaldehyde, by general method A with 1.93 g (48.3 mmol) of sodium hydride (60% in liquid paraffin) and 3.76 g (35.5 mmol) of methyl mercaptoacetate, 4.06 g (46% of theory) of the title compound are obtained.

$^1$H-NMR (200 MHz, DMSO-$d_6$): δ=8.42 (d, 1H), 8.22 (s, 1H), 7.98 (d, 1H), 7.65 (dd, 1H), 3.90 (s, 3H).

HPLC (method 1): $R_t$=5.3 min.

MS (ESIpos): m/z=270 (M$^+$).

EXAMPLE 10A

6-Bromo-1-benzothiophene-2-carboxylic acid

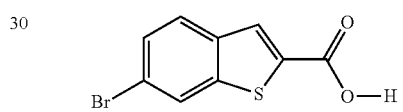

Starting from 4.0 g (14.8 mmol) of methyl 6-bromo-1-benzothiophene-2-carboxylate (from Example 9A), by general method B 3.55 g (94% of theory) of the desired product are obtained.

$^1$H-NMR (400 MHz, DMSO-$d_6$): δ=13.48 (br. s, 1H), 8.38 (s, 1H), 8.22 (s, 1H), 7.96 (d, 1H), 7.63 (m, 1H).

HPLC (method 1): $R_t$=4.5 min.

EXAMPLE 11A

N-[(3R)-1-Azabicyclo[2.2.2]oct-3-yl]-6-bromo-1-benzothiophene-2-carboxamide hydrochloride

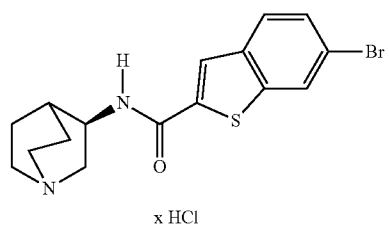 [SMILES: O=C(N[C@H]1CN2CCC1CC2)c1cc2ccc(Br)cc2s1]

900.0 mg (3.50 mmol) of 6-bromo-1-benzothiophene-2-carboxylic acid (Example 10A), 697.0 mg (3.50 mmol) of (R)-3-aminoquinuclidine dihydrochloride, 1597.1 mg (4.20 mmol) of HATU, 1628.7 mg (12.60 mmol) of N,N-diisopropylethylamine and 8.0 ml of DMF are reacted by general method C. The reaction mixture is purified by preparative HPLC. The product is dissolved in a 1:1 mixture of 4 M hydrogen chloride in dioxane and 1N hydrochloric acid, and the solution is then concentrated. Recrystallization from methanol/ethanol (1:10) affords 594 mg (42% of theory) of the title compound in the form of yellowish-brown crystals.

$^1$H-NMR (300 MHz, DMSO-d$_6$): δ=9.81 (br. s, 1H), 8.76 (m, 1H), 8.33 (s, 1H), 8.22 (s, 1H), 7.91 (d, 1H), 7.59 (dd, 1H), 4.15 (m, 1H), 3.51-2.93 (m, 6H), 2.12-1.92 (m, 2H), 1.79 (m, 2H), 1.58 (m, 1H).

HPLC (method 1): R$_t$=4.1 min.

MS (ESIpos): m/z=364 (M$^+$) (free base).

EXAMPLE 12A

Methyl 5-bromo-1-benzothiophene-2-carboxylate

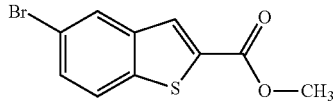

Starting from 2.99 g (14.7 mmol) of 5-bromo-2-fluorobenzaldehyde, by general method A with 0.88 g (22.1 mmol) of sodium hydride (60%) and 1.72 g (16.2 mmol) of methyl mercaptoacetate, 2.76 g (69.1% of theory) of the title compound are obtained.

$^1$H-NMR (200 MHz, DMSO-d$_6$): δ=8.29 (d, 1H), 8.18 (s, 1H), 8.08 (d, 1H), 7.69 (dd, 1H), 3.90 (s, 3H).

HPLC (method 1): R$_t$=5.2 min.

MS (ESIpos): m/z=270 (M$^+$).

EXAMPLE 13A

5-Bromo-1-benzothiophene-2-carboxylic acid

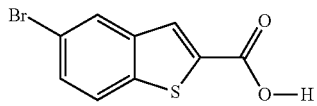

Starting from 2.7 g (9.96 mmol) of methyl 5-bromo-benzothiophene-2-carboxylate (from Example 12A), by general method B 2.41 g (94% of theory) of the desired product are obtained.

$^1$H-NMR (400 MHz, DMSO-d$_6$): δ=13.67 (br. s, 1H), 8.27 (m, 1H), 8.10 (s, 1H), 8.05 (d, 1H), 7.66 (dd, 1H).

HPLC (method 1): R$_t$=4.5 min.

EXAMPLE 14A

N-[(3R)-1-Azabicyclo[2.2.2]oct-3-yl]-5-bromo-1-benzothiophene-2-carboxamide hydrochloride

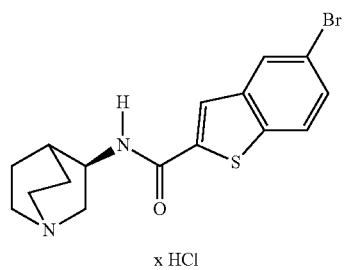 [SMILES: O=C(N[C@H]1CN2CCC1CC2)c1cc2cc(Br)ccc2s1]

133.7 mg (0.52 mmol) of 5-bromo-1-benzothiophene-2-carboxylic acid (Example 13A), 155.4 mg (0.78 mmol) of (R)-3-aminoquinuclidine dihydrochloride, 296.7 mg (0.78 mmol) of HATU, 369.8 mg (2.86 mmol) of N,N-diisopropylethylamine and 1.5 ml of DMF are reacted by general method C. The reaction mixture is purified by preparative HPLC. The product is dissolved in acetonitrile, and an excess of 1N hydrochloric acid is added. Finally, the solvent is removed. 175 mg (84% of theory) of the title compound are isolated.

$^1$H-NMR (200 MHz, DMSO-d$_6$): δ=9.44 (br. s, 1H), 8.95 (d, 1H), 8.30-8.10 (m, 2H), 8.03 (d, 1H), 7.60 (m, 1H), 4.38-4.20 (m, 1H), 3.80-3.55 (m, 1H), 3.42-3.05 (m, 5H), 2.25-2.00 (m, 2H), 1.98-1.62 (m, 3H).

HPLC (method 1): R$_t$=4.1 min.

MS (ESIpos): m/z=365 (M+H)$^+$ (free base).

EXAMPLE 15A 4-(4-Bromophenyl)morpholine

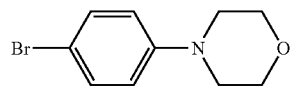

A solution of 6.94 ml (134.8 mmol) of bromine in 25 ml of acetic acid is slowly added dropwise over a period of 40 min to a solution of 20 g (122.5 mmol) of N-phenylmorpholine in 170 ml of acetic acid at room temperature. After stirring at room temperature for 30 min, the reaction mixture is stirred into 750 ml of water and adjusted to pH 11 with 45% strength sodium hydroxide solution. The resulting precipitate is filtered off with suction, washed with water and dried under high vacuum. Recrystallization from ethanol results in 18.6 g (62.9% of theory) of the title compound.

$^1$H-NMR (200 MHz, DMSO-d$_6$): δ=7.37 (m, 2H), 6.89 (m, 2H), 3.73 (m, 4H), 3.08 (m, 4H).

HPLC (method 1): R$_t$=3.9 min.

MS (ESIpos): m/z=242 (M+H)+.

EXAMPLE 16A 4-(4-Bromophenyl)-3-morpholinone

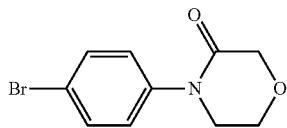

1.41 g (6.20 mmol) of benzyltriethylammonium chloride and 0.98 g (6.20 mmol) of potassium permanganate are added to a solution of 500 mg (2.07 mmol) of 4-(4-bromophenyl) morpholine (Example 15A) in 10 ml of dichloromethane. After 5 h under reflux, the contents of the flask are concentrated in vacuo, and the residue is purified by preparative HPLC. The concentrated product is dried under high vacuum. 217 mg (35.7% of theory) of the title compound are obtained.

LC-MS (method 4): $R_t$=2.9 min, m/z=255 (M+).

EXAMPLE 17A 3-(4-Morpholinyl)phenyl trifluoromethanesulphonate

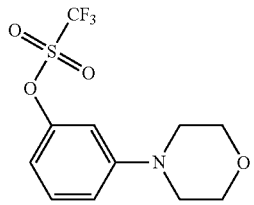 [SMILES: O=S(=O)(Oc1cccc(N2CCOCC2)c1)C(F)(F)F]

2.18 ml (12.9 mmol) of trifluoromethanesulphonic anhydride are slowly added dropwise to a solution, cooled to −10° C., of 1.54 g (8.6 mmol) of 3-(4-morpholinyl)-phenol and 3.59 ml (25.8 mmol) of triethylamine in 10 ml of dichloromethane. The mixture is stirred at −10° C. for 30 min and then at 0° C. for 30 min. It is washed successively with 10% strength sodium bicarbonate solution, water and saturated sodium chloride solution, dried over sodium sulphate and concentrated in vacuo, and the residue is dried under high vacuum. 2.41 g (90.1% of theory) of the title compound are obtained.

$^1$H-NMR (200 MHz, CDCl$_3$): δ=7.28 (m, 1H), 6.88 (m, 1H), 6.73 (m, 2H), 3.86 (m, 4H), 3.18 (m, 4H).

HPLC (method 1): $R_t$=4.8 min.

MS (ESIpos): m/z=312 (M+H)+.

EXAMPLE 18A 4-(4-Morpholinylcarbonyl)phenyl trifluoromethanesulphonate

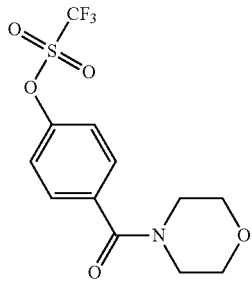 [SMILES: O=C(c1ccc(OS(=O)(=O)C(F)(F)F)cc1)N1CCOCC1]

1.23 ml (7.24 mmol) of trifluoromethanesulphonic anhydride are slowly added dropwise to a solution, cooled to −10° C., of 1.0 g (4.83 mmol) of 4-(4-morpholinyl-carbonyl)phenol and 2.02 ml (14.48 mmol) of triethylamine in 20 ml of dichloromethane. The mixture is stirred at −10° C. for 30 min and then at 0° C. for 30 min. It is washed successively with 10% strength sodium bicarbonate solution, water and saturated sodium chloride solution, dried over sodium sulphate and concentrated in vacuo, and the residue is dried under high vacuum. 1.71 g (94.6% of theory) of the title compound are obtained.

$^1$H-NMR (400 MHz, methanol-d$_4$): δ=7.62 (m, 2H), 7.49 (m, 2H), 3.86-3.34 (m, 8H).

HPLC (method 1): $R_t$=4.2 min.
MS (ESIpos): m/z=357 (M+NH$_4$)+.

EXAMPLE 19A

Methyl 7-[4-(4-morpholinyl)phenyl]-1-benzothiophene-2-carboxylate

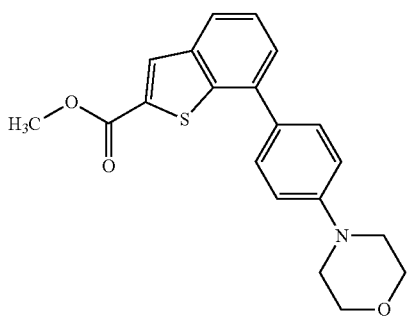 [SMILES: COC(=O)c1cc2cccc(-c3ccc(N4CCOCC4)cc3)c2s1]

3.42 ml of 2 M sodium carbonate solution and 83.5 mg (0.11 mmol) of PdCl$_2$(dppf) are added to a solution of 619.1 mg (2.28 mmol) of methyl 7-bromo-1-benzothiophene-2-carboxylate (Example 6A) and 520 mg (2.51 mmol) of 4-(4-morpholinyl)phenylboronic acid in 10 ml DMF. The mixture is heated at 80° C. for 16 h. Cooling is followed by filtration through kieselguhr and purification by preparative HPLC. The concentrated product is dried under high vacuum. 146.7 mg (16.4% of theory) of the title compound are obtained.

HPLC (method 1): $R_t$=4.6 min.

MS (ESIpos): m/z=354 (M+H)+.

EXAMPLE 20A

7-[4-(4-Morpholinyl)phenyl]-1-benzothiophene-2-carboxylic acid

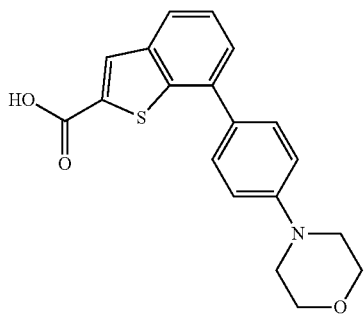 [SMILES: O=C(O)c1cc2cccc(-c3ccc(N4CCOCC4)cc3)c2s1]

A solution of 330 mg (0.77 mmol) of methyl 7-[4-(4-morpholinyl)phenyl]-1-benzothiophene-2-carboxylate (Example 19A) in 6 ml of a 1:1 mixture of methanol and 2N potassium hydroxide solution is stirred at room temperature for 2 h and at 50° C. for 1 h. The reaction mixture is concentrated in vacuo and, after addition of water, acidified with conc. hydrochloric acid. The resulting precipitate is filtered off with suction, washed twice with water and dried under high vacuum. 292 mg of crude product are obtained and reacted without further purification.

EXAMPLE 21A 7-(2-Methoxyphenyl)-1-benzofuran-2-carboxylic acid

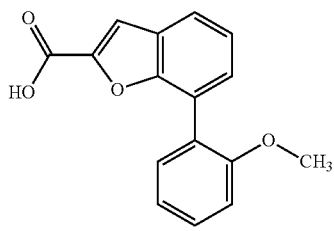

5.0 g (20.7 mmol) of 7-bromo-1-benzofuran-2-carboxylic acid (Example 29A) and 3.78 g (24.9 mmol) of 2-methoxyphenylboronic acid are introduced into 50 ml of DMF. Addition of 31.1 ml of 2 M sodium carbonate solution and 1.2 g (1.04 mmol) of Pd(PPh$_3$)$_4$ is followed by heating to 90° C. After 18 h, the solvent is distilled out. The residue is partitioned between 1N hydrochloric acid and ethyl acetate and extracted three times with 200 ml of ethyl acetate each time. The organic phase is dried over sodium sulphate and concentrated in vacuo. The residue is purified by flash chromatography (silica gel, mobile phase: dichloromethane/methanol/acetic acid 100:10:1). Concentration and drying under high vacuum result in 2.97 g (53.2% of theory) of the title compound.

$^1$H-NMR (300 MHz, DMSO-d$_6$): δ=13.46 (s, 1H), 7.73 (dd, 1H), 7.59 (s, 1H), 7.48-7.33 (m, 4H), 7.20 (d, 1H), 7.09 (m, 1H), 3.75 (s, 3H).

HPLC (method 1): R$_t$=4.5 min.
MS (ESIpos): m/z=286 (M+NH$_4$)+.

EXAMPLE 22A

N-[(3S)-1-Azabicyclo[2.2.2]oct-3-yl]-7-bromo-1-benzothiophene-2-carboxamide hydrochloride

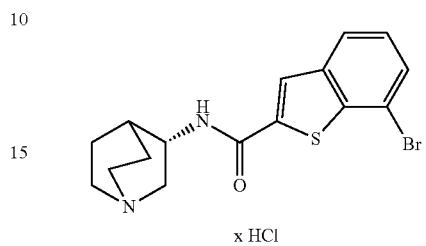

3.58 g (18.7 mmol) of EDC, 2.52 g (18.7 mmol) of HOBt and 7.8 ml (56 mmol) of triethylamine are added to a solution, cooled to 0° C., of 4.0 g (15.6 mmol) of 7-bromo-1-benzothiophene-2-carboxylic acid (Example 7A) and 3.10 g (15.6 mmol) of (S)-3-aminoquinuclidine dihydrochloride in 50 ml of DMF. The mixture is stirred at room temperature for 18 h. The reaction is stopped by adding 10% strength sodium bicarbonate solution. The precipitate resulting after addition of ethyl acetate is filtered off. The aqueous phase is extracted with ethyl acetate, the combined organic phases are dried over sodium sulphate and concentrated, and the residue is dried under high vacuum. 4.70 g (68% of theory) of the title compound are obtained.

The spectroscopic data agree with those of the enantiomeric compound (Example 8A).

EXAMPLE 23A

N-[(3R)-1-Azabicyclo[2.2.2]oct-3-yl]-6-(4-formylphenyl)-1-benzothiophene-2-carboxamide hydrochloride

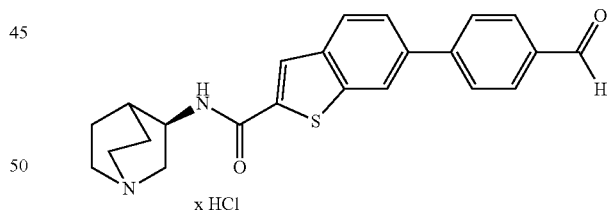

200 mg (0.50 mmol) of N-[(3R)-1-azabicyclo[2.2.2]oct-3-yl]-6-bromo-1-benzothiophene-2-carboxamide hydrochloride (Example 11A) and 74.6 mg (0.50 mmol) of 4-formylphenylboronic acid are introduced into 2 ml of DMF. Addition of 0.75 ml of 2 M sodium carbonate solution and 20.3 mg (0.02 mmol) of PdCl$_2$(dppf) is followed by heating to 80° C. After 18 h, the reaction mixture is filtered through kieselguhr and purified by preparative HPLC. The product fractions are concentrated, mixed with a 5:1 mixture of methanol and 4 N hydrogen chloride in dioxane and again concentrated. Drying under high vacuum results in 163.8 mg (75.0% of theory) of the title compound.

$^1$H-NMR (200 MHz, DMSO-d$_6$): δ=10.09 (s, 1H), 10.07 (br. s, 1H), 9.10 (d, 1H), 8.50 (m, 1H), 8.37 (s, 1H), 8.15-7.97

(m, 5H), 7.87 (dd, 1H), 4.33 (m, 1H), 3.68 (m, 1H), 3.45-3.12 (m, 5H), 2.23 (m, 1H), 2.16 (m, 1H), 1.91 (m, 2H), 1.76 (m, 1H).

HPLC (method 1): $R_t$=4.1 min.
MS (ESIpos): m/z=391 (M+H)$^+$ (free base).

EXAMPLE 24A

Methyl 6-cyano-1-benzothiophene-2-carboxylate

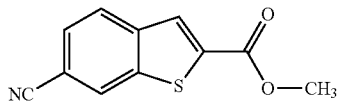

4.08 g (23.2 mmol) of 4-cyano-2-nitrobenzaldehyde, 2.46 g (23.2 mmol) of methyl mercaptoacetate and 6.46 ml (46.4 mmol) of triethylamine are heated in 12.3 ml of DMSO at 80° C. for 2.5 h. The reaction solution is added to 400 ml of ice-water. The precipitate resulting after addition of 4 ml of acetic acid is filtered off with suction, washed twice with water and dried in vacuo at 50° C. overnight. 4.19 g (83.2% of theory) of the title compound are obtained.

$^1$H-NMR (200 MHz, DMSO-d$_6$): δ=8.73 (d, 1H), 8.32 (s, 1H), 8.21 (d, 1H), 7.85 (dd, 1H), 3.92 (s, 3H).
HPLC (method 1): $R_t$=4.4 min.
MS (ESIpos): m/z=218 (M+H)$^+$.

EXAMPLE 25A

6-Cyano-1-benzothiophene-2-carboxylic acid

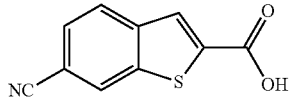

In accordance with general method B, 0.49 g (61.6% of theory) of the desired product is obtained starting from 0.6 g (2.76 mmol) of methyl 6-cyano-1-benzothiophene-2-carboxylate (Example 24A).

HPLC (method 1): $R_t$=3.9 min.
MS (ESIpos): m/z=222 (M+H)$^+$.

EXAMPLE 26A

N-[(3R)-1-Azabicyclo[2.2.2]oct-3-yl]-6-cyano-1-benzothiophene-2-carboxamide hydrochloride

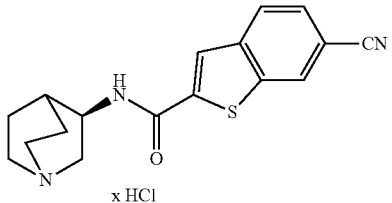 [SMILES: N#Cc1ccc2cc(C(=O)N[C@H]3CN4CCC3CC4)sc2c1]

320.8 mg (1.1 mmol) of 6-cyano-1-benzothiophene-2-carboxylic acid (Example 25A), 200 mg (1.0 mmol) of (R)-3-aminoquinuclidine dihydrochloride, 458.3 mg (1.21 mmol) of HATU, 467.3 mg (3.62 mmol) of N,N-diisopropylethylamine and 4.0 ml of DMF are reacted by general method C. The reaction mixture is purified by preparative HPLC. The product is dissolved in a mixture of methanol and 4 M hydrogen chloride in dioxane and then concentrated and dried under high vacuum. 222.1 mg (64% of theory) of the title compound are obtained.

$^1$H-NMR (300 MHz, DMSO-d$_6$): δ=9.80 (m, 1H), 9.12 (d, 1H), 8.68 (s, 1H), 8.37 (s, 1H), 8.16 (d, 1H), 7.83 (dd, 1H), 4.33 (m, 1H), 3.76-3.05 (m, 6H), 2.23 (m, 1H), 2.13 (m, 1H), 1.92 (m, 2H), 1.76 (m, 1H).
HPLC (method 1): $R_t$=3.6 min.
MS (ESIpos): m/z=312 (M+H)$^+$ (free base).

EXAMPLE 27A

6-[(Z)-Amino(hydroxyimino)methyl]-N-[(3R)-1-azabicyclo[2.2.2]oct-3-yl]-1-benzothiophene-2-carboxamide dihydrochloride

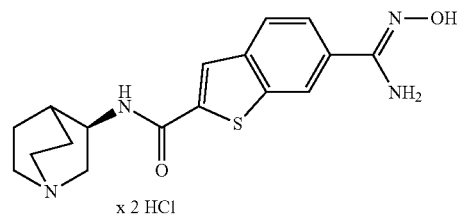 [SMILES: N/C(=N\O)c1ccc2cc(C(=O)N[C@H]3CN4CCC3CC4)sc2c1]

800 mg (2.0 mmol) of N-[(3R)-1-azabicyclo[2.2.2]oct-3-yl]-6-cyano-1-benzothiophene-2-carboxamide hydrochloride (Example 26A), 278.1 mg (4.0 mmol) of hydroxylamine hydrochloride and 829.5 mg (6.0 mmol) of potassium carbonate are heated in 8 ml of an 8:1 mixture of water and ethanol at 80° C. for 3 h. The mixture is purified by column chromatography on silica gel (mobile phase: dichloromethane/methanol/25% ammonia solution 100:20:4). The product fractions are combined, concentrated, mixed with methanol and 4 M hydrogen chloride in dioxane, then again concentrated and dried under high vacuum. 447.3 mg (53.6% of theory) of the title compound are obtained.

$^1$H-NMR (200 MHz, DMSO-d$_6$): δ=11.15 (m, 1H), 10.22 (m, 1H), 9.36 (d, 1H), 8.52 (s, 1H), 8.46 (m, 1H), 8.14 (d, 1H), 7.73 (dd, 1H), 4.33 (m, 1H), 3.93-3.10 (m, 6H), 2.32-2.05 (m, 2H), 1.93 (m, 2H), 1.75 (m, 1H).
HPLC (method 1): $R_t$=2.9 min.
MS (ESIpos): m/z=345 (M+H)$^+$ (free base).

EXAMPLE 28A

3-Bromo-2-hydroxybenzaldehyde

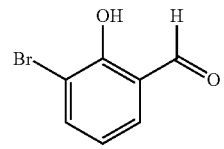

20.0 g (115.6 mmol) of 2-bromophenol are introduced into 500 ml of dry acetonitrile. 16.84 g (176.87 mmol) of dry magnesium chloride, 23.4 g of paraformaldehyde granules and 41.9 ml (300.6 mmol) of triethylamine are added. The reaction mixture is heated under reflux for 4 h and, after cooling to 0° C., 300 ml of 2N hydrochloric acid are added. The aqueous phase is extracted three times with 200 ml of diethyl ether each time. The organic phase is dried over magnesium sulphate, and the solvent is removed in vacuo. 24 g (64% of theory, 62% pure according to HPLC) of the title compound are isolated and reacted further without further purification.

HPLC (method I): $R_t$=4.25 min.
MS (ESIpos): m/z=202 (M+H)$^+$.

EXAMPLE 29A

7-Bromo-1-benzofuran-2-carboxylic acid

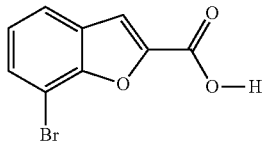 [SMILES: O=C(O)c1cc2cccc(Br)c2o1]

13.5 g (40.3 mmol) of 3-bromo-2-hydroxybenzaldehyde (Example 28A, 62% pure) are heated together with 9.18 g (84.62 mmol) of methyl chloroacetate, 1.49 g (4.03 mmol) of tetra-n-butylammonium iodide and 22.28 g (161.18 mmol) of potassium carbonate at 130° C. for 6 h. After cooling to RT, 100 ml of water and 100 ml of THF, and 13.57 g (241.77 mmol) of potassium hydroxide are added, and the mixture is stirred at RT overnight. The solvent is removed under reduced pressure, and the residue is taken up in 400 ml of water and washed four times with a total of 400 ml of diethyl ether. While cooling in ice, the pH is adjusted to 0 with concentrated hydrochloric acid and five extractions with a total of 700 ml of ethyl acetate are carried out. The organic phase is washed with 100 ml of saturated sodium chloride solution and then dried over magnesium sulphate. The crude product is completely freed of residual solvents under high vacuum and is stirred with 80 ml of diethyl ether. The product is filtered off and washed with a little ice-cold diethyl ether. 4.8 g (47% of theory) of the title compound are isolated.

$^1$H-NMR (200 MHz, DMSO-d$_6$): δ=13.5 (br. s, 1H), 7.86-7.72 (m, 2H), 7.79 (s, 1H), 7.31 (t, 1H).
MS (DCI/NH$_3$): m/z=258 (M+NH$_4$)$^+$.

EXAMPLE 30A

N-[(3R)-1-Azabicyclo[2.2.2]oct-3-yl]-7-bromo-1-benzofuran-2-carboxamide

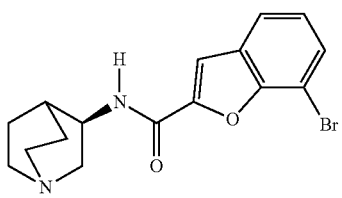 [SMILES: O=C(N[C@H]1CN2CCC1CC2)c1cc2cccc(Br)c2o1]

5.20 g (21.57 mmol) of 7-bromobenzofuran-2-carboxylic acid (Example 29A), 4.3 g (21.57 mmol) of (R)-3-aminoquinuclidine dihydrochloride, 9.84 g (25.89 mmol) of HATU, 13.53 ml (74.68 mmol) of N,N-diisopropylethylamine and 21 ml of DMF are reacted by general method C. The solvent is removed under reduced pressure, and the crude product is taken up in 100 ml of ethyl acetate and washed 15 times with a total of 1.5 l of 1N sodium hydroxide solution. The organic phase is dried over magnesium sulphate and freed of solvent. 5.2 g (69% of theory) of the title compound are isolated.

$^1$H-NMR (300 MHz, DMSO-d$_6$): δ=8.48 (d, 1H), 7.85-7.65 (m, 3H), 7.25 (t, 1H), 3.95 (m, 1H), 3.15 (m, 1H), 2.95 (m, 1H), 2.80-2.60 (m, 4H), 1.90 (m, 1H), 1.70 (m, 1H), 1.58 (m, 2H), 1.35 (m, 1H).
HPLC (method 1): $R_t$=3.79 min.
MS (ESIpos) m/z=349 (M+H)$^+$
$[α]^{20}_D$=26.9° (c=0.50, methanol).

In some exemplary embodiments, the corresponding hydrochloride is employed and is obtained by mixing the title compound with a 5:1 mixture of methanol and 1N hydrochloric acid and then concentrating and drying under high vacuum.

EXAMPLE 31A

N-[(3S)-1-Azabicyclo[2.2.2]oct-3-yl]-7-bromo-1-benzofuran-2-carboxamide

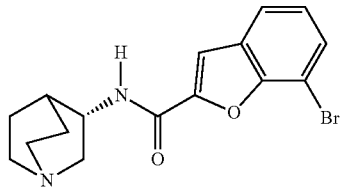 [SMILES: O=C(N[C@@H]1CN2CCC1CC2)c1cc2cccc(Br)c2o1]

4.0 g (16.59 mmol) of 7-bromobenzofuran-2-carboxylic acid (Example 29A), 3.3 g (16.59 mmol) of (S)-3-aminoquinuclidine dihydrochloride, 7.57 g (19.91 mmol) of HATU, 10.41 ml (59.74 mmol) of N,N-diisopropylethylamine and 21 ml of DMF are reacted by general method C. The solvent is removed under reduced pressure, and the crude product is taken up in 100 ml of ethyl acetate and washed 15 times with a total of 1.5 l of 1N sodium hydroxide solution. The organic phase is dried over magnesium sulphate and freed of solvent. 5.0 g (85% of theory) of the title compound are isolated.

The analytical data agree with those of Example 30A.
$[α]^{20}_D$=−28.0° (c=0.1, methanol).

EXAMPLE 32A 2-(4-Morpholinyl)phenyl trifluoromethanesulphonate

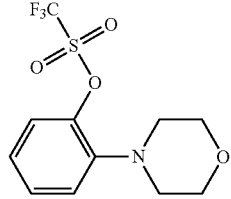 [SMILES: O=S(=O)(Oc1ccccc1N1CCOCC1)C(F)(F)F]

2.78 ml (16.4 mmol) of trifluoromethanesulphonic anhydride are slowly added dropwise to a solution, cooled to −10° C., of 2 g (10.9 mmol) of 2-(4-morpholinyl)-phenol and 4.57 ml (32.8 mmol) of triethylamine in 15 ml of dichloromethane. The mixture is stirred at −10° C. for 30 min and then at 0° C. for 30 min. It is washed successively with 10% strength sodium bicarbonate solution, water and saturated sodium chloride solution, dried over sodium sulphate and concentrated in vacuo, and the residue is dried under high vacuum. 3.48 g (87.6% of theory) of the title compound are obtained.

HPLC (method 1): $R_t$=4.9 min.

MS (ESIpos): m/z=312 (M+H)$^+$.

EXAMPLE 33A

N-[(3R)-1-Azabicyclo[2.2.2]oct-3-yl]-6-(3-formylphenyl)-1-benzothiophene-2-carboxamide hydrochloride

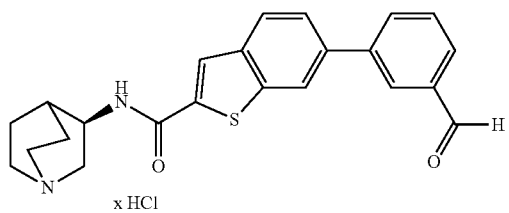 [SMILES: O=Cc1cccc(-c2ccc3cc(C(=O)N[C@H]4CN5CCC4CC5)sc3c2)c1]

200 mg (0.50 mmol) of N-[(3R)-azabicyclo[2.2.2]oct-3-yl]-6-bromo-1-benzothiophene-2-carboxamide hydrochloride (Example 11A) and 74.6 mg (0.50 mmol) of 3-formylphenylboronic acid are introduced into 1 ml of DMF. Addition of 0.75 ml of 2 M sodium carbonate solution and 20.3 mg (0.02 mmol) of PdCl$_2$(dppf) is followed by heating to 80° C. After 18 h, the reaction mixture is filtered through kieselguhr and purified by preparative HPLC. The product fractions are concentrated, mixed with a 5:1 mixture of methanol and 4N hydrogen chloride in dioxane and again concentrated. Drying under high vacuum results in 92.4 mg (39.5% of theory) of the title compound.

HPLC (method 1): $R_t$=4.11 min.

MS (ESIpos): m/z=391 (M+H)$^+$ (free base).

Exemplary Embodiments

General Method D:

1.5 eq. of bis(pinacolato)diboron, 3.25 eq. of dry potassium acetate, 1.3 eq. of the substituted haloaromatic compound or of the substituted aryl trifluoromethane-sulphonate are dissolved in DMF (about 1 ml/mmol of haloaromatic compound or aryl trifluoromethanesulphonate). Argon is passed through the reaction mixture for 15 minutes and then 0.05 eq. of PdCl$_2$(dppf) is added and the mixture is heated at 90° C. for 2 h. Then 1.0 eq. of the appropriate bromine-substituted N-[(3R)-1-azabicyclo[2.2.2]oct-3-yl]benzothiophene-2-carboxamide or N-[(3R)-1-azabicyclo-[2.2.2]oct-3-yl]benzofuran-2-carboxamide, 5 eq. of aqueous 2 M sodium carbonate solution and a further 0.05 eq. of PdCl$_2$(dppf) are added. The reaction mixture is heated at 90° C. for 6-12 h. Purification takes place by preparative HPLC. The resulting product (free base) is dissolved in methanol, and an excess of 1N hydrochloric acid is added. The solvent is removed under reduced pressure.

General Method E:

A solution of 50 mg (0.11 mmol) of 3-(2-{[(3R)-1-azabicyclo[2.2.2]oct-3-yl-amino]carbonyl}-1-benzothien-7-yl)benzoic acid hydrochloride (Example 75), 103 mg (0.27 mmol) of HATU and 52.5 mg (0.41 mmol) of N,N-diisopropylethylamine in 0.5 ml of DMF is added dropwise to a 2N solution of an amine (0.23 mmol) in DMF. After 16 h at room temperature, 0.1 ml of water is added to the reaction mixture, which is then filtered and purified by preparative HPLC. The product fractions are combined and, after addition of 2 ml of 1N hydrochloric acid, concentrated in vacuo and dried under high vacuum.

General Method F:

0.24 mmol of acid chloride and 84 µl (0.60 mmol) of triethylamine are added to a solution of 50 mg (0.12 mmol) of N—((3R)-quinuclidin-3-yl)-7-(3-amino-phenyl)benzo[b]thiophene-2-carboxamide hydrochloride (Example 21) in 0.5 ml of DMF. After one hour at room temperature, 0.5 ml of 1N sodium hydroxide solution and 15 ml of ethyl acetate are added to the reaction mixture, which is then filtered.

The concentrated organic phase is purified by preparative HPLC. The product fractions are combined and, after addition of 1N hydrochloric acid, again concentrated in vacuo and dried under high vacuum.

EXAMPLE 1

N-[(3R)-1-Azabicyclo[2.2.2]oct-3-yl]-6-[2-(hydroxymethyl)phenyl]-1-benzofuran-2-carboxamide

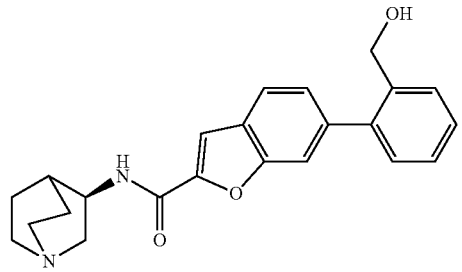 [SMILES: O=C(N[C@H]1CN2CCC1CC2)c1cc2ccc(-c3ccccc3CO)cc2o1]

A mixture of 130 mg (0.86 mmol) of 2-(hydroxymethyl)phenylboronic acid, 200 mg (0.57 mmol) of N-[(3R)-1-azabicyclo[2.2.2]oct-3-yl]-6-bromo-1-benzofuran-2-carboxamide (Example 2A), 1.72 ml (1.72 mmol) of 1N sodium hydroxide solution, 40 mg (0.06 mmol) of 1,1'-bis(diphenylphosphino)ferrocenepalladium(II) chloride and 2 ml of DMF is heated at 80-85° C. for 18 h. The solvent is removed under reduced pressure. The crude product is purified on silica gel 60 (Merck, Darmstadt; eluent: dichloromethane, dichloromethane/methanol 20:1, dichloromethane/methanol-/ammonia 80:20:2). The solvent is removed under reduced pressure. Finally, the last residues of solvent are removed under high vacuum. 149 mg (63% of theory) of the title compound are isolated.

$^1$H-NMR (200 MHz, CDCl$_3$): δ=7.71-7.28 (m, 8H), 6.77 (d, 1H), 4.62 (s, 2H), 4.28-4.12 (m, 1H), 3.56-3.38 (m, 1H), 3.04-2.78 (m, 4H), 2.75-2.59 (m, 1H), 2.16-2.02 (m, 1H), 1.93-1.66 (m, 3H), 1.66-1.45 (m, 1H).

HPLC (method 1): $R_t$=3.6 min.

LC-MS (method 2): $R_t$=1.49 min.

MS (ESIpos): m/z=377 (M+H)+.

EXAMPLE 2

N-[(3R)-1-Azabicyclo[2.2.2]oct-3-yl]-6-[3-(hydroxymethyl)phenyl]-1-benzofuran-2-carboxamide

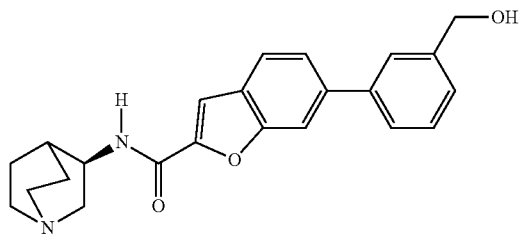 [SMILES: O=C(N[C@H]1CN2CCC1CC2)c1cc2ccc(-c3cccc(CO)c3)cc2o1]

A mixture of 130 mg (0.86 mmol) of 3-(hydroxymethyl)phenylboronic acid, 200 mg (0.57 mmol) of N-[(3R)-1-azabicyclo[2.2.2]oct-3-yl]-6-bromo-1-benzofuran-2-carboxamide (Example 2A), 1.72 ml (1.72 mmol) of 1N sodium hydroxide solution, 40 mg (0.06 mmol) of 1,1'-bis(diphenylphosphino)ferrocenepalladium(II) chloride and 2 ml of DMF is heated at 80-85° C. for 18 h. The solvent is removed under reduced pressure. The crude product is purified on silica gel 60 (Merck, Darmstadt; eluent: dichloromethane, dichloromethane/methanol 20:1, dichloromethane/methanol-/ammonia 80:20:2). The solvent is removed under reduced pressure. Finally, the last residues of solvent are removed under high vacuum. 127 mg (54% of theory) of the title compound are isolated.

1H-NMR (200 MHz, CDCl3): δ=7.86 (d, 1H), 7.72-7.28 (m, 7H), 6.77 (d, 1H), 4.62 (s, 2H), 4.28-4.12 (m, 1H), 3.56-3.38 (m, 1H), 3.04-2.78 (m, 4H), 2.75-2.59 (m, 1H), 2.16-2.02 (m, 1H), 1.93-1.66 (m, 3H), 1.66-1.45 (m, 1H).
HPLC (method 1): $R_t$=3.5 min.
LC-MS (method 2): $R_t$=1.50 min.
MS (ESIpos): m/z=377 (M+H)+.

EXAMPLE 3

N-[(3R)-1-Azabicyclo[2.2.2]oct-3-yl]-6-[4-(hydroxymethyl)phenyl]-1-benzofuran-2-carboxamide

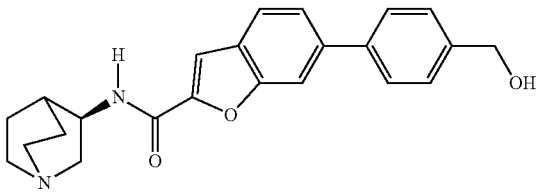 [SMILES: O=C(N[C@H]1CN2CCC1CC2)c1cc2ccc(-c3ccc(CO)cc3)cc2o1]

A mixture of 130 mg (0.86 mmol) of 4-(hydroxymethyl)phenylboronic acid, 200 mg (0.57 mmol) of N-[(3R)-1-azabicyclo[2.2.2]oct-3-yl]-6-bromo-1-benzofuran-2-carboxamide (Example 2A), 1.72 ml (1.72 mmol) of 1N sodium hydroxide solution, 40 mg (0.06 mmol) of 1,1'-bis(diphenylphosphino)ferrocenepalladium(II) chloride and 2 ml of DMF is heated at 80-85° C. for 18 h. The solvent is removed under reduced pressure. The crude product is purified on silica gel 60 (Merck, Darmstadt; eluent: dichloromethane, dichloromethane/methanol 20:1, dichloromethane/methanol-/ammonia 80:20:2). The solvent is removed under reduced pressure. Finally, the last residues of solvent are removed under high vacuum. 55 mg (23% of theory) of the title compound are isolated.

1H-NMR (200 MHz, CDCl3): δ=7.83 (d, 1H), 7.69-7.28 (m, 7H), 6.77 (d, 1H), 4.62 (s, 2H), 4.28-4.12 (m, 1H), 3.56-3.38 (m, 1H), 3.04-2.78 (m, 4H), 2.75-2.59 (m, 1H), 2.16-2.02 (m, 1H), 1.93-1.66 (m, 3H), 1.66-1.45 (m, 1H).
HPLC (method 1): $R_t$=3.5 min.
LC-MS (method 2): $R_t$=1.46 min.
MS (ESIpos): m/z=377 (M+H)+.

EXAMPLE 4

N-[(3R)-1-Azabicyclo[2.2.2]oct-3-yl]-6-[4-(4-morpholinyl)phenyl]-1-benzofuran-2-carboxamide

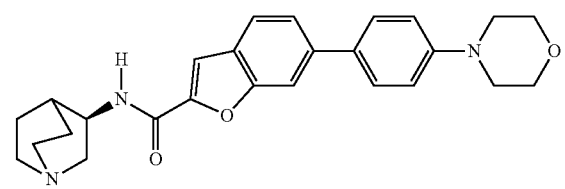 [SMILES: O=C(N[C@H]1CN2CCC1CC2)c1cc2ccc(-c3ccc(N4CCOCC4)cc3)cc2o1]

A mixture of 180 mg (0.86 mmol) of 4-(4-morpholinyl)phenylboronic acid, 200 mg (0.57 mmol) of N-[(3R)-1-azabicyclo[2.2.2]oct-3-yl]-6-bromo-1-benzofuran-2-carboxamide (Example 2A), 1.72 ml (1.72 mmol) of 1N sodium hydroxide solution, 40 mg (0.06 mmol) of 1,1'-bis(diphenylphosphino)ferrocenepalladium(II) chloride and 2 ml of DMF is heated at 80-85° C. for 18 h. The solvent is removed under reduced pressure. The crude product is purified on silica gel 60 (Merck, Darmstadt; eluent: dichloromethane, dichloromethane/methanol 20:1, dichloromethane/methanol-/ammonia 80:20:2). The solvent is removed under reduced pressure. Finally, the last residues of solvent are removed under high vacuum. 79 mg (32% of theory) of the title compound are isolated.

1H-NMR (200 MHz, CDCl3): δ=7.84-7.29 (m, 7H); 6.99 (d, 1H), 6.84-6.70 (m, 1H), 4.28-4.13 (m, 1H), 3.97-3.83 (m, 2H), 3.59-3.36 (m, 1H), 3.29-3.13 (m, 2H), 3.04-2.78 (m, 4H), 2.75-2.59 (m, 1H), 2.16-2.02 (m, 1H), 1.93-1.66 (m, 3H), 1.66-1.45 (m, 1H).
HPLC (method 1): $R_t$=3.5 min.
LC-MS (method 2): $R_t$=1.74 min.
MS (ESIpos): m/z=432 (M+H)+.

EXAMPLE 5

N-[(3R)-1-Azabicyclo[2.2.2]oct-3-yl]-6-[4-(methoxy)phenyl]-1-benzofuran-2-carboxamide

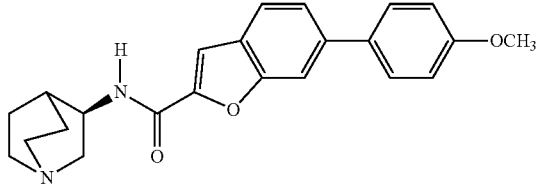 [SMILES: COc1ccc(-c2ccc3cc(C(=O)N[C@H]4CN5CCC4CC5)oc3c2)cc1]

A mixture of 130 mg (0.86 mmol) of 4-methoxyphenylboronic acid, 200 mg (0.57 mmol) of N-[(3R)-1-azabicyclo[2.2.2]oct-3-yl]-6-bromo-1-benzofuran-2-carboxamide (Example 2A), 1.72 ml (1.72 mmol) of 1N sodium hydroxide solution, 40 mg (0.06 mmol) of 1,1'-bis(diphenylphosphino)ferrocenepalladium(II) chloride and 2 ml of DMF is heated at 80-85° C. for 18 h. The solvent is removed under reduced pressure. The crude product is purified on silica gel 60 (Merck, Darmstadt; eluent: dichloromethane, dichloromethane/methanol 20:1, dichloromethane/methanol-/ammonia 80:20:2). The solvent is removed under reduced pressure. Finally, the last residues of solvent are removed under high vacuum. 160 mg (68% of theory) of the title compound are isolated.

$^1$H-NMR (200 MHz, CDCl$_3$): δ=7.84-7.75 (m, 1H), 7.62-7.45 (m, 5H), 6.99 (m, 2H), 6.84-6.70 (m, 1H), 4.28-4.13 (m, 1H), 3.87 (s, 3H), 3.59-3.36 (m, 1H), 3.04-2.78 (m, 4H), 2.75-2.59 (m, 1H), 2.16-2.02 (m, 1H), 1.93-1.66 (m, 3H), 1.66-1.45 (m, 1H).

HPLC (method 1): R$_t$=4.0 min.

LC-MS (method 3): R$_t$=3.2 min.

MS (ESIpos): m/z=377 (M+H)$^+$.

EXAMPLE 6

N-[(3R)-1-Azabicyclo[2.2.2]oct-3-yl]-6-[3-(methoxy)phenyl]-1-benzofuran-2-carboxamide

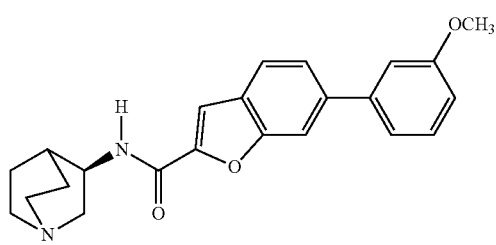 [SMILES: COc1cccc(-c2ccc3cc(C(=O)N[C@H]4CN5CCC4CC5)oc3c2)c1]

A mixture of 130 mg (0.86 mmol) of 3-methoxyphenylboronic acid, 200 mg. (0.57 mmol) of N-[(3R)-1-azabicyclo[2.2.2]oct-3-yl]-6-bromo-1-benzofuran-2-carboxamide (Example 2A), 1.72 ml (1.72 mmol) of 1N sodium hydroxide solution, 40 mg (0.06 mmol) of 1,1'-bis(diphenylphosphino)ferrocenepalladium(II) chloride and 2 ml of DMF is heated at 80-85° C. for 18 h. The solvent is removed under reduced pressure. The crude product is purified on silica gel 60 (Merck, Darmstadt; eluent: dichloromethane, dichloromethane/methanol 20:1, dichloromethane/methanol-/ammonia 80:20:2). The solvent is removed under reduced pressure. Finally, the last residues of solvent are removed under high vacuum. 151 mg (64% of theory) of the title compound are isolated.

$^1$H-NMR (200 MHz, CDCl$_3$): δ=7.90-7.80 (m, 1H), 7.72-7.08 (m, 5H), 6.95-6.85 (m, 1H), 6.84-6.70 (m, 1H), 4.28-4.13 (m, 1H), 3.87 (s, 3H), 3.59-3.36 (m, 1H), 3.04-2.78 (m, 4H), 2.75-2.59 (m, 1H), 2.16-2.02 (m, 1H), 1.93-1.66 (m, 3H), 1.66-1.45 (m, 1H).

HPLC (method 1): R$_t$=4.0 min.

LC-MS (method 2): R$_t$=1.87 min.

MS (ESIpos): m/z=377 (M+H)$^+$.

EXAMPLE 7

N-[(3R)-1-Azabicyclo[2.2.2]oct-3-yl]-6-(4-fluorophenyl)-1-benzofuran-2-carboxamide

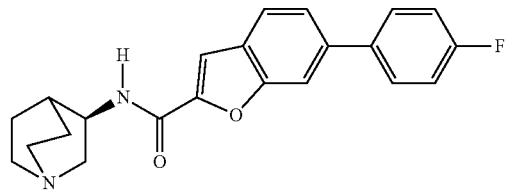 [SMILES: O=C(N[C@H]1CN2CCC1CC2)c1cc2ccc(-c3ccc(F)cc3)cc2o1]

A mixture of 120 mg (0.86 mmol) of 4-fluorophenylboronic acid, 200 mg (0.57 mmol) of N-[(3R)-1-azabicyclo[2.2.2]oct-3-yl]-6-bromo-1-benzofuran-2-carboxamide (Example 2A), 1.72 ml (1.72 mmol) of 1N sodium hydroxide solution, 40 mg (0.06 mmol) of 1,1'-bis(diphenylphosphino)ferrocenepalladium(II) chloride and 2 ml of DMF is heated at 80-85° C. for 18 h. The solvent is removed under reduced pressure. The crude product is purified on silica gel 60 (Merck, Darmstadt; eluent: dichloromethane, dichloromethane/methanol 20:1, dichloromethane/methanol-/ammonia 80:20:2). The solvent is removed under reduced pressure. Finally, the last residues of solvent are removed under high vacuum. 155 mg (68% of theory) of the title compound are isolated.

$^1$H-NMR (200 MHz, CDCl$_3$): δ=7.99 (s, 1H), 7.64-7.46 (m, 5H), 7.22-7.07 (m, 2H), 6.84-6.70 (m, 1H), 4.28-4.13 (m, 1H), 3.59-3.36 (m, 1H), 3.04-2.78 (m, 4H), 2.75-2.59 (m, 1H), 2.16-2.02 (m, 1H), 1.93-1.66 (m, 3H), 1.66-1.45 (m, 1H).

HPLC (method 1): R$_t$=4.1 min.

LC-MS (method 2): R$_t$=1.92 min.

MS (ESIpos): m/z=365 (M+H)$^+$.

EXAMPLE 8

N-[(3R)-1-Azabicyclo[2.2.2]oct-3-yl]-6-(4-trifluoromethoxyphenyl)-1-benzofuran-2-carboxamide

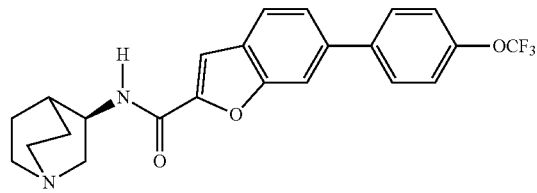 [SMILES: O=C(N[C@H]1CN2CCC1CC2)c1cc2ccc(-c3ccc(OC(F)(F)F)cc3)cc2o1]

A mixture of 180 mg (0.86 mmol) of 4-(trifluoromethoxy)phenylboronic acid, 200 mg (0.57 mmol) of N-[(3R)-1-azabicyclo[2.2.2]oct-3-yl]-6-bromo-1-benzofuran-2-carboxamide (Example 2A), 1.72 ml (1.72 mmol) of 1N sodium hydroxide solution, 40 mg (0.06 mmol) of 1,1'-bis(diphenylphosphino)ferrocenepalladium(II) chloride and 2 ml of DMF is heated at 80-85° C. for 18 h. The solvent is removed under reduced pressure. The crude product is purified on silica gel 60 (Merck, Darmstadt; eluent: dichloromethane, dichloromethane/methanol 20:1, dichloromethane/methanol/ammonia 80:20:2). The solvent is removed under reduced pressure. Finally, the last residues of solvent are removed under high vacuum. 155 mg (68% of theory) of the title compound are isolated.

$^1$H-NMR (200 MHz, CDCl$_3$): δ=7.82 (s, 1H), 7.72-7.45 (m, 5H), 7.36-7.27 (m, 2H), 6.84-6.70 (m, 1H), 4.28-4.13 (m, 1H), 3.59-3.36 (m, 1H), 3.04-2.78 (m, 4H), 2.75-2.59 (m, 1H), 2.16-2.02 (m, 1H), 1.93-1.66 (m, 3H), 1.66-1.45 (m, 1H).

HPLC (method 1): R$_t$=4.4 min.

LC-MS (method 2): R$_t$=2.22 min.

MS (ESIpos): m/z=431 (M+H)$^+$.

EXAMPLE 9

N-[(3R)-1-Azabicyclo[2.2.2]oct-3-yl]-6-(3-hydroxy-1-propynyl)-1-benzofuran-2-carboxamide

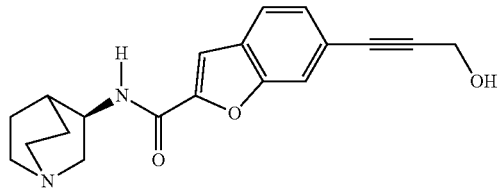 [SMILES: O=C(N[C@H]1CN2CCC1CC2)c1cc2ccc(C#CCO)cc2o1]

A mixture of 289 mg (5.15 mmol) of propargyl alcohol, 150 mg (0.43 mmol) of N-[(3R)-1-azabicyclo[2.2.2]oct-3-yl]-6-bromo-1-benzofuran-2-carboxamide (Example 2A), 1.6 mg (0.01 mmol) of copper(I) iodide, 15 mg (0.02 mmol) of bis(triphenylphosphine)palladium(II) chloride, 61 mg (0.86 mmol) of pyrrolidine and 1 ml of THF is heated under reflux overnight. The crude product is mixed with 10 ml of 1N sodium hydroxide solution and extracted three times with a total of 100 ml of ethyl acetate. The combined organic phases are dried over magnesium sulphate, and the solvent is removed under reduced pressure. The crude product is purified on silica gel 60 (Merck, Darmstadt; eluent: dichloromethane/triethylamine 100:1, then dichloromethane/methanol/triethylamine 100:1:1 to dichloromethane/methanol-/triethylamine 100:10:1). The solvent is removed under reduced pressure. Finally, the last residues of solvent are removed under high vacuum. 40 mg (27% of theory) of the title compound are isolated.

HPLC (method 1): R$_t$=3.3 min.

LC-MS (method 3): R$_t$=2.6 min.

MS (ESIpos): m/z=325 (M+H)$^+$.

EXAMPLE 10

N-[(3R)-1-Azabicyclo[2.2.2]oct-3-yl]-5-fluoro-7-(4-fluorophenyl)-1-benzofuran-2-carboxamide

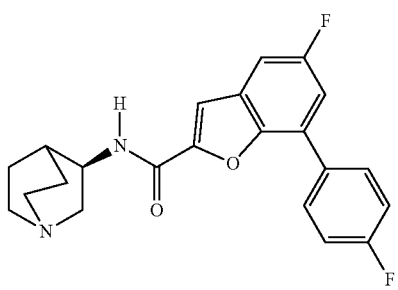 [SMILES: O=C(N[C@H]1CN2CCC1CC2)c1cc2cc(F)cc(-c3ccc(F)cc3)c2o1]

A mixture of 40 mg (0.29 mmol) of 4-fluorophenylboronic acid, 70 mg (0.1.9 mmol) of N-[(3R)-1-azabicyclo[2.2.2]oct-3-yl]-5-fluoro-7-bromo-1-benzofuran-2-carboxamide (Example 5A), 0.57 ml (0.57 mmol) of 1N sodium hydroxide solution, 14 mg (0.02 mmol) of 1,1'-bis(diphenylphosphino)ferrocenepalladium(II) chloride and 2 ml of DMF is heated at 85° C. overnight. The solvent is removed under reduced pressure. The crude product is mixed with 1N sodium hydroxide solution and extracted three times with a total of 100 ml of ethyl acetate. The combined organic phases are dried over magnesium sulphate, and the solvent is removed under reduced pressure. The crude product is taken up in methanol and shaken together with acidic ion exchanger (Dowex® WX2-200) for about 20 min. The loaded ion exchanger is washed three times with 30 ml of methanol each time, then with water, again with methanol, with dichloromethane, again with methanol, with THF and finally once more with methanol. The product is eluted with methanol/triethylamine 95:5. The solvent is removed in a rotary evaporator under reduced pressure. Silica gel 60 (Merck, Darmstadt; eluent: dichloromethane/triethylamine 100:1, then dichloromethane/methanol/triethylamine 100:1:1 to dichloromethane/methanol-/triethylamine 100:10:1) is used for final purification. The solvent is removed under reduced pressure. Finally, the last residues of solvent are removed under high vacuum. 51 mg (70% of theory) of the title compound are isolated.

$^1$H-NMR (400 MHz, methanol-d$_4$): δ=7.99-7.90 (m, 2H), 7.59 (s, 1H), 7.45-7.35 (m, 2H), 7.30-7.22 (m, 2H), 4.24-4.18 (m, 1H), 3.34-3.29 (m, 1H), 3.07-2.97 (m, 1H), 2.93-2.77 (m, 4H), 2.13-2.05 (m, 1H), 1.98-1.86 (m, 1H), 1.84-1.75 (m, 2H), 1.63-1.53 (m, 1H).

HPLC (method 1): R$_t$=4.3 min.

LC-MS (method 3): R$_t$=3.08 min.

MS (ESIpos): m/z=383 (M+H)+.

EXAMPLE 11

N-[(3R)-1-Azabicyclo[2.2.2]oct-3-yl]-5-fluoro-7-(4-trifluoromethoxyphenyl)-1-benzofuran-2-carboxamide

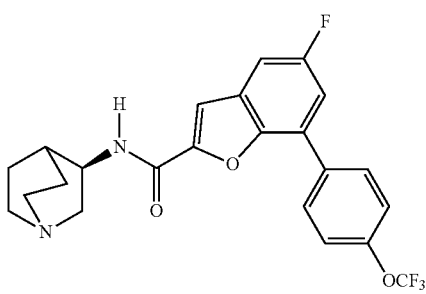 [SMILES: O=C(N[C@H]1CN2CCC1CC2)c1cc2cc(F)cc(-c3ccc(OC(F)(F)F)cc3)c2o1]

A mixture of 40 mg (0.29 mmol) of 4-(trifluoromethoxy)phenylboronic acid, 70 mg (0.19 mmol) of N-[(3R)-1-azabicyclo[2.2.2]oct-3-yl]-5-fluoro-7-bromo-1-benzofuran-2-carboxamide (Example 5A), 0.57 ml (0.57 mmol) of 1N sodium hydroxide solution, 14 mg (0.02 mmol) of 1,1'-bis(diphenyl-phosphino)ferrocenepalladium(II) chloride and 2 ml of DMF is heated at 85° C. overnight. The solvent is removed under reduced pressure. The crude product is mixed with 1N sodium hydroxide solution and extracted three times with a total of 100 ml of ethyl acetate. The combined organic phases are dried over magnesium sulphate, and the solvent is removed under reduced pressure. The crude product is taken up in methanol and shaken together with acidic ion exchanger (Dowex® WX2-200) for about 20 min. The loaded ion exchanger is washed three times with 30 ml of methanol each time, then with water, again with methanol, with dichloromethane, again with methanol, with THF and finally once more with methanol. The product is eluted with methanol/triethylamine 95:5. The solvent is removed in a rotary evaporator under reduced pressure. Silica gel 0.60 (Merck, Darmstadt; eluent: dichloromethane/triethylamine 100:1, then dichloromethane/methanol/triethylamine 100:1:1 to dichloromethane/methanol/triethylamine 100:10:1) is used for final purification. The solvent is removed under reduced pressure. Finally, the last residues of solvent are removed under high vacuum. 52 mg (61% of theory) of the title compound are isolated.

$^1$H-NMR (400 MHz, methanol-$d_4$): δ=8.08-8.00 (m, 2H), 7.59 (s, 1H), 7.49-741 (m, 4H), 4.24-4.18 (m, 1H), 3.34-3.29 (m, 1H), 3.07-2.97 (m, 1H), 2.93-2.77 (m, 4H), 2.13-2.05 (m, 1H), 1.98-1.86 (m, 1H), 1.84-1.75 (m, 2H), 1.63-1.53 (m, 1H).

HPLC (method 1): $R_t$=4.6 min.
LC-MS (method 3): $R_t$=3.37 min.

MS (ESIpos): m/z=449 (M+H)+.

EXAMPLE 12

N-[(3R)-1-Azabicyclo[2.2.2]oct-3-yl]-5-phenyl-1-benzothiophene-2-carboxamide hydrochloride

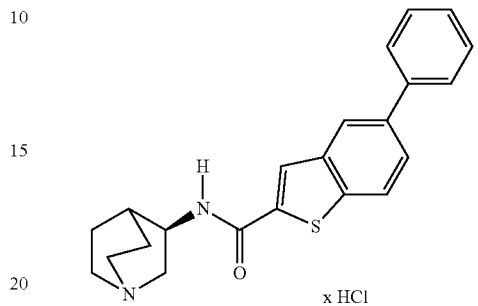

0.15 ml of 2 M aqueous sodium carbonate solution and 4.1 mg (0.005 mmol) of PdCl$_2$(dppf) are added to a mixture of 40 mg (0.10 mmol) of N-[(3R)-1-azabicyclo[2.2.2]oct-3-yl]-5-bromo-1-benzothiophene-2-carboxamide hydrochloride (Example 14A) and 12.1 mg (0.10 mmol) of phenylboronic acid in 1 ml of DMF. The reaction mixture is heated at 80° C. for 14 h, filtered through kieselguhr and evaporated to dryness. Purification of the crude product by preparative HPLC, subsequent addition of 1N hydrochloric acid and drying under high vacuum result in 7.3 mg (18% of theory) of the title compound.

HPLC (method 1): $R_t$=4.2 min.
MS (ESIpos): m/z=363 (M+H)+ (free base).

EXAMPLE 13

N-[(3R)-1-Azabicyclo[2.2.2]oct-3-yl]-6-phenyl-1-benzothiophene-2-carboxamide hydrochloride

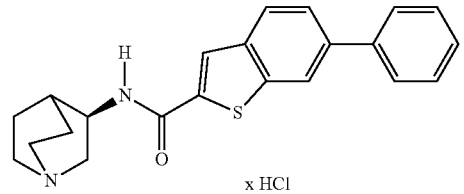 [SMILES: O=C(N[C@H]1CN2CCC1CC2)c1cc2ccc(-c3ccccc3)cc2s1]

0.15 ml of 2 M aqueous sodium carbonate solution and 4.1 mg (0.005 mmol) of PdCl$_2$(dppf) are added to a mixture of 40 mg (0.10 mmol) of N-[(3R)-1-azabicyclo[2.2.2]oct-3-yl]-6-bromo-1-benzothiophene-2-carboxamide hydrochloride (Example 11A) and 12.1 mg (0.10 mmol) of phenylboronic acid in 1 ml of DMF. The reaction mixture is heated at 80° C. for 14 h, filtered through kieselguhr and evaporated to dryness. Purification of the crude product by preparative HPLC, subsequent addition of 1N hydrochloric acid and drying under high vacuum result in 14.5 mg (37% of theory) of the title compound.

$^1$H-NMR (200 MHz, DMSO-$d_6$): δ=9.91 (m, 1H), 9.02 (d, 1H), 8.38 (m, 1H), 8.32 (m, 1H), 8.06 (d, 1H), 7.78 (m, 3H), 7.58-7.37 (m, 3H), 4.32 (m, 1H), 3.78-3.03 (m, 6H), 2.28-2.05 (m, 2H), 1.93 (m, 2H), 1.78 (m, 1H).

HPLC (method 1): R_t=4.2 min.
MS (ESIpos): m/z=363 (M+H)⁺ (free base).

EXAMPLE 14

N-[(3R)-1-Azabicyclo[2.2.2]oct-3-yl]-6-(3-methoxyphenyl)-1-benzothiophene-2-carboxamide hydrochloride

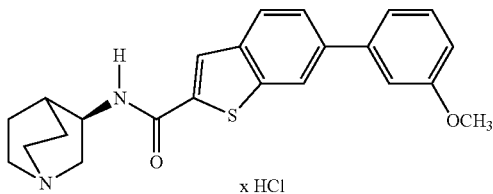 [SMILES: COc1cccc(-c2ccc3cc(C(=O)N[C@H]4CN5CCC4CC5)sc3c2)c1]

0.3 ml of 2 M aqueous sodium carbonate solution and 4.1 mg (0.005 mmol) of PdCl$_2$(dppf) are added to a mixture of 40 mg (0.10 mmol) of N-[(3R)-1-azabicyclo[2.2.2]oct-3-yl]-6-bromo-1-benzothiophene-2-carboxamide hydrochloride (Example 11A) and 15.1 mg (0.10 mmol) of 3-methoxyphenylboronic acid in 1 ml of DMF. The reaction mixture is heated at 80° C. for 14 h, filtered through kieselguhr and evaporated to dryness. Purification of the crude product by preparative HPLC, subsequent addition of 1N hydrochloric acid and drying under high vacuum result in 25.5 mg (57% of theory) of the title compound.

$^1$H-NMR (200 MHz, DMSO-d$_6$): δ=9.70 (s, 1H), 8.97 (d, 1H), 8.38 (m, 1H), 8.28 (m, 1H), 7.99 (m, 1H), 7.78 (m, 1H), 7.37 (m, 3H), 6.98 (m, 1H), 4.33 (m, 1H), 3.86 (s, 3H), 3.79-3.12 (m, 6H), 2.28-2.00 (m, 2H), 1.99-1.68 (m, 3H).

HPLC (method 1): R_t=4.2 min.
MS (ESIpos): m/z=393 (M+H)⁺ (free base).

EXAMPLE 15

N-[(3R)-1-Azabicyclo[2.2.2]oct-3-yl]-6-(3-hydroxy-1-propynyl)-1-benzothiophene-2-carboxamide

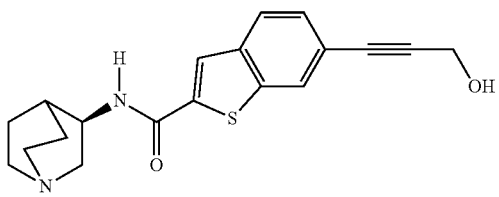 [SMILES: O=C(N[C@H]1CN2CCC1CC2)c1cc2ccc(C#CCO)cc2s1]

120 mg (0.30 mmol) of N-[(3R)-1-azabicyclo[2.2.2]oct-3-yl]-6-bromo-1-benzothiophene-2-carboxamide hydrochloride (Example 11A), 10.5 mg (0.01 mmol) of PdCl$_2$(PPh$_3$)$_2$ and 4.6 mg (0.02 mmol) of copper(I) iodide are dissolved in 1.5 ml of triethylamine/DMF (2:1) under argon and stirred at 60° C. for 1 h. Addition of 25.1 mg (0.45 mmol) of propargyl alcohol is followed by heating at 70° C. for a further 16 h. Cooling is followed by filtration through kieselguhr and purification by preparative HPLC, concentration and drying of the product under high vacuum. 12 mg (11% of theory) of the title compound are obtained.

$^1$H-NMR (200 MHz, DMSO-d$_6$): δ=8.73 (d, 1H), 8.20 (m, 2H), 7.96 (d, 1H), 7.46 (dd, 1H), 4.34 (s, 2H), 4.09 (m, 1H), 3.32 (m, 1H), 3.16-2.77 (m, 5H), 1.99 (m, 1H), 1.91 (m, 1H), 1.70 (m, 2H), 1.49 (m, 1H).

HPLC (method 1): R_t=3.4 min.
MS (ESIpos): m/z=341 (M+H)⁺.

EXAMPLE 16

N-[(3R)-1-Azabicyclo[2.2.2]oct-3-yl]-7-phenyl-1-benzothiophene-2-carboxamide hydrochloride

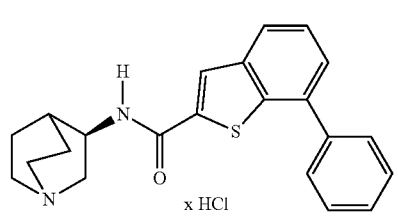 [SMILES: O=C(N[C@H]1CN2CCC1CC2)c1cc2cccc(-c3ccccc3)c2s1]

0.14 ml of 2M aqueous sodium carbonate solution and 5.7 mg (0.007 mmol) of PdCl$_2$(dppf) are added to a mixture of 56mg (0.14 mmol) of N-[(3R)-1-azabicyclo[2.2.2]oct-3-yl]-7-bromo-1-benzothiophene-2-carboxamide hydrochloride (Example 8A) and 18.7 mg (0.15 mmol) of phenylboronic acid in 1 ml of DMF. The reaction mixture is heated to 80° C. After 3 h at this temperature, a further 5.7 mg (0.007 mmol) of PdCl$_2$(dppf) are added, and the mixture is stirred at 80° C. for a further 12 h. The reaction mixture is filtered through kieselguhr and evaporated to dryness. Purification of the crude product by preparative HPLC, subsequent addition of 1N hydrochloric acid and drying under high vacuum result in 10.6 mg (18% of theory) of the title compound.

HPLC (method 1): R_t=4.2 min.
MS (ESIpos): m/z=363 (M+H)⁺ (free base).

EXAMPLE 17

N-[(3R)-1-Azabicyclo[2.2.2]oct-3-yl]-7-(3-methoxyphenyl)-1-benzothiophene-2-carboxamide hydrochloride

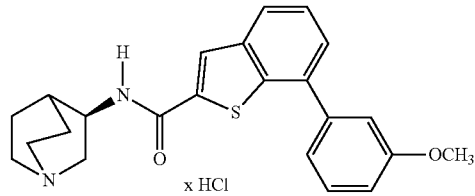 [SMILES: COc1cccc(-c2cccc3cc(C(=O)N[C@H]4CN5CCC4CC5)sc23)c1]

0.16 ml of 2 M aqueous sodium carbonate solution and 4.2 mg (0.005 mmol) of PdCl$_2$(dppf) are added to a mixture of 49 mg (0.10 mmol) of N-[(3R)-1-azabicyclo[2.2.2]oct-3-yl]-7-bromo-1-benzothiophene-2-carboxamide hydrochloride (Example 8A) and 15.8 mg (0.10 mmol) of 3-methoxyphenylboronic acid in 1 ml of DMF. The reaction mixture is heated at 80° C. for 14 h, then filtered through kieselguhr and evaporated to dryness. Purification of the crude product by preparative HPLC, subsequent addition of 1N hydrochloric acid and drying under high vacuum result in 8.0 mg (18% of theory) of the title compound.

HPLC (method 1): R_t=4.2 min.

MS (ESIpos): m/z=393 (M+H)+ (free base).

EXAMPLE 18

N-[(3R)-1-Azabicyclo[2.2.2]oct-3-yl]-7-(2-methoxyphenyl)-1-benzothiophene-2-carboxamide hydrochloride

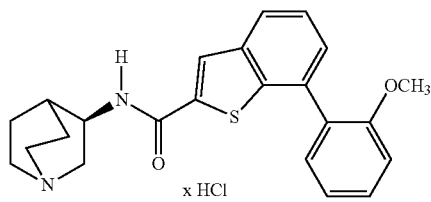 [SMILES: COc1ccccc1-c1cccc2cc(C(=O)N[C@H]3CN4CCC3CC4)sc12]

0.22 ml of 2 M aqueous sodium carbonate solution and 6.1 mg (0.007 mmol) of PdCl$_2$(dppf) are added to a mixture of 60 mg (0.15 mmol) of N-[(3R)-1-azabicyclo[2.2.2]oct-3-yl]-7-bromo-1-benzothiophene-2-carboxamide hydrochloride (Example 8A) and 22.7 mg (0.15 mmol) of 2-methoxyphenylboronic acid in 1 ml of DMF. The reaction mixture is heated at 80° C. for 14 h, then filtered through kieselguhr and evaporated to dryness. Purification of the crude product by preparative HPLC, subsequent addition of 1N hydrochloric acid and drying under high vacuum result in 12.8 mg (18% of theory) of the title compound.

HPLC (method 1): R$_t$=4.2 min.
MS (ESIpos): m/z=393 (M+H)+ (free base).

EXAMPLE 19

N-[(3R)-1-Azabicyclo[2.2.2]oct-3-yl]-7-[4-(4-morpholinyl)phenyl]-1-benzothiophene-2-carboxamide hydrochloride

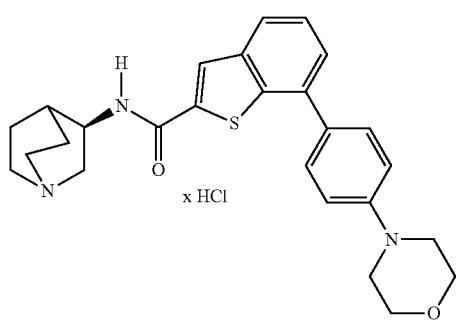 [SMILES: O=C(N[C@H]1CN2CCC1CC2)c1cc2cccc(-c3ccc(N4CCOCC4)cc3)c2s1]

0.22 ml of 2 M aqueous sodium carbonate solution and 6.1 mg (0.007 mmol) of PdCl$_2$(dppf) are added to a mixture of 60 mg (0.15 mmol) of N-[(3R)-1-azabicyclo[2.2.2]oct-3-yl]-7-bromo-1-benzothiophene-2-carboxamide hydrochloride (Example 8A) and 30.9 mg (0.15 mmol) of 4-(4-morpholinyl)phenylboronic acid in 1 ml of DMF. The reaction mixture is heated to 80° C. After 4.5 h, a further 6.1 mg (0.007 mmol) of PdCl$_2$(dppf) are added. After a further 12 h, the reaction mixture is filtered through kieselguhr and evaporated to dryness. The crude product is purified by preparative HPLC. The product is dissolved in methanol, and an excess of 4N hydrogen chloride in dioxane is added. Drying under high vacuum results in 20.6 mg (25% of theory) of the title compound.

$^1$H-NMR (300 MHz, methanol-d$_4$): δ=8.21 (s, 1H), 7.97 (m, 2H), 7.93 (s, 1H), 7.83 (m, 2H), 7.57 (dd, 1H), 7.52 (m, 1H), 4.46 (m, 1H), 4.13 (m, 4H), 3.83 (m, 1H), 3.78 (m, 4H), 3.49 (m, 1H), 3.43-3.17 (m, 4H), 2.38 (m, 1H), 2.28 (m, 1H), 2.10 (m, 2H), 1.96 (m, 1H).

HPLC (method 1): R$_t$=4.3 min.
MS (ESIpos): m/z=448 (M+H)+ (free base).

EXAMPLE 20

N-[(3R)-1-Azabicyclo[2.2.2]oct-3-yl]-7-[4-(hydroxymethyl)phenyl]-1-benzothiophene-2-carboxamide hydrochloride

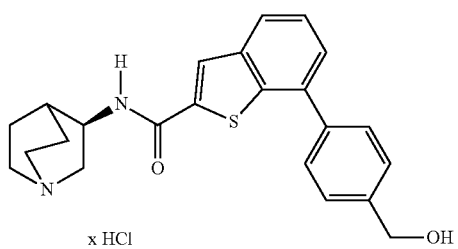 [SMILES: O=C(N[C@H]1CN2CCC1CC2)c1cc2cccc(-c3ccc(CO)cc3)c2s1]

60 mg (0.15 mmol) of N-[(3R)-1-azabicyclo[2.2.2]oct-3-yl]-7-bromo-1-benzothiophene-2-carboxamide hydrochloride (Example 8A) and 22.7 mg (0.15 mmol) of 4-(hydroxymethyl)phenylboronic acid are introduced into 1 ml of DMF. Addition of 0.22 ml of 2 M aqueous sodium carbonate solution and 6.1 mg (0.01 mmol) of PdCl$_2$(dppf) is followed by heating to 80° C. After 14 h, the reaction mixture is filtered through kieselguhr and evaporated to dryness. The crude product is purified by preparative HPLC. The product is dissolved in methanol and an excess of 4N hydrogen chloride in dioxane is added. Drying under high vacuum results in 9 mg (9% of theory) of the title compound.

HPLC (method 1): R$_t$=3.8 min.
MS (ESIpos): m/z=393 (M+H)+ (free base).

The compounds listed in the following table are obtained in an analogous manner:

TABLE 2

| Example No. | R | R$_t$ [min.] (method 5) | MS (ESIpos): m/z [M + H]+ (free base) |
|---|---|---|---|
| 21 | 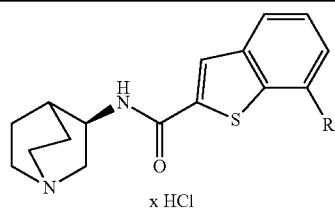 | 1.27 | 378 |

TABLE 2-continued

[Structure: quinuclidine-NH-C(O)-benzothiophene-R, × HCl]

| Example No. | R | R$_t$ [min.] (method 5) | MS (ESIpos): m/z [M + H]$^+$ (free base) |
|---|---|---|---|
| 22 | 4-methoxyphenyl | 1.51 | 393 |
| 23 | 4-acetylphenyl | 1.46 | 405 |
| 24 | 4-formylphenyl | 1.44 | 391 |
| 25 | 3-propionylphenyl | 1.51 | 420 |
| 26 | 3-formylphenyl | 1.45 | 391 |
| 27 | 4-propionylphenyl | 1.53 | 420 |
| 28 | 3-acetylphenyl | 1.46 | 405 |
| 29 | 4-(methylthio)phenyl | 1.59 | 410 |
| 30 | thiophen-3-yl | 1.48 | 369 |
| 31 | 3-(trifluoromethyl)phenyl | 1.61 | 431 |

TABLE 2-continued

| Example No. | R | R$_t$ [min.] (method 5) | MS (ESIpos): m/z [M + H]$^+$ (free base) |
|---|---|---|---|
| 32 | 4-fluorophenyl | 1.52 | 381 |
| 33 | 2-(N-Boc)-pyrrolyl | 1.6 | 453 |
| 34 | 3-cyanophenyl | 1.48 | 388 |
| 35 | 4-cyanophenyl | 1.45 | 388 |
| 36 | 2,4-difluorophenyl | 1.53 | 399 |
| 37 | 2,5-difluorophenyl | 1.52 | 399 |
| 38 | 2-(methylthio)phenyl | 1.54 | 410 |
| 39 | 2-fluorophenyl | 1.51 | 381 |
| 40 | 3-(methylthio)phenyl | 1.6 | 410 |
| 41 | 2-furyl | 1.43 | 353 |
| 42 | 3-ethoxyphenyl | 1.58 | 408 |

TABLE 2-continued

[Structure: N-(azabicyclo[2.2.2]oct-3-yl)-7-R-benzothiophene-2-carboxamide × HCl]

| Example No. | R | R_t [min.] (method 5) | MS (ESIpos): m/z [M + H]⁺ (free base) |
|---|---|---|---|
| 43 | 2,4-dimethoxyphenyl | 1.52 | 424 |
| 44 | 2-acetylphenyl | 1.42 | 405 |
| 45 | 2,5-dimethoxyphenyl | 1.48 | 424 |
| 46 | 5-fluoro-2-methoxyphenyl | 1.53 | 411 |
| 47 | 4-methoxy-2-methylphenyl | 1.56 | 408 |
| 48 | 4-fluoro-2-methylphenyl | 1.58 | 395 |
| 49 | 2-formylphenyl | 1.43 | 391 |
| 50 | 2-formylthiophen-3-yl | 1.38 | 397 |

EXAMPLE 51

7-[3-(Acetylamino)phenyl]-N-[(3R)-1-azabicyclo[2.2.2]oct-3-yl]-1-benzothiophene-2-carboxamide hydrochloride

[Structure of product × HCl]

0.75 ml of 2 M aqueous sodium carbonate solution and 20.3 mg (0.02 mmol) of PdCl₂(dppf) are added to a mixture of 200 mg (0.50 mmol) of N-[(3R)-1-azabicyclo[2.2.2]oct-3-yl]-7-bromo-1-benzothiophene-2-carboxamide hydrochloride (Example 8A) and 89.1 mg (0.50 mmol) of 3-(acetamido)phenylboronic acid in 2 ml of DMF. The reaction mixture is heated at 80° C. for 17 h. A further 89.1 mg (0.50 mmol) of 3-(acetamido)phenylboronic acid, 1.5 ml of 1N sodium hydroxide solution and 81.3 mg (0.1 mmol) of PdCl₂(dppf) are added, and the mixture is heated at 80° C. for a further 18 h. After cooling, it is filtered-through kieselguhr and purified by preparative HPLC. The resulting crude product is further purified by flash chromatography on silica gel (mobile phase: dichloromethane/methanol/ammonia 100:10:2). The product fractions are concentrated, taken up in a 5:1 mixture of methanol and 1N hydrochloric acid and again concentrated. Drying under high vacuum results in 243.2 mg (86.6% of theory) of the title compound.

$^1$H-NMR (300 MHz, DMSO-$d_6$): δ=10.16 (s, 1H), 10.10 (br. s, 1H), 9.03 (d, 1H), 8.38 (s, 1H), 8.06 (m, 1H), 7.98 (dd, 1H), 7.65 (m, 1H), 7.59 (dd, 1H), 7.51 (m, 1H), 7.48 (m, 1H), 7.37 (m, 1H), 4.33 (m, 1H), 3.66 (m, 1H), 3.45-3.13 (m, 5H), 2.22 (m, 1H), 2.14 (m, 1H), 2.08 (s, 3H), 1.91 (m, 2H), 1.75 (m, 1H).

HPLC (method 1): R$_t$=3.9 min.

MS (ESIpos): m/z=420 (M+H)$^+$ (free base).

EXAMPLE 52

N-[(3R)-1-Azabicyclo[2.2.2]oct-3-yl]-6-[4-(4-morpholinyl)phenyl]-1-benzothiophene-2-carboxamide hydrochloride

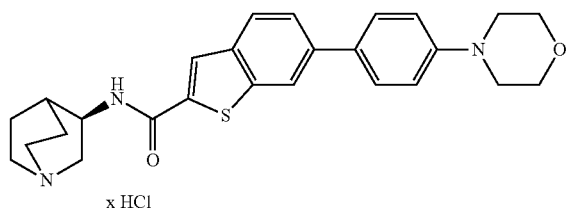 [SMILES: O=C(N[C@H]1CN2CCC1CC2)c1cc2ccc(-c3ccc(N4CCOCC4)cc3)cc2s1]

x HCl 100 mg (0.25 mmol) of N-[(3R)-1-azabicyclo[2.2.2]oct-3-yl]-6-bromo-1-benzothiophene-2-carboxamide hydrochloride (Example 11A) and 51.5 mg (0.25 mmol) of 4-morpholinophenylboronic acid are introduced into 1 ml of DMF. Addition of 0.37 ml of 2 M sodium carbonate solution and 10.2 mg (0.01 mmol) of PdCl$_2$(dppf) is followed by heating to 80° C. After 16 h, a further 51.5 mg (0.25 mmol) of 4-morpholinophenylboronic acid, 0.37 ml of 2 M sodium carbonate solution and 10.2 mg (0.01 mmol) of PdCl$_2$(dppf) are added. The mixture is heated at 80° C. for a further 4 h. After cooling, the reaction mixture is filtered through kieselguhr and purified by preparative HPLC. The product fractions are concentrated and, after addition of a 5:1 mixture of methanol and 4 M hydrogen chloride in dioxane, again concentrated. Drying under high vacuum results in 83 mg (69% of theory) of the title compound.

$^1$H-NMR (200 MHz, DMSO-$d_6$): δ=10.20 (br. s, 1H), 9.07 (d, 1H), 8.33 (s, 1H), 8.27 (s, 1H), 7.97 (d, 1H), 7.71 (m, 3H), 7.10 (m, 2H), 4.33 (m, 1H), 3.78 (m, 4H), 3.73-3.07 (m, 10H), 2.22 (m, 1H), 2.17 (m, 1H), 1.93 (m, 2H), 1.75 (m, 1H).

HPLC (method 1): R$_t$=3.8 min.

MS (ESIpos): m/z=448 (M+H)$^+$ (free base).

EXAMPLE 53

N-[(3R)-1-Azabicyclo[2.2.2]oct-3-yl]-6-(5-methyl-1,2,4-oxadiazol-3-yl)-1-benzothiophene-2-carboxamide hydrochloride

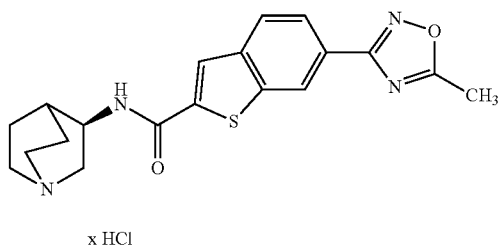 [SMILES: Cc1nc(-c2ccc3cc(C(=O)N[C@H]4CN5CCC4CC5)sc3c2)no1]

x HCl 154 mg (0.37 mmol) of 6-[amino(hydroxyimino)methyl]-N-[(3R)-1-azabicyclo[2.2.2]-oct-3-yl]-1-benzothiophene-2-carboxamide dihydrochloride (Example 27A) are dissoved in 2 ml of DMF and 0.75 ml of THF. 250 mg of 4 Å molecular sieves are added, and the mixture is stirred at room temperature for 30 min. Addition of 44.4 mg (1.11 mmol) of sodium hydride (60% suspension in mineral oil) is followed by heating at 60° C. for 20 min and then cooling to room temperature. A solution of 90 µl (1.11 mmol) of methyl acetate in 1 ml of THF is then added to the reaction mixture, after which it is heated at 80° C. for 14 h. Addition of a further 29.6 mg (0.74 mmol) of sodium hydride (60% suspension in mineral oil) and 0.88 ml (11.1 mmol) of methyl acetate in 1 ml of THF is followed by heating at 70° C. for a further 24 h. The reaction is stopped by adding water. Purification takes place by preparative HPLC. The product fractions are concentrated and, after addition of a 5:1 mixture of methanol and 4N hydrogen chloride in dioxane, again concentrated. Drying under high vacuum results in 41.9 mg (23.6% of theory) of the title compound.

$^1$H-NMR (300 MHz, DMSO-$d_6$): δ=10.15 (br. s, 1H), 9.14 (d, 1H), 8.70 (m, 1H), 8.41 (s, 1H), 8.13 (d, 1H), 8.05 (m, 1H), 4.34 (m, 1H), 3.75-3.13 (m, 6H), 2.70 (s, 3H), 2.23 (m, 1H), 2.15 (m, 1H), 1.92 (m, 2H), 1.77 (m, 1H).

HPLC (method I): R$_t$=3.8 min.

MS (ESIpos): m/z=369 (M+H)$^+$ (free base).

EXAMPLE 54

N-[(3R)-1-Azabicyclo[2.2.2]oct-3-yl]-6-[2-(hydroxymethyl)phenyl]-1-benzothiophene-2-carboxamide hydrochloride

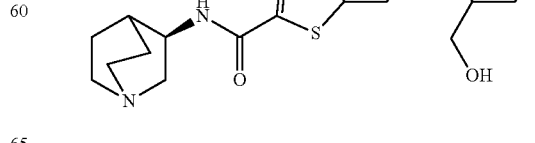

x HCl 100 mg (0.25 mmol) of N-[(3R)-1-azabicyclo[2.2.2]oct-3-yl]-6-bromo-1-benzothiophene-2-carboxamide hydrochloride (Example 11A) and 37.8 mg (0.25 mmol) of 2-(hydroxymethyl)phenylboronic acid are introduced into 1 ml of DMF. Addition of 0.37 ml of 2 M sodium carbonate solution and 10.2 mg (0.01 mmol) of $PdCl_2(dppf)$ is followed by heating to 80° C. After 14 h, the reaction mixture is filtered through kieselguhr and purified by separation twice by preparative HPLC. The product fractions are concentrated and, after addition of a 5:1 mixture of methanol and 4N hydrogen chloride in dioxane, again concentrated. Drying under high vacuum results in 27 mg (24.4% of theory) of the title compound.

$^1$H-NMR (200 MHz, DMSO-$d_6$): δ=10.10 (br. s, 1H), 9.06 (d, 1H), 8.36 (s, 1H), 8.02 (m, 2H), 7.61 (m, 1H), 7.54-7.36 (m, 4H), 4.43 (s, 2H), 4.33 (m, 1H), 3.67 (m, 1H), 3.55-3.12 (m, 5H), 2.23 (m, 1H), 2.16 (m, 1H), 1.92 (m, 2H), 1.77 (m, 1H).

HPLC (method 1): $R_t$=3.9 min.

MS (ESIpos): m/z=393 (M+H)$^+$ (free base).

EXAMPLE 55

N-[(3R)-1-Azabicyclo[2.2.2]oct-3-yl]-6-(5-phenyl-1, 2,4-oxadiazol-3-yl)-1-benzothiophene-2-carboxamide hydrochloride

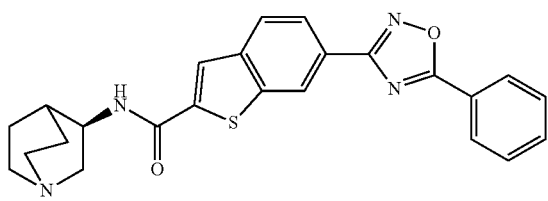

x HCl 110 mg (0.26 mmol) of 6-[amino(hydroxyimino)methyl]-N-[(3R)-1-azabicyclo-[2.2.2]oct-3-yl]-1-benzothiophene-2-carboxamide dihydrochloride (Example 27A) are dissolved in 2 ml of DMF and 0.75 ml of THF. 250 mg of 4 Å molecular sieves are added and the mixture is stirred at room temperature for 30 min. Addition of 31.2 mg (0.79 mmol) of sodium hydride (60% suspension in mineral oil) is followed by heating at 60° C. for 20 min and then cooling to room temperature. A solution of 100 μl (0.79 mmol) of methyl benzoate in 1 ml of THF is added to the reaction mixture, and it is heated at 80° C. for 14 h. A further 20.8 mg (0.52 mmol) of sodium hydride (60% suspension in mineral oil) and 0.99 ml (7.91 mmol) of methyl benzoate in 1 ml of THF are added, and the mixture is heated at 70° C. for a further 24 h. The reaction is stopped by adding water. Purification takes place by preparative HPLC. The product fractions are concentrated and, after addition of a 5:1 mixture of methanol and 4N hydrogen chloride in dioxane, again concentrated. Drying under high vacuum results in 45.7 mg (32% of theory) of the title compound.

HPLC (method 1): $R_t$=4.5 min.

MS (ESIpos): m/z=431 (M+H)$^+$ (free base).

EXAMPLE 56

N-[(3R)-1-Azabicyclo[2.2.2]oct-3-yl]-6-(5-benzyl-1, 2,4-oxadiazol-3-yl)-1-benzothiophene-2-carboxamide hydrochloride

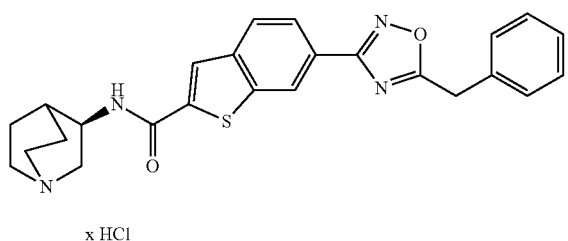 [SMILES: O=C(N[C@H]1CN2CCC1CC2)c1cc2ccc(-c3noc(Cc4ccccc4)n3)cc2s1]

x HCl 110 mg (0.26 mmol) of 6-[amino(hydroxyimino)methyl]-N-[(3R)-1-azabicyclo[2.2.2]oct-3-yl]-1-benzothiophene-2-carboxamide dihydrochloride (Example 27A) are dissolved in 2 ml of DMF and 0.75 ml of THF. 250 mg of 4 Å molecular sieves are added, and the mixture is stirred at room temperature for 30 min. Addition of 31.2 mg (0.79 mmol) of sodium hydride (60% suspension in mineral oil) is followed by heating at 60° C. for 20 min and then cooling to room temperature. A solution of 110 μl (0.79 mmol) of methyl phenylacetate in 1 ml of THF is added, and the mixture is heated at 80° C. for 14 h. Addition of a further 20.8 mg (0.52 mmol) of sodium hydride (60% suspension in mineral oil) and 1.14 ml (7.91 mmol) of methyl phenylacetate in 1 ml of THF is followed by heating at 70° C. for a further 24 h. The reaction is stopped by adding water. Purification takes place by preparative HPLC. The product fractions are concentrated and, after addition of a 5:1 mixture of methanol and 4N hydrogen chloride in dioxane, again concentrated. Drying under high vacuum results in 4.1 mg (3% of theory) of the title compound.

$^1$H-NMR (300 MHz, methanol-$d_4$): δ=8.63 (s, 1H), 8.11 (m, 2H), 8.04 (d, 1H), 7.43-7.27 (m, 5H), 4.47 (m, 1H), 4.38 (s, 2H), 3.87 (m, 1H), 3.52-3.20 (m, 5H), 2.40 (m, 1H), 2.28 (m, 1H), 2.11 (m, 2H), 1.97 (m, 1H).

HPLC (method 1): $R_t$=4.4 min.

MS (ESIpos): m/z=445 (M+H)$^+$ (free base).

EXAMPLE 57

N-[(3R)-1-Azabicyclo[2.2.2]oct-3-yl]-6-[4-(4-morpholinylmethyl)phenyl]-1-benzothiophene-2-carboxamide dihydrochloride

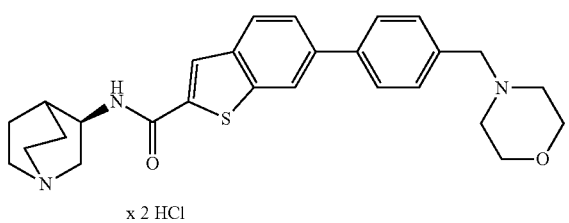 [SMILES: O=C(N[C@H]1CN2CCC1CC2)c1cc2ccc(-c3ccc(CN4CCOCC4)cc3)cc2s1]

x 2 HCl 330 mg (3.75 mmol) of morpholine and 40 mg (0.56 mmol) of sodium cyanoborohydride are successively added to a solution of 80 mg (0.19 mmol) of.

N-[(3R)-1-azabicyclo[2.2.2]oct-3-yl]-6-(4-formylphenyl)-1-benzothiophene-2-carboxamide hydrochloride (Example 23A) in 1.5 ml of a 6:1 mixture of methanol and acetic acid. 2 h at room temperature and 6 h at 80° C. are followed by purification by preparative HPLC. The product fractions are concentrated and, after addition of a 5:1 mixture of methanol and 1N hydrochloric acid, again concentrated. Drying under high vacuum results in 87.7 mg (88% of theory) of the title compound.

$^1$H-NMR (400 MHz, DMSO-d$_6$): δ=11.26 (br. s, 1H), 10.29 (br. s, 1H), 9.18 (d, 1H), 8.41 (m, 2H), 8.06 (d, 1H), 7.89 (m, 2H), 7.81 (d, 1H), 7.74 (m, 2H), 4.39 (m, 2H), 4.34 (m, 1H), 4.05-3.03 (m, 6H), 2.23 (m, 1H), 2.16 (m, 1H), 1.92 (m, 2H), 1.76 (m, 1H).

HPLC (method 1): R$_t$=3.5 min.

MS (ESIpos): m/z=462 (M+H)$^+$ (free base).

EXAMPLE 58

N-[(3R)-1-Azabicyclo[2.2.2]oct-3-yl]-7-[4-(dimethylamino)phenyl]-1-benzothiophene-2-carboxamide hydrochloride

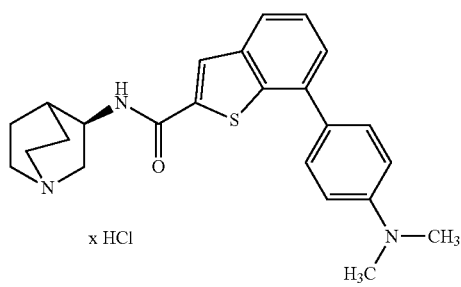 [SMILES: CN(C)c1ccc(-c2cccc3cc(C(=O)N[C@H]4CN5CCC4CC5)sc23)cc1]

0.33 ml of 2 M sodium carbonate solution and 9.1 mg (0.01 mmol) of PdCl$_2$(dppf) are added to a mixture of 100 mg (0.22 mmol) of N-[(3R)-1-azabicyclo[2.2.2]oct-3-yl]-7-bromo-1-benzothiophene-2-carboxamide hydrochloride (Example 8A) and 36.8 mg (0.22 mmol) of 4-(dimethylamino)phenylboronic acid in 1 ml of DMF. The reaction mixture is heated at 80° C. for 16 h. A further 36.8 mg (0.22 mmol) of 4-(dimethylamino)phenylboronic acid, 36.5 mg (0.04 mmol) of PdCl$_2$(dppf) and 0.67 ml of 1N sodium hydroxide solution are added, and the mixture is heated at 80° C. for a further 3 h. Cooling is followed by filtration through kieselguhr and purification by preparative HPLC. The product fractions are concentrated, taken up in a 5:1 mixture of methanol and 1N hydrochloric acid and again concentrated. Drying under high vacuum results in 50.6 mg-(47% of theory) of the title compound.

$^1$H-NMR (300 MHz, methanol-d$_4$): δ=8.26 (s, 1H), 7.95 (m, 3H), 7.80 (m, 2H), 7.58 (dd, 1H), 7.53 (m, 1H), 4.46 (m, 1H), 3.82 (m, 1H), 3.51 (m, 1H), 3.45-3.16 (m, 10H), 2.37 (m, 1H), 2.29 (m, 1H), 2.10 (m, 2H), 1.95 (m, 1H).

HPLC (method 1): R$_t$=3.6 min.

MS (ESIpos): m/z=406 (M+H)$^+$ (free base).

EXAMPLE 59

N-[(3R)-1-Azabicyclo[2.2.2]oct-3-yl]-7-(2-thienyl)-1-benzothiophene-2-carboxamide formate

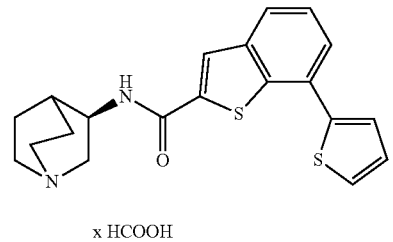 [SMILES: O=C(N[C@H]1CN2CCC1CC2)c1cc2cccc(-c3cccs3)c2s1]

100 mg (0.25 mmol) of N-[(3R)-1-azabicyclo[2.2.2]oct-3-yl]-7-bromo-1-benzothiophene-2-carboxamide hydrochloride (Example 8A) and 31.9 mg (0.25 mmol) of 2-thiopheneboronic acid are introduced into 1.5 ml of DMF. Addition of 0.37 ml of 2 M sodium carbonate solution and 9.11 mg (0.01 mmol) of PdCl$_2$(dppf) is followed by heating to 85° C. After 14 h, the reaction mixture is filtered through kieselguhr and purified by preparative HPLC (eluent A: acetonitrile, eluent B: water+0.1% formic acid; gradient: 10% A→95% A). The product fractions are concentrated and dried under high vacuum. 30 mg (28% of theory) of the title compound are obtained.

$^1$H-NMR (200 MHz, DMSO-d$_6$): δ=8.80 (d, 1H), 8.33 (s, 1H), 8.23 (s, 1H), 7.97 (m, 1H), 7.72 (m, 3H), 7.55 (dd, 1H), 7.28 (dd, 1H), 4.12 (m, 1H), 3.36 (m, 1H), 3.18-2.80 (m, 5H), 2.03 (m, 1H), 1.95 (m, 1H), 1.74 (m, 2H), 1.52 (m, 1H):

HPLC (method 1): R$_t$=4.2 min.

MS (ESIpos): m/z=369 (M+H)$^+$ (free base).

EXAMPLE 60

7-(5-Acetyl-2-thienyl)-N-[(3R)-1-azabicyclo[2.2.2]oct-3-yl]-1-benzothiophene-2-carboxamide hydrochloride

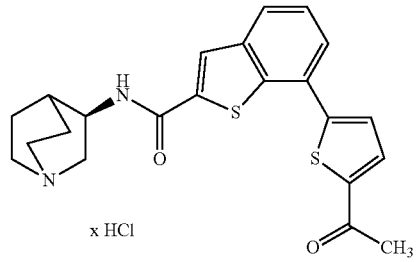 [SMILES: CC(=O)c1ccc(-c2cccc3cc(C(=O)N[C@H]4CN5CCC4CC5)sc23)s1]

100 mg (0.25 mmol) of N-[(3R)-1-azabicyclo[2.2.2]oct-3-yl]-7-bromo-1-benzothiophene-2-carboxamide hydrochloride (Example 8A) and 42.3 mg (0.25 mmol) of 5-acetyl-2-thienylboronic acid are introduced into 1.5 ml of DMF. Addition of 0.37 ml of 2 M sodium carbonate solution and 9.11 mg (0.01 mmol) of PdCl$_2$(dppf) is followed by heating to 85° C. After 14 h, the reaction mixture is filtered through kieselguhr and purified by preparative HPLC. The product fractions are concentrated, taken up in a 5:1 mixture of methanol and 1N hydrochloric acid, again concentrated and dried under high vacuum. 52 mg (46% of theory) of the title compound are obtained.

$^1$H-NMR (200 MHz, DMSO-$d_6$): δ=10.25 (br: s, 1H), 9.23 (d, 1H), 8.49 (s, 1H), 8.08 (d, 1H), 8.06 (m, 1H), 7.89 (m, 1H), 7.82 (d, 1H), 7.61 (dd, 1H), 4.36 (m, 1H), 3.73-3.13 (m, 5H), 2.60 (s, 3H), 2.23 (m, 1H), 2.15 (m, 1H), 1.93 (m, 2H), 1.76 (m, 1H).

HPLC (method 1): $R_t$=4.1 min.

MS (ESIpos): m/z=411 (M+H)$^+$ (free base).

EXAMPLE 61

N-[(3R)-1-Azabicyclo[2.2.2]oct-3-yl]-7-[4-(6-oxo-2-piperidinyl)phenyl]-1-benzothiophene-2-carboxamide hydrochloride

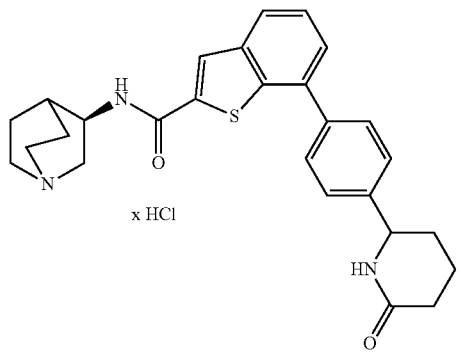 [SMILES: O=C1CCCC(c2ccc(-c3cccc4cc(C(=O)N[C@H]5CN6CCC5CC6)sc34)cc2)N1]

123.4 mg (0.49 mmol) of 6-(4-bromophenyl)-2-piperidinone, 142.2 mg (0.56 mmol) of bis(pinacolato)diboron, 146.6 mg (1.49 mmol) of potassium acetate, 13.7 mg (0.02 mmol) of PdCl$_2$(dppf), 150 mg (0.37 mmol) of N-[(3R)-1-azabicyclo[2.2.2]oct-3-yl]-7-bromo-1-benzothiophene-2-carboxamide hydrochloride (Example 8A), 0.93 ml of 2 M sodium carbonate solution and a further 13.7 mg (0.02 mmol) of PdCl$_2$(dppf) in 2 ml of DMF are reacted by general method D. Drying under high vacuum results in 7.3 mg (4% of theory) of the title compound.

HPLC (method 1): $R_t$=3.9 min.

MS (ESIpos): m/z=460 (M+H)$^+$ (free base).

EXAMPLE 62

N-[(3R)-1-Azabicyclo[2.2.2]oct-3-yl]-7-[3-(hydroxymethyl)phenyl]-1-benzothiophene-2-carboxamide hydrochloride

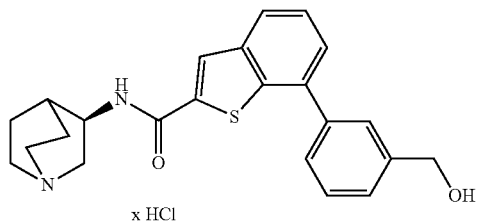 [SMILES: O=C(N[C@H]1CN2CCC1CC2)c1cc2cccc(-c3cccc(CO)c3)c2s1]

200 mg (0.45 mmol) of N-[(3R)-1-azabicyclo[2.2.2]oct-3-yl]-7-bromo-1-benzothiophene-2-carboxamide hydrochloride (Example 8A) and 74.6 mg (0.49 mmol) of 3-(hydroxymethyl)phenylboronic acid are introduced into 3 ml of DMF. Addition of 0.67 ml of 2 M sodium carbonate solution and 1.8.2 mg (0.02 mmol) of PdCl$_2$(dppf) is followed by heating to 80° C. After 14 h, the reaction mixture is filtered through kieselguhr and purified by separation by preparative HPLC. The product fractions are concentrated and, after addition of a 5:1 mixture of methanol and 4N hydrogen chloride in dioxane, again concentrated. Drying under high vacuum results in 40 mg (19% of theory) of the title compound.

$^1$H-NMR (300 MHz, DMSO-$d_6$): δ=10.47 (br. s, 1H), 9.17 (d, 1H), 8.47 (s, 1H), 7.96 (d, 1H), 7.67 (s, 1H), 7.63-7.47 (m, 4H), 7.43 (d, 1H), 4.61 (s, 2H), 4.33 (m, 1H), 3.62 (m, 1H), 3:39 (m, 2H), 3.20 (m, 3H), 2.11 (m, 1H), 2.15 (m, 1H), 1.91 (m, 2H), 1.75 (m, 1H).

HPLC (method 1): $R_t$=3.9 min.

MS (ESIpos): m/z=393 (M+H)$^+$ (free base).

EXAMPLE 63

N-[(3R)-1-Azabicyclo[2.2.2]oct-3-yl]-7-[2-(4-morpholinyl)phenyl]-1-benzothiophene-2-carboxamide hydrochloride

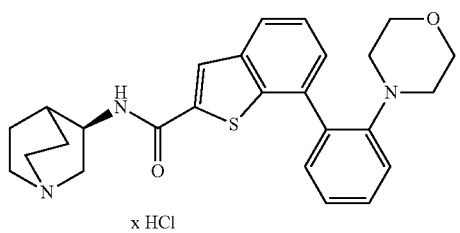 [SMILES: O=C(N[C@H]1CN2CCC1CC2)c1cc2cccc(-c3ccccc3N3CCOCC3)c2s1]

100 mg (0.41 mmol) of 4-(2-bromophenyl)morpholine, 121.0 mg (0.48 mmol) of bis(pinacolato)diboron, 101.3 mg (1.03 mmol) of potassium acetate, 11.6 mg (0.02 mmol) of PdCl$_2$(dppf), 127.6 mg (0.32 mmol) of N-[(3R)-1-azabicyclo[2.2.2]oct-3-yl]-7-bromo-1-benzothiophene-2-carboxamide hydrochloride (Example 8A), 0.79 ml of 2 M sodium carbonate solution and a further 11.6 mg (0.02 mmol) of PdCl$_2$(dppf) in 2 ml of DMF are reacted by general method D. Drying under high vacuum results in 38.9 mg (48% of theory) of the title compound.

$^1$H-NMR (200 MHz, DMSO-$d_6$): δ=10.20 (br. s, 1H), 9.04 (d, 1H), 8.36 (s, 1H), 7.93 (dd, 1H), 7.55 (m, 2H), 7.45 (d, 1H), 7.37 (dd, 1H), 7.17 (m, 2H), 4.32 (m, 1H), 3.62 (m, 1H), 3.48-3.10 (m, 9H), 2.69 (m, 4H), 2.19 (m, 1H), 2.10 (m, 1H), 1.90 (m, 2H), 1.73 (m, 1H).

HPLC (method 1): $R_t$=4.3 min.

MS (ESIpos): m/z=448 (M+H)+ (free base).

EXAMPLE 64

2-(2-{[(3R)-1-Azabicyclo[2.2.2]oct-3-ylamino]carbonyl}-1-benzothien-7-yl)-benzyl ethylcarbamate hydrochloride

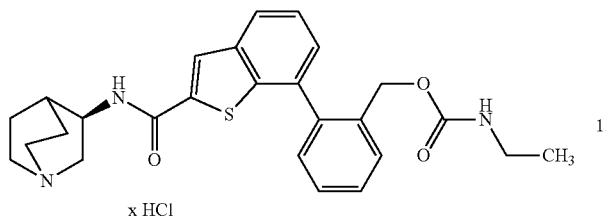

32.5 µl (0.23 mmol) of triethylamine and 16.6 mg (0.23 mmol) of ethyl isocyanate are added to a suspension of 50 mg (0.12 mmol) of N-[(3R)-1-azabicyclo[2.2.2]oct-3-yl]-7-[2-(hydroxymethyl)phenyl]-1-benzothiophene-2-carboxamide hydrochloride (Example 131) in 1 ml of a 5:1 mixture of THF and DMF. After 18 h at room temperature, a further 16.6 mg (0.23 mmol) of ethyl isocyanate and a catalytic amount of 4-N,N-dimethylaminopyridine are added. The mixture is stirred at room temperature for a further 18 h. The reaction mixture is concentrated in vacuo and purified by preparative HPLC. The product fractions are concentrated and, after addition of a 5:1 mixture of methanol and 1N hydrochloric acid, again concentrated. Drying under high vacuum results in 28 mg (47% of theory) of the title compound.

HPLC (method 1): $R_t$=4.2 min.
MS (ESIpos): m/z=464 (M+H)+ (free base).

EXAMPLE 65

2-(2-{[(3R)-1-Azabicyclo[2.2.2]oct-3-ylamino]carbonyl}-1-benzothien-7-yl)benzyl methylcarbamate hydrochloride

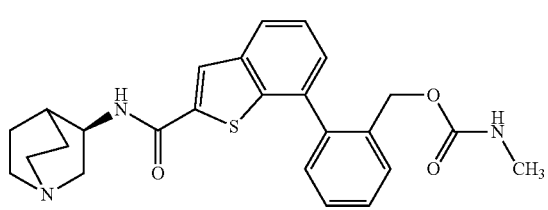

32.5 µl (0.23 mmol) of triethylamine and 13.3 mg (0.23 mmol) of methyl isocyanate are added to a suspension of 50 mg (0.12 mmol) of N-[(3R)-1-azabicyclo[2.2.2]oct-3-yl]-7-[2-(hydroxymethyl)phenyl]-1-benzothiophene-2-carboxamide hydrochloride (Example 131) in 1 ml of a 5:1 mixture of THF and DMF. After 18 h at room temperature, a further 13.3 mg (0.23 mmol) of methyl isocyanate and a catalytic amount of 4-N,N-dimethylaminopyridine are added. The mixture is stirred at room temperature for a further 18 h. The reaction mixture is concentrated in vacuo and purified by preparative HPLC. The product fractions are concentrated and, after addition of a 5:1 mixture of methanol and 1N hydrochloric acid, again concentrated. Drying under high vacuum results in 18 mg (30% of theory) of the title compound.

$^1$H-NMR (400 MHz, methanol-$d_4$): δ=8.18 (s, 1H), 7.95 (m, 1H), 7.63-7.42 (m, 4H), 7.38 (m, 2H), 4.42 (m, 1H), 3.81 (m, 1H), 3.47 (m, 1H), 3.40-3.25 (m, 4H), 2.57 (m, 3H), 2.37 (m, 1H), 2.26 (m, 1H), 2.09 (m, 2H), 1.94 (m, 1H).

LC-MS (method 4): $R_t$=2.7 min., m/z=464 (M+H)+ (free base).

EXAMPLE 66

N-[(3R)-1-Azabicyclo[2.2.2]oct-3-yl]-7-[4-(2-oxo-1-pyrrolidinyl)phenyl]-1-benzothiophene-2-carboxamide hydrochloride

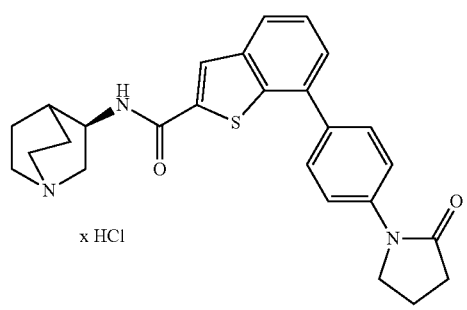 [SMILES: O=C(N[C@H]1CN2CCC1CC2)c1cc2cccc(-c3ccc(N4CCCC4=O)cc3)c2s1]

116.5 mg (0.49 mmol) of 1-(4-bromophenyl)-2-pyrrolidinone, 142.2 mg (0.56 mmol) of bis(pinacolato)diboron, 119.1 mg (1.21 mmol) of potassium acetate, 13.7 mg (0.02 mmol) of PdCl$_2$(dppf), 150 mg (0.37 mmol) of N-[(3R)-1-azabicyclo[2.2.2]oct-3-yl]-7-bromo-1-benzothiophene-2-carboxamide hydrochloride (Example 8A), 0.93 ml of 2 M sodium carbonate solution and a further 13.7 mg (0.02 mmol) of PdCl$_2$(dppf) in 2 ml of DMF are reacted by general method D. Drying under high vacuum results in 71 mg (39% of theory) of the title compound.

$^1$H-NMR (400 MHz, methanol-$d_4$): δ=8.16 (s, 1H), 7.91 (d, 1H), 7.80 (m, 2H), 7.75 (m, 2H), 7.54 (dd, 1H), 7.51 (dd, 1H), 4.46 (m, 1H), 4.01 (m, 2H), 3.85 (m, 1H), 3.47 (m, 1H), 3.42-3.26 (m, 4H), 2.65 (m, 2H), 2.39 (m, 1H), 2.24 (m, 3H), 2.10 (m, 2H), 1.96 (m, 1H).

HPLC (method 1): $R_t$=4.0 min.

MS (ESIpos): m/z=446 (M+H)+ (free base).

EXAMPLE 67

N-[(3R)-1-Azabicyclo[2.2.2]oct-3-yl]-7-[4-(1-piperazinyl)phenyl]-1-benzothiophene-2-carboxamide dihydrochloride

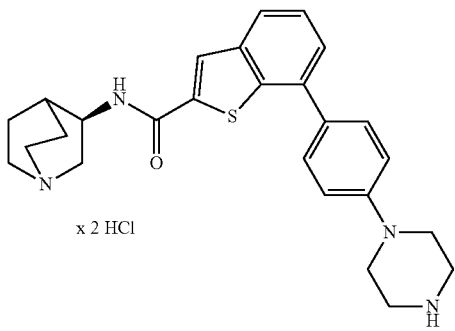 [SMILES: O=C(N[C@H]1CN2CCC1CC2)c1cc2cccc(-c3ccc(N4CCNCC4)cc3)c2s1]

x 2 HCl 165.6 mg (0.49 mmol) of tert-butyl 4-(4-bromophenyl)-1-piperazinecarboxylate, 142.2 mg (0.56 mmol) of bis(pinacolato)diboron, 119.1 mg (1.21 mmol) of potassium acetate, 13.7 mg (0.02 mmol) of PdCl$_2$(dppf), 150 mg (0.37 mmol) of N-[(3R)-1-azabicyclo[2.2.2]oct-3-yl]-7-bromo-1-benzothiophene-2-carboxamide hydrochloride (Example 8A), 0.93 ml of 2 M sodium carbonate solution and a further 13.7 mg (0.02 mmol) of PdCl$_2$(dppf) in 2 ml of DMF are reacted by general method D. The compound purified by preparative HPLC is dissolved in 3 ml of methanol and, after addition of 3 ml of 4 M hydrogen chloride in dioxane, stirred at room temperature for 30 min. The contents of the flask are concentrated in vacuo, and the residue is azeotropically distilled with toluene twice. Drying under high vacuum results in 54 mg (28% of theory) of the title compound.

$^1$H-NMR (300 MHz, methanol-d$_4$): δ=8.17 (s, 1H), 7.87 (dd, 1H), 7.66 (m, 2H), 7.52 (dd, 1H), 7.45 (dd, 1H), 7.18 (m, 2H), 4.45 (m, 1H), 3.83 (m, 1H), 3.75-3.13 (m, 13H), 2.38 (m, 1H), 2.28 (m, 1H), 2.10 (m, 2H), 1.95 (m, 1H).

HPLC (method 1): R$_t$=3.7 min.

MS (ESIpos): m/z=447 (M+H)+ (free base).

EXAMPLE 68

N-[(3R)-1-Azabicyclo[2.2.2]oct-3-yl]-7-[4-(3-oxo-4-morpholinyl)phenyl]-1-benzothiophene-2-carboxamide hydrochloride

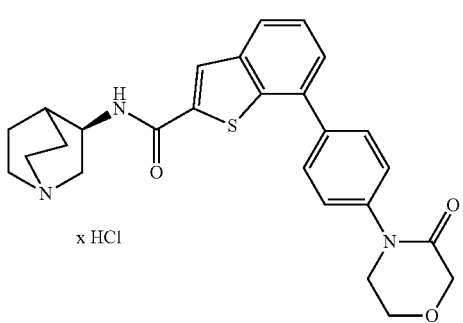 [SMILES: O=C(N[C@H]1CN2CCC1CC2)c1cc2cccc(-c3ccc(N4CCOCC4=O)cc3)c2s1]

x HCl 120 mg (0.39 mmol) of 4-(4-bromophenyl)-3-morpholinone, 115.3 mg (0.45 mmol) of bis(pinacolato)diboron, 96.6 mg (0.98 mmol) of potassium acetate, 11.1 mg (0.02 mmol) of PdCl$_2$(dppf), 121.6 mg (0.30 mmol) of N-[(3R)-1-azabicyclo[2.2.2]oct-3-yl]-7-bromo-1-benzothiophene-2-carboxamide hydrochloride (Example 8A), 0.76 ml of 2 M sodium carbonate solution and a further 11.1 mg (0.02 mmol) of PdCl$_2$(dppf) in 2 ml of DMF are reacted by general method D. Drying under high vacuum results in 24 mg (16% of theory) of the title compound.

$^1$H-NMR (400 MHz, methanol-d$_4$): δ=8.17 (s, 1H), 7.93 (d, 1H), 7.80 (m, 2H), 7.55 (m, 4H), 4.46 (m, 1H), 4.33 (s, 2H), 4.09 (m, 2H), 3.88 (m, 2H), 3.84 (m, 1H), 3.47 (m, 1H), 3.41-3.26 (m, 4H), 2.39 (m, 1H), 2.28 (m, 1H), 2.10 (m, 2H), 1.95 (m, 1H).

HPLC (method 1): R$_t$=3.8 min.

MS (ESIpos): m/z=462 (M+H)+ (free base).

EXAMPLE 69

N-[(3R)-1-Azabicyclo[2.2.2]oct-3-yl]-7-[3-(1-pyrrolidinyl)phenyl]-1-benzothiophene-2-carboxamide hydrochloride

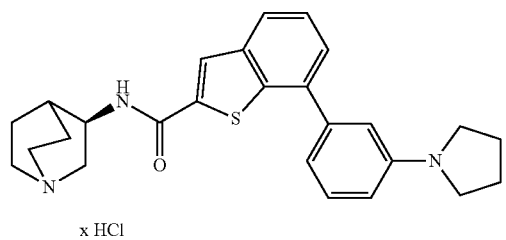 [SMILES: O=C(N[C@H]1CN2CCC1CC2)c1cc2cccc(-c3cccc(N4CCCC4)c3)c2s1]

x HCl 109.8 mg (0.49 mmol) of 1-(3-bromophenyl)pyrrolidine, 142.2 mg (0.56 mmol) of bis(pinacolato)diboron, 119.1 mg (1.21 mmol) of potassium acetate, 13.7 mg (0.02 mmol) of PdCl$_2$(dppf), 150.0 mg (0.37 mmol) of N-[(3R)-1-azabicyclo[2.2.2]oct-3-yl]-7-bromo-1-benzothiophene-2-carboxamide hydrochloride (Example 8A), 0.93 ml of 2 M sodium carbonate solution and a further 13.7 mg (0.02 mmol) of PdCl$_2$(dppf) in 2 ml of DMF are reacted by general method D. Drying under high vacuum results in 88.4 mg (51% of theory) of the title compound.

$^1$H-NMR (200 MHz, DMSO-d$_6$): δ=10.28 (br. s, 1H), 9.11 (d, 1H), 8.42 (s, 1H), 7.95 (dd, 1H), 7.55 (m, 2H), 7.36 (dd, 1H), 6.96 (d, 1H), 6.87 (s, 1H), 6.68 (m, 1H), 4.33 (m, 1H), 3.80-3.10 (m, 10H), 2.21 (m, 1H), 2.11 (m, 1H), 2.95 (m, 6H), 1.75 (m, 1H).

HPLC (method 1): R$_t$=4.2 min.

MS (ESIpos): m/z=432 (M+H)+ (free base).

EXAMPLE 70

N-[(3R)-1-Azabicyclo[2.2.2]oct-3-yl]-7-[3-(4-morpholinyl)phenyl]-1-benzothiophene-2-carboxamide hydrochloride

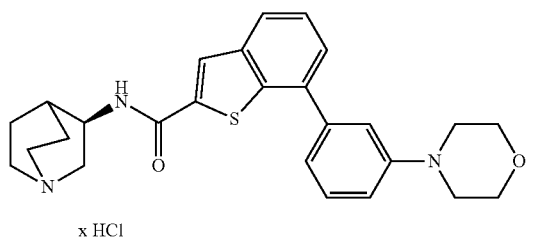 [SMILES: O=C(N[C@H]1CN2CCC1CC2)c1cc2cccc(-c3cccc(N4CCOCC4)c3)c2s1]

151.1 mg (0.49 mmol) of 3-(4-morpholinyl)phenyl trifluoromethanesulphonate (Example 17A), 142.2 mg (0.56 mmol) of bis(pinacolato)diboron, 119.1 mg (1.21 mmol) of potassium acetate, 13.7 mg (0.02 mmol) of PdCl$_2$(dppf), 150.0 mg (0.37 mmol) of N-[(3R)-1-azabicyclo[2.2.2]oct-3-yl]-7-bromo-1-benzothiophene-2-carboxamide hydrochloride (Example 8A), 0.93 ml of 2 M sodium carbonate solution and a further 13.7 mg (0.02 mmol) of PdCl$_2$(dppf) in 2 ml of DMF are reacted by general method D. Drying under high vacuum results in 125.3 mg (68% of theory) of the title compound.

$^1$H-NMR (400 MHz, methanol-d$_4$): δ=8.26 (s, 1H), 7.99 (m, 2H), 7.86 (d, 1H), 7.75 (m, 2H), 7.59 (m, 2H), 4.47 (m, 1H), 4.10 (m, 4H), 3.83 (m, 1H), 3.76 (m, 4H), 3.73 (m, 1H), 3.52 (m, 1H), 3.37 (m, 3H), 2.38 (m, 1H), 2.29 (m, 1H), 2.10 (m, 2H), 1.96 (m, 11H).

HPLC (method 1): R$_t$=3.9 min.

MS (ESIpos): m/z=448 (M+H)+ (free base).

EXAMPLE 71

N-[(3R)-1-Azabicyclo[2.2.2]oct-3-yl]-7-[4-(1-pyrrolidinyl)phenyl]-1-benzothiophene-2-carboxamide dihydrochloride

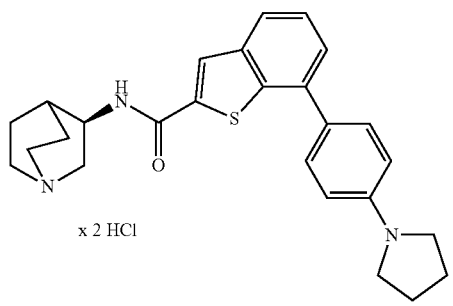 [SMILES: O=C(N[C@H]1CN2CCC1CC2)c1cc2cccc(-c3ccc(N4CCCC4)cc3)c2s1]

109.8 mg (0.49 mmol) of 1-(4-bromophenyl)pyrrolidine, 142.2 mg (0.56 mmol) of bis(pinacolato)diboron, 119.1 mg (1.21 mmol) of potassium acetate, 13.7 mg (0.02 mmol) of PdCl$_2$(dppf), 150.0 mg (0.37 mmol) of N-[(3R)-1-azabicyclo[2.2.2]oct-3-yl]-7-bromo-1-benzothiophene-2-carboxamide hydrochloride (Example 8A), 0.93 ml of 2 M sodium carbonate solution and a further 13.7 mg (0.02 mmol) of PdCl$_2$(dppf) in 2.5 ml of DMF are reacted by general method D. Drying under high vacuum results in 24.8 mg (13% of theory) of the title compound.

$^1$H-NMR (400 MHz, methanol-d$_4$): δ=8.26 (s, 1H), 7.98 (d, 1H), 7.92 (m, 2H), 7.75 (m, 2H), 7.58 (dd, 1H), 7.53 (d, 1H), 4.47 (m, 1H), 3.92-3.76 (m, 5H), 3.51 (m, 1H), 3.45-3.18 (m, 4H), 2.42-2.23 (m, 6H), 2.10 (m, 2H), 1.96 (m, 1H).

HPLC (method 1): R$_t$=4.1 min.

MS (ESIpos): m/z=432 (M+H)+ (free base).

EXAMPLE 72

N-[(3R)-1-Azabicyclo[2.2.2]oct-3-yl]-7-[4-(4-morpholinylcarbonyl)phenyl]-1-benzothiophene-2-carboxamide hydrochloride

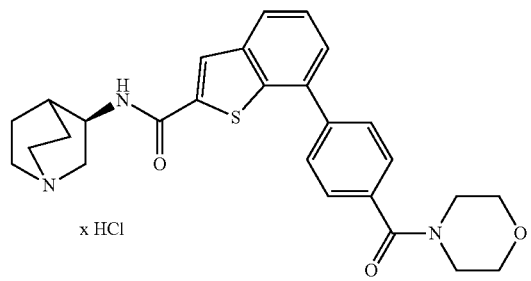 [SMILES: O=C(N[C@H]1CN2CCC1CC2)c1cc2cccc(-c3ccc(C(=O)N4CCOCC4)cc3)c2s1]

164.7 mg (0.49 mmol) of 4-(4-morpholinylcarbonyl)phenyl trifluoromethane-sulphonate (Example 18A), 142.2 mg (0.56 mmol) of bis(pinacolato)diboron, 119.1 mg (1.21 mmol) of potassium acetate, 13.7 mg (0.02 mmol) of PdCl$_2$(dppf), 150.0 mg (0.37 mmol) of N-[(3R)-1-azabicyclo[2.2.2]oct-3-yl]-7-bromo-1-benzothiophene-2-carboxamide hydrochloride (Example 8A), 0.93 ml of 2 M sodium carbonate solution and a further 13.7 mg (0.02 mmol) of PdCl$_2$(dppf) in 2.5 ml of DMF are reacted by general method D. An initial purification by preparative HPLC is followed by column chromatography on silica gel (mobile phase: dichloromethane/methanol/ammonia 90:9:1). Drying under high vacuum results in 24.8 mg (13% of theory) of the title compound.

$^1$H-NMR (400 MHz, methanol-d$_4$): δ=8.22 (s, 1H), 7.97 (d, 1H), 7.83 (m, 2H), 7.62 (m, 2H), 7.55 (m, 2H), 4.47 (m, 1H), 3.90-3.26 (m, 14H), 2.38 (m, 1H), 2.28 (m, 1H), 2.10 (m, 2H), 1.96 (m, 1H).

HPLC (method 1): R$_t$=3.8 min.

MS (ESIpos): m/z=476 (M+H)⁺ (free base).

EXAMPLE 73

7-[2-(Aminomethyl)phenyl]-N-[(3R)-1-azabicyclo[2.2.2]oct-3-yl]-1-benzothiophene-2-carboxamide dihydrochloride

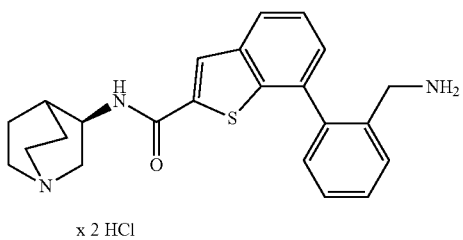 [SMILES: NCc1ccccc1-c1cccc2cc(C(=O)N[C@H]3CN4CCC3CC4)sc12]

x 2 HCl 534.2 mg (1.87 mmol) of tert-butyl 2-bromobenzylcarbamate, 474.1 mg (1.87 mmol) of bis(pinacolato)diboron, 397.0 mg (4.04 mmol) of potassium acetate, 45.5 mg (0.06 mmol) of PdCl₂(dppf), 500 mg (1.24 mmol) of N-[(3R)-1-azabicyclo[2.2.2]oct-3-yl]-7-bromo-1-benzothiophene-2-carboxamide hydrochloride (Example 8A), 3.11 ml of 2 M sodium carbonate solution and a further 45.5 mg (0.06 mmol) of PdCl₂(dppf) in 6.0 ml of DMF are reacted by general method D. Purification by preparative HPLC is followed by concentration of the combined product fractions, taking up in methanol, addition of 1N hydrochloric acid, and stirring at room temperature for 30 min. Concentration and drying under high vacuum result in 121 mg (20% of theory) of the title compound.

HPLC (method 1): $R_t$=3.6 min.
MS (ESIpos): m/z=392 (M+H)⁺ (free base).

EXAMPLE 74

N-[(3R)-1-Azabicyclo[2.2.2]oct-3-yl]-7-{3-[(2,2-dimethylpropanoyl)amino]phenyl}-1-benzothiophene-2-carboxamide hydrochloride

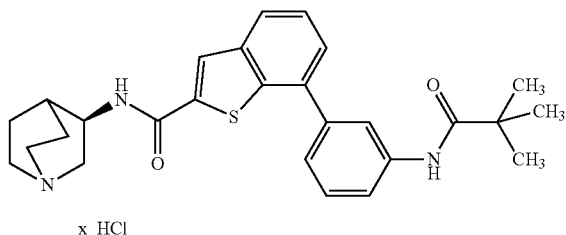 [SMILES: CC(C)(C)C(=O)Nc1cccc(-c2cccc3cc(C(=O)N[C@H]4CN5CCC4CC5)sc23)c1]

x HCl 143.5 mg (0.56 mmol) of N-(3-bromophenyl)-2,2-dimethylpropanamide, 142.2 mg (0.56 mmol) of bis(pinacolato)diboron, 119.1 mg (1.21 mmol) of potassium acetate, 13.7 mg (0.02 mmol) of PdCl₂(dppf), 150.0 mg (0.37 mmol) of N-[(3R)-1-azabicyclo[2.2.2]oct-3-yl]-7-bromo-1-benzothiophene-2-carboxamide hydrochloride (Example 8A), 0.93 ml of 2 M sodium carbonate solution and a further 13.7 mg (0.02 mmol) of PdCl₂(dppf) in 2.0 ml of DMF are reacted by general method D. An initial purification by preparative HPLC is followed by column chromatography on silica gel (mobile phase: dichloromethane/methanol/ammonia 90:9:1). Drying under high vacuum results in 32.4 mg (17% of theory) of the title compound.

¹H-NMR (400 MHz, methanol-d₄): δ=8.16 (s, 1H), 8.01 (m, 1H), 7.92 (m, 1H), 7.63-7.48 (m, 3H), 7.47 (m, 2H), 4.44 (m, 1H), 3.84 (m, 1H), 3.47 (m, 1H), 3.41-3.27 (m, 4H), 2.38 (m, 1H), 2.28 (m, 1H), 2.10 (m, 2H), 1.96 (m, 1H), 1.32 (s, 9H).

HPLC (method 1): $R_t$=4.3 min.
MS (ESIpos): m/z=462 (M+H)⁺ (free base).

EXAMPLE 75

3-(2-{[(3R)-1-Azabicyclo[2.2.2]oct-3-ylamino]carbonyl}-1-benzothien-7-yl)-benzoic acid hydrochloride

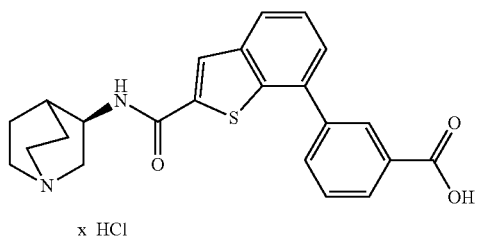 [SMILES: O=C(O)c1cccc(-c2cccc3cc(C(=O)N[C@H]4CN5CCC4CC5)sc23)c1]

x HCl 200 mg (0.50 mmol) of N-[(3R)-1-azabicyclo[2.2.2]oct-3-yl]-7-bromo-1-benzothiophene-2-carboxamide hydrochloride (Example 8A) and 82.6 mg (0.50 mmol) of 3-carboxyphenylboronic acid are introduced into 1.5 ml of DMF. Addition of 0.78 ml of 2 M sodium carbonate solution and 20.3 mg (0.02 mmol) of PdCl₂(dppf) is followed by heating at 60° C. After 18 h, a further 20.3 mg (0.02 mmol) of PdCl₂(dppf) are added, and the mixture is heated at 90° C. for a further 18 h. After cooling, the reaction mixture is filtered through kieselguhr and purified by preparative HPLC. The product fractions are concentrated and, after addition of a 3:1 mixture of acetonitrile and 1N hydrochloric acid, again concentrated. Drying under high vacuum results in 103 mg (45% of theory) of the title compound.

¹H-NMR (300 MHz, DMSO-d₆): δ=10.28 (br. s, 1H), 9.13 (d, 1H), 8.46 (s, 1H), 8.29 (m, 1H), 8.08-7.95 (m, 3H), 7.71 (dd, 1H), 7.60 (m, 2H), 4.33 (m, 1H), 3.85-3.12 (m, 6H), 2.22 (m, 1H), 2.15 (m, 1H), 1.91 (m, 2H), 1.75 (m, 1H).

HPLC (method 1): $R_t$=3.9 min.

MS (ESIpos): m/z=407 (M+H)+ (free base).

EXAMPLE 76

N-[(3R)-1-Azabicyclo[2.2.2]oct-3-yl]-7-[2-({[(methylamino)carbonyl]amino}-methyl)phenyl]-1-benzothiophene-2-carboxamide hydrochloride

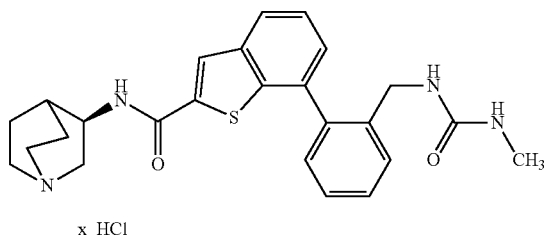 [SMILES: CNC(=O)NCc1ccccc1-c1cccc2cc(C(=O)N[C@H]3CN4CCC3CC4)sc12]

x HCl 51.0 µl (0.37 mmol) of triethylamine and 43.5 ld (0.73 mmol) of methyl isocyanate are added to a suspension of 85 mg (0.18 mmol) of 7-[2-(aminomethyl)phenyl]-N-[(3R)-1-azabicyclo[2.2.2]oct-3-yl]-1-benzothiophene-2-carboxamide dihydrochloride (Example 73) in 1 ml of a 5:1 mixture of THF and DMF. After 18 h at room temperature, the reaction mixture is concentrated in vacuo and purified by preparative HPLC. The product fractions are concentrated and, after addition of a 5:1 mixture of methanol and 1N hydrochloric acid, again concentrated. Drying under high vacuum results in 65.5 mg (74% of theory) of the title compound.

$^1$H-NMR (400 MHz, methanol-d$_4$): δ=8.18 (s, 1H), 7.94 (d, 1H), 7.58-7.44 (m, 3H), 7.43-7.29 (m, 3H); 4.43 (m, 1H), 4.15 (m, 2H), 3.82 (m, 1H), 3.47 (m, 1H), 3.41-3.27 (m, 4H), 2.62 (s, 3H), 2.37 (m, 1H), 2.26 (m, 1H), 2.08 (m, 2H), 1.94 (m, 1H).

HPLC (method 1): R$_t$=3.8 min.
LC-MS (method 4): R$_t$=2.5 min.
MS (ESIpos): m/z=448 (M+H)+ (free base).

EXAMPLE 77

N-[(3R)-1-Azabicyclo[2.2.2]oct-3-yl]-7-[3-(1H-pyrrol-1-yl)phenyl]-1-benzothiophene-2-carboxamide hydrochloride

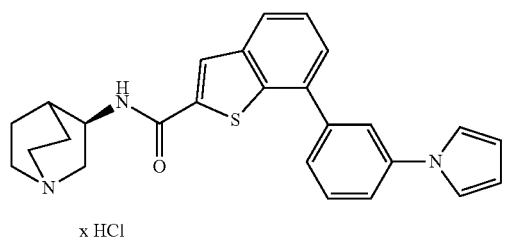 [SMILES: O=C(N[C@H]1CN2CCC1CC2)c1cc2cccc(-c3cccc(-n4cccc4)c3)c2s1]

x HCl 124.4 mg (0.56 mmol) of 1-(3-bromophenyl)-1H-pyrrole, 142.2 mg (0.56 mmol) of bis(pinacolato)diboron, 119.1 mg (1.21 mmol) of potassium acetate, 13.7 mg (0.02 mmol) of PdCl$_2$(dppf), 150.0 mg (0.37 mmol) of N-[(3R)-1-azabicyclo[2.2.2]oct-3-yl]-7-bromo-1-benzothiophene-2-carboxamide hydrochloride (Example 8A), 0.93 ml of 2 M sodium carbonate solution and a further 13.7 mg (0.02 mmol) of PdCl$_2$(dppf) in 2.0 ml of DMF are reacted by general method D. Drying under high vacuum results in 86.9 mg (48% of theory) of the title compound.

$^1$H-NMR (400 MHz, DMSO-d$_6$): δ=9.92 (br. s, 1H), 9.03 (d, 1H), 8.39 (m, 1H), 8.02 (m, 1H), 7.88 (s, 1H), 7.77-7.57 (m, 5H), 7.49 (m, 2H), 6.31 (m, 2H), 4.32 (m, 1H), 3.67 (m, 1H), 3.57-3.13 (m, 5H), 2.21 (m, 1H), 2.13 (m, 1H), 1.90 (m, 2H), 1.75 (m, 1H).

HPLC (method 1): R$_t$=4.5 min.
MS (ESIpos): m/z=428 (M+H)+ (free base).

EXAMPLE 78

N-[(3R)-1-Azabicyclo[2.2.2]oct-3-yl]-7-[3-(4-morpholinylcarbonyl)phenyl]-1-benzothiophene-2-carboxamide hydrochloride

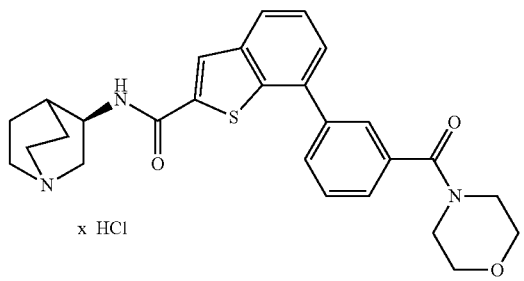 [SMILES: O=C(N[C@H]1CN2CCC1CC2)c1cc2cccc(-c3cccc(C(=O)N4CCOCC4)c3)c2s1]

x HCl 103 mg (0.27 mmol) of HATU and 70.8 µl (0.41 mmol) of N,N-diisopropylethylamine are added to a solution of 50 mg (0.11 mmol) of 3-(2-{[(3R)-1-azabicyclo[2.2.2]oct-3-ylamino]carbonyl}-1-benzothien-7-yl)benzoic acid hydrochloride (Example 75) and 19.7 µl (0.23 mmol) of morpholine in 0.5 ml of DMF at 0° C. The mixture is stirred at room temperature for 18 h. After purification by preparative HPLC, the product fractions are concentrated and, after addition of a 3:1 mixture of acetonitrile and 1N hydrochloric acid, again concentrated. Drying under high vacuum results in 43 mg (74% of theory) of the title compound.

$^1$H-NMR (200 MHz, DMSO-d$_6$): δ=10.66 (br. s, 1H), 9.33 (d, 1H), 8.56 (s, 1H), 7.98 (dd, 1H), 7.87-7.45 (m, 6H), 4.34 (m, 1H), 3.87-3.06 (m, 14H), 2.18 (m, 2H), 1.90 (m, 2H), 1.74 (m, 1H).

HPLC (method 1): R$_t$=3.8 min.

MS (ESIpos): m/z=476 (M+H)⁺ (free base).

EXAMPLE 79

N-[(3S)-1-Azabicyclo[2.2.2]oct-3-yl]-7-[4-(4-morpholinyl)phenyl]-1-benzothiophene-2-carboxamide hydrochloride

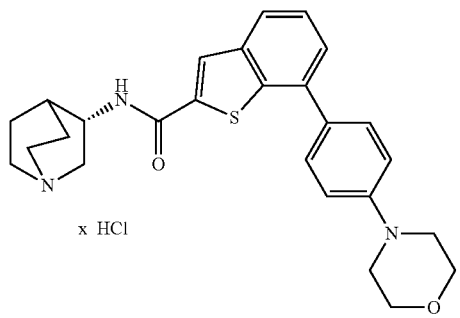 [SMILES: O=C(N[C@@H]1CN2CCC1CC2)c1cc2cccc(-c3ccc(N4CCOCC4)cc3)c2s1]

330.7 mg (0.87 mmol) of HATU and 112.4 mg (0.87 mmol) of N,N-diisopropylethylamine are added to a mixture of 144.3 mg (0.72 mmol) of S-3-aminoquinuclidine dihydrochloride and 300 mg (0.72 mmol) of 7-[4-(4-morpholinyl)phenyl]-1-benzothiophene-2-carboxylic acid (Example 20A) in 3 ml of DMF at 0° C. After 30 min at 0° C., a further 224.8 mg (1.74 mmol) of N,N-diisopropylethylamine are added, and the mixture is stirred at room temperature for 19 h. The reaction solution is mixed with a little water and acetonitrile and purified by preparative HPLC. The product fractions are concentrated and, after addition of a 3:1 mixture of methanol and 1N hydrochloric acid, again concentrated. Drying under high vacuum results in 158 mg (45% of theory) of the title compound.

The spectroscopic data agree with those of the enantiomeric compound (Example 19).

EXAMPLE 80

N-[(3R)-1-Azabicyclo[2.2.2]oct-3-yl]-7-[3-(4-morpholinyl)phenyl]-1-benzofuran-2-carboxamide hydrochloride

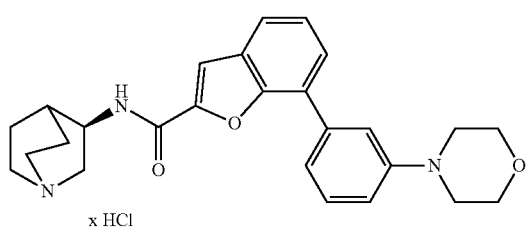 [SMILES: O=C(N[C@H]1CN2CCC1CC2)c1cc2cccc(-c3cccc(N4CCOCC4)c3)c2o1]

151.1 mg (0.49 mmol) of 3-(4-morpholinyl)phenyl trifluoromethanesulphonate (Example 17A), 142.2 mg (0.56 mmol) of bis(pinacolato)diboron, 119.1 mg (1.21 mmol) of potassium acetate, 13.7 mg (0.02 mmol) of PdCl₂(dppf), 144 mg (0.37 mmol) of N-[(3R)-1-azabicyclo[2:2.2]oct-3-yl]-7-bromo-1-benzofuran-2-carboxamide hydrochloride (Example 30A), 0.93 ml of 2 M sodium carbonate solution and a further 13.7 mg (0.02 mmol) of PdCl₂(dppf) in 2 ml of DMF are reacted by general method D. Drying under high vacuum results in 32 mg (18% of theory) of the title compound.

¹H-NMR (300 MHz, DMSO-d₆): δ=10.27 (br. s, 1H), 8.96 (d, 1H), 7.85 (s, 1H), 7.78 (m, 1H), 7.68 (m, 1H), 7.62 (m, 1H), 7.43 (m, 3H), 7.17 (m; 1H), 4.36 (m, 1H), 3.82 (m, 4H), 3.63 (m, 1H), 3.44-3.10 (m, 9H), 2.22 (m, 1H), 2.12 (m, 1H), 1.91 (m, 2H), 1.75 (m, 1H).

HPLC (method 1): R$_f$=3.8 min.

MS (ESIpos): m/z=432 (M+H)⁺ (free base).

EXAMPLE 81

7-(3-Aminophenyl)-N-[(3R)-1-azabicyclo[2.2.2]oct-3-yl]-1-benzothiophene-2-carboxamide hydrochloride

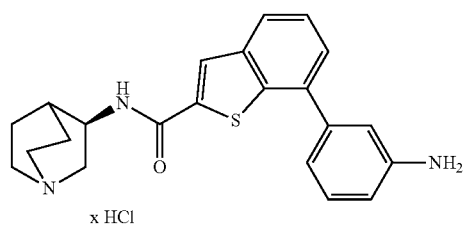 [SMILES: Nc1cccc(-c2cccc3cc(C(=O)N[C@H]4CN5CCC4CC5)sc23)c1]

200 mg (0.50 mmol) of N-[(3R)-1-azabicyclo[2.2.2]oct-3-yl]-7-bromo-1-benzothiophene-2-carboxamide hydrochloride (Example 8A) and 68.2 mg (0.50 mmol) of 3-aminophenylboronic acid are introduced into 1.5 ml of DMF. Addition of 0.78 ml of 2 M sodium carbonate solution and 20.3 mg (0.02 mmol) of PdCl₂(dppf) is followed by heating at 60° C. for 18 h. After cooling, the reaction mixture is filtered through kieselguhr and purified by separation by preparative HPLC. The product fractions are concentrated and, after addition of a 3:1 mixture of acetonitrile and 1N hydrochloric acid, again concentrated. Drying under high vacuum results in 201 mg (98% of theory) of the title compound.

¹H-NMR (200 MHz, DMSO-d₆): δ=10.63 (br. s, 1H), 9.33 (d, 1H), 8.57 (s, 1H), 8.00 (dd, 1H), 7.76-7.58 (m, 4H), 7.55 (m, 1H), 7.43 (m, 1H), 4.34 (m, 1H), 3.62 (m, 1H), 3.42 (m, 2H), 3.19 (m, 3H), 2.19 (m, 2H), 1.90 (m, 2H), 1.73 (m, 1H).

HPLC (method 1): R$_f$=3.5 min.

MS (ESIpos): m/z=378 (M+H)⁺ (free base).

EXAMPLE 82

N-[(3R)-1-Azabicyclo[2.2.2]oct-3-yl]-7-{3-[(methoxyacetyl)amino]phenyl}-1-benzothiophene-2-carboxamide hydrochloride

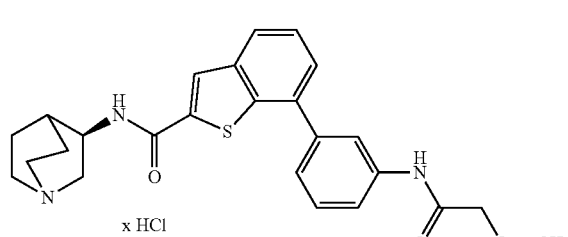

96.4 mg (0.25 mmol) of HATU and 71.5 μl (0.41 mmol) of N,N-diisopropylethylamine are added to a solution of 50 mg (0.12 mmol) of 7-(3-aminophenyl)-N-[(3R)-1-azabicyclo[2.2.2]oct-3-yl]-1-benzothiophene-2-carboxamide hydrochloride (Example 81) and 18.5 µl (0.24 mmol) of methoxyacetic acid in 0.5 ml of DMF at 0° C. The mixture is stirred at room temperature for 3 h. Purification by preparative HPLC is followed by concentration of the product fractions and, after addition of a 3:1 mixture of acetonitrile and 1N hydrochloric acid, concentration again. Drying under high vacuum results in 7 mg (11% of theory) of the title compound.

$^1$H-NMR (300 MHz, DMSO-$d_6$): δ=10.13 (br. s, 1H), 9.97 (s, 1H), 9.04 (d, 1H), 8.39 (s, 1H), 8.13 (m, 1H), 7.98 (d, 1H), 7.76 (d, 1H), 7.58 (dd, 1H), 7.50 (m, 2H), 7.42 (m, 1H), 4.33 (m, 1H), 4.03 (s, 2H), 3.66 (m, 1H), 3.56-3.12 (m, 8H), 2.22 (m, 1H), 2.14 (m, 1H), 1.91 (m, 2H), 1.75 (m, 1H).

HPLC (method 1): $R_t$=4.0 min.

MS (ESIpos): m/z=450 (M+H)$^+$ (free base).

EXAMPLE 83

N-[(3R)-1-Azabicyclo[2.2.2]oct-3-yl]-7-[4-(2-oxo-1-pyrrolidinyl)phenyl]-1-benzofuran-2-carboxamide hydrochloride

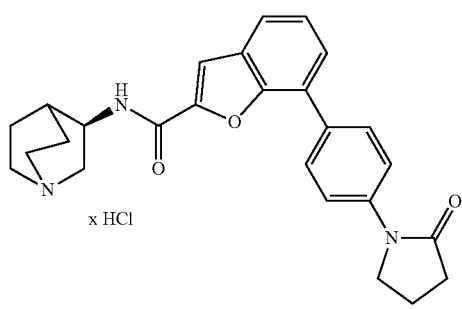 [SMILES: O=C(N[C@H]1CN2CCC1CC2)c1cc2cccc(-c3ccc(N4CCCC4=O)cc3)c2o1]

161.9 mg (0.67 mmol) of 1-(4-bromophenyl)-2-pyrrolidinone, 197.5 mg (0.78 mmol) of bis(pinacolato)diboron, 165.4 mg (1.69 mmol) of potassium acetate, 19.0 mg (0.03 mmol) of PdCl$_2$(dppf), 200 mg (0.52 mmol) of N-[(3R)-1-azabicyclo[2.2.2]oct-3-yl]-7-bromo-1-benzofuran-2-carboxamide hydrochloride (Example 30A), 1.30 ml of 2 M sodium carbonate solution and a further 19.0 mg (0.03 mmol) of PdCl$_2$(dppf) in 2.5 ml of DMF are reacted by general method D. Drying under high vacuum results in 166.6 mg (65% of theory) of the title compound.

$^1$H-NMR (200 MHz, DMSO-$d_6$): δ=10.06 (br. s, 1H), 8.96 (d, 1H), 7.97 (m, 1H), 7.94 (s, 1H), 7.83 (m, 3H), 7.78 (dd, 1H), 7.69 (dd, 1H), 7.43 (dd, 1H), 4.33 (m, 1H), 4.00-3.75 (m, 2H), 3.66 (m, 1H), 3.49-3.10 (m, 5H), 2.55 (m, 2H), 2.23 (m, 1H), 2.10 (m, 3H), 1.91 (m, 2H), 1.75 (m, 1H).

HPLC (method 1): $R_t$=4.0 min.

MS (ESIpos): m/z=430.5 (M+H)$^+$ (free base).

EXAMPLE 84

7-[3-(Acetylamino)phenyl]-N-[(3S)-1-azabicyclo[2.2.2]oct-3-yl]-1-benzothiophene-2-carboxamide hydrochloride

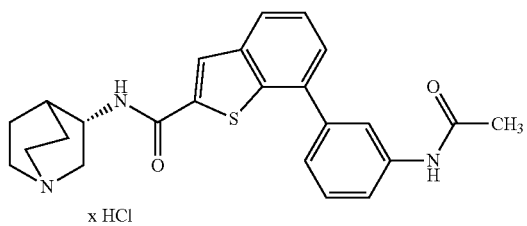 [SMILES: CC(=O)Nc1cccc(-c2cccc3cc(C(=O)N[C@@H]4CN5CCC4CC5)sc23)c1]

0.67 ml of 2 M sodium carbonate solution and 18.3 mg (0.02 mmol) of PdCl$_2$(dppf) are added to a mixture of 200 mg (0.45 mmol) of N-[(3S)-1-azabicyclo[2.2.2]oct-3-yl]-7-bromo-1-benzothiophene-2-carboxamide hydrochloride (Example 22A) and 80.2 mg (0.45 mmol) of 3-(acetamido)phenylboronic acid in 2 ml of DMF. The reaction mixture is heated at 80° C. for 17 h. A further 40.1 mg (0.22 mmol) of 3-(acetamido)phenylboronic acid, 1.34 ml of 1N sodium hydroxide solution and 73.2 mg (0.09 mmol) of PdCl$_2$(dppf) are added, and the mixture is heated at 70° C. for a further 18 h. Cooling is followed by filtration through kieselguhr and purification by preparative HPLC. The product fractions are concentrated, taken up in a 5:1 mixture of methanol and 1N hydrochloric acid and again concentrated. Drying under high vacuum results in 124.5 mg (59% of theory) of the title compound.

The spectroscopic data agree with those of the enantiomeric compound (Example 51).

EXAMPLE 85

N-[(3S)-1-Azabicyclo[2.2.2]oct-3-yl]-7-(3-methoxyphenyl)-1-benzothiophene-2-carboxamide hydrochloride

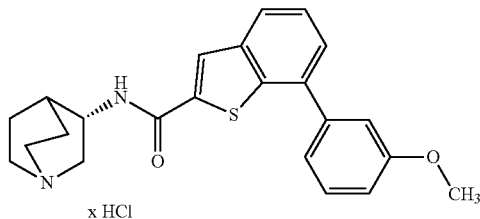 [SMILES: COc1cccc(-c2cccc3cc(C(=O)N[C@@H]4CN5CCC4CC5)sc23)c1]

0.67 ml of 2 M aqueous sodium carbonate solution and 18.3 mg (0.02 mmol) of PdCl$_2$(dppf) are added to a mixture of 200 mg (0.45 mmol) of N-[(3S)-1-azabicyclo[2.2.2]oct-3-yl]-7-bromo-1-benzothiophene-2-carboxamide hydrochloride (Example 22A) and 68.1 mg (0.45 mmol) of 3-methoxyphenylboronic acid in 2 ml of DMF. The reaction mixture is heated at 80° C. for 17 h, filtered through kieselguhr and evaporated to dryness. A purification by preparative HPLC is followed by column chromatography on silica gel (mobile phase: dichloromethane/methanol-/ammonia 90:9:1). The product fractions are concentrated, taken up in a 5:1 mixture of methanol and 1N hydrochloric acid and again concentrated. Drying under high vacuum results in 97.7 mg (48% of theory) of the title compound.

$^1$H-NMR (200 MHz, DMSO-d$_6$): δ=10.25 (br. s, 1H), 9.11 (d, 1H), 8.42 (s, 1H), 7.97 (dd, 1H), 7.56 (m, 2H), 7.47 (d, 1H), 7.30 (d, 1H), 7.24 (m, 1H), 7.06 (m, 1H), 4.32 (m, 1H), 3.83 (s, 3H), 3.63 (m, 1H), 3.49-3.10 (m, 5H), 2.20 (m, 1H), 2.13 (m, 1H), 1.90 (m, 2H), 1.74 (m, 1H).

The analytical data agree with those of the enantiomeric compound (Example 17).

EXAMPLE 86

4-(2-{[(3R)-1-Azabicyclo[2.2.2]oct-3-ylamino]carbonyl}-1-benzofuran-7-yl)-benzoic acid hydrochloride

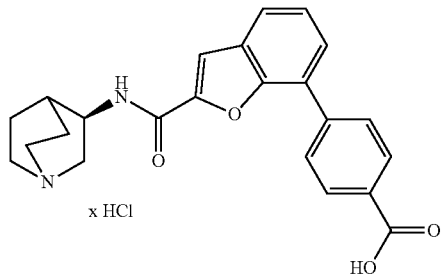 [SMILES: O=C(O)c1ccc(-c2cccc3cc(C(=O)N[C@H]4CN5CCC4CC5)oc23)cc1]

150 mg (0.43 mmol) of N-[(3R)-1-azabicyclo[2.2.2]oct-3-yl]-7-bromo-1-benzofuran-2-carboxamide hydrochloride (Example 30A) and 71.3 mg (0.43 mmol) of 4-carboxyphenylboronic acid are introduced into 1.5 ml of DMF. Addition of 0.64 ml of 2 M sodium carbonate solution and 17.5 mg (0.02 mmol) of PdCl$_2$(dppf) is followed by heating at 80° C. for 18 h. After cooling, the reaction mixture is filtered through kieselguhr, and the filtrate is concentrated and partitioned between water and ethyl acetate. The aqueous phase is washed with ethyl acetate and then concentrated. The crude product is purified by preparative HPLC. The product fractions are combined and concentrated and, after addition of a 3:1 mixture of acetonitrile and 1N hydrochloric acid, again concentrated. The crude product is stirred with acetonitrile. The precipitate is filtered off with suction and dried under high vacuum to result in 37 mg (20% of theory) of the title compound.

$^1$H-NMR (300 MHz, DMSO-d$_6$): δ=10.37 (br. s, 1H), 9.15 (d, 1H), 8.08 (m, 4H), 7.93 (s, 1H), 7.85 (dd, 1H), 7.76 (dd, 1H), 7.47 (dd, 1H), 4.36 (m, 1H), 3.77-3.32 (m, 3H), 3.32 (m, 3H), 2.23 (m, 1H), 2.12 (m, 1H), 1.92 (m, 2H), 1.76 (m, 1H).

HPLC (method 1): R$_t$=3.9 min.

MS (ESIpos): m/z=391 (M+H)$^+$ (free base).

EXAMPLE 87

N-[(3R)-1-Azabicyclo[2.2.2]oct-3-yl]-7-[3-(trifluoromethoxy)phenyl]-1-benzofuran-2-carboxamide hydrochloride

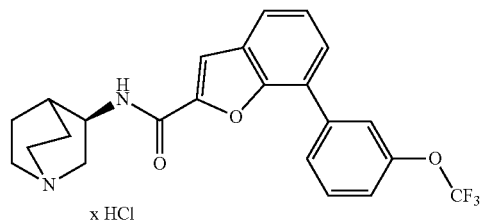 [SMILES: O=C(N[C@H]1CN2CCC1CC2)c1cc2cccc(-c3cccc(OC(F)(F)F)c3)c2o1]

200 mg (0.52 mmol) of N-[(3R)-1-azabicyclo[2.2.2]oct-3-yl]-7-bromo-1-benzofuran-2-carboxamide hydrochloride (Example 30A) and 106.8 mg (0.52 mmol) of 3-(trifluoromethoxy)phenylboronic acid are introduced into 2.0 ml of DMF. Addition of 0.78 ml of 2 M sodium carbonate solution and 21.2 mg (0.03 mmol) of PdCl$_2$(dppf) is followed by heating at 70° C. for 17 h. After cooling, the reaction mixture is filtered through kieselguhr and purified by preparative HPLC. The product fractions are combined and concentrated and, after addition of a 5:1 mixture of methanol and 1N hydrochloric acid, again concentrated. Drying under high vacuum results in 48.8 mg (20% of theory) of the title compound.

$^1$H-NMR (200 MHz, DMSO-d$_6$): δ=10.18 (br. s, 1H), 9.00 (d, 1H), 7.95 (m, 2H), 7.89 (s, 1H), 7.86 (m, 1H), 7.77 (m, 1H), 7.68 (m, 1H), 7.47 (m, 2H), 4.34 (m, 1H), 3.65 (m, 1H), 3.35 (m, 2H), 3.23 (m, 3H), 2.22 (m, 1H), 2.12 (m, 1H), 1.92 (m, 2H), 1.76 (m, 1H).

HPLC (method 1): R$_t$=4.5 min.
MS (ESIpos): m/z=431 (M+H)$^+$ (free base).

EXAMPLE 88

N-[(3S)-1-Azabicyclo[2.2.2]oct-3-yl]-7-(2-methoxyphenyl)-1-benzothiophene-2-carboxamide hydrochloride

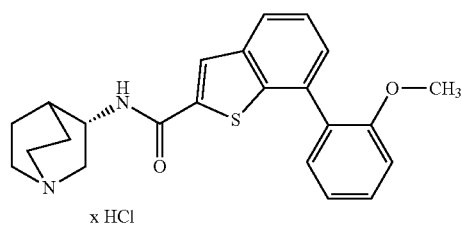 [SMILES: COc1ccccc1-c1cccc2cc(C(=O)N[C@@H]3CN4CCC3CC4)sc12]

0.67 ml of 2 M sodium carbonate solution and 18.3 mg (0.02 mmol) of PdCl$_2$(dppf) are added to a mixture of 200 mg (0.45 mmol) of N-[(3S)-1-azabicyclo[2.2.2]oct-3-yl]-7-bromo-1-benzothiophene-2-carboxamide hydrochloride (Example 22A) and 68.1 mg (0.45 mmol) of 2-methoxyphenylboronic acid in 2 ml of DMF. The reaction mixture is heated at 70° C. for 17 h and, after cooling, filtered through kieselguhr and purified by preparative HPLC. The product fractions are concentrated, taken up in a 5:1 mixture of methanol and 1N hydrochloric acid and again concentrated. Drying under high vacuum results in 112 mg (58% of theory) of the title compound.

$^1$H-NMR (400 MHz, DMSO-d$_6$): δ=10.38 (br. s, 1H), 9.07 (d, 1H), 8.38 (s, 1H), 7.95 (m, 1H), 7.50 (dd, 1H), 7.47 (m, 1H), 7.37 (m, 2H), 7.20 (d, 1H), 7.09 (dd, 1H), 4.31 (m, 1H), 3.73 (s, 3H), 3.62 (m; 1H), 3.35 (m, 2H), 3.19 (m, 3H), 2.19 (m, 1H), 2.13 (m, 1H), 1.90 (m, 2H), 1.73 (m, 1H).

The other analytical data agree with those of the enantiomeric compound (Example 18).

EXAMPLE 89

N-[(3R)-1-Azabicyclo[2.2.2]oct-3-yl]-7-[3-(hydroxymethyl)phenyl]-1-benzofuran-2-carboxamide hydrochloride

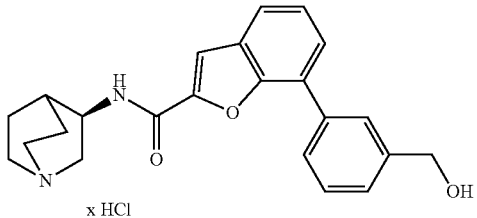 [SMILES: O=C(N[C@H]1CN2CCC1CC2)c1cc2cccc(-c3cccc(CO)c3)c2o1]

150 mg (0.43 mmol) of N-[(3R)-1-azabicyclo[2.2.2]oct-3-yl]-7-bromo-1-benzofuran-2-carboxamide hydrochloride (Example 30A) and 65.3 mg (0.43 mmol) of 3-(hydroxymethyl)phenylboronic acid are introduced into 1.5 ml of DMF. Addition of 0.64 ml of 2 M sodium carbonate solution and 17.5 mg (0.02 mmol) of PdCl$_2$(dppf) is followed by heating at 60° C. for 18 h. A further 17.5 mg (0.02 mmol) of PdCl$_2$(dppf) are added and the mixture is stirred at 90° C. for a further 18 h. After cooling, the reaction mixture is filtered through kieselguhr. A first purification by preparative HPLC is followed by column chromatography on silica gel (mobile phase: dichloromethane/methanol/ammonia 90:9:1). The product fractions are combined and concentrated and, after addition of a 5:1 mixture of methanol and 4N hydrogen chloride in dioxane, again concentrated. Drying under high vacuum results in 45 mg (24% of theory) of the title compound.

$^1$H-NMR (400 MHz, methanol-d$_4$): δ=7.98 (m, 1H), 7.74 (m, 2H), 7.65 (m, 2H), 7.52 (dd, 1H), 7.42 (m, 2H), 4.72 (s, 2H), 4.51 (m, 1H), 3.87-3.26 (m, 6H), 2.39 (m, 1H), 2.23 (m, 1H), 2.10 (m, 2H), 1.95 (m, 1H).

HPLC (method 1): R$_t$=3.9 min.

MS (ESIpos): m/z=377 (M+H)$^+$ (free base).

EXAMPLE 90

N-[(3R)-1-Azabicyclo[2.2.2]oct-3-yl]-7-[4-(3-oxo-4-morpholinyl)phenyl]-1-benzofuran-2-carboxamide hydrochloride

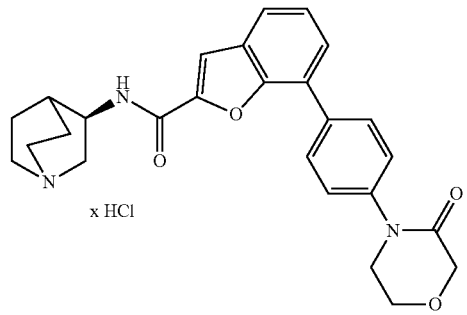 [SMILES: O=C(N[C@H]1CN2CCC1CC2)c1cc2cccc(-c3ccc(N4CCOCC4=O)cc3)c2o1]

205.4 mg (0.70 mmol) of 4-(4-bromophenyl)-3-morpholinone (Example 16A), 204.4 mg (0.81 mmol) of bis(pinacolato)diboron, 171.2 mg (1.74 mmol) of potassium acetate, 19.6 mg (0.03 mmol) of PdCl$_2$(dppf), 207 mg (0.54 mmol) of N-[(3R)-1-azabicyclo[2.2.2]oct-3-yl]-7-bromo-1-benzofuran-2-carboxamide hydrochloride (Example 30A), 1.34 ml of 2 M sodium carbonate solution and a further 19.6 mg (0.03 mmol) of PdCl$_2$(dppf) in 2 ml of DMF are reacted by general method D. Drying under high vacuum results in 233 mg (85% of theory) of the title compound.

$^1$H-NMR (200 MHz, DMSO-d$_6$): δ=10.32 (br. s, 1H), 9.07 (d, 1H), 7.95 (m, 3H), 7.80 (dd, 1H), 7.70 (dd, 1H), 7.59 (m, 2H), 7.44 (dd, 1H), 4.33 (m, 1H), 4.26 (s, 2H), 4.02 (m, 2H), 3.83 (m, 2H), 3.64 (m, 1H), 3.37 (m, 2H), 3.21 (m, 3H), 2.23 (m, 1H), 2.11 (m, 1H), 1.91 (m, 2H), 1.74 (m, 1H).

HPLC (method 1): R$_t$=4.5 min.

MS (ESIpos): m/z=446 (M+H)$^+$ (free base).

EXAMPLE 91

N-[(3R)-1-Azabicyclo[2.2.2]oct-3-yl]-7-[2-(4-morpholinyl)phenyl]-1-benzofuran-2-carboxamide hydrochloride

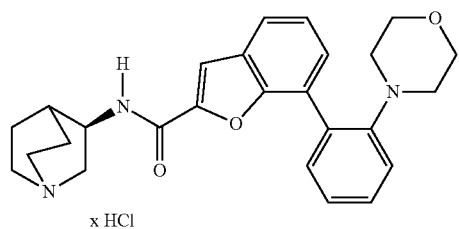 [SMILES: O=C(N[C@H]1CN2CCC1CC2)c1cc2cccc(-c3ccccc3N3CCOCC3)c2o1]

225 mg (0.93 mmol) of 2-(4-morpholinyl)phenyl trifluoromethanesulphonate (Example 32A), 272 mg (1.07 mmol) of bis(pinacolato)diboron, 228 mg (2.33 mmol) of potassium acetate, 26 mg (0.04 mmol) of PdCl$_2$(dppf), 250 mg (0.72 mmol) of N-[(3R)-1-azabicyclo[2.2.2]oct-3-yl]-7-bromo-1-benzofuran-2-carboxamide (Example 30A), 1.8 ml of 2 M sodium carbonate solution and a further 26 mg (0.04 mmol)

of PdCl$_2$(dppf) in 2 ml of DMF are reacted by general method D. Drying under high vacuum results in 82 mg (24% of theory) of the title compound.

$^1$H-NMR (400 MHz, DMSO-d$_6$): δ=9.76 (s, 1H), 8.82 (d, 1H), 7.79 (s, 1H), 7.77 (d, 1H), 7.55 (d, 1H), 7.46-7.37 (m, 3H), 7.23-7.14 (m, 2H), 4.33 (m, 1H), 3.83-3.04 (m, 6H), 3.55 (s, 4H), 2.68 (s, 4H), 2.16 (m, 1H), 2.04 (m, 1H), 1.95-1.84 (m, 2H), 1.79-1.67 (m, 1H).

HPLC (method 1): R$_t$=4.1 min.

MS (ESIpos): m/z=432 (M+H)$^+$ (free base).

EXAMPLE 92

N-[(3R)-1-Azabicyclo[2.2.2]oct-3-yl]-7-[4-(4-morpholinyl)phenyl]-1-benzofuran-2-carboxamide hydrochloride

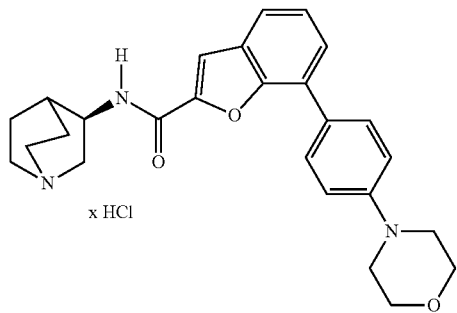 [SMILES: O=C(N[C@H]1CN2CCC1CC2)c1cc2cccc(-c3ccc(N4CCOCC4)cc3)c2o1]

x HCl 444 mg (2.15 mmol) of 4-(4-morpholinyl)phenylboronic acid and 4.3 ml of 1N sodium hydroxide solution are added to a mixture of 0.500 mg (0.143 mmol) of N-[(3R)-1-azabicyclo [2.2.2]oct-3-yl]-7-bromo-1-benzofuran-2-carboxamide hydrochloride (Example 30A) and 105 mg (0.14 mmol) of PdCl$_2$(dppf) in 5 ml of DMF. The reaction mixture is heated at 100° C. overnight. The solvent is removed under reduced pressure, and the crude product is taken up in methanol and filtered through kieselguhr. Purification takes place by preparative HPLC. The product fractions are concentrated and dissolved in methanol, and an excess of 1N hydrochloric acid is added. The solvent is removed under reduced pressure. Drying under high vacuum results in 393 mg (59% of theory) of the title compound.

$^1$H-NMR (200 MHz, DMSO-d$_6$): δ=10.45 (s, 1H), 9.10 (d, 1H), 7.91 (s, 1H), 7.87 (d, 1H), 7.75-7.55 (m, 2H), 7.40 (t, 1H), 7.18 (d, 2H), 4.40 (m, 1H), 3.80 (m, 4H), 3.75-3.00 (m, 6H), 3.20 (m, 4H), 2.30-2.02 (m, 2H), 2.00-1.62 (m, 3H).

HPLC (method 1): R$_t$=3.79 min.

MS (ESIpos): m/z=432 (M+H)$^+$ (free base).

EXAMPLE 93

N-[(3R)-1-Azabicyclo[2.2.2]oct-3-yl]-5-[4-(4-morpholinyl)phenyl]-1-benzofuran-2-carboxamide hydrochloride

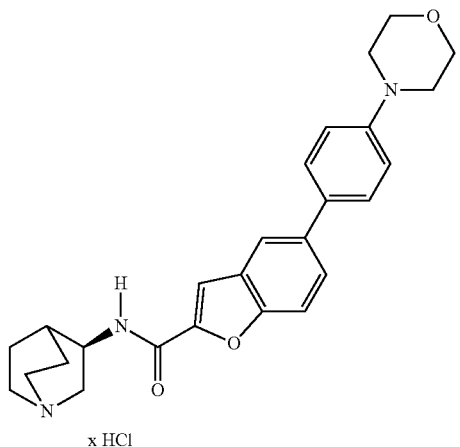 [SMILES: O=C(N[C@H]1CN2CCC1CC2)c1cc2cc(-c3ccc(N4CCOCC4)cc3)ccc2o1]

x HCl 177 mg (0.86 mmol) of 4-(4-morpholinyl)phenylboronic acid and 2.15 ml of 1N sodium hydroxide solution are added to a mixture of 250 mg (0.72 mmol) of N-[(3R)-1-azabicyclo [2.2.2]oct-3-yl]-5-bromo-1-benzofuran-2-carboxamide (Example 3A) and 52 mg (0.07 mmol) of PdCl$_2$(dppf) in 3 ml of DMF. The reaction mixture is heated at 90° C. overnight. The solvent is removed under reduced pressure, and the crude product is taken up in methanol and filtered through kieselguhr. Purification takes place by preparative HPLC. The product fractions are concentrated and dissolved in acetonitrile/water, and an excess of 1N hydrochloric acid is added. The solvent is removed under reduced pressure. Drying under high vacuum results in 23 mg (7% of theory) of the title compound.

$^1$H-NMR (200 MHz, DMSO-d$_6$): δ=10.40 (s, 1H), 9.15 (d, 1H), 7.98 (s, 1H), 7.76-7.68 (m, 2H), 7.67-7.58 (m, 2H), 7.20-7.10 (d, 2H), 4.45 (m, 1H), 3.80 (m, 4H), 3.75-3.30 (m, 0.6H), 3.20 (m, 4H), 2.30-2.02 (m, 2H), 2.00-1.62 (m, 3H).

HPLC (method 1): R$_t$=3.52 min.

MS (ESIpos): m/z=432 (M+H)+ (free base).

EXAMPLE 94

N-[(3R)-1-Azabicyclo[2.2.2]oct-3-yl]-5-[4-(hydroxymethyl)phenyl]-1-benzofuran-2-carboxamide

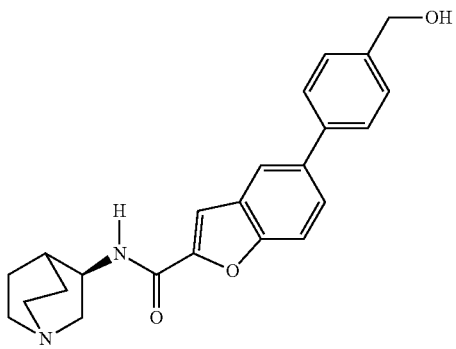 [SMILES: O=C(N[C@H]1CN2CCC1CC2)c1cc2cc(-c3ccc(CO)cc3)ccc2o1]

110 mg (0.73 mmol) of 4-(hydroxymethyl)phenylboronic acid and 1.46 ml of 1N sodium hydroxide solution are added to a mixture of 170 mg (0.49 mmol) of N-[(3R)-1-azabicyclo[2.2.2]oct-3-yl]-5-bromo-1-benzofuran-2-carboxamide (Example 3A) and 35 mg (0.05 mmol) of PdCl$_2$(dppf) in 2 ml of DMF. The reaction mixture is heated at 85° C. overnight. The solvent is removed under reduced pressure. Addition of a mixture of 1N sodium hydroxide solution and ethyl acetate to the residue is followed by extraction of the aqueous phase once more with ethyl acetate. The combined organic phases are washed twice with each of 1N sodium hydroxide solution and saturated sodium chloride solution, dried over magnesium sulphate and concentrated in a rotary evaporator under reduced pressure. The crude product is taken up in methanol and shaken together with acidic ion exchanger (Dowex® WX2-200) for about 20 min. The loaded ion exchanger is washed three times with 30 ml of methanol each time, then with DMF, again with methanol, with dichloromethane, again with methanol, with water and finally with methanol again. The product is eluted with methanol/triethylamine 95:5. The solvent is removed in a rotary evaporator under reduced pressure. 148 mg (80% of theory) of the title compound are isolated.

$^1$H-NMR (200 MHz, CDCl$_3$): δ=7.85 (s, 1H), 7.70-7.35 (m, 7H), 6.77 (d, 1H), 4.62 (s, 2H), 4.28-4.12 (m, 1H), 3.56-3.38 (m, 1H), 3.04-2.78 (m, 4H), 2.75-2.59 (m, 1H), 2.16-2.02 (m, 1H), 1.93-1.66 (m, 3H), 1.66-1.50 (m, 1H).

HPLC (method 1): R$_t$=3.65 min.

MS (ESIpos): m/z=377 (M+H)+.

EXAMPLE 95

N-[(3R)-1-Azabicyclo[2.2.2]oct-3-yl]-5-[2-(hydroxymethyl)phenyl]-1-benzofuran-2-carboxamide

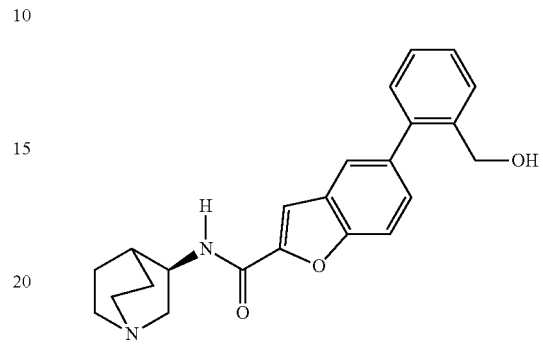

110 mg (0.73 mmol) of 2-(hydroxymethyl)phenylboronic acid and 1.46 ml of 1N sodium hydroxide solution are added to a mixture of 170 mg (0.49 mmol) of N-[(3R)-1-azabicyclo[2.2.2]oct-3-yl]-5-bromo-1-benzofuran-2-carboxamide (Example 3A) and 35 mg (0.05 mmol) of PdCl$_2$(dppf) in 2 ml of DMF. The reaction mixture is heated at 85° C. overnight. The solvent is removed under reduced pressure. Addition of a mixture of 1N sodium hydroxide solution and ethyl acetate to the residue is followed by extraction of the aqueous phase once more with ethyl acetate. The combined organic phases are washed twice with each of 1N sodium hydroxide solution and saturated sodium chloride solution, dried over magnesium sulphate and concentrated in a rotary evaporator under reduced pressure. The crude product is taken up in methanol and shaken together with acidic ion exchanger (Dowex® WX2-200) for about 20 min. The loaded ion exchanger is washed three times with 30 ml of methanol each time, then with DMF, again with methanol, with dichloromethane, again with methanol, with water and finally with methanol again. The product is eluted with methanol/triethylamine 95:5. The solvent is removed in a rotary evaporator under reduced pressure. 140 mg (76% of theory) of the title compound are isolated.

$^1$H-NMR (300 MHz, CDCl$_3$): δ=7.70-7.25 (m, 8H), 6.75 (d, 1H), 4.62 (s, 2H), 4.28-4.12 (m, 1H), 3.56-3.38 (m, 1H), 3.04-2.78 (m, 4H), 2.75-2.59 (m, 1H), 2.16-2.02 (m, 1H), 1.93-1.66 (m, 3H), 1.66-1.50 (m, 1H).

HPLC (method 1): R$_t$=3.76 min.

MS (ESIpos): m/z=377 (M+H)+.

EXAMPLE 96

N-[(3R)-1-Azabicyclo[2.2.2]oct-3-yl]-5-[4-(dimethylamino)phenyl]-1-benzofuran-2-carboxamide

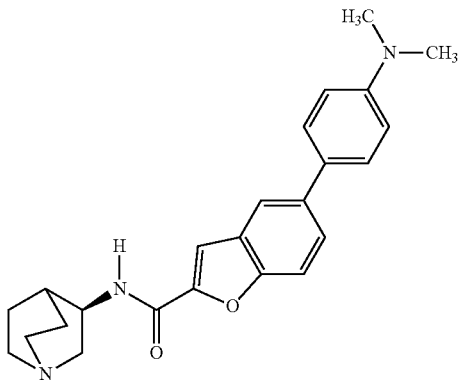 [SMILES: CN(C)c1ccc(-c2ccc3oc(C(=O)N[C@H]4CN5CCC4CC5)cc3c2)cc1]

120 mg (0.73 mmol) of 4-(dimethylamino)phenylboronic acid and 1.46 ml of 1N sodium hydroxide solution are added to a mixture of 170 mg (0.49 mmol) of N-[(3R)-1-azabicyclo[2.2.2]oct-3-yl]-5-bromo-1-benzofuran-2-carboxamide (Example 3A) and 35 mg (0.05 mmol) of PdCl$_2$(dppf) in 2 ml of DMF. The reaction mixture is heated at 85° C. overnight. The solvent is removed under reduced pressure. Addition of a mixture of 1N sodium hydroxide solution and ethyl acetate to the residue is followed by extraction of the aqueous phase once more with ethyl acetate. The combined organic phases are washed twice with each of 1N sodium hydroxide solution and saturated sodium chloride solution, dried over magnesium sulphate and concentrated in a rotary evaporator under reduced pressure. The crude product is taken up in methanol and shaken together with acidic ion exchanger (Dowex® WX2-200) for about 20 min. The loaded ion exchanger is washed three times with 30 ml of methanol each time, then with DMF, again with methanol, with dichloromethane, again with methanol, with water and finally with methanol again. The product is eluted with methanol/triethylamine 95:5. The solvent is removed in a rotary evaporator under reduced pressure. 138 mg (73% of theory) of the title compound are isolated.

$^1$H-NMR (200 MHz, CDCl$_3$): δ=7.78 (d, 1H) 7.70-7.39 (m, 4H), 6.88-6.75 (m, 3H), 4.28-4.12 (m, 1H), 3.56-3.38 (m, 1H), 3.04-2.78 (m, 4H), 3.00 (s, 6H), 2.75-2.59 (m, 1H), 2.16-2.02 (m, 1H), 1.93-1.66 (m, 3H), 1.66-1.50 (m, 1H).

HPLC (method 1): R$_t$=3.36 min.

MS (ESIpos): m/z=390 (M+H)+.

EXAMPLE 97

N-[(3R)-1-Azabicyclo[2.2.2]oct-3-yl]-5-[4-(methoxy)phenyl]-1-benzofuran-2-carboxamide hydrochloride

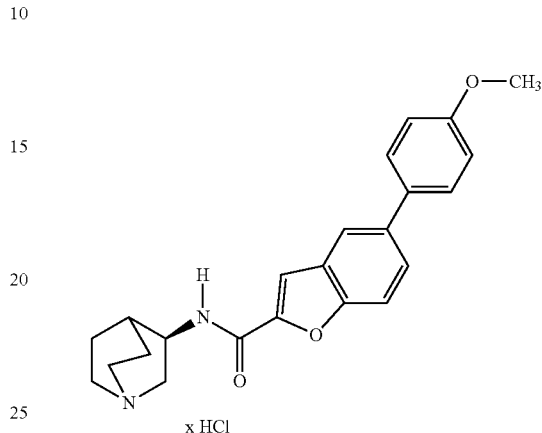

130 mg (0.86 mmol) of 4-(methoxy)phenylboronic acid and 2.15 ml of 1N sodium hydroxide solution are added to a mixture of 250 mg (0.72 mmol) of N-[(3R)-1-azabicyclo[2.2.2]oct-3-yl]-5-bromo-1-benzofuran-2-carboxamide (Example 3A) and 52 mg (0.07 mmol) of PdCl$_2$(dppf) in 3 ml of DMF. The reaction mixture is heated at 90° C. overnight. The solvent is removed under reduced pressure, and the crude product is taken up in methanol and filtered through kieselguhr. Purification takes place by preparative HPLC. The product fractions are mixed with an excess of 1N hydrochloric acid. The solvent is removed under reduced pressure. Drying under high vacuum results in 127 mg (39% of theory) of the title compound.

$^1$H-NMR (200 MHz, DMSO-d$_6$): δ=9.90 (s, 1H), 9.10 (d, 1H), 7.95 (m, 2H), 7.75-7.60 (m, 4H), 7.10-7.02 (m, 2H), 4.40 (m, 1H), 3.85 (m, 3H), 3.75-3.00 (m, 6H), 3.20 (m, 4H), 2.30-2.02 (m, 2H), 2.00-1.62 (m, 3H).

HPLC (method 1): R$_t$=4.15 min,

MS (ESIpos): m/z=377 (M+H)+ (free base).

EXAMPLE 98

N-[(3R)-1-Azabicyclo[2.2.2]oct-3-yl]-5-[3-(methoxy)phenyl]-1-benzofuran-2-carboxamide hydrochloride

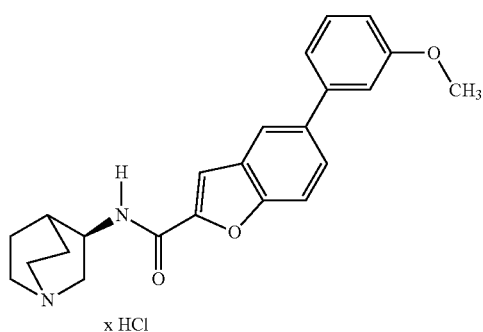 [SMILES: COc1cccc(-c2ccc3oc(C(=O)N[C@H]4CN5CCC4CC5)cc3c2)c1]

130 mg (0.86 mmol) of 3-(methoxy)phenylboronic acid and 2.15 ml of 1N sodium hydroxide solution are added to a mixture of 250 mg (0.72 mmol) of N-[(3R)-1-azabicyclo[2.2.2]oct-3-yl]-5-bromo-1-benzofuran-2-carboxamide (Example 3A) and 52 mg (0.07 mmol) of PdCl$_2$(dppf) in 3 ml of DMF. The reaction mixture is heated at 90° C. overnight. The solvent is removed under reduced pressure, and the crude product is taken up in methanol and filtered through kieselguhr. Purification takes place by preparative HPLC. The product fractions are mixed with an excess of 1N hydrochloric acid. The solvent is removed under reduced pressure. Drying under high vacuum results in 208 mg (63% of theory) of the title compound.

$^1$H-NMR (300 MHz, DMSO-d$_6$): δ=10.0 (s, 1H), 9.10 (d, 1H), 8.05 (s, 1H), 7.80-7.65 (m, 3H), 7.42-7.18 (m, 3H), 6.93 (m, 1H), 4.35 (m, 1H), 3.85 (s, 3H), 3.75-3.00 (m, 6H), 3.20 (m, 4H), 2.30-2.02 (m, 2H), 2.00-1.62 (m, 3H).

HPLC (method 1): R$_t$=4.19 min.
MS (ESIpos): m/z=377 (M+H)+ (free base).

EXAMPLE 99

N-[(3R)-1-Azabicyclo[2.2.2]oct-3-yl]-7-[4-(methoxy)phenyl]-1-benzofuran-2-carboxamide hydrochloride

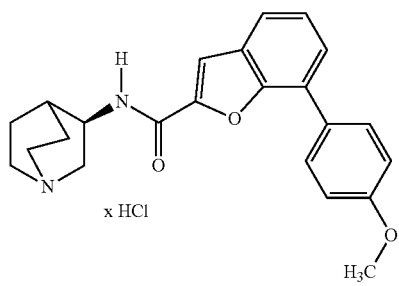 [SMILES: COc1ccc(-c2cccc3cc(C(=O)N[C@H]4CN5CCC4CC5)oc23)cc1]

130 mg (0.86 mmol) of 4-(methoxy)phenylboronic acid and 2.58 ml of 1N sodium hydroxide solution are added to a mixture of 300 mg (0.86 mmol) of N-[(3R)-1-azabicyclo[2.2.2]oct-3-yl]-7-bromo-1-benzofuran-2-carboxamide (Example 30A) and 63 mg (0.09 mmol) of PdCl$_2$(dppf) in 4 ml of DMF. The reaction mixture is heated at 95° C. overnight. The solvent is removed under reduced pressure, and the crude product is taken up in methanol and filtered through kieselguhr. Purification takes place by preparative HPLC. The product fractions are mixed with an excess of 1N hydrochloric acid. The solvent is removed under reduced pressure. Drying under high vacuum results in 165 mg (47% of theory) of the title compound.

$^1$H-NMR (300 MHz, DMSO-d$_6$): δ=10.4 (s, 1H), 9.00 (d, 1H), 8.05 (s, 1H), 7.90-7.82 (m, 3H), 7.75 (d, 1H), 7.62 (d, 1H), 7.40 (t, 1H), 7.15-7.05 (m, 2H), 4.35 (m, 1H), 3.85 (s, 3H), 3.65 (m, 1H), 3.48-3.30 (m, 2H), 3.25-3.10 (m, 3H), 2.25 (m, 1H), 2.18-2.05 (m, 1H), 1.98-1.88 (m, 2H), 1.80-1.63 (m, 1H).

HPLC (method 1): R$_t$=4.18 min.
MS (ESIpos): m/z=377 (M+H)+ (free base).

EXAMPLE 100

N-[(3S)-1-Azabicyclo[2.2.2]oct-3-yl]-7-(2-methoxyphenyl)-1-benzofuran-2-carboxamide hydrochloride

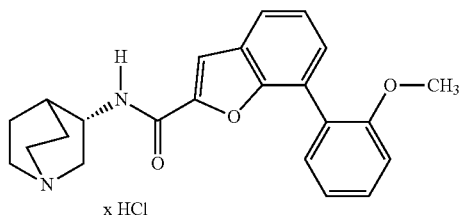 [SMILES: COc1ccccc1-c1cccc2cc(C(=O)N[C@@H]3CN4CCC3CC4)oc12]

3.4 g (8.95 mmol) of HATU and 2.34 ml (13.42 mmol) of N,N-diisopropylethylamine are added to a mixture of 890 mg (4.47 mmol) of S-3-aminoquinuclidine dihydrochloride and 1000 mg (3.73 mmol) of 7-(2-methoxyphenyl)-1-benzofuran-2-carboxylic acid (Example 21A) in 10 ml of DMF at 0° C. After stirring at room temperature for 18 h, the reaction solution is purified by preparative HPLC. The product fractions are concentrated and, after addition of 5 ml of 1N hydrochloric acid, again concentrated. Drying under high vacuum results in 209 mg (13.6% of theory) of the title compound.

EXAMPLE 101

N-[(3R)-1-Azabicyclo[2.2.2]oct-3-yl]-7-[3-(methoxy)phenyl]-1-benzofuran-2-carboxamide hydrochloride

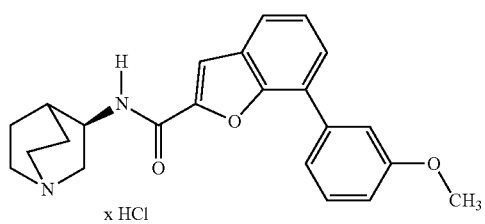 [SMILES: COc1cccc(-c2cccc3cc(C(=O)N[C@H]4CN5CCC4CC5)oc23)c1]

98 mg (0.64 mmol) of 3-(methoxy)phenylboronic acid and 1.29 ml of 1N sodium hydroxide solution are added to a mixture of 150 mg (0.43 mmol) of N-[(3R)-1-azabicyclo[2.2.2]oct-3-yl]-7-bromo-1-benzofuran-2-carboxamide (Example 30A) and 31 mg (0.04 mmol) of PdCl$_2$(dppf) in 2 ml of DMF. The reaction mixture is heated at 90° C. overnight. The solvent is removed under reduced pressure, and the crude product is taken up in methanol and filtered through kieselguhr. Purification takes place by preparative HPLC. The product is dissolved in methanol and mixed with an excess of 1N hydrochloric acid. The solvent is removed under reduced pressure, and the residue is recrystallized from a little isopropanol. Drying under high vacuum results in 159 mg (85% of theory) of the title compound.

$^1$H-NMR (400 MHz, DMSO-d$_6$): δ=10.05 (s, 1H), 8.95 (d, 1H), 7.85 (s, 1H), 7.80 (d, 1H), 7.70 (d, 1H), 7.50-7.40 (m, 4H), 7.00 (m, 1H), 4.35 (m, 1H), 3.85 (s, 3H), 3.65 (m, 1H), 3.48-3.30 (m, 2H), 3.25-3.15 (m, 3H), 2.25 (m, 1H), 2.18-2.05 (m, 1H), 1.98-1.88 (m, 2H), 1.80-1.63 (m, 1H).

HPLC (method 1): R$_t$=4.21 min.
MS (ESIpos): m/z=377 (M+H)$^+$ (free base).

EXAMPLE 102

N-[(3R)-1-Azabicyclo[2.2.2]oct-3-yl]-7-[2-(methoxy)phenyl]-1-benzofuran-2-carboxamide hydrochloride

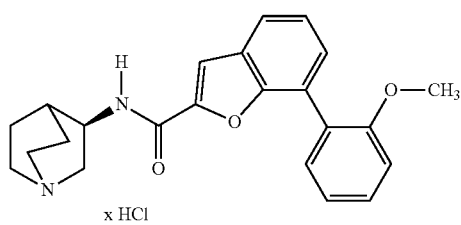 [SMILES: COc1ccccc1-c1cccc2cc(C(=O)N[C@H]3CN4CCC3CC4)oc12]

Method a):

98 mg (0.64 mmol) of 2-(methoxy)phenylboronic acid and 1.29 ml of 1N sodium hydroxide solution are added to a mixture of 150 mg (0.43 mmol) of N-[(3R)-1-azabicyclo[2.2.2]oct-3-yl]-7-bromo-1-benzofuran-2-carboxamide (Example 30A) and 31 mg (0.04 mmol) of PdCl$_2$(dppf) in 2 ml of DMF. The reaction mixture is heated at 85° C. overnight. The solvent is removed under reduced pressure, and the crude product is taken up in methanol and filtered through kieselguhr. Further purification takes place by preparative HPLC. The product is dissolved in methanol and mixed with an excess of 1N hydrochloric acid. The solvent is removed under reduced pressure, and the residue is recrystallized from a little isopropanol. Drying under high vacuum results in 100 mg (62% of theory) of the title compound.

$^1$H-NMR (400 MHz, DMSO-d$_6$): δ=10.08 (s, 1H), 8.91 (d, 1H), 7.87 (s, 1H), 7.84-7.74 (m, 2H), 7.53-7.33 (m, 3H), 7.25-7.00 (m, 2H), 4.35 (m, 1H), 3.75 (s, 3H), 3.65 (m, 1H), 3.48-3.30 (m, 2H), 3.25-3.15 (m, 3H), 2.25 (m, 1H), 2.18-2.05 (m, 1H), 1.98-1.88 (m, 2H), 1.80-1.63 (m, 1H).

HPLC (method 1): R$_t$=4.16 min.
MS (ESIpos): m/z=377 (M+H)$^+$ (free base).

Method b):

2.51 g (13.1 mmol) of EDC, 1.77 g (13.1 mmol) of HOBt and 5.47 ml (39.2 mmol) of triethylamine are added to a solution of 2.92 g (10.9 mmol) of 7-(2-methoxyphenyl)-1-benzofuran-2-carboxylic acid (Example 21A) and 2.17 g (10.9 mmol) of (R)-3-aminoquinuclidine dihydrochloride in 35 ml of DMF at 0° C. After stirring at room temperature for 18 hours, a further 434 mg (2.2 mmol) of (R)-3-aminoquinuclidine dihydrochloride and 418 mg (2.2 mmol) of EDC are added. After 2 h at 55° C., the reaction solution is concentrated and the residue is partitioned between 200 ml each of ethyl acetate and 2N sodium hydroxide solution. The organic phase is washed. 15 times with 100 ml of 2N sodium hydroxide solution each time.

The combined aqueous phases are back-extracted with 250 ml of ethyl acetate. The combined organic phases are dried over sodium sulphate and concentrated and, after addition of a 5:1 mixture of methanol and 1N hydrochloric acid to the residue, again concentrated and dried under high vacuum. Recrystallization of the residue from 10 ml of a 10:1 mixture of isopropanol and ethanol results in 2.73 g (60.5% of theory) of the title compound.

EXAMPLE 103

N-[(3R)-1-Azabicyclo[2.2.2]oct-3-yl]-7-[4-(methoxy)-3-pyridinyl]-1-benzofuran-2-carboxamide hydrochloride

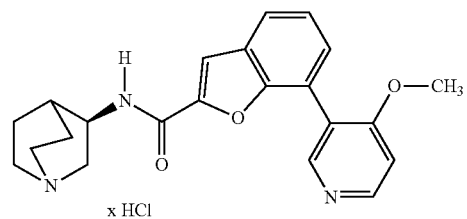 [SMILES: COc1ccncc1-c1cccc2cc(C(=O)N[C@H]3CN4CCC3CC4)oc12]

98 mg (0.64 mmol) of 4-methoxy-3-pyridinylboronic acid and 0.86 ml of 1N sodium hydroxide solution are added to a mixture of 100 mg (0.29 mmol) of N-[(3R)-1-azabicyclo[2.2.2]oct-3-yl]-7-bromo-1-benzofuran-2-carboxamide (Example 30A) and 21 mg (0.03 mmol) of PdCl$_2$(dppf) in 2 ml of DMF. The reaction mixture is heated at 85° C. overnight. The solvent is removed under reduced pressure, and the crude product is taken up in methanol and filtered through kieselguhr. Purification takes place by preparative HPLC. The product fractions are mixed with an excess of 1N hydrochloric acid. The solvent is removed under reduced pressure. Drying under high vacuum results in 58 mg (49% of theory) of the title compound.

$^1$H-NMR (400 MHz, DMSO-d$_6$): δ=10.55 (s, 1H), 9.20 (d, 1H), 9.05 (s, 1H), 8.95 (d, 1H), 7.96-7.89 (m, 2H), 7.82 (d, 1H), 7.65 (d, 1H), 7.50 (t, 1H), 4.35 (m, 1H), 4.10 (s, 3H), 3.65-3.15 (m, 6H), 2.20 (m, 1H), 2.18-2.05 (m, 1H), 1.98-1.88 (m, 2H), 1.80-1.63 (m, 1H).

HPLC (method 1): R$_t$=3.35 min.
MS (ESIpos): m/z=378 (M+H)$^+$ (free base).

EXAMPLE 104

N-[(3R)-1-Azabicyclo[2.2.2]oct-3-yl]-7-[4-(4-morpholinylcarbonyl)phenyl]-1-benzofuran-2-carboxamide hydrochloride

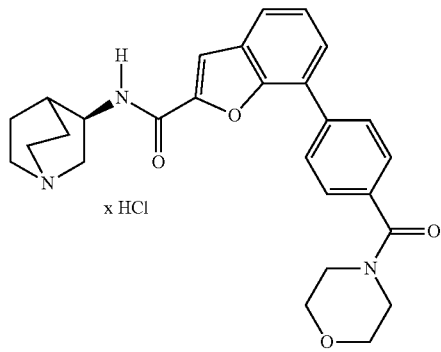 [SMILES: O=C(N[C@H]1CN2CCC1CC2)c1cc2cccc(-c3ccc(C(=O)N4CCOCC4)cc3)c2o1]

631 mg (1.43 mmol) of 4-(4-morpholinylcarbonyl)phenyl trifluoromethane-sulphonate (Example 18A), 545 mg (2.15 mmol) of bis(pinacolato)diboron, 456 mg (4.65 mmol) of potassium acetate, 52 mg (0.07 mmol) of PdCl$_2$(dppf), 500 mg (1.43 mmol) of N-[(3R)-1-azabicyclo[2.2.2]oct-3-yl]-7-bromo-1-benzofuran-2-carboxamide (Example 30A), 3.6 ml of 2 M sodium carbonate solution and a further 52 mg (0.07 mmol) of PdCl$_2$(dppf) in 8 ml of DMF are reacted by general method D. Drying under high vacuum results in 455 mg (61% of theory) of the title compound.

$^1$H-NMR (400 MHz, DMSO-d$_6$): δ=10.45 (s, 1H), 9.10 (d, 1H), 8.02-7.92 (m, 3H), 7.78 (d, 1H), 7.71 (d, 1H), 7.60 (d, 2H), 7.45 (t, 1H), 4.35 (m, 1H), 3.75-3.35 (m, 11H), 3.25-3.15 (m, 3H), 2.25 (m, 1H), 2.18-2.05 (m, 1H), 1.98-1.88 (m, 2H), 1.80-1.63 (m, 1H).

HPLC (method 1): R$_t$=3.79 min.
MS (ESIpos): m/z=460 (M+H)$^+$ (free base).

EXAMPLE 105

N-[(3R)-1-Azabicyclo[2.2.2]oct-3-yl]-7-[3-(1-piperidinyl)phenyl]-1-benzofuran-2-carboxamide dihydrochloride

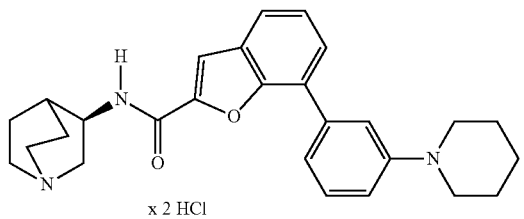 [SMILES: O=C(N[C@H]1CN2CCC1CC2)c1cc2cccc(-c3cccc(N4CCCCC4)c3)c2o1]

311 mg (1.29 mmol) of 3-(1-piperidinyl)phenylboronic acid and 3.44 ml of 1N sodium hydroxide solution are added to a mixture of 300 mg (0.86 mmol) of N-[(3R)-1-azabicyclo[2.2.2]oct-3-yl]-7-bromo-1-benzofuran-2-carboxamide (Example 30A) and 63 mg (0.09 mmol) of PdCl$_2$(dppf) in 4 ml of DMF. The reaction mixture is heated at 95° C. overnight. The solvent is removed under reduced pressure, and the crude product is taken up in methanol and filtered through kieselguhr. Purification takes place by preparative HPLC. The product is dissolved in methanol, and an excess of 1N hydrochloric acid is added. The solvent is removed under reduced pressure. Drying under high vacuum results in 164 mg (41% of theory) of the title compound.

$^1$H-NMR (200 MHz, DMSO-d$_6$): δ=10.55 (s, 1H), 9.10 (d, 1H), 8.75 (s, 1H), 7.95-7.63 (m, 7H), 7.45 (t, 1H), 4.35 (m, 1H), 4.13-3.40 (m, 7H), 3.35-3.10 (m, 3H), 2.15-1.50 (m, 11H).

HPLC (method 1): R$_t$=3.72 min.
MS (ESIpos): m/z=430 (M+H)$^+$ (free base).

EXAMPLE 106

N-[(3R)-1-Azabicyclo[2.2.2]oct-3-yl]-7-(3-pyridinyl)-1-benzofuran-2-carboxamide dihydrochloride

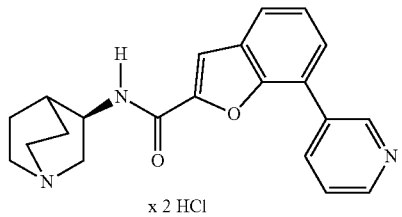 [SMILES: O=C(N[C@H]1CN2CCC1CC2)c1cc2cccc(-c3cccnc3)c2o1]

70 mg (0.57 mmol) of 3-pyridineboronic acid and 0.86 ml of 1N sodium hydroxide solution are added to a mixture of 100 mg (0.86 mmol) of N-[(3R)-1-azabicyclo[2.2.2]oct-3-yl]-7-bromo-1-benzofuran-2-carboxamide (Example 30A) and 63 mg (0.09 mmol) of PdCl$_2$(dppf) in 4 ml of DMF. The reaction mixture is heated at 95° C. overnight. The solvent is removed under reduced pressure, and the crude product is taken up in methanol and filtered through kieselguhr. Purification takes place by preparative HPLC. The product is dissolved in methanol, and an excess of 1N hydrochloric acid is added. The solvent is removed under reduced pressure. Drying under high vacuum results in 49 mg (45% of theory) of the title compound.

$^1$H-NMR (300 MHz, DMSO-d$_6$): δ=10.55 (s, 1H), 9.51 (s, 1H), 9.30 (d, 1H), 9.20 (s, 1H), 8.94-8.80 (m, 2H), 8.07-7.80 (m, 4H), 7.55 (t, 1H), 4.35 (m, 1H), 3.65-3.15 (m, 6H), 2.20 (m, 1H), 2.18-2.05 (m, 1H), 1.98-1.88 (m, 2H), 1.80-1.63 (m, 1H).

HPLC (method 1): R$_t$=3.27 min.

MS (ESIpos): m/z=348 (M+H)$^+$ (free base).

EXAMPLE 107

N-[(3R)-1-Azabicyclo[2.2.2]oct-3-yl]-7-(3-{[(methylamino)carbonyl]amino}phenyl)-1-benzofuran-2-carboxamide hydrochloride

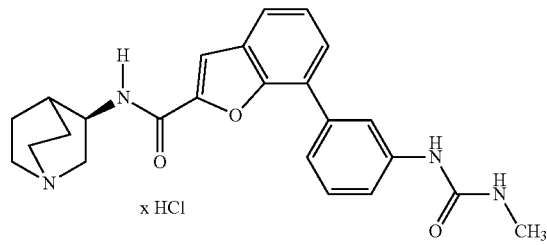 [SMILES: CNC(=O)Nc1cccc(-c2cccc3cc(C(=O)N[C@H]4CN5CCC4CC5)oc23)c1]

63 mg (0.18 mmol) of 7-(3-aminophenyl)-N-[(3R)-1-azabicyclo[2.2.2]oct-3-yl]-1-benzofuran-2-carboxamide (Example 114), 40 mg (0.70 mmol) of methyl isocyanate and 0.12 ml (0.88 mmol) of triethylamine are heated in 3 ml of THF/DMF (1:1) at 40° C. overnight. A further 40 mg (0.70 mmol) of methyl isocyanate and a catalytic amount of DMAP are added, and the mixture is heated at 50° C. overnight. Cooling is followed by addition of water, filtration and removal of the solvent under reduced pressure. Purification takes place by preparative HPLC. The product is dissolved in methanol, and an excess of 1N hydrochloric acid is added. The solvent is removed under reduced pressure. Drying under high vacuum results in 18 mg (23% of theory) of the title compound.

$^1$H-NMR (400 MHz, DMSO-d$_6$): δ=9.98 (s, 1H), 8.85 (s, 1H), 8.63 (d, 1H), 8.15 (s, 1H), 7.80 (m, 2H), 7.65 (d, 1H), 7.45 (t, 1H), 7.38 (s, 2H), 6.20 (m, 1H), 4.35 (m, 1H), 3.75-3.63 (m, 1H), 3.60-3.15 (m, 5H), 2.65 (s, 3H), 2.30 (m, 1H), 2.18-2.05 (m, 1H), 1.98-1.88 (m, 2H), 1.80-1.63 (m, 1H).

HPLC (method 1): R$_t$=3.89 min.

MS (ESIpos): m/z=419 (M+H)$^+$ (free base).

EXAMPLE 108

N-[(3R)-1-Azabicyclo[2.2.2]oct-3-yl]-7-(3-{[(ethylamino)carbonyl]amino}phenyl)-1-benzofuran-2-carboxamide hydrochloride

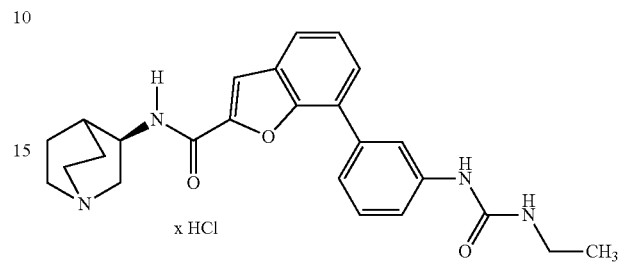

63 mg (0.18 mmol) of 7-(3-aminophenyl)-N-[(3R)-1-azabicyclo[2.2.2]oct-3-yl]-1-benzofuran-2-carboxamide (Example 114), 50 mg (0.70 mmol) of ethyl isocyanate and 0.12 ml (0.88 mmol) of triethylamine are heated in 3 ml of THF/DMF (1:1) at 40° C. overnight. A further 50 mg (0.70 mmol) of ethyl isocyanate and a catalytic amount of DMAP are added, and the mixture is heated at 50° C. overnight. Cooling is followed by addition of water, filtration and removal of the solvent under reduced pressure. Purification takes place by preparative HPLC. The product is dissolved in methanol, and an excess of 1N hydrochloric acid is added. The solvent is removed under reduced pressure. Drying under high vacuum results in 15 mg (18% of theory) of the title compound.

$^1$H-NMR (400 MHz, DMSO-d$_6$): δ=9.80 (s, 1H), 8.74 (s, 1H), 8.63 (d, 1H), 8.10 (s, 1H), 7.80 (m, 2H), 7.60 (d, 1H), 7.45 (t, 1H), 7.38 (s, 2H), 6.20 (m, 1H), 4.35 (m, 1H), 3.75-3.63 (m, 1H), 3.60-3.15 (m, 5H), 3.10 (m, 2H), 2.65 (s, 3H), 2.30 (m, 1H), 2.18-2.05 (m, 1H), 1.98-1.88 (m, 2H), 1.80-1.63 (m, 1H), 1.05 (t, 3H).

HPLC (method 1): R$_t$=4.01 min.

MS (ESIpos): m/z=433 (M+H)$^+$ (free base).

EXAMPLE 109

N-[(3R)-1-Azabicyclo[2.2.2]oct-3-yl]-7-[3-({[(1-methylethyl)amino]carbonyl}-amino)phenyl]-1-benzofuran-2-carboxamide hydrochloride

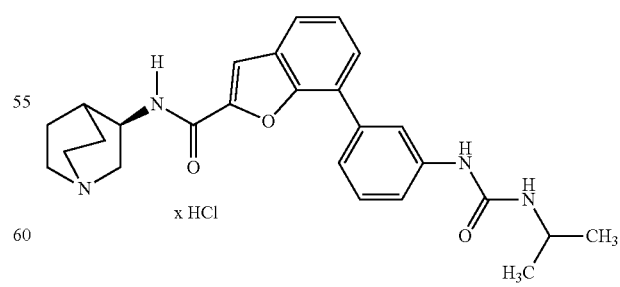

50 mg (0.14 mmol) of 7-(3-aminophenyl)-N-[(3R)-1-azabicyclo[2.2.2]oct-3-yl]-1-benzofuran-2-carboxamide (Example 114), 47 mg (0.55 mmol) of isopropyl isocyanate and 0.12 ml (0.88 mmol) of triethylamine are heated in 3 ml of THF/DMF (1:1) at 40° C. overnight. A further 47 mg (0.55 mmol) of isopropyl isocyanate and a catalytic amount of DMAP are added, and the mixture is heated at 50° C. overnight. Cooling is followed by addition of water, filtration and removal of the solvent under reduced pressure. Purification takes place by preparative HPLC. The product is dissolved in methanol, and an excess of 1N hydrochloric acid is added. The solvent is removed under reduced pressure. Drying under high vacuum results in 13 mg (18% of theory) of the title compound.

$^1$H-NMR (400 MHz, DMSO-d$_6$): δ=9.80 (s, 1H), 8.70 (d, 1H), 8.65 (s, 1H), 8:05 (s, 1H), 7.80 (m, 2H), 7.60 (d, 1H), 7:45 (t, 1H), 7.38 (s, 2H), 6.20 (m, 1H), 4.35 (m, 1H), 3.80-3.72 (m, 1H), 3.70-3.63 (m, 1H), 3.50-3.05 (m, 5H), 2.30 (m, 1H), 2.18-2.05 (m, 1H), 1.98-1.88 (m, 2H), 1.80-1.63 (m, 1H), 1.10 (d, 6H).

HPLC (method 1): R$_t$=4.12 min.

MS (ESIpos): m/z=447 (M+H)$^+$ (free base).

EXAMPLE 110

N-[(3R)-1-Azabicyclo[2.2.2]oct-3-yl]-7-[3-({[(1,1-dimethylethyl)amino]carbonyl}-amino)phenyl]-1-benzofuran-2-carboxamide hydrochloride

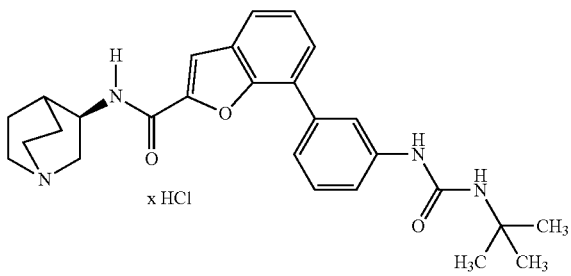 [SMILES: CC(C)(C)NC(=O)Nc1cccc(-c2cccc3cc(C(=O)N[C@H]4CN5CCC4CC5)oc23)c1]

63 mg (0.14 mmol) of 7-(3-aminophenyl)-N-[(3R)-L-azabicyclo[2.2.2]oct-3-yl]-1-benzofuran-2-carboxamide (Example 114), 69 mg (0.70 mmol) of tert-butyl isocyanate and 0.12 ml (0.88 mmol) of triethylamine are heated in 3 ml of THF/DMF (1:1) at 40° C. overnight. A further 69 mg (0.70 mmol) of tert-butyl isocyanate and a catalytic amount of DMAP are added, and the mixture is heated at 50° C. overnight.

Cooling is followed by addition of water, filtration and removal of the solvent under reduced pressure. Purification takes place by preparative HPLC. The product is dissolved in methanol, and an excess of 1N hydrochloric acid is added. The solvent is removed under reduced pressure. Drying under high vacuum results in 8 mg (9% of theory) of the title compound.

$^1$H-NMR (400 MHz, DMSO-d$_6$): δ=9.70 (s, 1H), 8.80 (d, 1H), 8.55 (s, 1H), 7.85 (s, 1H), 7.80 (m, 2H), 7.60 (d, 1H), 7.45 (t, 1H), 7.38 (s, 2H), 6.10 (m, 1H), 4.35 (m, 1H), 3.70-3.63 (m, 1H), 3.50-3.05 (m, 5H), 2.30 (m, 1H), 2.18-2.05 (m, 1H), 1.98-1.88 (m, 2H), 1.80-1.63 (m, 1H), 1.30 (s, 9H).

HPLC (method 1): R$_t$=4.27 min.

MS (ESIpos): m/z=461 (M+H)$^+$ (free base).

EXAMPLE 111

N-[(3R)-1-Azabicyclo[2.2.2]oct-3-yl]-7-{3-[(methylsulphonyl)amino]phenyl}-1-benzofuran-2-carboxamide hydrochloride

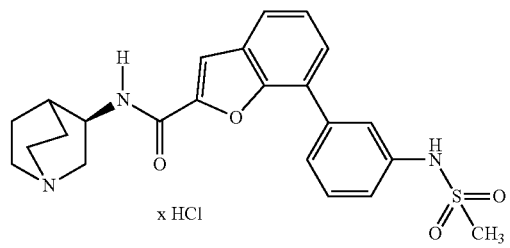 [SMILES: CS(=O)(=O)Nc1cccc(-c2cccc3cc(C(=O)N[C@H]4CN5CCC4CC5)oc23)c1]

73 mg (0.20 mmol) of 7-(3-aminophenyl)-N-[(3R)-1-azabicyclo[2.2.2]oct-3-yl]-1-benzofuran-2-carboxamide (Example 114), 69 mg (0.61 mmol) of methansulphonyl chloride and 0.14 ml (1.01 mmol) of triethylamine are heated in 3 ml of THF/DMF (1:1) at 50° C. overnight. Cooling is followed by addition of water, filtration and removal of the solvent under reduced pressure. Purification takes place by preparative HPLC. The product is dissolved in methanol, and an excess of 1N hydrochloric acid is added. The solvent is removed under reduced pressure. Drying under high vacuum results in 16 mg (14% of theory) of the title compound.

$^1$H-NMR (300 MHz, DMSO-d$_6$): δ=10.15 (s, 1H), 9.90 (s, 1H), 8.76 (d, 1H), 7.90 (s, 1H), 7.85-7.75 (m, 2H), 7.66-7.60 (m, 2H), 7.55-7.53 (m, 2H), 7.25 (m, 1H), 4.37 (m, 1H), 3.70-3.63 (m, 1H), 3.45-3.05 (m, 5H), 3:10 (s, 3H), 2.30 (m, 1H), 2.18-2.05 (m, 1H), 1.98-1.88 (m, 2H), 1.80-1.63 (m, 1H).

HPLC (method 1): R$_t$=3.97 min.

MS (ESIpos): m/z=440 (M+H)$^+$ (free base).

EXAMPLE 112

N-[(3R)-1-Azabicyclo[2.2.2]oct-3-yl]-7-{2-[(cyclobutylcarbonyl)amino]phenyl}-1-benzofuran-2-carboxamide hydrochloride

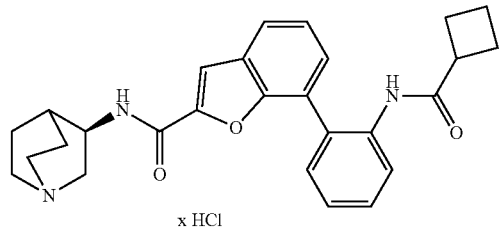 [SMILES: O=C(N[C@H]1CN2CCC1CC2)c1cc2cccc(-c3ccccc3NC(=O)C3CCC3)c2o1]

60 mg (0.15 mmol) of 7-(2-aminophenyl)-N-[(3R)-1-azabicyclo[2.2.2]oct-3-yl]-1-benzofuran-2-carboxamide (Example 132), 26 mg (0.22 mmol) of cyclobutanecarbonyl chloride and 0.06 ml (0.44 mmol) of triethylamine are shaken in 2 ml of THF/DMF (1:1) at RT overnight. The solvent is removed under reduced pressure. Purification takes place by preparative HPLC. The product is dissolved in methanol, and an excess of 1N hydrochloric acid is added. The solvent is removed under reduced pressure. Drying under high vacuum results in 39 mg (56% of theory) of the title compound.

$^1$H-NMR (300 MHz, DMSO-d$_6$): δ=10.15 (s, 1H), 9.05 (s, 1H), 8.40 (d, 1H), 7.95 (s, 1H), 7.80-7.70 (m, 2H), 7.55-7.30 (m, 6H), 4.32 (m, 1H), 3.70-3.63 (m, 1H), 3.45-3.05 (m, 5H), 2.98-2.88 (m, 1H), 2.30 (m, 1H), 2.18-2.05 (m, 1H), 1.98-1.55 (m, 9H).

HPLC (method 1): R$_t$=3.95 min.

MS (ESIpos): m/z=444 (M+H)$^+$ (free base).

EXAMPLE 113

N-[(3R)-1-Azabicyclo[2.2.2]oct-3-yl]-5-(5-pyrimidinyl)-1-benzofuran-2-carboxamide hydrochloride

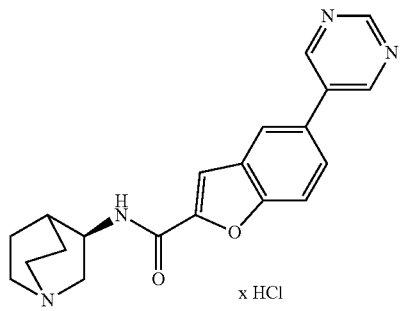 [SMILES: O=C(N[C@H]1CN2CCC1CC2)c1cc2cc(-c3cncnc3)ccc2o1]

177 mg (0.86 mmol) of 5-(4,4,5,5-tetramethyl-1,3,2-dioxaborolan-2-yl)pyrimidine and 2.15 ml of 1N sodium hydroxide solution are added to a mixture of 250 mg (0.72 mmol) of N-[(3R)-1-azabicyclo[2.2.2]oct-3-yl]-5-bromo-1-benzofuran-2-carboxamide (Example 3A) and 52 mg (0.07 mmol) of PdCl$_2$(dppf) in 3 ml of DMF. The reaction mixture is heated at 90° C. overnight. The solvent is removed under reduced pressure, and the crude product is taken up in methanol and filtered through kieselguhr. Purification takes place by preparative HPLC. The product is dissolved in methanol, and an excess of 1N hydrochloric acid is added. The solvent is removed under reduced pressure. Recrystallization of the residue from isopropanol and drying under high vacuum results in 28 mg (10% of theory) of the title compound.

$^1$H-NMR (300 MHz, DMSO-d$_6$): δ=10.30 (s, 1H), 9.22-9.13 (m, 4H), 8.24 (m, 1H), 7.93-7.81 (m, 3H), 4.39 (m, 1H), 3.68-3.48 (m, 1H), 3.45-3.13 (m, 5H), 2.28-2.20 (m, 1H), 2.18-2.07 (m, 1H), 1.97-1.88 (m, 2H), 1.80-1.57 (m, 1H).

HPLC (method 1): R$_t$=3.26 min.

MS (ESIpos): m/z=349 (M+H)$^+$ (free base).

EXAMPLE 114

7-(3-Aminophenyl)-N-[(3R)-1-azabicyclo[2.2.2]oct-3-yl]-1-benzofuran-2-carboxamide

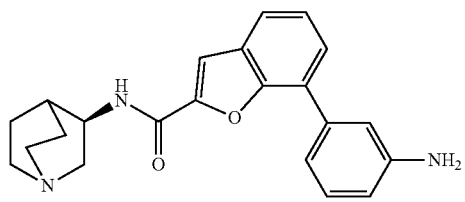 [SMILES: Nc1cccc(-c2cccc3cc(C(=O)N[C@H]4CN5CCC4CC5)oc23)c1]

Method a):

622 mg (1.68 mmol) of 3-aminophenylboronic acid hemisulphate and 11.2 ml of 1N sodium hydroxide solution are added to a mixture of 978 mg (2.80 mmol) of N-[(3R)-1-azabicyclo[2.2.2]oct-3-yl]-7-bromo-1-benzofuran-2-carboxamide (Example 30A) and 205 mg (0.28 mmol) of PdCl$_2$(dppf) in 15 ml of DMF. The reaction mixture is heated at 95° C. overnight. The crude product is filtered through kieselguhr, washed with DMF and freed of solvent under reduced pressure. The residue is mixed with 200 ml of 1N sodium hydroxide solution and 200 ml of ethyl acetate. After separation of the phases, the organic phase is washed twice more with 100 ml of 1N sodium hydroxide solution each time and then once more with 100 ml of a saturated sodium chloride solution. Drying over magnesium sulphate is followed by purification of the crude product by preparative HPLC. After removal of the solvent in a rotary evaporator it is possible to obtain–875 mg (73% of theory) of the title compound in the form of a white foam by twice adding dichloromethane and concentrating again.

$^1$H-NMR (300 MHz, DMSO-d$_6$): δ=8.48 (d, 1H), 8.21 (s, 1H), 7.76-7.69 (m, 1H), 7.54 (d, 1H), 7.45-7.37 (m, 1H), 7.20-7.00 (m, 3H); 6.67-6.61 (m, 1H), 4.13-4.06 (m, 11H), 3.48-3.26 (m, 1H), 3.10-3.01 (m, 1H), 2.93-2.79 (m, 4H), 2.03 (m, 1H), 2.00-1.88 (m, 1H), 1.79-1.67 (m, 2H), 1.58-1.42 (m, 1H).

HPLC (method 1): R$_t$=3.46 min.

MS (ESIpos): m/z=362 (M+H)$^+$.

Method b):

419 mg (1.13 mmol) of bis[3-(dihydroxyboranyl)anilinium]sulphate and 7.56 ml of 1N sodium hydroxide solution are added to a mixture of 660 mg (1.89 mmol) of N-[(3R)-1-azabicyclo[2.2.2]oct-3-yl]-7-bromo-1-benzofuran-2-carboxamide (Example 30A) and 138 mg (0.19 mmol) of PdCl$_2$(dppf) in 8 ml of DMF. The reaction mixture is heated at 95° C. overnight. The solvent is removed under reduced pressure, and the crude product is taken up in methanol and filtered through kieselguhr. Further purification takes place by preparative HPLC. The solvent is removed from the product fractions under reduced pressure. Drying under high vacuum results in 485 mg (71% of theory) of the title compound.

$^1$H-NMR (300 MHz, DMSO-d$_6$): δ=8.48 (d, 1H), 8.21 (s, 1H), 7.70 (s, 1H), 7.55 (m, 1H), 7.40 (t, 1H), 7.18 (t, 1H), 7.10-7.00 (m, 2H), 6.66 (m, 1H), 4.20 (br. s, 2H), 4.05 (m, 1H), 3.25 (m, 1H), 3.05 (m, 1H), 2.90-2.70 (m, 4H), 2.05 (m, 1H), 1.70 (m, 1H), 1.65 (m, 2H), 1.45 (m, 1H).

HPLC (method 1): R$_t$=3.50 min.

MS (ESIpos): m/z=362 (M+H)+.

EXAMPLE 115

7-[3-(Acetylamino)phenyl]-N-[(3R)-azabicyclo[2.2.2]oct-3-yl]-1-benzofuran-2-carboxamide hydrochloride

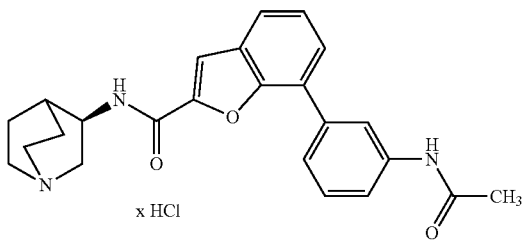 [SMILES: CC(=O)Nc1cccc(-c2cccc3cc(C(=O)N[C@H]4CN5CCC4CC5)oc23)c1]

75 mg (0.16 mmol) of 7-(3-aminophenyl)-N-[(3R)-1-azabicyclo[2.2.2]oct-3-yl]-1-benzofuran-2-carboxamide (Example 114), 18 µl (0.24 mmol) of acetyl chloride and 68 µl (0.49 mmol) of triethylamine are stirred in 2 ml of THF at RT overnight. The solvent is removed under reduced pressure. Purification takes place by preparative HPLC. The product is dissolved in methanol, and an excess of 1N hydrochloric acid is added. Removal of the solvent under reduced pressure and drying under high vacuum results in 51 mg (72% of theory) of the title compound.

$^1$H-NMR (300 MHz, DMSO-$d_6$): δ=10.37 (s, 1H), 10.30 (br. s, 1H), 8.67-8.59 (m, 2H), 7.82-7.68 (m, 3H), 7.58-7.41 (m, 4H), 4.40 (m, 1H), 3.73-3.60 (m, 1H), 3.48-3.37 (m, 1H), 3.78-3.15 (m, 4H), 2.29 (m, 1H), 2.19-2.09 (m, 1H), 2.13 (s, 3H), 1.98-1.90 (m, 2H), 1.81-1.69 (m, 1H).

HPLC (method 1): $R_t$=4.04 min.
MS (ESIpos): m/z=404 (M+H)+ (free base).

EXAMPLE 116

N-[(3R)-1-Azabicyclo[2.2.2]oct-3-yl]-7-{3-[(cyclopropylcarbonyl)amino]phenyl}-1-benzofuran-2-carboxamide hydrochloride

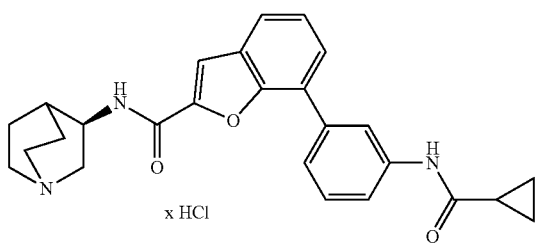 [SMILES: O=C(N[C@H]1CN2CCC1CC2)c1cc2cccc(-c3cccc(NC(=O)C4CC4)c3)c2o1]

75 mg (0.21 mmol) of 7-(3-aminophenyl)-N-[(3R)-1-azabicyclo[2.2.2]oct-3-yl]-1-benzofuran-2-carboxamide (Example 114), 28 µl (0.31 mmol) of cyclopropylcarbonyl chloride and 87 µl (0.62 mmol) of triethylamine are stirred in 2 ml of THF at RT overnight. After addition of water, the solvent is removed under reduced pressure. Purification takes place by preparative HPLC. The product is dissolved in methanol, and an excess of 1N hydrochloric acid is added. Removal of the solvent under reduced pressure and drying under high vacuum result in 55 mg (57% of theory) of the title compound.

$^1$H-NMR (300 MHz, DMSO-$d_6$): δ=10.53 (s, 1H), 10.08 (br. s, 1H), 8.83 (m, 1H), 8.28 (s, 1H), 7.82-7.75 (m, 2H), 7.71 (d, 1H), 7.62 (d, 1H), 7.58-7.50 (m, 1H), 7.48-7.41 (m, 2H), 4.38 (m, 1H), 3.71-3.60 (m, 1H), 3.50-3.15 (m, 5H), 2.27 (m, 1H), 2.21-2.11 (m, 1H), 1.99-1.82 (m, 3H), 1.80-1.71 (m, 1H), 0.88-0.77 (m, 4H).

HPLC (method 1): $R_t$=4.07 min.
MS (ESIpos): m/z=430 (M+H)+ (free base).

EXAMPLE 117

N-[(3R)-1-Azabicyclo[2.2.2]oct-3-yl]-7-(3-{[(methoxy)acetyl]amino}phenyl)-1-benzofuran-2-carboxamide hydrochloride

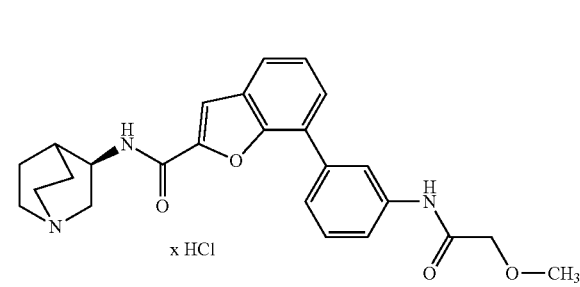 [SMILES: COCC(=O)Nc1cccc(-c2cccc3cc(C(=O)N[C@H]4CN5CCC4CC5)oc23)c1]

75 mg (0.21 mmol) of 7-(3-aminophenyl)-N-[(3R)-1-azabicyclo[2.2.2]oct-3-yl]-1-benzofuran-2-carboxamide (Example 114), 21 µl (0.31 mmol) of methoxyacetyl chloride and 87 µl (0.62 mmol) of triethylamine are stirred in 2 ml of THF at RT overnight. After addition of water, the solvent is removed under reduced pressure.

Purification takes place by preparative HPLC. The product is dissolved in methanol, and an excess of 1N hydrochloric acid is added. Removal of the solvent under reduced pressure and drying under high vacuum result in 56 mg (55% of theory) of the title compound.

$^1$H-NMR (300 MHz, DMSO-$d_6$): δ=10.17 (br. s, 1H), 10.10 (s, 1H), 8.63-8.55 (m, 2H), 7.82-7.68 (m, 3H), 7.64-7.57 (m, 2H), 7.52-7.41 (m, 2H), 4.39 (m, 1H), 4.10 (s, 2H), 3.71-3.61 (m, 1H), 3.49-3.14 (m, 5H), 3.41 (s, 3H), 2.29 (m, 1H), 2.19-2.05 (m, 1H), 1.99-1.89 (m, 2H), 1.80-1.69 (m, 1H).

HPLC (method 1): $R_t$=4.07 min.
MS (ESIpos): m/z=434 (M+H)+ (free base).

EXAMPLE 118

N-[(3R)-1-Azabicyclo[2.2.2]oct-3-yl]-7-{3-[(cyclobutylcarbonyl)amino]phenyl}-1-benzofuran-2-carboxamide hydrochloride 75 mg (0.21 mmol) of 7-(3-aminophenyl)-N-[(3R)-1-azabicyclo[2.2.2]oct-3-yl]-1-benzofuran-2-carboxamide (Example 114), 37 mg (0.31 mmol) of cyclobutanecarbonyl chloride and 87 µl (0.62 mmol) of triethylamine are stirred in 2 ml of THF at RT overnight. After addition of water, the solvent is removed under reduced pressure. Purification takes place by preparative HPLC. The product is dissolved in methanol, and an excess of 1N hydrochloric acid is added. Removal of the solvent under reduced pressure and drying under high vacuum result in 57 mg (57% of theory) of the title compound.

$^1$H-NMR (300 MHz, DMSO-d$_6$): δ=10.14 (br. s, 1H), 10.07 (s, 1H), 8.82 (d, 1H), 8.35 (s, 1H), 7.80-7.78 (m, 2H), 7.74-7.61 (m, 2H), 7.57-7.41 (m, 3H), 4.36 (m, 1H), 3.70-3.61 (m, 1H), 3.45-3.13 (m, 5H), 2.30-1.67 (m, 12H).

HPLC (method 1): R$_t$=4.22 min.

MS (ESIpos): m/z=444 (M+H)$^+$ (free base).

EXAMPLE 119

N-[(3R)-1-Azabicyclo[2.2.2]oct-3-yl]-7-{2-[(cyclopropylcarbonyl)amino]phenyl}-1-benzofuran-2-carboxamide hydrochloride

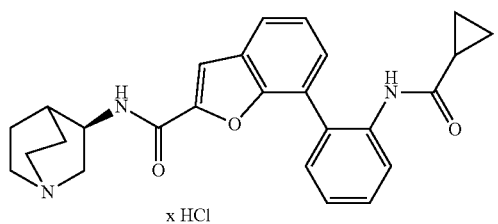 [SMILES: O=C(N[C@H]1CN2CCC1CC2)c1cc2cccc(-c3ccccc3NC(=O)C3CC3)c2o1]

60 mg (0.15 mmol) of 7-(2-aminophenyl)-N-[(3R)-1-azabicyclo[2.2.2]oct-3-yl]-1-benzofuran-2-carboxamide (Example 132), 20 µl (0.31 mmol) of cyclopropylcarbonyl chloride and 87 µl (0.62 mmol) of triethylamine are stirred in 2 ml of THF/DMF (1:1) at RT overnight. After addition of water, the solvent is removed under reduced pressure. Purification takes place by preparative HPLC. The product is dissolved in methanol, and an excess of 1N hydrochloric acid is added. Removal of the solvent under reduced pressure and drying under high vacuum result in 27 mg (40% of theory) of the title compound.

$^1$H-NMR (300 MHz, DMSO-d$_6$): δ=10.07 (br. s, 1H), 9.48 (s, 1H), 8.84 (d, 1H), 7.83-7.77 (m, 1H), 7.72 (m, 1H), 7.54-7.31 (m, 6H), 4.30 (m, 1H), 3.70-3.61 (m, 1H), 3.37-3.03 (m, 5H), 2.23 (m, 1H), 2.14-2.03 (m, 1H), 1.95-1.83 (m, 2H), 1.79-1.68 (m, 1H), 1.53 (m, 1H), 1.31-1.15 (m, 4H).

HPLC (method 1): R$_t$=3.85 min.

MS (ESIpos): m/z=430 (M+H)$^+$ (free base).

EXAMPLE 120

N-[(3R)-1-Azabicyclo[2.2.2]oct-3-yl]-7-(2-{[(methoxy)acetyl]amino}phenyl)-1-benzofuran-2-carboxamide hydrochloride

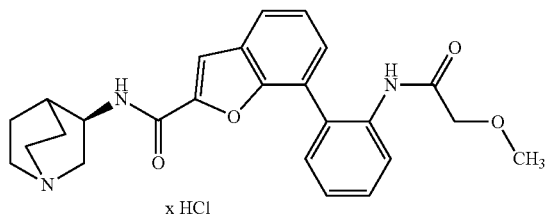 [SMILES: COCC(=O)Nc1ccccc1-c1cccc2cc(C(=O)N[C@H]3CN4CCC3CC4)oc12]

60 mg (0.15 mmol) of 7-(2-aminophenyl)-N-[(3R)-1-azabicyclo[2.2.2]oct-3-yl]-1-benzofuran-2-carboxamide (Example 132), 201 (0.22 mmol) of methoxyacetyl chloride and 61 µl (0.44 mmol) of triethylamine are stirred in 2 ml of THF/DMF (1:1) at RT overnight. After addition of water, the solvent is removed under reduced pressure. Purification takes place by preparative HPLC. The product is dissolved in methanol, and an excess of 1N hydrochloric acid is added. Removal of the solvent under reduced pressure and drying under high vacuum result in 29 mg (40% of theory) of the title compound.

$^1$H-NMR (300 MHz, DMSO-d$_6$): δ=10.15 (br. s, 1H), 9.05 (s, 1H), 8.53 (d, 1H), 7.88-7.73 (m, 3H), 7.52-7.34 (m, 5H), 4.33 (m, 1H), 3.77 (s, 2H), 3.69-3.59 (m, 1H), 3.44-3.14 (m, 5H), 3.04 (s, 3H), 2.22 (m, 1H), 2.18-2.05 (m, 1H), 1.96-1.84 (m, 2H), 1.80-1.67 (m, 1H).

HPLC (method 1): R$_t$=3.84 min.

MS (ESIpos): m/z=434 (M+H)$^+$ (free base).

EXAMPLE 121

N-[(3S)-1-Azabicyclo[2.2.2]oct-3-yl]-7-[4-(4-morpholinyl)phenyl]-1-benzofuran-2-carboxamide hydrochloride

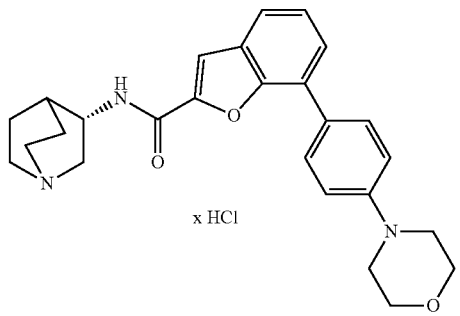 [SMILES: O=C(N[C@@H]1CN2CCC1CC2)c1cc2cccc(-c3ccc(N4CCOCC4)cc3)c2o1]

107 mg (0.52 mmol) of 4-morpholinophenylboronic acid and 1.72 ml of 1N sodium hydroxide solution are added to a mixture of 150 mg (0.43 mmol) of N-[(3S)-1-azabicyclo[2.2.2]oct-3-yl]-7-bromo-1-benzofuran-2-carboxamide (Example 31A) and 35 mg (0.04 mmol) of PdCl$_2$(dppf) in 4 ml of DMF. The reaction mixture is heated at. 95° C. overnight. The crude product is filtered through kieselguhr, and, after washing with DMF, the solvent is removed under reduced pressure. To remove the last residues of catalyst, a further filtration through silica gel is carried out, washing with dichloromethane and methanol. The crude product is purified by preparative HPLC. The product is dissolved in methanol, and an excess of 1N hydrochloric acid is added. Removal of the solvent under reduced pressure and drying under high vacuum result in 84 mg (42% of theory) of the title compound.

$^1$H-NMR (300 MHz, DMSO-d$_6$): δ=10.48 (br. s, 1H), 9.05 (d, 1H), 7.90-7.82 (m, 3H), 7.70 (d, 1H), 7.63 (d, 1H), 7.42-7.35 (m, 1H), 7.20-7.12 (m, 2H), 4.40-4.31 (m, 1H), 3.84-3.77 (m, 4H), 3.69-3.57 (m, 1H), 3.48-3.12 (m, 9H), 2.22 (m, 1H), 2.19-2.08 (m, 1H), 1.96-1.85 (m, 2H), 1.80-1.71 (m, 1H).

HPLC (method 1): R$_t$=3.82 min.

MS (ESIpos): m/z=432 (M+H)$^+$.

EXAMPLE 122

N-[(3S)-1-Azabicyclo[2.2.2]oct-3-yl]-7-[2-(hydroxymethyl)phenyl]-1-benzofuran-2-carboxamide hydrochloride

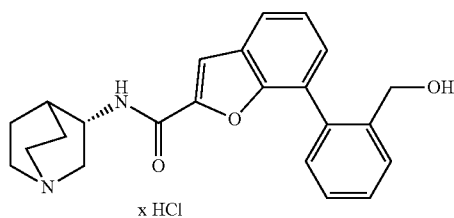 [SMILES: O=C(N[C@@H]1CN2CCC1CC2)c1cc2cccc(-c3ccccc3CO)c2o1]

x HCl 78 mg (0.52 mmol) of 2-(hydroxymethyl)phenylboronic acid and 1.72 ml of 1N sodium hydroxide solution are added to a mixture of 150 mg (0.43 mmol) of N-[(3S)-1-azabicyclo[2.2.2]oct-3-yl]-7-bromo-1-benzofuran-2-carboxamide (Example 31A) and 35 mg (0.04 mmol) of PdCl$_2$(dppf) in 3 ml of DMF. The reaction mixture is heated at 95° C. overnight. The crude product is filtered through kieselguhr, and, after washing with DMF, the solvent is removed under reduced pressure. To remove the last residues of catalyst, a further filtration through silica gel is carried out, washing with dichloromethane and methanol. The crude product is purified by preparative HPLC. The product is dissolved in methanol, and an excess of 1N hydrochloric acid is added. Removal of the solvent under reduced pressure and drying under high vacuum result in 81 mg (46% of theory) of the title compound.

$^1$H-NMR (300 MHz, DMSO-d$_6$): δ=10.12 (br. s, 1H), 8.94 (d, 1H), 7.91-7.79 (m, 3H), 7.69 (d, 1H), 7.53-7.32 (m, 5H), 4.33-4.22 (m, 3H), 3.68-3.57 (m, 1H), 3.48-3.12 (m, 5H), 2.19 (m, 1H), 2.15-2.04 (m, 1H), 1.94-1.83 (m, 2H), 1.79-1.67 (m, 1H).

HPLC (method 1): R$_t$=3.87 min.

MS (ESIpos): m/z=377 (M+H)$^+$.

EXAMPLE 123

N-[(3S)-1-Azabicyclo[2.2.2]oct-3-yl]-7-(3-pyridinyl)-1-benzofuran-2-carboxamide hydrochloride

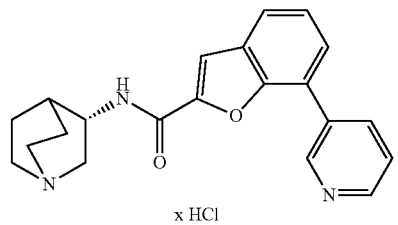 [SMILES: O=C(N[C@@H]1CN2CCC1CC2)c1cc2cccc(-c3cccnc3)c2o1]

x HCl 63 mg (0.57 mmol) of 3-pyridineboronic acid and 1.72 ml of 1N sodium hydroxide solution are added to a mixture of 150 mg (0.43 mmol) of N-[(3S)-1-azabicyclo[2.2.2]oct-3-yl]-7-bromo-1-benzofuran-2-carboxamide (Example 31A) and 35 mg (0.04 mmol) of PdCl$_2$(dppf) in 4 ml of DMF. The reaction mixture is heated at 95° C. overnight. The solvent is removed under reduced pressure and the crude product is taken up in methanol and filtered through kieselguhr. To remove the last residues of catalyst, a further filtration through silica gel is carried out, washing with dichloromethane and methanol. Purification takes place by preparative HPLC. The product is dissolved in methanol, and an excess of 1N hydrochloric acid is added. The solvent is removed under reduced pressure. Drying under high vacuum results in 76 mg (42% of theory) of the title compound.

$^1$H-NMR (300 MHz, DMSO-d$_6$): δ=10.49 (s, 1H), 9.51 (s, 1H), 9.30 (d, 1H), 8.94-8.80 (m, 2H), 8.07-7.80 (m, 4H), 7.55 (t, 1H), 4.35 (m, 1H), 3.65-3.15 (m, 6H), 2.20 (m, 1H), 2.18-2.05 (m, 1H), 1.98-1.88 (m, 2H), 1.80-1.63 (m, 1H).

HPLC (method 1): R$_t$=3.30 min.

MS (ESIpos): m/z=348 (M+H)$^+$ (free base).

EXAMPLE 124

N-[(3S)-1-Azabicyclo[2.2.2]oct-3-yl]-7-[4-(methoxy)phenyl]-1-benzofuran-2-carboxamide hydrochloride

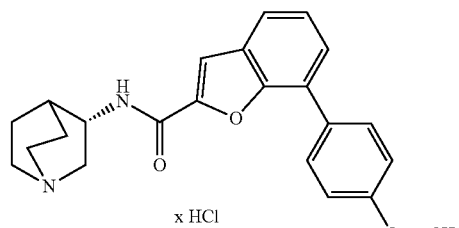

x HCl 78 mg (0.52 mmol) of 4-(methoxy)phenylboronic acid and 1.72 ml of 1N sodium hydroxide solution are added to a mixture of 150 mg (0.43 mmol) of N-[(3S)-1-azabicyclo[2.2.2]oct-3-yl]-7-bromo-1-benzofuran-2-carboxamide (Example 31A) and 35 mg (0.04 mmol) of PdCl$_2$(dppf) in 4 ml of DMF. The reaction mixture is heated at 95° C. overnight. The solvent is removed under reduced pressure and the crude product is taken up in methanol and filtered through kieselguhr. To remove the last residues of catalyst, a further filtration through silica gel is carried out, washing with dichloromethane and methanol. Purification takes place by preparative HPLC. An excess of 1N hydrochloric acid is added to the product fractions. The solvent is removed under reduced pressure. Drying under high vacuum results in 27 mg (15% of theory) of the title compound.

The analytical data agree with those of the enantiomeric compound (Example 99).

EXAMPLE 125

N-[(3S)-1-Azabicyclo[2.2.2]oct-3-yl]-7-[3-(methoxy)phenyl]-1-benzofuran-2-carboxamide hydrochloride

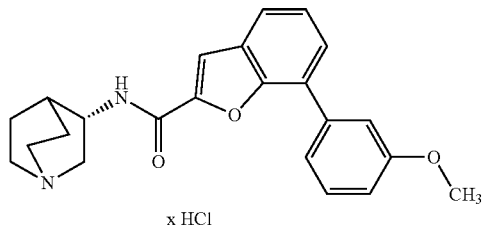 [SMILES: COc1cccc(-c2cccc3cc(C(=O)N[C@@H]4CN5CCC4CC5)oc23)c1]

78 mg (0.52 mmol) of 3-(methoxy)phenylboronic acid and 1.72 ml of 1N sodium hydroxide solution are added to a mixture of 150 mg (0.43 mmol) of N-[(3S)-1-azabicyclo[2.2.2]oct-3-yl]-7-bromo-1-benzofuran-2-carboxamide (Example 31A) and 35 mg (0.04 mmol) of PdCl$_2$(dppf) in 3 ml of DMF. The reaction mixture is heated at 95° C. overnight. The solvent is removed under reduced pressure and the crude product is taken up in methanol and filtered through kieselguhr. To remove the last residues of catalyst, a further filtration through silica gel is carried out, washing with dichloromethane and methanol. Purification takes place by preparative HPLC. The product is dissolved in methanol, and an excess of 1N hydrochloric acid is added. The solvent is removed under reduced pressure. Drying under high vacuum results in 23 mg (13% of theory) of the title compound.

The analytical data agree with those of the enantiomeric compound (Example 101).

EXAMPLE 126

N-[(3R)-1-Azabicyclo[2.2.2]oct-3-yl]-7-[2-({[(1-methylethyl)amino]carbonyl}-amino)phenyl]-1-benzofuran-2-carboxamide hydrochloride

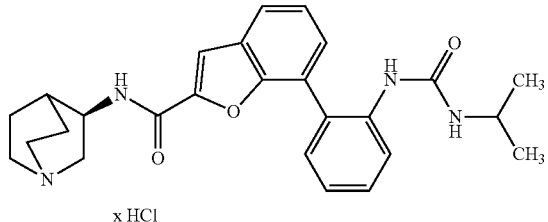 [SMILES: CC(C)NC(=O)Nc1ccccc1-c1cccc2cc(C(=O)N[C@H]3CN4CCC3CC4)oc12]

75 mg (0.16 mmol) of 7-(2-aminophenyl)-N-[(3R)-1-azabicyclo[2.2.2]oct-3-yl]-1-benzofuran-2-carboxamide (Example 132), 65 µl (0.66 mmol) of isopropyl isocyanate and 114 µl (0.82 mmol) of triethylamine are heated in 3 ml of THF/DMF (1:1) at 50° C. for 48 h. Cooling is followed by addition of water, filtration and removal of the solvent under reduced pressure. Purification takes place by preparative HPLC. The product is dissolved in methanol, and an excess of 1N hydrochloric acid is added. The solvent is removed under reduced pressure. Drying under high vacuum results in 21 mg (26% of theory) of the title compound.

$^1$H-NMR (300 MHz, DMSO-d$_6$): δ=10.09 (br. s, 1H), 8.60 (d, 1H), 7.88-7.77 (m, 3H), 7.46-7.33 (m, 3H), 7.29 (dd, 1H), 7.19-7.10 (m, 1H), 6.22 (br. s, 1H), 4.29 (m, 1H), 3.75-3.54 (m, 2H), 3.39-3.13 (m, 5H), 2.22 (m, 1H), 2.15-2.02 (m, 1H), 1.96-1.86 (m, 2H), 1.80-1.69 (m, 1H), 0.96 (d, 6H).

HPLC (method 1): R$_t$=3.92 min.

MS (ESIpos): m/z=447 (M+H)$^+$ (free base).

EXAMPLE 127

N-[(3R)-1-Azabicyclo[2.2.2]oct-3-yl]-7-(2-{[[(ethylamino)carbonyl]amino}phenyl)-1-benzofuran-2-carboxamide hydrochloride

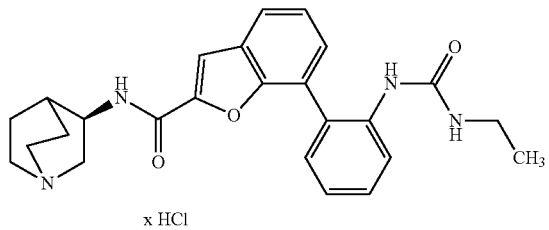 [SMILES: CCNC(=O)Nc1ccccc1-c1cccc2cc(C(=O)N[C@H]3CN4CCC3CC4)oc12]

75 mg (0.16 mmol) of 7-(2-aminophenyl)-N-[(3R)-1-azabicyclo[2.2.2]oct-3-yl]-1-benzofuran-2-carboxamide (Example 132), 50 µl (0.66 mmol) of ethyl isocyanate and 110 µl (0.82 mmol) of triethylamine are heated together with a catalytic amount of DMAP in 3 ml of THF/DMF (1:1) at 50° C. for 48 h. Cooling is followed by addition of water, filtration and removal of the solvent under reduced pressure. Purification takes place by preparative HPLC. The product is dissolved in methanol, and an excess of 1N hydrochloric acid is added. The solvent is removed under reduced pressure. Drying under high vacuum results in 10 mg (12% of theory) of the title compound.

$^1$H-NMR (300 MHz, DMSO-d$_6$): δ=10.41 (br. s, 1H), 9.30 (d, 1H), 8.69 (d, 1H), 7.96-7.78 (m, 3H), 7.59-7.11 (m, 4H), 4.30 (m, 1H), 3.69-3.54 (m, 1H), 3.40-3.13 (m, 5H), 2.99 (q, 2H), 2.24-2.19 (m, 1H), 2.17-2.04 (m, 1H), 1.96-1.84 (m, 2H), 1.80-1.64 (m, 1H), 0.92 (t, 3H).

HPLC (method 1): R$_t$=3.86 min.

MS (ESIpos): m/z=433 (M+H)+ (free base).

EXAMPLE 128

N-[(3R)-1-Azabicyclo[2.2.2]oct-3-yl]-7-(2-{[(methylamino)carbonyl]amino}phenyl)-1-benzofuran-2-carboxamide hydrochloride

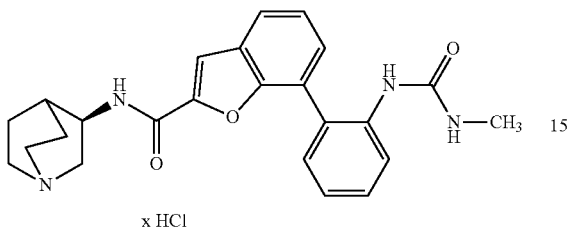

x HCl 75 mg (0.16 mmol) of 7-(2-aminophenyl)-N-[(3R)-1-azabicyclo[2.2.2]oct-3-yl]-1-benzofuran-2-carboxamide (Example 132), 37 mg (0.66 mmol) of methyl isocyanate and 110 μl (0.82 mmol) of triethylamine are heated together with a catalytic amount of DMAP in 3 ml of THF/DMF (1:1) at 50° C. overnight. Cooling is followed by addition of water, filtration and removal of the solvent under reduced pressure.

Purification takes place by preparative HPLC. The product is dissolved in methanol, and an excess of 1N hydrochloric acid is added. The solvent is removed under reduced pressure. Drying under high vacuum results in 29 mg (35% of theory) of the title compound.

$^1$H-NMR (300 MHz, DMSO-d$_6$): δ=10.22 (br. s, 1H), 8.60 (d, 1H), 8.69 (d, 1H), 7.86-7.74 (m, 3H), 7.51-7.28 (m, 5H), 7.18-7.11 (m, 1H), 6.21 (br. s, 1H), 4.29 (m, 1H), 3.69-3.58 (m, 1H), 3.38-3.13 (m, 5H), 2.51 (s, 3H), 2.28-2.22 (m, 1H), 2.18-2.04 (m, 1H), 1.99-1.87 (m, 2H), 1.82-1.68 (m, 1H).

HPLC (method 1): R$_t$=3.72 min.
MS (ESIpos): m/z=419 (M+H)+ (free base).

EXAMPLE 129

N-[(3R)-1-Azabicyclo[2.2.2]oct-3-yl]-7-[2-({[(1,1-dimethylethyl)amino]carbonyl}-amino)phenyl]-1-benzofuran-2-carboxamide hydrochloride

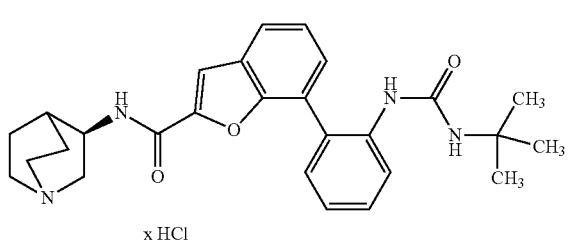 [SMILES: CC(C)(C)NC(=O)Nc1ccccc1-c1cccc2cc(C(=O)N[C@H]3CN4CCC3CC4)oc12]

x HCl 75 mg (0.16 mmol) of 7-(2-aminophenyl)-N-[(3R)-1-azabicyclo[2.2.2]oct-3-yl]-1-benzofuran-2-carboxamide (Example 132), 65 mg (0.66 mmol) of 1,1-dimethylethyl isocyanate and 110 μl (0.82 mmol) of triethylamine are heated together with a catalytic amount of DMAP in 3 ml of THF/DMF (1:1) at 50° C. overnight. Cooling is followed by addition of water, filtration and removal of the solvent under reduced pressure. Purification takes place by preparative HPLC. The product is dissolved in methanol, and an excess of 1N hydrochloric acid is added. The solvent is removed under reduced pressure. Drying under high vacuum results in 10 mg (12% of theory) of the title compound.

HPLC (method 1): R$_t$=4.06 min.
MS (ESIpos): m/z=461 (M+H)+ (free base).

EXAMPLE 130

N-[(3R)-1-Azabicyclo[2.2.2]oct-3-yl]-7-[2-(methoxy)phenyl]-1-benzofuran-2-carboxamide

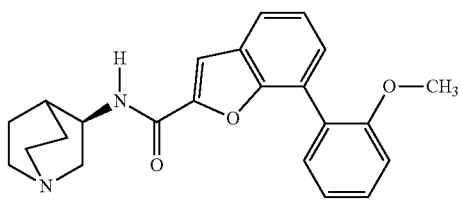 [SMILES: COc1ccccc1-c1cccc2cc(C(=O)N[C@H]3CN4CCC3CC4)oc12]

600 mg (1.45 mmol) of N-[(3R)-1-azabicyclo[2.2.2]oct-3-yl]-7-[2-(methoxy)phenyl]-1-benzofuran-2-carboxamide hydrochloride (Example 102) are dissolved in 15 ml of ethyl acetate and extracted three times with 1N sodium hydroxide solution. The organic phase is dried over sodium sulphate and then concentrated. Drying under high vacuum results in 534 mg (97.6% of theory) of the title compound.

$^1$H-NMR (200 MHz, DMSO-d$_6$): δ=8.34 (d, 1H), 7.72 (dd, 1H), 7.70 (s, 1H), 7.50-7.30 (m, 4H), 7.20 (m, 1H), 7.08 (m, 1H), 3.93 (m, 1H), 3.76 (s, 3H), 3.11 (m, 1H), 2.86 (m, 1H), 2.69 (m, 4H), 1.86 (m, 1H), 1.75 (m, 1H), 1.58 (m, 2H), 1.32 (m, 1H).

HPLC (method 1): R$_t$=4.1 min.
MS (ESIpos): m/z=377 (M+H)+.

EXAMPLE 131

N-[(3R)-1-Azabicyclo[2.2.2]oct-3-yl]-7-[2-(hydroxymethyl)phenyl]-1-benzothiophene-2-carboxamide hydrochloride

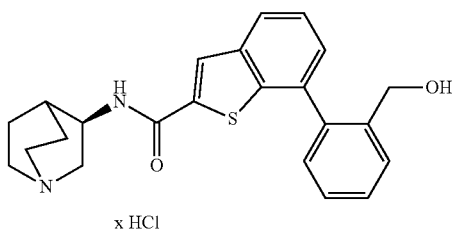 [SMILES: O=C(N[C@H]1CN2CCC1CC2)c1cc2cccc(-c3ccccc3CO)c2s1]

x HCl 200 mg (0.45 mmol) of N-[(3R)-1-azabicyclo[2.2.2]oct-3-yl]-7-bromo-1-benzothiophene-2-carboxamide hydrochloride (Example 8A) and 67.9 mg (0.45 mmol) of 2-(hydroxymethyl)phenylboronic acid are introduced into 2 ml of DMF. Addition of 0.67 ml of 2 M sodium carbonate solution and 18.2 mg (0.02 mmol) of PdCl$_2$(dppf) is followed by heating at 80° C. After 18 h, the reaction mixture is filtered through kieselguhr and purified by separation by preparative HPLC. The product fractions are concentrated and, after addition of a 5:1 mixture of methanol and 4N hydrogen chloride in dioxane, again concentrated. Drying under high vacuum results in 148 mg (72% of theory) of the title compound.

$^1$H-NMR (300 MHz, DMSO-d$_6$): δ=10.30 (br. s, 1H), 9.10 (d, 1H), 8.47 (s, 1H), 8.07 (d, 1H), 7.78 (d, 1H), 7.68-7.54 (m, 2H), 7.52-7.39 (m, 3H), 4.40 (m, 1H), 4.36 (s, 2H), 3.72 (m, 1H), 3.53-3.20 (m, 5H), 2.29 (m, 1H), 2.21 (m, 1H), 2.00 (m, 2H), 1.82 (m, 1H).

HPLC (method 1): R$_t$=3.9 min.

MS (ESIpos): m/z=393 (M+H)$^+$ (free base).

EXAMPLE 132

7-(2-Aminophenyl)-N-[(3R)-1-azabicyclo[2.2.2]oct-3-yl]-1-benzofuran-2-carboxamide

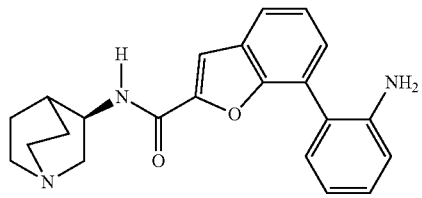 [SMILES: Nc1ccccc1-c1cccc2cc(C(=O)N[C@H]3CN4CCC3CC4)oc12]

752 mg (3.44 mmol) of 2-(4,4,5,5-tetramethyl-1,3,2-dioxaborolan-2-yl)phenylamine and 11.45 ml of 1N sodium hydroxide solution are added to a mixture of 1.0 g (2.86 mmol) of N-[(3R)-1-azabicyclo[2.2.2]oct-3-yl]-7-bromo-1-benzofuran-2-carboxamide (Example 30A) and 234 mg (0.29 mmol) of PdCl$_2$(dppf) in 15 ml of DMF. The reaction mixture is heated at 95° C. overnight and then filtered through kieselguhr. The solvent is then removed under reduced pressure, and the residue is taken up in 100 ml of ethyl acetate and 100 ml of 1N sodium hydroxide solution. The organic phase is washed twice with 1N sodium hydroxide solution and once with saturated sodium chloride solution. The combined organic phases are dried over magnesium sulphate, and the solvent is removed in a rotary evaporator under reduced pressure. The crude product is taken up in methanol and shaken together with acidic ion exchanger (Dowex® WX2-200) for about 30 min. The loaded ion exchanger is washed three times with 30 ml of methanol each time and then with DMF. It is washed successively with methanol, dichloromethane, methanol, water, methanol, dichloromethane, methanol, THF and finally once again with methanol. The product is eluted with methanol/triethylamine 95:5. The solvent is removed in a rotary evaporator under reduced pressure. Drying under high vacuum results in 601 mg (48% of theory) of the title compound in sufficient purity for further reactions.

HPLC (method 1): R$_t$=3.51 min.

MS (ESIpos): m/z=362 (M+H)$^+$.

EXAMPLE 133

N-[(3S)-1-Azabicyclo[2.2.2]oct-3-yl]-7-[4-(4-morpholinylcarbonyl)phenyl]-1-benzothiophene-2-carboxamide hydrochloride

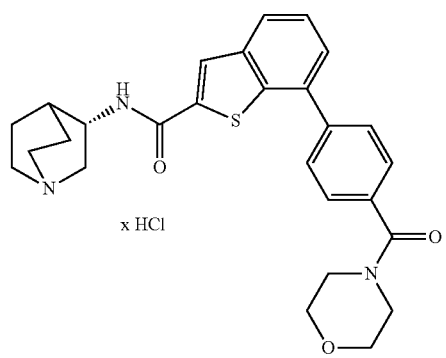 [SMILES: O=C(N[C@@H]1CN2CCC1CC2)c1cc2cccc(-c3ccc(C(=O)N4CCOCC4)cc3)c2s1]

244.0 mg (0.65 mmol) of 4-(4-morpholinylcarbonyl)phenyl trifluoromethane-sulphonate (Example 18A), 189.6 mg (0.75 mmol) of bis(pinacolato)diboron, 158.8 mg (1.62 mmol) of potassium acetate, 18.2 mg (0.02 mmol) of PdCl$_2$(dppf), 200.0 mg (0.50 mmol) of N-[(3S)-1-azabicyclo[2.2.2]oct-3-yl]-7-bromo-1-benzothiophene-2-carboxamide hydrochloride (Example 22A), 1.24 ml of 2 M sodium carbonate solution and a further 18.2 mg (0.02 mmol) of PdCl$_2$(dppf) in 2.5 ml of DMF are reacted by general method D. Drying under high vacuum results in 76.8 mg (30.1% of theory) of the title compound.

The spectroscopic data agree with those of the enantiomeric compound (Example 72).

EXAMPLE 134

N-[(3S)-1-Azabicyclo[2.2.2]oct-3-yl]-7-[3-(4-morpholinyl)phenyl]-1-benzothiophene-2-carboxamide hydrochloride

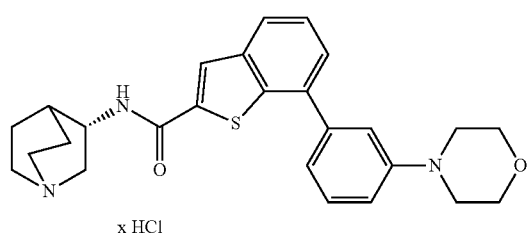 [SMILES: O=C(N[C@@H]1CN2CCC1CC2)c1cc2cccc(-c3cccc(N4CCOCC4)c3)c2s1]

143.3 mg (0.49 mmol) of 3-(4-morpholinyl)phenyl trifluoromethanesulphonate (Example 17A), 142.2 mg (0.56 mmol) of bis(pinacolato)diboron, 119.1 mg (1.21 mmol) of potassium acetate, 13.7 mg (0.02 mmol) of PdCl$_2$(dppf), 150 mg (0.37 mmol) of N-[(3S)-1-azabicyclo[2.2.2]oct-3-yl]-7-bromo-1-benzothiophene-2-carboxamide hydrochloride (Example 22A), 0.93 ml of 2 M sodium carbonate solution and a further 13.7 mg (0.02 mmol) of PdCl$_2$(dppf) in 2.0 ml of DMF are reacted by general method D. Drying under high vacuum results in 67 mg (37.1% of theory) of the title compound.

The spectroscopic data agree with those of the enantiomeric compound (Example 0.70).

EXAMPLE 135

N-[(3R)-1-Azabicyclo[2.2.2]oct-3-yl]-7-{3-[(cyclopropylamino)carbonyl]phenyl}-1-benzothiophene-2-carboxamide hydrochloride

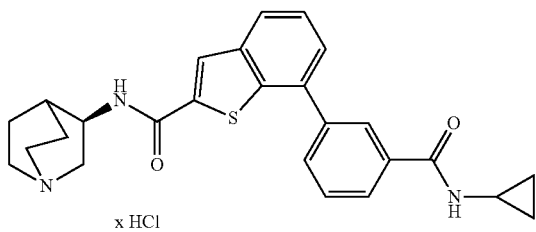 [SMILES: O=C(NC1CC1)c1cccc(-c2cccc3cc(C(=O)N[C@H]4CN5CCC4CC5)sc23)c1]

50 mg (0.11 mmol) of 3-(2-{[(3R)-1-azabicyclo[2.2.2]oct-3-ylamino]carbonyl}-1-benzothien-7-yl)benzoic acid hydrochloride (Example 75) and 12.9 mg (0.23 mmol) of cyclopropylamine are reacted together by general method E. 17.6 mg (31.1% of theory) of the title compound are obtained.

$^1$H-NMR (400 MHz, methanol-$d_4$): δ=8.18 (s, 1H), 8.15 (s, 1H), 7.93 (d, 1H), 7.88 (m, 2H), 7.62 (dd, 1H), 7.56 (m, 2H), 4.45 (m, 1H), 3.84 (m, 1H), 3.48 (m, 1H), 3.42-3.27 (m, 4H), 2.89 (m, 1H), 2.38 (m, 1H), 2.28 (m, 1H), 2.10 (m, 2H), 1.96 (m, 1H), 0.82 (m, 2H), 0.67 (m, 2H).

HPLC (method 1): $R_t$=3.95 min.

LC-MS (method 6): $R_t$=3.36 min.; m/z=445 (M+H)$^+$ (free base).

EXAMPLE 136

N-[(3R)-1-Azabicyclo[2.2.2]oct-3-yl]-7-(3-{[ethyl(methyl)amino]carbonyl}phenyl)-1-benzothiophene-2-carboxamide hydrochloride

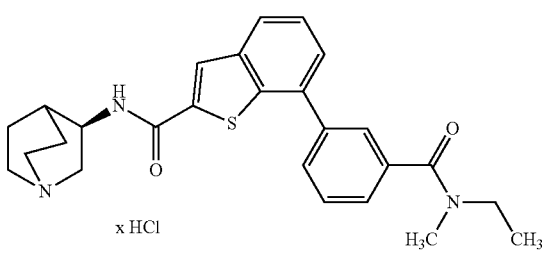 [SMILES: CCN(C)C(=O)c1cccc(-c2cccc3cc(C(=O)N[C@H]4CN5CCC4CC5)sc23)c1]

50 mg (0.11 mmol) of 3-(2-{[(3R)-1-azabicyclo[2.2.2]oct-3-ylamino]carbonyl}-1-benzothien-7-yl)benzoic acid hydrochloride (Example 75) and 13.3 mg (0.23 mmol) of ethylmethylamine are reacted together by general method E. 20.1 mg (36.8% of theory) of the title compound are obtained.

$^1$H-NMR (400 MHz, methanol-$d_4$): δ=8.19 (s, 1H), 7.95 (d, 1H), 7.82 (d, 1H), 7.73 (m, 1H), 7.64 (dd, 1H), 7.60-7.46 (m, 3H), 4.45 (m, 1H), 3.83 (m, 1H), 3.61 (m, 1H), 3.51-3.28 (m, 6H), 3.10 (m, 3H), 2.39 (m, 1H), 2.28 (m, 1H), 2.10 (m, 2H), 1.96 (m, 1H), 1.23 (m, 3H).

HPLC (method 1): $R_t$=4.00 min.

LC-MS (method 6): $R_t$=3.40 min.; m/z=447 (M+H)$^+$ (free base).

EXAMPLE 137

N-[(3R)-1-Azabicyclo[2.2.2]oct-3-yl]-7-[3-(2,5-dihydro-1H-pyrrol-1-ylcarbonyl)-phenyl]-1-benzothiophene-2-carboxamide hydrochloride

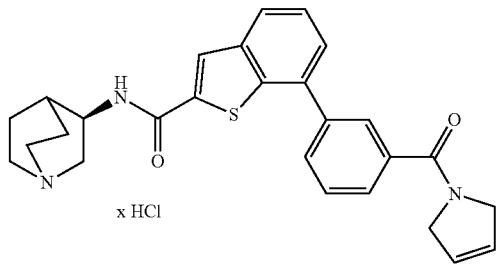 [SMILES: O=C(N[C@H]1CN2CCC1CC2)c1cc2cccc(-c3cccc(C(=O)N4CC=CC4)c3)c2s1]

50 mg (0.11 mmol) of 3-(2-{[(3R)-1-azabicyclo[2.2.2]oct-3-ylamino]carbonyl}-1-benzothien-7-yl)benzoic acid hydrochloride (Example 75) and 15.6 mg (0.23 mmol) of 3-pyrroline are reacted together by general method E. 20 mg (35.9% of theory) of the title compound are obtained.

HPLC (method 1): $R_t$=4.00 min.

LC-MS (method 6): $R_t$=3.40 min.; m/z=457 (M+H)$^+$ (free base).

EXAMPLE 138

N-[(3R)-Azabicyclo[2.2.2]oct-3-yl]-7-(3-{[(3-methoxypropyl)amino]carbonyl}-phenyl)-1-benzothiophene-2-carboxamide hydrochloride

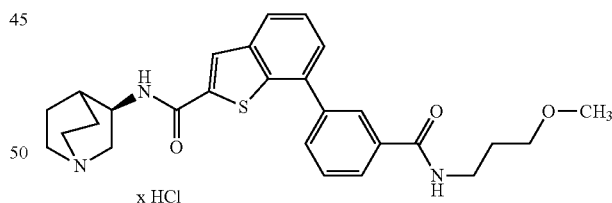

50 mg (0.11 mmol) of 3-(2-{[(3R)-1-azabicyclo[2.2.2]oct-3-ylamino]carbonyl}-1-benzothien-7-yl)benzoic acid hydrochloride (Example 75) and 20.1 mg (0.23 mmol) of 3-methoxypropylamine are reacted together by general method E. 29.2 mg (49.8% of theory) of the title compound are obtained.

HPLC (method 1): $R_t$=3.94 min.

LC-MS (method 6): $R_t$=3.37 min.; m/z=477 (M+H)⁺ (free base).

EXAMPLE 139

N-[(3R)-1-Azabicyclo[2.2.2]oct-3-yl]-7-(3-{[(2-methoxyethyl)(methyl)amino]-carbonyl}phenyl)-1-benzothiophene-2-carboxamide hydrochloride

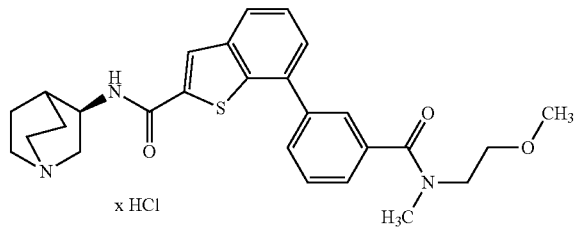

50 mg (0.11 mmol) of 3-(2-{[(3R)-1-azabicyclo[2.2.2]oct-3-ylamino]carbonyl}-1-benzothien-7-yl)benzoic acid hydrochloride (Example 75) and 20.1 mg (0.23 mmol) of (2-methoxyethyl)methylamine are reacted together by general method E. 20.5 mg (31.8% of theory) of the title compound are obtained.

HPLC (method 1): $R_t$=3.93 min.
LC-MS (method 6): $R_t$=3.35 min.; m/z=477 (M+H)⁺ (free base).

EXAMPLE 140

N-[(3R)-1-Azabicyclo[2.2.2]oct-3-yl]-7-(3-{[(3-ethoxypropyl)amino]carbonyl}-phenyl)-1-benzothiophene-2-carboxamide hydrochloride

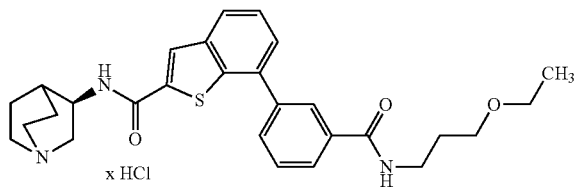 [SMILES: CCOCCCNC(=O)c1cccc(-c2cccc3cc(C(=O)N[C@H]4CN5CCC4CC5)sc23)c1]

50 mg (0:11 mmol) of 3-(2-{[(3R)-1-azabicyclo[2.2.2]oct-3-ylamino]carbonyl}-1-benzothien-7-yl)benzoic acid hydrochloride (Example 75) and 20.1 mg (0.23 mmol) of 3-ethoxypropylamine are reacted together by general method E. 23.4 mg (37.1% of theory) of the title compound are obtained.

¹H-NMR (400 MHz, methanol-d₄): δ=8.18 (s, 1H), 8.15 (s, 1H), 7.94 (d, 1H), 7.89 (m, 2H), 7.64 (dd, 1H), 7.56 (m, 2H), 4.45 (m, 1H), 3.84 (m, 1H), 3.55 (m, 2H), 3.53-3.25 (m, 9H), 2.39 (m, 1H), 2.28 (m, 1H), 2.10 (m, 2H), 1.96 (m, 1H), 1.91 (m, 2H), 1.17 (m, 3H).

HPLC (method 1): $R_t$=4.07 min.

LC-MS (method 6): $R_t$=3.46 min.; m/z=491 (M+H)⁺ (free base).

EXAMPLE 141

N-[(3R)-1-Azabicyclo[2.2.2]oct-3-yl]-7-{3-[(4-methyl-1-piperazinyl)carbonyl]-phenyl}-1-benzothiophene-2-carboxamide dihydrochloride

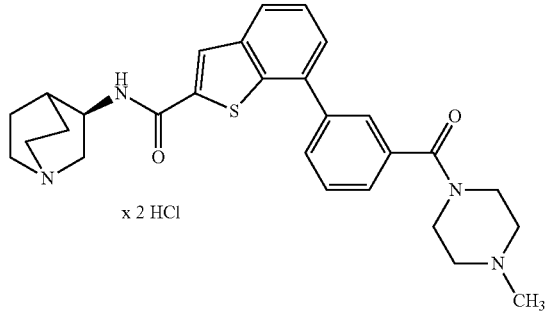 [SMILES: CN1CCN(C(=O)c2cccc(-c3cccc4cc(C(=O)N[C@H]5CN6CCC5CC6)sc34)c2)CC1]

50 mg (0.11 mmol) of 3-(2-{[(3R)-1-azabicyclo[2.2.2]oct-3-ylamino]carbonyl}-1-benzothien-7-yl)benzoic acid hydrochloride (Example 75) and 22.6 mg (0.23 mmol) of N-methylpiperazine are reacted together by general method E. 4.2 mg (6.6% of theory) of the title compound are obtained.

¹H-NMR (400 MHz, methanol-d₄): δ=8.23 (s, 1H), 7.97 (dd, 1H), 7.88 (m, 2H), 7.69 (m, 1H), 7.57 (m, 3H), 4.46 (m, 1H), 3.84 (m, 1H), 3.50 (m, 1H), 3.46-3.25 (m, 12H), 2.97 (s, 3H), 2.39 (m, 1H), 2.29 (m, 1H), 2.10 (m, 2H), 1.96 (m, 1H).

HPLC (method 1): $R_t$=3.62 min.
LC-MS (method 6): $R_t$=2.94 min.; m/z=488 (M+H)⁺ (free base).

EXAMPLE 142

N-[(3R)-1-Azabicyclo[2.2.2]oct-3-yl]-7-{3-[(cyclobutylcarbonyl)amino]phenyl}-1-benzothiophene-2-carboxamide hydrochloride

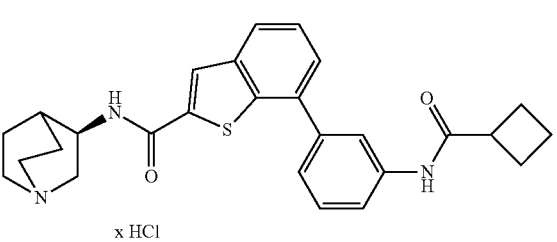 [SMILES: O=C(N[C@H]1CN2CCC1CC2)c1cc2cccc(-c3cccc(NC(=O)C4CCC4)c3)c2s1]

50 mg (0.12 mmol) of 7-(3-aminophenyl)-N-[(3R)-1-azabicyclo[2.2.2]oct-3-yl]-1-benzothiophene-2-carboxamide hydrochloride (Example 21) and 28.6 mg (0.24 mmol) of cyclobutanecarbonyl chloride are reacted together by general method F. 38 mg (61.3% of theory) of the title compound are obtained.

HPLC (method 1): $R_t$=4.22 min.

MS (ESIpos): m/z=460 (M+H)⁺ (free base).

EXAMPLE 143

N-[3-(2-{[(3R)-1-Azabicyclo[2.2.2]oct-3-ylamino] carbonyl}-1-benzothien-7-yl)-phenyl]-5-isoxazole-carboxamide hydrochloride

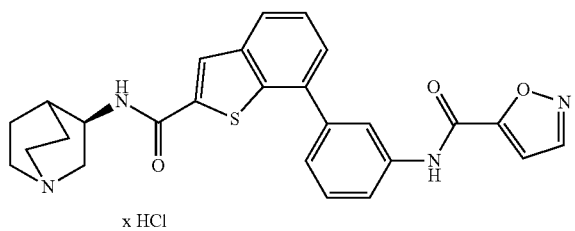 [SMILES: O=C(Nc1cccc(-c2cccc3cc(C(=O)N[C@H]4CN5CCC4CC5)sc23)c1)c1ccno1]

x HCl 50 mg (0.12 mmol) of 7-(3-aminophenyl)-N-[(3R)-1-azabicyclo[2.2.2]oct-3-yl]-1-benzothiophene-2-carboxamide hydrochloride (Example 21) and 31.8 mg (0.24 mmol) of isoxazole-5-carbonyl chloride are reacted together by general method F. 44.4 mg (72.6% of theory) of the title compound are obtained.

¹H-NMR (400 MHz, methanol-d₄): δ=8.58 (d, 1H), 8.18 (s, 2H), 7.93 (dd, 1H), 7.79 (m, 1H), 7.55 (m, 4H), 7.13 (m, 1H), 4.45 (m, 1H), 3.83 (m, 1H), 3.48 (m, 1H), 3.42-3.27 (m, 4H), 2.39 (m, 1H), 2.28 (m, 1H), 2.10 (m, 2H), 1.96 (m, 1H).

HPLC (method 1): R_f=4.12 min.

MS (ESIpos): m/z=473 (M+H)⁺ (free base).

EXAMPLE 144

N-[(3R)-1-Azabicyclo[2.2.2]oct-3-yl]-7-{3-[(cyclopentylcarbonyl)amino]phenyl}-1-benzothiophene-2-carboxamide hydrochloride

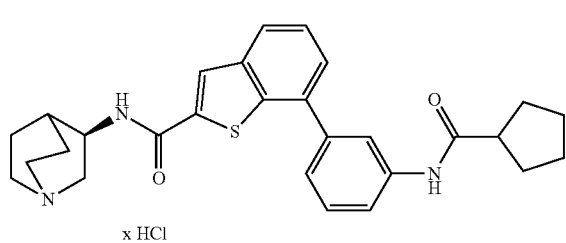 [SMILES: O=C(N[C@H]1CN2CCC1CC2)c1cc2cccc(-c3cccc(NC(=O)C4CCCC4)c3)c2s1]

x HCl 50 mg (0.12 mmol) of 7-(3-aminophenyl)-N-[(3R)-1-azabicyclo[2.2.2]oct-3-yl]-1-benzothiophene-2-carboxamide hydrochloride (Example 21) and 32 mg (0.24 mmol) of cyclopentylcarbonyl chloride are reacted together by general method F. 30.5 mg (52.8% of theory) of the title compound are obtained.

¹H-NMR (400 MHz, methanol-d₄): δ=8.17 (s, 1H), 8.03 (m, 1H), 7.91 (dd, 1H), 7.60 (m, 1H), 7.57-7.38 (m, 4H), 4.45 (m, 1H), 3.83 (m, 1H), 3.48 (m, 1H), 3.42-3.27 (m, 4H), 2.86 (m, 1H), 2.38 (m, 1H), 2.28 (m, 1H), 2.10 (m, 2H), 1.96 (m, 3H), 1.90-1.72 (m, 4H), 1.66 (m, 2H).

HPLC (method 1): R_f=4.40 min.

MS (ESIpos) m/z=474 (M+H)⁺ (free base).

EXAMPLE 145

N-[(3R)-1-Azabicyclo[2.2.2]oct-3-yl]-7-{3-[(cyclohexylcarbonyl)amino]phenyl}-1-benzothiophene-2-carboxamide hydrochloride

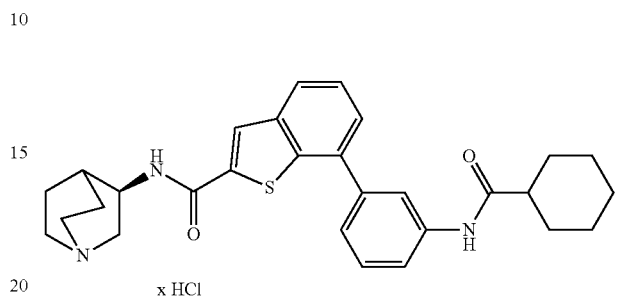

x HCl 50 mg (0.12 mmol) of 7-(3-aminophenyl)-N-[(3R)-1-azabicyclo[2.2.2]oct-3-yl]-1-benzothiophene-2-carboxamide hydrochloride (Example 21) and 35.4 mg (0.24 mmol) of cyclohexylcarbonyl chloride are reacted together by general method F. 9.8 mg (16.2% of theory) of the title compound are obtained.

HPLC (method 1): R_f=4.51 min.

MS (ESIpos): m/z=488 (M+H)⁺ (free base).

EXAMPLE 146

N-[(3R)-1-Azabicyclo[2.2.2]oct-3-yl]-7-{3-[(tetrahydro-2-furanylcarbonyl)amino]-phenyl}-1-benzothiophene-2-carboxamide hydrochloride

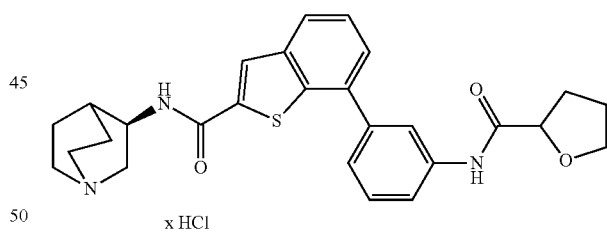

x HCl 50 mg (0.12 mmol) of 7-(3-aminophenyl)-N-[(3R)-1-azabicyclo[2.2.2]oct-3-yl]-1-benzothiophene-2-carboxamide hydrochloride (Example 21) and 32.5 mg (0.24 mmol) of tetrahydrofuran-2-carbonyl chloride are reacted together by general method F. 40.9 mg (68.1% of theory) of the title compound are obtained.

¹H-NMR (400 MHz, methanol-d₄): δ=8.17 (s, 1H), 8.04 (s, 1H), 7.91 (d, 1H), 7.61 (m, 1H), 7.58-7.40 (m, 4H), 4.46 (m, 1H), 4.04 (dd, 1H), 3.92 (m, 2H), 3.83 (m, 2H), 3.48 (m, 1H), 3.42-3.27 (m, 4H), 3.23 (m, 1H), 2.38 (m, 1H), 2.28 (m, 1H), 2.22 (m, 2H), 2.10 (m, 2H), 1.96 (m, 1H).

HPLC (method 1): R_f=3.99 min.

MS (ESIpos): m/z=476 (M+H)+ (free base).

EXAMPLE 147

N-[(3R)-1-Azabicyclo[2.2.2]oct-3-yl]-7-[3-(isobutyrylamino)phenyl]-1-benzothiophene-2-carboxamide hydrochloride

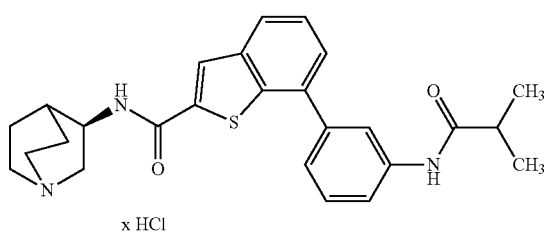 [SMILES: CC(C)C(=O)Nc1cccc(-c2cccc3cc(C(=O)N[C@H]4CN5CCC4CC5)sc23)c1]

50 mg (0.12 mmol) of 7-(3-aminophenyl)-N-[(3R)-1-azabicyclo[2.2.2]oct-3-yl]-1-benzothiophene-2-carboxamide hydrochloride (Example 21) and 25.7 mg (0.24 mmol) of isobutyryl chloride are reacted together by general method F. 35.1 mg (64.9% of theory) of the title compound are obtained.

$^1$H-NMR (400 MHz, methanol-$d_4$): δ=8.17 (s, 1H), 8.03 (s, 1H), 7.90 (d, 1H), 7.61 (m, 1H), 7.57-7.40 (m, 4H), 4.45 (m, 1H), 3.83 (m, 1H), 3.48 (m, 1H), 3.42-3.27 (m, 4H), 2.68 (m, 1H), 2.38 (m, 1H), 2.28 (m, 1H), 2.10 (m, 2H), 1.96 (m, 1H), 1.21 (d, 6H).

HPLC (method 1): $R_t$=4.19 min.
MS (ESIpos): m/z=448 (M+H)+ (free base).

EXAMPLE 148

N-[(3R)-1-Azabicyclo[2.2.2]oct-3-yl]-7-[3-(2-furoylamino)phenyl]-1-benzothiophene-2-carboxamide hydrochloride

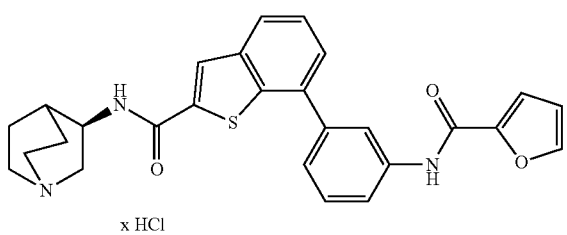 [SMILES: O=C(Nc1cccc(-c2cccc3cc(C(=O)N[C@H]4CN5CCC4CC5)sc23)c1)c1ccco1]

50 mg (0.12 mmol) of 7-(3-aminophenyl)-N-[(3R)-1-azabicyclo[2.2.2]oct-3-yl]-1-benzothiophene-2-carboxamide hydrochloride (Example 21) and 31.5 mg (0.24 mmol) of furan-2-carbonyl chloride are reacted together by general method F. 29.1 mg (51.1% of theory) of the title compound are obtained.

$^1$H-NMR (400 MHz, methanol-$d_4$): δ=8.17 (s, 2H), 7.91 (d, 1H), 7.74 (m, 2H), 7.58-7.47 (m, 4H), 7.29 (d, 1H), 6.65 (m, 1H), 4.44 (m, 1H), 3.83 (m, 1H), 3.47 (m, 1H), 3.42-3.27 (m, 4H), 2.38 (m, 1H), 2.28 (m, 1H), 2.10 (m, 2H); 1.96 (m, 1H).

HPLC (method 1): $R_t$=4.19 min.

MS (ESIpos): m/z=472 (M+H)+ (free base).

EXAMPLE 149

3-(2-{[(3R)-1-Azabicyclo[2.2.2]oct-3-ylamino]carbonyl}-1-benzofuran-7-yl)-benzoic acid hydrochloride

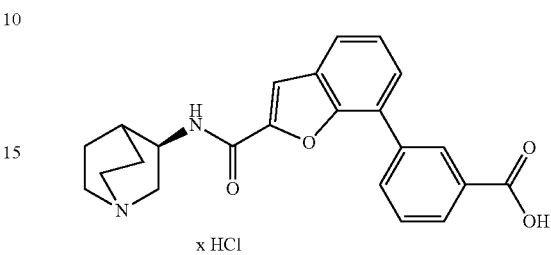

4.3 ml of 2 M aqueous sodium carbonate solution and 116.9 mg (0.14 mmol) of PdCl$_2$(dppf) are added to a mixture of 1104 mg (2.86 mmol) of N-[(3R)-1-azabicyclo[2.2.2]oct-3-yl]-7-bromo-1-benzofuran-2-carboxamide hydrochloride (Example 30A) and 475 mg (2.86 mmol) of 3-carboxyphenylboronic acid in 10 ml of DMF. The reaction mixture is heated at 90° C. for 18 h and then filtered through kieselguhr and evaporated to dryness. Purification of the crude product by preparative HPLC, subsequent addition of a 3:1 mixture of acetonitrile and 1N hydrochloric acid, concentrating and drying under high vacuum result in 724 mg (59.2% of theory) of the title compound.

$^1$H-NMR (400 MHz, methanol-$d_4$): δ=8.62 (s, 1H), 8.11 (d, 1H), 8.08 (d, 1H), 7.76 (d, 1H), 7.73-7.61 (m, 3H), 7.46 (dd, 1H), 4.49 (m, 1H), 3.83 (m, 1H), 3.48 (m, 1H), 3.43-3.27 (m, 4H), 2.40 (m, 1H), 2.28 (m, 1H), 2.10 (m, 2H), 1.96 (m, 1H).

HPLC (method 1): $R_t$=3.89 min.
MS (ESIpos): m/z=391 (M+H)+ (free base).

EXAMPLE 150

N-[(3R)-1-Azabicyclo[2.2.2]oct-3-yl]-7-[2-(hydroxymethyl)phenyl]-1-benzofuran-2-carboxamide hydrochloride

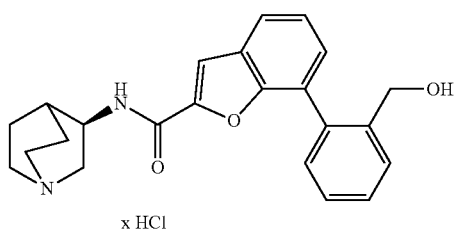 [SMILES: O=C(N[C@H]1CN2CCC1CC2)c1cc2cccc(-c3ccccc3CO)c2o1]

0.64 ml of 2 M aqueous sodium carbonate solution and 17.5 mg (0.02 mmol) of PdCl$_2$(dppf) are added to a mixture of 150 mg (0.43 mmol) of N-[(3R)-1-azabicyclo[2.2.2]oct-3-yl]-7-bromo-1-benzofuran-2-carboxamide hydrochloride (Example 30A) and 65.3 mg (0.43 mmol) of 2-(hydroxymethyl)phenylboronic acid in 1.5 ml of DMF. The reaction mixture is heated at 90° C. for 18 h and then filtered through kieselguhr and evaporated to dryness. Purification of the crude product by preparative HPLC, subsequent addition of a 3:1 mixture of acetonitrile and 1N hydrochloric acid, concentration and drying under high vacuum result in 13 mg (7.1% of theory) of the title compound.

HPLC (method 1): R$_t$=3.87 min.

MS (ESIpos): m/z=377 (M+H)$^+$ (free base).

EXAMPLE 151

N-[(3R)-1-Azabicyclo[2.2.2]oct-3-yl]-7-(2,5-dimethoxyphenyl)-1-benzofuran-2-carboxamide hydrochloride

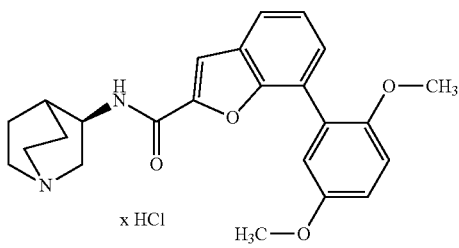 [SMILES: COc1ccc(OC)c(-c2cccc3cc(C(=O)N[C@H]4CN5CCC4CC5)oc23)c1]

0.78 ml of 2 M aqueous sodium carbonate solution and 21.2 mg (0.03 mmol) of PdCl$_2$(dppf) are added to a mixture of 200 mg (0.52 mmol) of N-[(3R)-1-azabicyclo[2.2.2]oct-3-yl]-7-bromo-1-benzofuran-2-carboxamide hydrochloride (Example 30A) and 94.4 mg (0.52 mmol) of 2,5-dimethoxyphenylboronic acid in 2 ml of DMF. The reaction mixture is heated at 70° C. for 17 h and then filtered through kieselguhr and evaporated to dryness. Purification of the crude product by preparative HPLC, subsequent addition of a 3:1 mixture of methanol and 1N hydrochloric acid, concentration and drying under high vacuum result in 75 mg (31.7% of theory) of the title compound.

HPLC (method 1): R$_t$=4.15 min.

MS (ESIpos): m/z=407 (M+H)$^+$ (free base).

EXAMPLE 152

7-[2-(Aminomethyl)phenyl]-N-[(3R)-1-azabicyclo[2.2.2]oct-3-yl]-1-benzofuran-2-carboxamide dihydrochloride

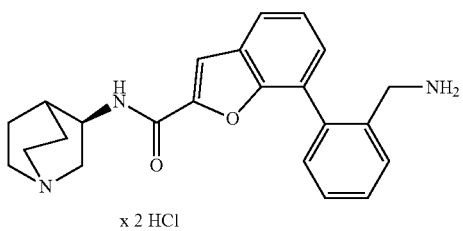 [SMILES: NCc1ccccc1-c1cccc2cc(C(=O)N[C@H]3CN4CCC3CC4)oc12]

500 mg (1.75 mmol) of tert-butyl 2-bromobenzylcarbamate, 512 mg (2.02 mmol) of bis(pinacolato)diboron, 428.7 mg (4.37 mmol) of potassium acetate, 49.2 mg (0.07 mmol) of PdCl$_2$(dppf), 518.4 mg (1.34 mmol) of N-[(3R)-1-azabicyclo[2.2.2]oct-3-yl]-7-bromo-1-benzofuran-2-carboxamide hydrochloride (Example 30A), 3.36 ml of 2 M sodium carbonate solution and a further 49.2 mg (0.07 mmol) of PdCl$_2$ (dppf) in 5 ml of DMF are reacted by general method D. The crude product which has been dried under high vacuum is stirred in 8 ml of a 1:1 mixture of methanol and 4 M hydrogen chloride in dioxane at room temperature for 2 h. The reaction solution is concentrated and the resulting crude product is purified by preparative HPLC. The product fractions are concentrated and, after addition of a 3:1 mixture of methanol and 1N hydrochloric acid, again concentrated and dried under high vacuum. 245.5 mg (44.5% of theory) of the title compound are obtained.

$^1$H-NMR (300 MHz, DMSO-d$_6$): δ=10.48 (br. s, 1H), 9.26 (d, 1H), 8.47 (br. s, 3H), 8.05 (s, 1H), 7.88 (dd, 1H), 7.80 (d, 1H), 7.62-7.40 (m, 5H), 4.31 (m, 1H), 3.86 (m, 2H), 3.48 (m, 1H), 3.51-3.10 (m, 5H), 2.18 (m, 1H), 2.11 (m, 1H), 1.90 (m, 2H), 1.71 (m, 1H).

HPLC (method 7): R$_t$=3.55 min.

MS (ESIpos): m/z=376 (M+H)$^+$ (free base).

EXAMPLE 153

3-(2-{[[(3S)-1-Azabicyclo[2.2.2]oct-3-ylamino]carbonyl}-1-benzofuran-7-yl)-benzoic acid hydrochloride

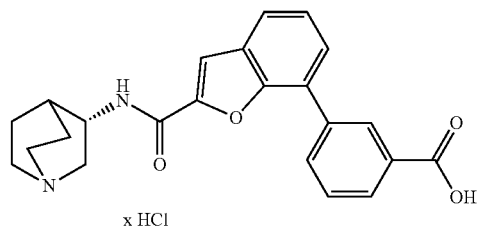 [SMILES: O=C(O)c1cccc(-c2cccc3cc(C(=O)N[C@@H]4CN5CCC4CC5)oc23)c1]

3.89 ml of 2 M aqueous sodium carbonate solution and 105.9 mg (0.13 mmol) of PdCl$_2$(dppf) are added to a mixture of 1000 mg (2.59 mmol) of N-[(3S)-1-azabicyclo[2.2.2]oct-3-yl]-7-bromo-1-benzofuran-2-carboxamide hydrochloride (free base: Example 31A) and 430.2 mg (2.59 mmol) of 3-carboxyphenylboronic acid in. 8 ml of DMF. The reaction mixture is heated at 70° C. for 18 h and then filtered through kieselguhr and evaporated to dryness. Purification of the crude product by preparative HPLC, subsequent addition of a 3:1 mixture of methanol and 1N hydrochloric acid, concentration and drying under high vacuum result in 142.5 mg 1.5 (12% of theory) and a further 627.9 mg (of 80% purity) of the title compound.

The spectroscopic data agree with those of the enantiomeric compound (Example 149).

EXAMPLE 154

N-[(3R)-1-Azabicyclo[2.2.2]oct-3-yl]-7-{3-[(cyclopropylamino)carbonyl]phenyl}-1-benzofuran-2-carboxamide hydrochloride

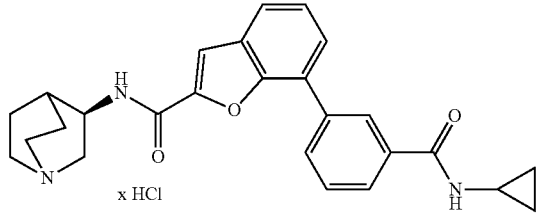 [SMILES: O=C(NC1CC1)c1cccc(-c2cccc3cc(C(=O)N[C@H]4CN5CCC4CC5)oc23)c1]

50 mg (0.12 mmol) of 3-(2-{[(3R)-1-azabicyclo[2.2.2]oct-3-ylamino]carbonyl}-1-benzofuran-7-yl)benzoic acid hydrochloride (Example 149) and 13.4 mg (0.23 mmol) of cyclopropylamine are reacted together by general method E. 20 mg (32.2% of theory) of the title compound are obtained.

HPLC (method 1): $R_t$=3.93 min.

LC-MS (method 6): $R_t$=3.33 min.; m/z=429 (M+H)$^+$ (free base).

EXAMPLE 155

N-[(3R)-1-Azabicyclo[2.2.2]oct-3-yl]-7-(3-{[ethyl(methyl)amino]carbonyl}phenyl)-1-benzofuran-2-carboxamide hydrochloride

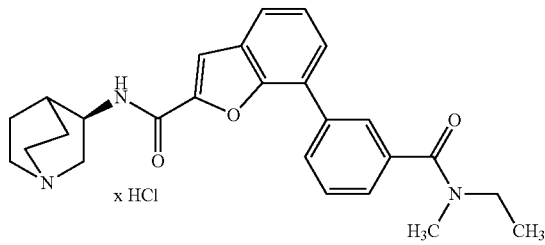 [SMILES: CCN(C)C(=O)c1cccc(-c2cccc3cc(C(=O)N[C@H]4CN5CCC4CC5)oc23)c1]

50 mg (0.12 mmol) of 3-(2-{[(3R)-1-azabicyclo[2.2.2]oct-3-ylamino]carbonyl}-1-benzofuran-7-yl)benzoic acid hydrochloride (Example 149) and 13.9 mg (0.23 mmol) of methylethylamine are reacted together by general method E. 19.8 mg (29.4% of theory) of the title compound are obtained.

HPLC (method 1): $R_t$=4.03 min.

LC-MS (method 6): $R_t$=3.38 min.; m/z=431 (M+H)$^+$ (free base).

EXAMPLE 156

N-[(3R)-1-Azabicyclo[2.2.2]oct-3-yl]-7-{3-[(butylamino)carbonyl]phenyl}-1-benzofuran-2-carboxamide hydrochloride

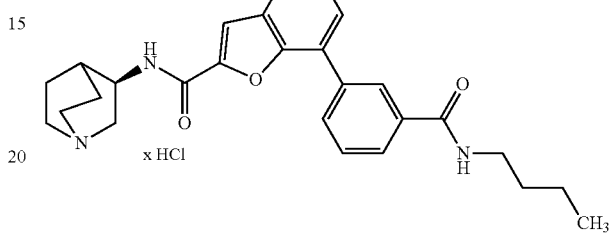

50 mg (0.12 mmol) of 3-(2-{[(3R)-1-azabicyclo[2.2.2]oct-3-ylamino]carbonyl}-1-benzofuran-7-yl)benzoic acid hydrochloride (Example 149) and 17.1 mg (0.23 mmol) of n-butylamine are reacted together by general method E. 15.2 mg (26.2% of theory) of the title compound are obtained.

HPLC (method 1): $R_t$=4.21 min.

LC-MS (method 6): $R_t$=3.49 min.; m/z=445 (M+H)$^+$ (free base).

EXAMPLE 157

N-[(3R)-1-Azabicyclo[2.2.2]oct-3-yl]-7-{3-[(isobutylamino)carbonyl]phenyl}-1-benzofuran-2-carboxamide hydrochloride

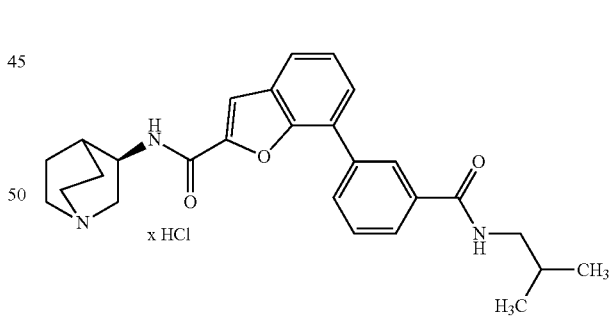

50 mg (0.12 mmol) of 3-(2-{[(3R)-azabicyclo[2.2.2]oct-3-ylamino]carbonyl}-1-benzofuran-7-yl)benzoic acid hydrochloride (Example 149) and 17.1 mg (0.23 mmol) of isobutylamine are reacted together by general method E. 15.2 mg (26.9% of theory) of the title compound are obtained.

HPLC (method 1): $R_t$=4.18 min.

LC-MS (method 6): $R_t$=3.49 min.; m/z=445 (M+H)$^+$ (free base).

EXAMPLE 158

N-[(3R)-1-Azabicyclo[2.2.2]oct-3-yl]-7-[3-(1-piperidinylcarbonyl)phenyl]-1-benzofuran-2-carboxamide hydrochloride

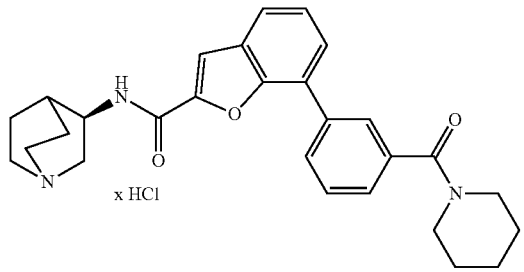 [SMILES: O=C(N[C@H]1CN2CCC1CC2)c1cc2cccc(-c3cccc(C(=O)N4CCCCC4)c3)c2o1]

50 mg (0.12 mmol) of 3-(2-{[(3R)-1-azabicyclo[2.2.2]oct-3-ylamino]carbonyl}-1-benzofuran-7-yl)benzoic acid hydrochloride (Example 149) and 20.0 mg (0.23 mmol) of piperidine are reacted together by general method E. 16.4 mg (27.6% of theory) of the title compound are obtained.

HPLC (method 1): $R_t$=4.22 min.

LC-MS (method 6): $R_t$=3.51 min.; m/z=457 (M+H)$^+$ (free base).

EXAMPLE 159

N-[(3R)-1-Azabicyclo[2.2.2]oct-3-yl]-7-[3-({[2-(dimethylamino)ethyl]amino}-carbonyl)phenyl]-1-benzofuran-2-carboxamide hydrochloride

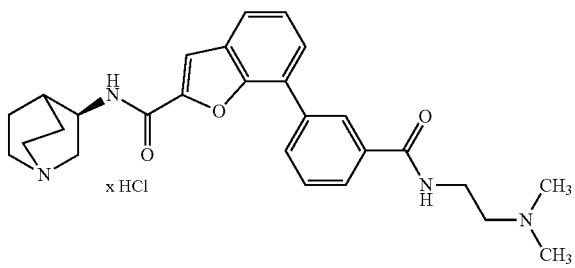 [SMILES: CN(C)CCNC(=O)c1cccc(-c2cccc3cc(C(=O)N[C@H]4CN5CCC4CC5)oc23)c1]

50 mg (0.12 mmol) of 3-(2-{[(3R)-1-azabicyclo[2.2.2]oct-3-ylamino]carbonyl}-1-benzofuran-7-yl)benzoic acid hydrochloride (Example 149) and 20.7 mg (0.23 mmol) of N-(2-aminoethyl)-N,N-dimethylamine are reacted together by general method E. 17.4 mg (24.8% of theory) of the title compound are obtained.

HPLC (method 1): $R_t$=3.64 min.

LC-MS (method 6): $R_t$=2.93 min.; m/z=460 (M+H)$^+$ (free base).

EXAMPLE 160

N-[(3R)-1-Azabicyclo[2.2.2]oct-3-yl]-7-(3-{[(3-methoxypropyl)amino]carbonyl}-phenyl)-1-benzofuran-2-carboxamide hydrochloride

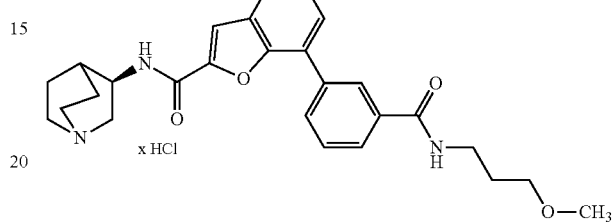

50 mg (0.12 mmol) of 3-(2-{[(3R)-1-azabicyclo[2.2.2]oct-3-ylamino]carbonyl}-1-benzofuran-7-yl)benzoic acid hydrochloride (Example 149) and 20.9 mg (0.23 mmol) of 3-methoxypropylamine are reacted together by general method E. 22.7 mg (36.4% of theory) of the title compound are obtained.

HPLC (method 1): $R_t$=3.93 min.

LC-MS (method 6): $R_t$=3.36 min.; m/z=461 (M+H)$^+$ (free base).

EXAMPLE 161

N-[(3R)-1-Azabicyclo[2.2.2]oct-3-yl]-7-(3-{[(2-methoxyethyl)(methyl)amino]-carbonyl}phenyl)-1-benzofuran-2-carboxamide hydrochloride

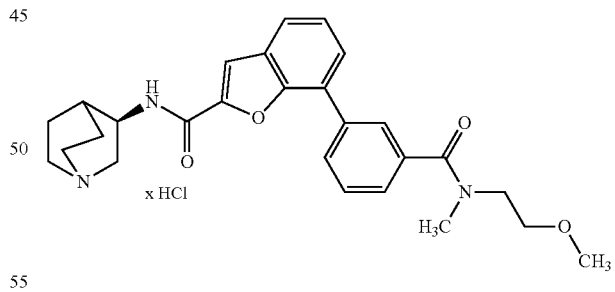

50 mg (0.12 mmol) of 3-(2-{[(3R)-1-azabicyclo[2.2.2]oct-3-ylamino]carbonyl}-1-benzofuran-7-yl)benzoic acid hydrochloride (Example 149) and 20.9 mg (0.23 mmol) of N-(2-methoxyethyl)-N-methylamine are reacted together by general method E. 20.4 mg (31.3% of theory) of the title compound are obtained.

HPLC (method 1): $R_t$=3.96 min.

LC-MS (method 6): $R_t$=3.34 min.; m/z=461 (M+H)$^+$ (free base).

EXAMPLE 162

N-[(3R)-1-Azabicyclo[2.2.2]oct-3-yl]-7-(3-{[(3-ethoxypropyl)amino]carbonyl}-phenyl)-1-benzofuran-2-carboxamide hydrochloride

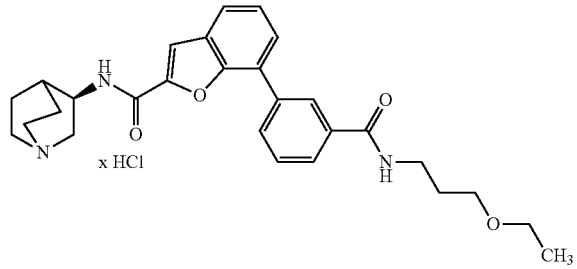 [SMILES: CCOCCCNC(=O)c1cccc(-c2cccc3cc(C(=O)N[C@H]4CN5CCC4CC5)oc23)c1]

50 mg (0.12 mmol) of 3-(2-{[(3R)-1-azabicyclo[2.2.2]oct-3-ylamino]carbonyl}-1-benzofuran-7-yl)benzoic acid hydrochloride (Example 149) and 24.2 mg (0.23 mmol) of 3-ethoxypropylamine are reacted together by general method E. 17.8 mg (28.9% of theory) of the title compound are obtained.

HPLC (method 1): $R_t$=4.06 min.

LC-MS (method 6): $R_t$=3.43 min.; m/z=475 (M+H)$^+$ (free base).

EXAMPLE 163

N-[(3R)-1-Azabicyclo[2.2.2]oct-3-yl]-7-{3-[(4-methyl-1-piperazinyl)carbonyl]-phenyl}-1-benzofuran-2-carboxamide dihydrochloride

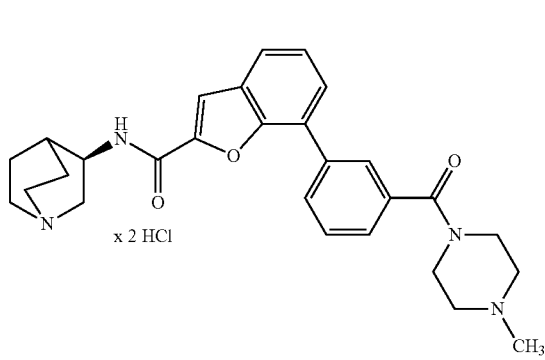 [SMILES: CN1CCN(C(=O)c2cccc(-c3cccc4cc(C(=O)N[C@H]5CN6CCC5CC6)oc34)c2)CC1]

50 mg (0.12 mmol) of 3-(2-{[(3R)-1-azabicyclo[2.2.2]oct-3-ylamino]carbonyl}-1-benzofuran-7-yl)benzoic acid hydrochloride (Example 149) and 23.5 mg (0.23 mmol) of N-methylpiperazine are reacted together by general method E. 29.6 mg (41.9% of theory) of the title compound are obtained.

HPLC (method 1): $R_t$=3.60 min.

LC-MS (method 6): $R_t$=2.91 min.; m/z=472 (M+H)$^+$ (free base).

EXAMPLE 164

N-[(3S)-1-Azabicyclo[2.2.2]oct-3-yl]-7-(3-{[ethyl(methyl)amino]carbonyl}phenyl)-1-benzofuran-2-carboxamide hydrochloride

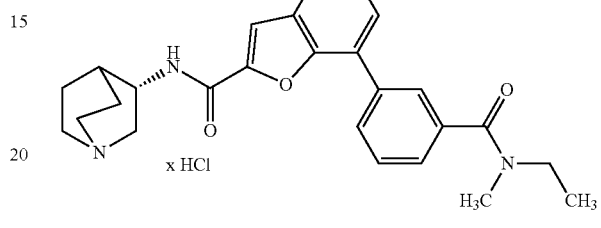

50 mg (0.12 mmol) of 3-(2-{[(3S)-1-azabicyclo[2.2.2]oct-3-ylamino]carbonyl}-1-benzofuran-7-yl)benzoic acid hydrochloride (Example 153) and 13.9 mg (0.23 mmol) of methylethylamine are reacted together by general method E. 50.1 mg (91.4% of theory) of the title compound are obtained.

The spectroscopic data agree with those of the enantiomeric compound (Example 155).

EXAMPLE 165

N-[(3S)-1-Azabicyclo[2.2.2]oct-3-yl]-7-{3-[(butylamino)carbonyl]phenyl}-1-benzofuran-2-carboxamide hydrochloride

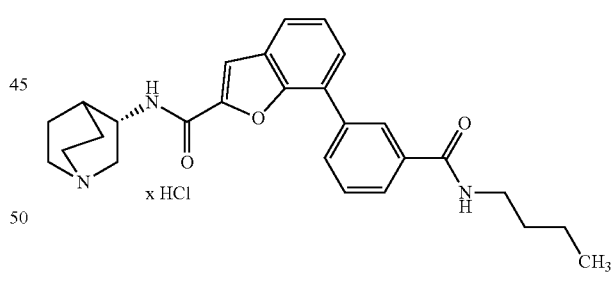

50 mg (0.12 mmol) of 3-(2-{[(3S)-1-azabicyclo[2.2.2]oct-3-ylamino]carbonyl}-1-benzofuran-7-yl)benzoic acid hydrochloride (Example 153) and 17.1 mg (0.23 mmol) of n-butylamine are reacted together by general method E. 49.4 mg (87.5% of theory) of the title compound are obtained.

The spectroscopic data agree with those of the enantiomeric compound (Example 156).

EXAMPLE 166

N-[(3S)-1-Azabicyclo[2.2.2]oct-3-yl]-7-{3-[(isobutylamino)carbonyl]phenyl}-1-benzofuran-2-carboxamide hydrochloride

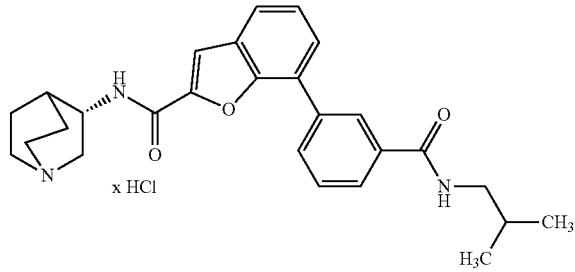 [SMILES: CC(C)CNC(=O)c1cccc(-c2cccc3cc(C(=O)N[C@@H]4CN5CCC4CC5)oc23)c1]

50 mg (0.12 mmol) of 3-(2-{[(3S)-1-azabicyclo[2.2.2]oct-3-ylamino]carbonyl}-1-benzofuran-7-yl)benzoic acid hydrochloride (Example 153) and 17.1 mg (0.23 mmol) of iso-butylamine are reacted together by general method E. 40.3 mg (71.4% of theory) of the title compound are obtained.

The spectroscopic data agree with those of the enantiomeric compound (Example 157).

EXAMPLE 167

N-[(3S)-1-Azabicyclo[2.2.2]oct-3-yl]-7-[3-(1-piperidinylcarbonyl)phenyl]-1-benzofuran-2-carboxamide hydrochloride

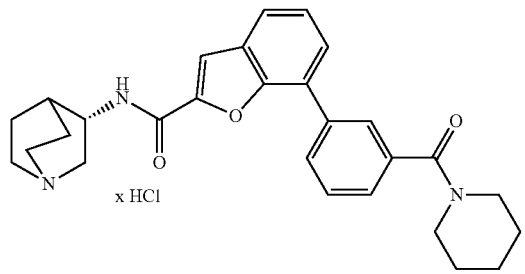 [SMILES: O=C(N[C@@H]1CN2CCC1CC2)c1cc2cccc(-c3cccc(C(=O)N4CCCCC4)c3)c2o1]

50 mg (0.12 mmol) of 3-(2-{[(3S)-1-azabicyclo[2.2.2]oct-3-ylamino]carbonyl}-1-benzofuran-7-yl)benzoic acid hydrochloride (Example 153) and 20.0 mg (0.23 mmol) of piperidine are reacted together by general method E. 29.7 mg (49.9% of theory) of the title compound are obtained.

The spectroscopic data agree with those of the enantiomeric compound (Example 158).

EXAMPLE 168

N-[(3S)-1-Azabicyclo[2.2.2]oct-3-yl]-7-[3-({[2-(dimethylamino)ethyl]amino}-carbonyl)phenyl]-1-benzofuran-2-carboxamide hydrochloride

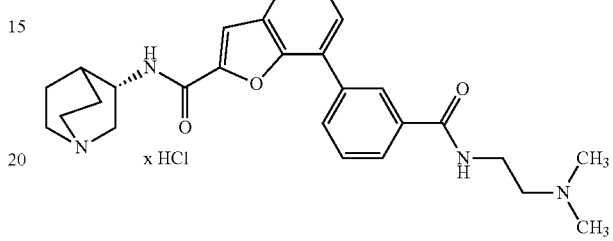

50 mg (0.12 mmol) of 3-(2-{[(3S)-1-azabicyclo[2.2.2]oct-3-ylamino]carbonyl}-1-benzofuran-7-yl)benzoic acid hydrochloride (Example 153) and 20.7 mg (0.23 mmol) of N-(2-aminoethyl)-N,N-dimethylamine are reacted together by general method E. 42.5 mg (64.5% of theory) of the title compound are obtained.

The spectroscopic data agree with those of the enantiomeric compound (Example 159).

EXAMPLE 169

N-[(3S)-1-Azabicyclo[2.2.2]oct-3-yl]-7-(3-{[(3-methoxypropyl)amino]carbonyl}-phenyl)-1-benzofuran-2-carboxamide hydrochloride

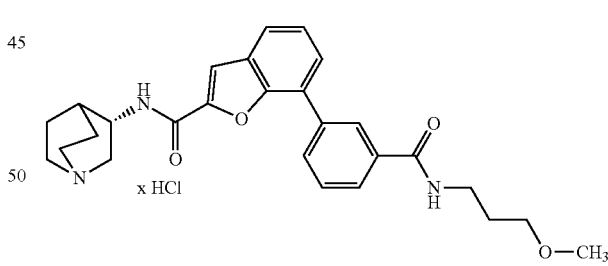

50 mg (0.12 mmol) of 3-(2-{[(3S)-1-azabicyclo[2.2.2]oct-3-ylamino]carbonyl}-1-benzofuran-7-yl)benzoic acid hydrochloride (Example 153) and 20.9 mg (0.23 mmol) of 3-methoxypropylamine are reacted together by general method E. 29.8 mg (44.5% of theory) of the title compound are obtained.

The spectroscopic data agree with those of the enantiomeric compound (Example 160):

EXAMPLE 170

N-[(3S)-1-Azabicyclo[2.2.2]oct-3-yl]-7-(3-{[(2-methoxyethyl)(methyl)amino]-carbonyl}phenyl)-1-benzofuran-2-carboxamide hydrochloride

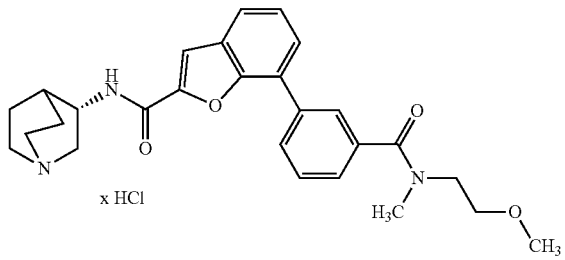 [SMILES: COCCN(C)C(=O)c1cccc(-c2cccc3cc(C(=O)N[C@@H]4CN5CCC4CC5)oc23)c1]

50 mg (0.12 mmol) of 3-(2-{[(3S)-1-azabicyclo[2.2.2]oct-3-ylamino]carbonyl}-1-benzofuran-7-yl)benzoic acid hydrochloride (Example 153) and 20.9 mg (0.23 mmol) of N-(2-methoxyethyl)-N-methylamine are reacted together by general method E. 22.1 mg (35.1% of theory) of the title compound are obtained.

The spectroscopic data agree with those of the enantiomeric compound (Example 161).

EXAMPLE 171

N-[(3S)-1-Azabicyclo[2.2.2]oct-3-yl]-7-(3-({[(3-ethoxypropyl)amino]carbonyl}-phenyl)-1-benzofuran-2-carboxamide hydrochloride

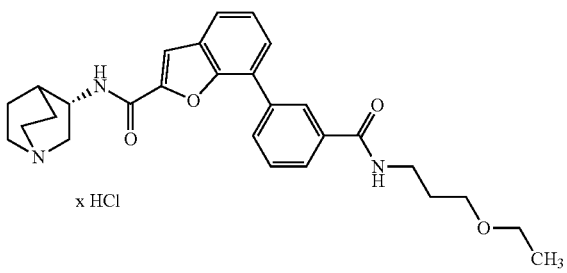 [SMILES: CCOCCCNC(=O)c1cccc(-c2cccc3cc(C(=O)N[C@@H]4CN5CCC4CC5)oc23)c1]

50 mg (0.12 mmol) of 3-(2-{[(3S)-1-azabicyclo[2.2.2]oct-3-ylamino]carbonyl}-1-benzofuran-7-yl)benzoic acid hydrochloride (Example 153) and 24.2 mg (0.23 mmol) of 3-ethoxypropylamine are reacted together by general method E. 23.6 mg (36.9% of theory) of the title compound are obtained.

The spectroscopic data agree with those of the enantiomeric compound (Example 162).

EXAMPLE 172

N-[(3S)-1-Azabicyclo[2.2.2]oct-3-yl]-7-{3-[(4-methyl-1-piperazinyl)carbonyl]-phenyl}-1-benzofuran-2-carboxamide dihydrochloride

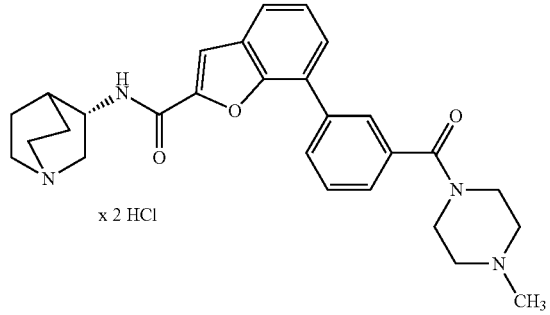 [SMILES: CN1CCN(C(=O)c2cccc(-c3cccc4cc(C(=O)N[C@@H]5CN6CCC5CC6)oc34)c2)CC1]

50 mg (0.12 mmol) of 3-(2-{[(3S)-1-azabicyclo[2.2.2]oct-3-ylamino]carbonyl}-1-benzofuran-7-yl)benzoic acid hydrochloride (Example 153) and 23.5 mg (0.23 mmol) of N-methylpiperazine are reacted together by general method E. 9.2 mg (15.4% of theory) of the title compound are obtained.

The spectroscopic data agree with those of the enantiomeric compound (Example 163).

EXAMPLE 173

N-[(3R)-1-Azabicyclo[2.2.2]oct-3-yl]-7-[3-(1-pyrrolidinyl)phenyl]-1-benzofuran-2-carboxamide hydrochloride

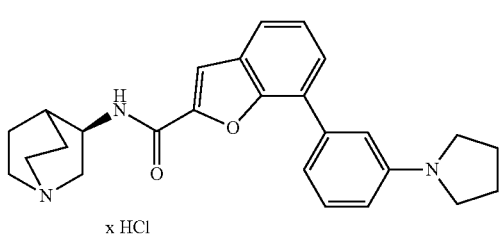 [SMILES: O=C(N[C@H]1CN2CCC1CC2)c1cc2cccc(-c3cccc(N4CCCC4)c3)c2o1]

114.3 mg (0.51 mmol) of 1-(3-bromophenyl)pyrrolidine, 148.1 mg (0.58 mmol) of bis(pinacolato)diboron, 124.1 mg (1.26 mmol) of potassium acetate, 14.2 mg (0.02 mmol) of $PdCl_2$(dppf), 150 mg (0.39 mmol) of N-[(3R)-1-azabicyclo[2.2.2]oct-3-yl]-7-bromo-1-benzofuran-2-carboxamide hydrochloride (Example 30A), 0.97 ml of 2 M sodium carbonate solution and a further 14.2 mg (0.02 mmol) of $PdCl_2$(dppf) in 2.0 ml of DMF are reacted by general method D. Drying under high vacuum results in 95.6 mg (54.4% of theory) of the title compound.

HPLC (method 1): $R_f$=3.85 min.

MS (ESIpos): m/z=416 (M+H)+ (free base).

EXAMPLE 174

7-[2-(Aminomethyl)phenyl]-N-[(3S)-azabicyclo[2.2.2]oct-3-yl]-1-benzofuran-2-carboxamide dihydrochloride

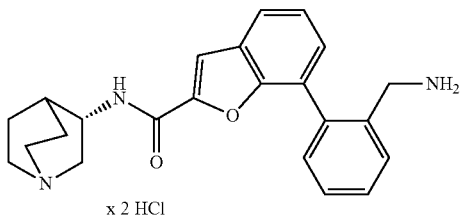 [SMILES: NCc1ccccc1-c1cccc2cc(C(=O)N[C@@H]3CN4CCC3CC4)oc12]

x 2 HCl 500 mg (1.75 mmol) of tert-butyl 2-bromobenzylcarbamate, 512 mg (2.02 mmol) of bis(pinacolato)diboron, 428.7 mg (4.37 mmol) of potassium acetate, 49.2 mg (0.07 mmol) of PdCl$_2$(dppf), 518.4 mg (1.34 mmol) of N-[(3S)-1-azabicyclo[2.2.2]oct-3-yl]-7-bromo-1-benzofuran-2-carboxamide hydrochloride (free base: Example 31A), 3.36 ml of 2 M sodium carbonate solution and a further 49.2 mg (0.07 mmol) of PdCl$_2$(dppf) in 5 ml of DMF are reacted by general method D. The crude product which has been dried under high vacuum is stirred in 4 ml of a 1:1 mixture of methanol and 4 M hydrogen chloride in dioxane at room temperature for 2 h. The reaction solution is concentrated, and the resulting crude product is purified by preparative HPLC. The product fractions are concentrated and, after addition of a 3:1 mixture of methanol and 1N hydrochloric acid, again concentrated and dried under high vacuum. 121.6 mg (22.4% of theory) of the title compound are obtained.

The spectroscopic data agree with those of the enantiomeric compound (Example 152).

EXAMPLE 175

N-[(3R)-1-Azabicyclo[2.2.2]oct-3-yl]-7-[2-({[(methylamino)carbonyl]amino}-methyl)phenyl]-1-benzofuran-2-carboxamide hydrochloride

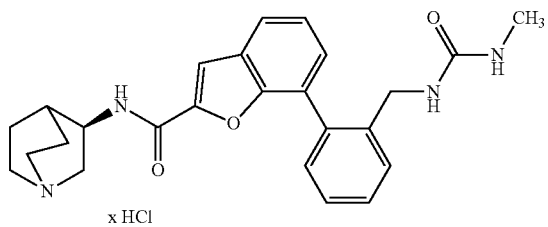 [SMILES: CNC(=O)NCc1ccccc1-c1cccc2cc(C(=O)N[C@H]3CN4CCC3CC4)oc12]

x HCl 62.2 μl (0.45 mmol) of triethylamine and 53 μl (0.89 mmol) of methyl isocyanate are added to a solution of 100 mg (0.22 mmol) of 7-[2-(aminomethyl)phenyl]-N-[(3R)-1-azabicyclo[2.2.2]oct-3-yl]-1-benzofuran-2-carboxamide dihydrochloride (Example 152) in 1 ml of a 5:1 mixture of THF and DMF. After 18 h at room temperature, the reaction mixture is concentrated and purified by preparative HPLC. The product fractions are concentrated and, after addition of a 3:1 mixture of methanol and 1N hydrochloric acid, again concentrated and dried under high vacuum. 75 mg (66% of theory) of the title compound are obtained.

$^1$H-NMR (400 MHz, methanol-d$_4$): δ=7.78 (m, 1H), 7.68 (s, 1H), 7.52-7.30 (m, 6H), 4.47 (m, 1H), 4.23 (m, 2H), 3.77 (m, 1H), 3.53-3.25 (m, 5H), 2.69 (s, 3H), 2.37 (m, 1H), 2.20 (m, 1H), 2.08 (m, 2H), 1.88 (m, 1H).

HPLC (method 1): R$_t$=3.78 min.

MS (ESIpos): m/z=433 (M+H)+ (free base).

EXAMPLE 176

N-[(3S)-1-Azabicyclo[2.2.2]oct-3-yl]-7-[2-({[(methylamino)carbonyl]amino}-methyl)phenyl]-1-benzofuran-2-carboxamide hydrochloride

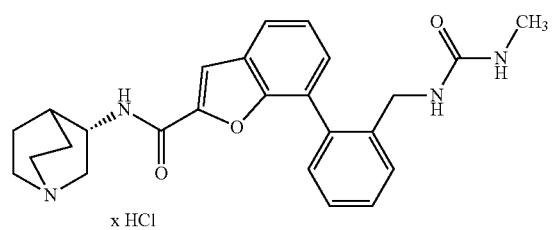 [SMILES: CNC(=O)NCc1ccccc1-c1cccc2cc(C(=O)N[C@@H]3CN4CCC3CC4)oc12]

x HCl

36 μl (0.26 mmol) of triethylamine and 29.5 μl (0.52 mmol) of methyl isocyanate are added to a solution of 57.9 mg (0.13 mmol) of 7-[2-(aminomethyl)phenyl]-N-[(3S)-1-azabicyclo[2.2.2]oct-3-yl]-1-benzofuran-2-carboxamide dihydrochloride (Example 174) in 0.7 ml of a 5:1 mixture of THF and DMF. After 18 h at room temperature, the reaction mixture is concentrated and purified by preparative HPLC. The product fractions are concentrated and, after addition of a 3:1 mixture of methanol and 1N hydrochloric acid, again concentrated and dried under high vacuum. 49.2 mg (81.2% of theory) of the title compound are obtained.

The spectroscopic data agree with those of the enantiomeric compound (Example 175).

EXAMPLE 177

N-[(3R)-1-Azabicyclo[2.2.2]oct-3-yl]-7-{3-[(2,2-dimethylpropanoyl)amino]phenyl}-1-benzofuran-2-carboxamide hydrochloride

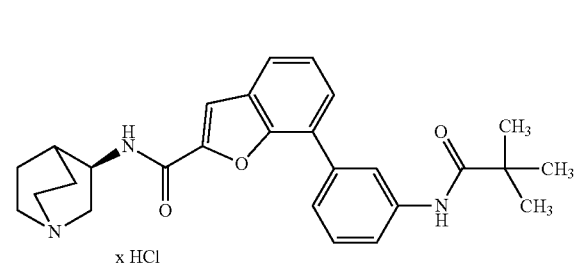 [SMILES: CC(C)(C)C(=O)Nc1cccc(-c2cccc3cc(C(=O)N[C@H]4CN5CCC4CC5)oc23)c1]

x HCl 50 mg (0.14 mmol) of 7-(3-aminophenyl)-N-[(3R)-1-azabicyclo[2.2.2]oct-3-yl]-1-benzofuran-2-carboxamide (Example 114) and 33.4 mg (0.28 mmol) of pivaloyl chloride are reacted together by general method F. 15.2 mg (20.7% of theory) of the title compound are obtained.

HPLC (method 1): R$_t$=4.30 min.

MS (ESIpos): m/z=446 (M+H)⁺ (free base).

EXAMPLE 178

N-[3-(2-{[(3R)-1-Azabicyclo[2.2.2]oct-3-ylamino]carbonyl}-1-benzofuran-7-yl)-phenyl]-5-isoxazolecarboxamide hydrochloride

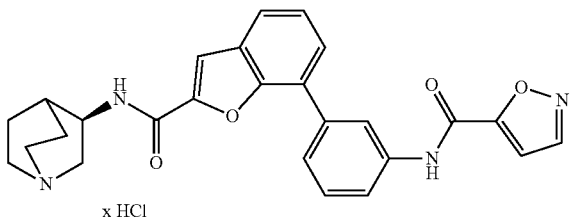 [SMILES: O=C(Nc1cccc(-c2cccc3cc(C(=O)N[C@H]4CN5CCC4CC5)oc23)c1)c1ccno1]

50 mg (0.14 mmol) of 7-(3-aminophenyl)-N-[(3R)-1-azabicyclo[2.2.2]oct-3-yl]-1-benzofuran-2-carboxamide (Example 114) and 36.4 mg (0.28 mmol) of 5-isoxazolecarbonyl chloride are reacted together by general method F. 39.6 mg (53.3% of theory) of the title compound are obtained.

HPLC (method 1): $R_t$=4.18 min.

MS (ESIpos): m/z=457 (M+H)⁺ (free base).

EXAMPLE 179

N-[(3R)-1-Azabicyclo[2.2.2]oct-3-yl]-7-{3-[(cyclopentylcarbonyl)amino]phenyl}-1-benzofuran-2-carboxamide hydrochloride

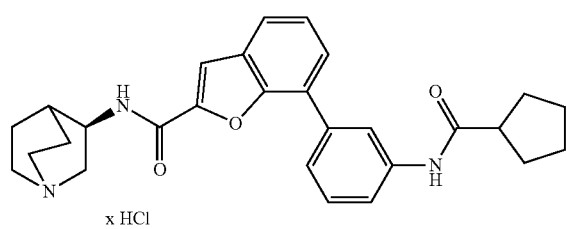 [SMILES: O=C(N[C@H]1CN2CCC1CC2)c1cc2cccc(-c3cccc(NC(=O)C4CCCC4)c3)c2o1]

50 mg (0.14 mmol) of 7-(3-aminophenyl)-N-[(3R)-1-azabicyclo[2.2.2]oct-3-yl]-1-benzofuran-2-carboxamide (Example 114) and 36.7 mg (0.28 mmol) of cyclopentanecarbonyl chloride are reacted together by general method F. 33.2 mg (45.1% of theory) of the title compound are obtained.

HPLC (method 1): $R_t$=4.38 min.

MS (ESIpos): m/z=458 (M+H)⁺ (free base).

EXAMPLE 180

N-[(3R)-1-Azabicyclo[2.2.2]oct-3-yl]-7-[3-(isobutyrylamino)phenyl]-1-benzofuran-2-carboxamide hydrochloride

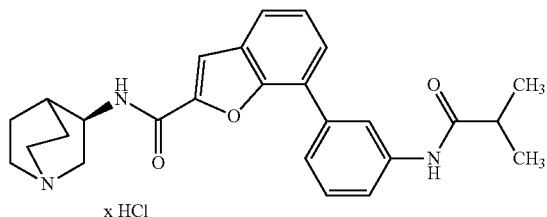 [SMILES: CC(C)C(=O)Nc1cccc(-c2cccc3cc(C(=O)N[C@H]4CN5CCC4CC5)oc23)c1]

50 mg (0.14 mmol) of 7-(3-aminophenyl)-N-[(3R)-1-azabicyclo[2.2.2]oct-3-yl]-1-benzofuran-2-carboxamide (Example 114) and 29.5 mg (0.28 mmol) of isobutyryl chloride are reacted together by general method F. 12.8 mg (19.5% of theory) of the title compound are obtained.

HPLC (method 1): $R_t$=4.19 min.

MS (ESIpos): m/z=432 (M+H)⁺ (free base).

EXAMPLE 181

N-[(3R)-1-Azabicyclo[2.2.2]oct-3-yl]-7-[3-(2-furoylamino)phenyl]-1-benzofuran-2-carboxamide hydrochloride

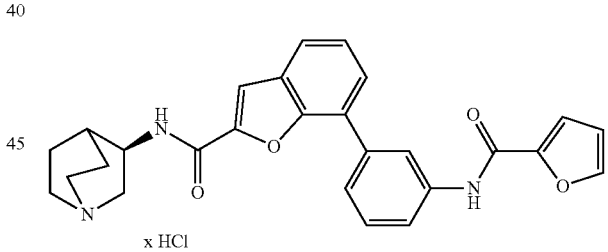

50 mg (0.14 mmol) of 7-(3-aminophenyl)-N-[(3R)-1-azabicyclo[2.2.2]oct-3-yl]-1-benzofuran-2-carboxamide (Example 114) and 36.1 mg (0.28 mmol) of furan-2-carbonyl chloride are reacted together by general method F. 7.4 mg (10.6% of theory) of the title compound are obtained.

HPLC (method 1): $R_t$=4.27 min.

MS (ESIpos): m/z=456 (M+H)⁺ (free base).

EXAMPLE 182

N-[(3R)-1-Azabicyclo[2.2.2]oct-3-yl]-7-(2-methoxyphenyl)-1-benzofuran-2-carboxamide acetate

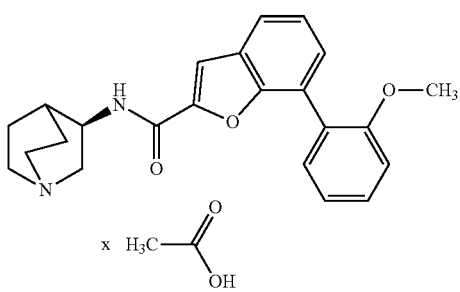

95.9 mg (0.25 mmol) of N-[(3R)-1-azabicyclo[2.2.2]oct-3-yl]-7-(2-methoxyphenyl)-1-benzofuran-2-carboxamide (Example 130) are dissolved in 2 ml of methanol. After addition of 15.3 mg (0.25 mmol) of acetic acid, the mixture is concentrated and the residue is dried under high vacuum. 114.9 mg (99.7% of theory) of the title compound are obtained.

¹H-NMR (200 MHz, DMSO-$d_6$): δ=8.37 (d, 1H), 7.74 (dd, 1H), 7.71 (s, 1H), 7.50-7.33 (m, 4H), 7.20 (d, 1H), 7.08 (m, 1H), 3.93 (m, 1H), 3.76 (s, 3H), 3.10 (m, 1H), 2.87 (m, 1H), 2.78-2.60 (m, 4H), 1.90 (s, 3H), 1.87 (m, 1H), 1.75 (m, 1H), 1.58 (m, 2H), 1.33 (m, 1H).

EXAMPLE 183

N-[(3R)-1-Azabicyclo[2.2.2]oct-3-yl]-7-(2-methoxyphenyl)-1-benzofuran-2-carboxamide tosylate

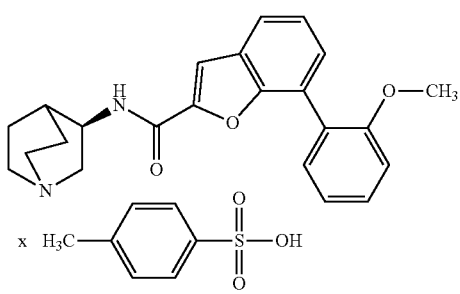

95.9 mg (0.25 mmol) of N-[(3R)-1-azabicyclo[2.2.2]oct-3-yl]-7-(2-methoxyphenyl)-1-benzofuran-2-carboxamide (Example 130) are dissolved in 2 ml of methanol. After addition of 49.2 mg (0.25 mmol) of p-toluenesulphonic acid, the mixture is concentrated and the residue is dried under high vacuum. 143 mg (99.4% of theory) of the title compound are obtained.

¹H-NMR (200 MHz, DMSO-$d_6$): δ=9.34 (br. s, 1H), 8.70 (d, 1H), 7.77 (dd, 1H), 7.72 (s, 1H), 7.52-7.35 (m, 6H), 7.21 (d, 1H), 7.15-7.04 (m, 3H), 4.30 (m, 1H), 3.76 (s, 3H), 3.68 (m, 1H), 3.33-3.11 (m, 5H), 2.29 (s, 3H), 2.19 (m, 1H), 2.07 (m, 1H), 1.91 (m, 2H), 1.74 (m, 1H).

EXAMPLE 184

N-[(3R)-1-Azabicyclo[2.2.2]oct-3-yl]-7-(2-methoxyphenyl)-1-benzofuran-2-carboxamide fumarate

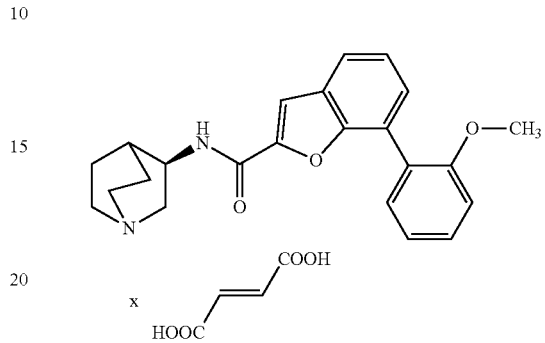

95.9 mg (0.25 mmol) of N-[(3R)-1-azabicyclo[2.2.2]oct-3-yl]-7-(2-methoxyphenyl)-1-benzofuran-2-carboxamide (Example 130) are dissolved in 1.5 ml of acetone. After addition of 29.6 mg (0.25 mmol) of fumaric acid in 1 ml of hot isopropanol, the mixture is stirred at 50° C. for 30 min and then concentrated, and the residue is dried under high vacuum. 124.2 mg (99% of theory) of the title compound are obtained.

¹H-NMR (200 MHz, DMSO-$d_6$): δ=8.62 (d, 1H), 7.76 (dd, 1H), 7.72 (s, 1H), 7.49-7.33 (m, 4H), 7.21 (d, 1H), 7.09 (m, 1H), 6.50 (s, 2H), 4.16 (m, 1H), 3.76 (s, 3H), 3.38 (m, 1H), 3.11 (m, 1H), 3.06-2.85 (m, 4H), 2.03 (m, 1H), 1.92 (m, 1H), 1.76 (m, 2H), 1.56 (m, 1H).

EXAMPLE 185

N-[(3R)-1-Azabicyclo[2.2.2]oct-3-yl]-7-(2-methoxyphenyl)-1-benzofuran-2-carboxamide oxalate

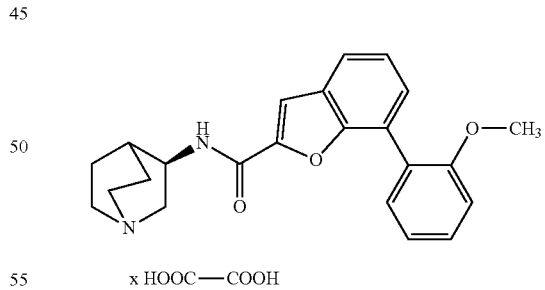

95.9 mg (0.25 mmol) of N-[(3R)-1-azabicyclo[2.2.2]oct-3-yl]-7-(2-methoxyphenyl)-1-benzofuran-2-carboxamide (Example 130) are dissolved in 1.5 ml of acetone. After addition of 22.9 mg (0.25 mmol) of oxalic acid in 1 ml of hot isopropanol, the mixture is stirred at 50° C. for 30 min and then concentrated, and the residue is dried under high vacuum. 117.6 mg (99% of theory) of the title compound are obtained.

¹H-NMR (200 MHz, DMSO-$d_6$): δ=8.75 (d, 1H), 7.77 (dd, 1H), 7.72 (s, 1H), 7.50-7.33 (m, 4H), 7.20 (d, 1H), 7.09 (m,

1H), 4.28 (m, 1H), 3.75 (s, 3H), 3.62 (m, 1H), 3.32-3.08 (m, 5H), 2.17 (m, 1H), 2.04 (m, 1H), 1.89 (m, 2H), 1.71 (m, 1H).

EXAMPLE 186

N-[(3R)-1-Azabicyclo[2.2.2]oct-3-yl]-7-(2-hydroxyphenyl)-1-benzofuran-2-carboxamide

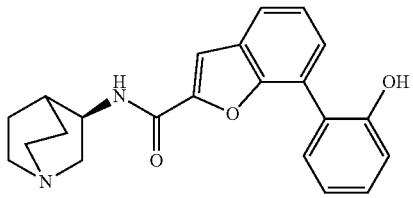 [SMILES: O=C(N[C@H]1CN2CCC1CC2)c1cc2cccc(-c3ccccc3O)c2o1]

2.42 ml of a 1 M boron tribromide solution in dichloromethane are added dropwise to a suspension, cooled to −20° C., of 200 mg (0:48 mmol) of N-[(3R)-1-azabicyclo[2.2.2]oct-3-yl]-7-(2-methoxyphenyl)-1-benzofuran-2-carboxamide hydrochloride (Example 102) in 8 ml of dichloromethane. After 2 h, the reaction is stopped by adding diethyl ether. The mixture is stirred at room temperature for 30 min and, after addition of water, neutralized with 1N sodium hydroxide solution. After extraction with ethyl acetate, the organic phases are combined and dried over sodium sulphate. Concentration and drying under high vacuum result in 125.9 mg (71.7% of theory) of the title compound.

HPLC (method 1): $R_t$=3.84 min.
MS (ESIpos): m/z=363 (M+H)$^+$.

EXAMPLE 187

(3R)-3-({[7-(2-Methoxyphenyl)-1-benzofuran-2-yl]carbonyl}amino)-1-methyl-1-azoniabicyclo[2.2.2]octane chloride

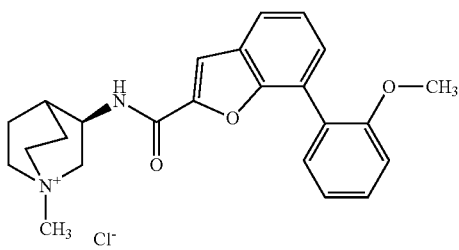 [SMILES: COc1ccccc1-c1cccc2cc(C(=O)N[C@H]3C[N+]4(C)CCC3CC4)oc12 ; [Cl-]]

60.5 mg (1.51 mmol) of sodium hydride (60% suspension in mineral oil) are added to a solution, cooled to −20° C., of 250 mg (0.61 mmol) of N-[(3R)-1-azabicyclo[2.2.2]oct-3-yl]-7-(2-methoxyphenyl)-1-benzofuran-2-carboxamide hydrochloride (Example 102) in 2.5 ml of DMF. After 30 min at room temperature and renewed cooling to −20° C., 33.9 μl (0.54 mmol) of iodomethane are added. After 18 h at room temperature, the reaction is stopped by adding water. The reaction mixture is purified by preparative HPLC. The product fractions are concentrated, codistilled with 1N hydrochloric acid, again concentrated and dried under high vacuum. 206 mg (79.7% of theory) of the title compound are obtained.

$^1$H-NMR (200 MHz, DMSO-d$_6$): δ=9.23 (d, 1H), 8.02 (s, 1H), 7.77 (d; 1H), 7.46 (dd, 1H), 7.39 (m, 3H), 7.20 (d, 1H), 7.09 (dd, 1H), 4.32 (m, 1H), 3.83 (m, 1H), 3.75 (s, 3H), 3.63 (m, 1H), 3.49-3.33 (m, 4H), 2.96 (s, 3H), 2.27 (m, 1H), 2.20 (m, 1H), 1.97 (m, 2H), 1.83 (m, 1H).

HPLC (method 1): $R_t$=4.19 min.
MS (ESIpos): m/z=391 (M+H)$^+$.

EXAMPLE 188

(3R)-1-Benzyl-3-({[7-(2-methoxyphenyl)-1-benzofuran-2-yl]carbonyl}amino)-1-azoniabicyclo[2.2.2]octane bromide

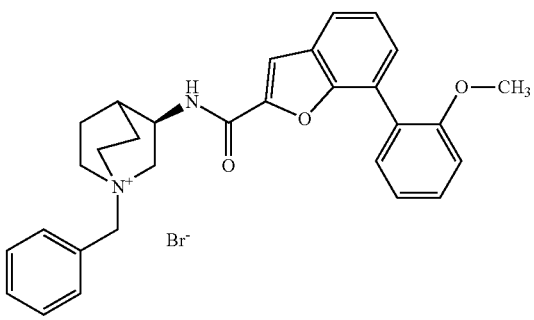 [SMILES: COc1ccccc1-c1cccc2cc(C(=O)N[C@H]3C[N+]4(Cc5ccccc5)CCC3CC4)oc12 ; [Br-]]

288 μl (2.42 mmol) of benzyl bromide and 502 mg (3.63 mmol) of potassium carbonate are added to a solution of 500 mg (1.21 mmol) of N-[(3R)-1-azabicyclo[2.2.2]oct-3-yl]-7-(2-methoxyphenyl)-1-benzofuran-2-carboxamide hydrochloride (Example 102) in 12.5 ml of DMF. After 20 h at 50° C., the reaction mixture is purified by preparative HPLC. The product fractions are concentrated and, after addition of 50% strength hydrobromic acid, again concentrated and dried under high vacuum. Recrystallization from cyclohexane/acetone affords 537 mg (77% of theory) of the title compound.

HPLC (method 1): $R_t$=4.44 min.
MS (ESIpos): m/z=467 (M+H)$^+$.

EXAMPLE 189

(3R)-3-[{[7-(2-Methoxyphenyl)-1-benzofuran-2-yl]carbonyl}(methyl)amino]-1-methyl-1-azoniabicyclo[2.2.2]octane chloride

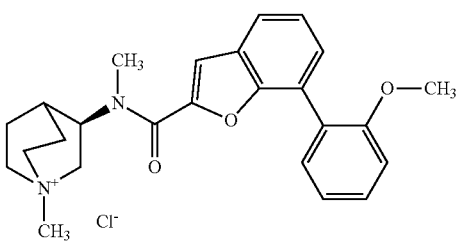 [SMILES: COc1ccccc1-c1cccc2cc(C(=O)N(C)[C@H]3C[N+]4(C)CCC3CC4)oc12 ; [Cl-]]

84.8 mg (2.12 mmol) of sodium hydride (60% suspension in mineral oil) are added to a solution, cooled to −20° C., of 250 mg (0.61 mmol) of N-[(3R)-1-azabicyclo[2.2.2]oct-3-yl]-7-(2-methoxyphenyl)-1-benzofuran-2-carboxamide hydrochloride (Example 102) in 2.5 ml of DMF. After 30 min at room temperature and renewed cooling to −20° C., 94.2 μl (1.51 mmol) of iodomethane are added. After 18 h at room temperature, the reaction is stopped by adding water. The reaction mixture is purified by preparative HPLC. The product fractions are concentrated, codistilled with a 1:1 mixture of methanol and 4 M hydrogen chloride in dioxane, again concentrated and dried under high vacuum. 58 mg (21.7% of theory) of the title compound are obtained.

HPLC (method 1): $R_t$=4.17 min.
MS (ESIpos): m/z=405 (M+H)$^+$.

EXAMPLE 190

7-(2-Methoxyphenyl)-N-[(3R)-1-oxido-1-azabicyclo[2.2.2]oct-3-yl]-1-benzofuran-2-carboxamide

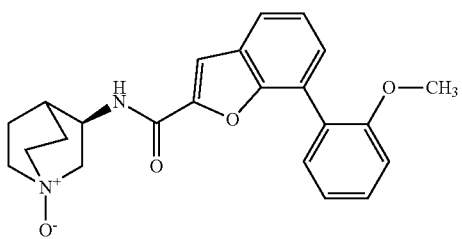 [SMILES: COc1ccccc1-c1cccc2cc(C(=O)N[C@H]3C[N+]4([O-])CCC3CC4)oc12]

35.8 μl (0.35 mmol) of 30% strength hydrogen peroxide are added to a solution, cooled to 0° C., of 110 mg (0.29 mmol) of N-[(3R)-1-azabicyclo[2.2.2]oct-3-yl]-7-(2-methoxyphenyl)-1-benzofuran-2-carboxamide (Example 130) in 2 ml of methanol. After 18 h at room temperature, a further 35.8 μl (0.35 mmol) of 30% strength hydrogen peroxide are added. After a further 18 h at room temperature, the reaction solution is concentrated, and the residue is dried under high vacuum. 111.5 mg (97.2% of theory) of the title compound are obtained.

$^1$H-NMR (400 MHz, methanol-$d_4$): δ=7.69 (d, 1H), 7.59 (s, 1H), 7.41 (m, 3H), 7.37 (dd, 1H), 7.16 (d, 1H), 7.08 (dd, 1H), 4.57 (m, 1H), 3.78 (s, 3H), 3.75 (m, 1H), 3.43-3.30 (m, 5H), 2.22 (m, 2H), 2.13 (m, 2H), 1.99 (m, 1H).
HPLC (method 1): $R_t$=4.18 min.
MS (ESIpos): m/z=393 (M+H)$^+$.

EXAMPLE 191

N-[(3R)-1-Azabicyclo[2.2.2]oct-3-yl]-6-[3-(4-morpholinylmethyl)phenyl]-1-benzothiophene-2-carboxamide dihydrochloride

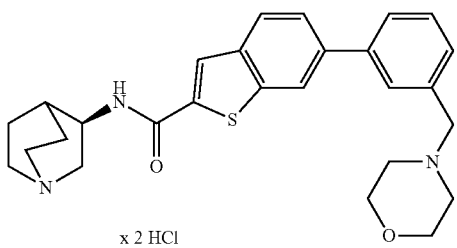 [SMILES: O=C(N[C@H]1CN2CCC1CC2)c1cc2ccc(-c3cccc(CN4CCOCC4)c3)cc2s1]

290 mg (3.32 mmol) of morpholine and 31 mg (0.50 mmol) of sodium cyanoborohydride are successively added to a solution of 80 mg (0.17 mmol) of N-[(3R)-1-azabicyclo[2.2.2]oct-3-yl]-6-(3-formylphenyl)-1-benzothiophene-2-carboxamide hydrochloride (Example 33A) in 1.0 ml of a 6:1 mixture of methanol and acetic acid. After 18 h at. 80° C., purification is carried out by preparative HPLC.

The product fractions are concentrated and, after addition of a 5:1 mixture of methanol and 1N hydrochloric acid, again concentrated: Drying under high vacuum results in 47 mg (49.8% of theory) of the title compound.

HPLC (method 1): $R_t$=3.64 min.
MS (ESIpos): m/z=462 (M+H)$^+$ (free base).

EXAMPLE 192

7-(5-Acetyl-2-thienyl)-N-[(3R)-1-azabicyclo[2.2.2]oct-3-yl]-1-benzofuran-2-carboxamide hydrochloride

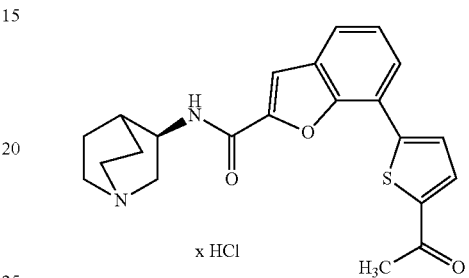

0.58 ml of 2 M aqueous sodium carbonate solution and 15.9 mg (0.02 mmol) of PdCl$_2$(dppf) are added to a mixture of 150 mg (0.39 mmol) of N-[(3R)-1-azabicyclo[2.2.2]oct-3-yl]-7-bromo-1-benzofuran-2-carboxamide hydrochloride (Example 30A) and 66.1 mg (0.39 mmol) of 5-acetyl-2-thienylboronic acid in 2 ml of DMF. The reaction mixture is heated at 70° C. for 18 h and then filtered through kieselguhr and evaporated to dryness. Purification of the crude product by preparative HPLC, subsequent addition of a 1:1 mixture of methanol and 1N hydrochloric acid, concentration and drying under high vacuum result in 83.6 mg (49.9% of theory) of the title compound.

$^1$H-NMR (400 MHz, DMSO-$d_6$): δ=10.29 (br. s, 1H), 9.10 (d, 1H), 8.07 (m, 2H), 7.95 (m, 1H), 7.93 (d, 1H), 7.87 (d, 1H), 7.46 (dd, 1H), 4.38 (m, 1H), 3.63 (m, 1H), 3.40 (m, 2H), 3.23 (m, 3H), 2.60 (s, 3H), 2.27 (m, 1H), 2.16 (m, 1H), 1.94 (m, 2H), 1.77 (m, 1H).
HPLC (method 1): $R_t$=3.99 min.
MS (ESIpos): m/z=495 (M+H)$^+$ (free base).

The invention claimed is:

1. A method for improving memory in patient in need thereof, comprising administering to the patient a therapeutically effective amount of a compound represented by a compound of formula (I):

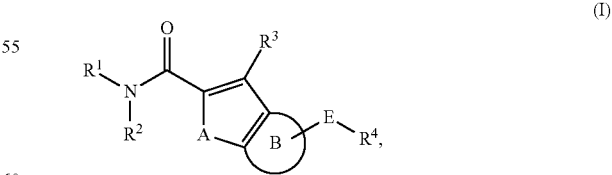

wherein:
R$^1$ is 1-azabicyclo[2.2.2]oct-3-yl, which is optionally substituted via the nitrogen atom by a radical selected from the group of C$_1$-C$_4$-alkyl, benzyl and oxy,
R$^2$ is hydrogen or C$_1$-C$_6$-alkyl,
R$^3$ is hydrogen, halogen or C$_1$-C$_6$-alkyl, R[4] is hydrogen, halogen, cyano, amino, trifluoromethyl, trifluoromethoxy, $C_1$-$C_6$-alkyl, $C_1$-$C_6$-alkylcarbonyl, $C_1$-$C_6$-alkylamino, formyl, hydroxycarbonyl, $C_1$-$C_6$-alkoxy, $C_1$-$C_6$-alkoxycarbonyl, $C_1$-$C_6$-alkylthio, $C_1$-$C_6$-alkylcarbonylamino, $C_1$-$C_6$-alkylaminocarbonyl, $C_1$-$C_4$-alkylsulphonylamino, $C_3$-$C_8$-cycloalkylcarbonylamino, $C_3$-$C_6$-cycloalkylaminocarbonyl, pyrrolyl, $C_1$-$C_6$-alkylaminocarbonylamino, hydroxyl, phenyl morpholinyl, oxypiperidinyl, oxopyrrolidinyl, oxomorpholinyl, pyrrolidinyl, morpholinylcarbonyl, piperidinyl, pyridinyl, dihydropyrrolylcarbonyl, $C_1$-$C_6$-alkylpiperizinylcarbonyl, isoxazolecarbonylamino, tetrahydrofuranylcarbonylamino, furoylamino, piperidinylcarbonyl, or piperidinylcarbonyl,
  where $C_1$-$C_6$-alkyl may optionally be substituted by hydroxyl, cyano, amino, $C_1$-$C_6$-alkylaminocarbonylamino, $C_1$-$C_6$-alkylaminocarboxyl, morpholinyl or aryl,
  $C_1$-$C_6$-alkylaminocarbonyl may optionally be substituted by $C_1$-$C_6$-alkoxy or $C_1$-$C_6$-alkylamino, and
  $C_1$-$C_6$-alkylcarbonylamino may optionally be substituted by $C_1$-$C_6$-alkoxy,
A is oxygen or sulphur,
the ring B is benzo or pyrido, each of which are optionally substituted by radicals from the series halogen, cyano, formyl, trifluoromethyl, trifluoromethoxy, nitro, amino, $C_1$-$C_6$-alkyl and $C_1$-$C_6$-alkoxy,
and
E is C≡C, phenylene, thienylene, oxadizolylene, pyrrolylene, furanylene, pyrimidinylene, or pyridinylene wherein each ring system respectively may be substituted by radicals from the series halogen, cyano, trifluoromethyl, trifluoromethoxy, nitro, amino, $C_1$-$C_6$-alkoxy and $C_1$-$C_6$-alkyl,
or a salt thereof.

2. The method of claim 1, wherein the patient suffers from Alzheimer's disease or schizophrenia.

3. The method of claim 1, wherein:
R[1] is 1-azabicyclo[2.2.2]oct-3-yl,
R[2] is hydrogen or $C_1$-$C_4$-alkyl,
R[3] is hydrogen, fluorine, chlorine, bromine or $C_1$-$C_4$-alkyl,
R[4] is hydrogen, fluorine, chlorine, bromine, cyano, amino, trifluoromethyl, trifluoromethoxy, $C_1$-$C_4$-alkyl, $C_1$-$C_4$-alkylcarbonyl, $C_1$-$C_4$-alkylamino, formyl, hydroxycarbonyl, $C_1$-$C_4$-alkoxy, $C_1$-$C_4$-alkoxycarbonyl, $C_1$-$C_4$-alkylthio, $C_1$-$C_4$-alkylcarbonylamino, $C_1$-$C_4$-alkylaminocarbonyl, $C_1$-$C_4$-alkylsulphonylamino, $C_3$-$C_6$-cycloalkylcarbonylamino, $C_3$-$C_6$-cycloalkylaminocarbonyl, pyrrolyl, $C_1$-$C_4$-alkylaminocarbonylamino, hydroxyl, phenyl morpholinyl, oxypiperidinyl, oxopyrrolidinyl, oxomorpholinyl, pyrrolidinyl, morpholinylcarbonyl, piperidinyl, pyridinyl, dihydropyrrolylcarbonyl, $C_1$-$C_4$-alkylpiperizinylcarbonyl, isoxazolecarbonylamino, tetrahydrofuranylcarbonylamino, furoylamino, piperidinylcarbonyl, or piperidinylcarbonyl,
  where $C_1$-$C_4$-alkyl may optionally be substituted by hydroxyl, cyano, amino, $C_1$-$C_4$-alkylaminocarbonylamino, $C_1$-$C_4$-alkylaminocarboxyl, morpholinyl or aryl,
  $C_1$-$C_4$-alkylaminocarbonyl may optionally be substituted by $C_1$-$C_4$-alkoxy or $C_1$-$C_4$-alkylamino, and
  $C_1$-$C_4$-alkylcarbonylamino may optionally be substituted by $C_1$-$C_4$-alkoxy,
A is oxygen or sulphur,
the ring B is benzo or pyrido, each of which are optionally substituted by radicals from the series halogen, cyano, trifluoromethyl, trifluoromethoxy and $C_1$-$C_4$-alkyl,
and
E is C≡C, phenylene, thienylene, oxadizolylene, pyrrolylene, furanylene, pyrimidinylene, or pyridinylene wherein each ring system respectively may be substituted by radicals from the series halogen, cyano, trifluoromethyl, trifluoromethoxy, nitro, amino, $C_1$-$C_4$-alkoxy and $C_1$-$C_4$-alkyl
or a salt thereof.

4. The method of claim 1, wherein:
R[1] is 1-azabicyclo[2.2.2]oct-3-yl,
R[2] and R[3] are hydrogen,
R[4] is hydrogen, fluorine, chlorine, bromine, cyano, amino, trifluoromethyl, trifluoromethoxy, $C_1$-$C_4$-alkyl, $C_1$-$C_4$-alkylcarbonyl, $C_1$-$C_4$-alkylamino, formyl, hydroxycarbonyl, $C_1$-$C_4$-alkoxy, $C_1$-$C_4$-alkoxycarbonyl, $C_1$-$C_6$-alkylthio, $C_1$-$C_4$-alkylcarbonylamino, $C_1$-$C_4$-alkylaminocarbonyl, $C_1$-$C_4$-alkylsulphonylamino, $C_3$-$C_6$-cycloalkylcarbonylamino, $C_3$-$C_6$-cycloalkylaminocarbonyl, pyrrolyl, $C_1$-$C_4$-alkylaminocarbonylamino, hydroxyl, phenyl morpholinyl, oxypiperidinyl, oxopyrrolidinyl, oxomorpholinyl, pyrrolidinyl, morpholinylcarbonyl, piperidinyl, pyridinyl, dihydropyrrolylcarbonyl, $C_1$-$C_4$-alkylpiperizinylcarbonyl, isoxazolecarbonylamino, tetrahydrofuranylcarbonylamino, furoylamino, piperidinylcarbonyl, or piperidinylcarbonyl,
  where $C_1$-$C_4$-alkyl may optionally be substituted by hydroxyl, cyano, amino, $C_1$-$C_4$-alkylaminocarbonylamino, $C_1$-$C_4$-alkylaminocarboxyl, morpholinyl or aryl,
  $C_1$-$C_4$-alkylaminocarbonyl may optionally be substituted by $C_1$-$C_4$-alkoxy or $C_1$-$C_4$-alkylamino, and
  $C_1$-$C_4$-alkylcarbonylamino may optionally be substituted by $C_1$-$C_4$-alkoxy,
A is oxygen,
the ring B is benzo or pyrido, each of which are optionally substituted by radicals from the series halogen, cyano, trifluoromethyl, trifluoromethoxy and $C_1$-$C_4$-alkyl,
and
E is C≡C, phenylene, thienylene, oxadizolylene, pyrrolylene, furanylene, pyrimidinylene, or pyridinylene wherein each ring system respectively may be substituted by radicals from the series halogen, cyano, trifluoromethyl, trifluoromethoxy, nitro, amino, $C_1$-$C_4$-alkoxy and $C_1$-$C_4$-alkyl
or a salt thereof.

5. The method of claim 1, wherein which
R[1] is 1-azabicyclo[2.2.2]oct-3-yl,
R[2] is hydrogen or $C_1$-$C_6$-alkyl,
R[3] is hydrogen, halogen or $C_1$-$C_6$-alkyl,
R[4] is hydrogen, halogen, cyano, amino, trifluoromethyl, trifluoromethoxy, $C_1$-$C_6$-alkyl, $C_1$-$C_6$-alkylcarbonyl, $C_1$-$C_6$-alkylamino, formyl, hydroxycarbonyl, $C_1$-$C_6$-alkoxy, $C_1$-$C_6$-alkoxycarbonyl, $C_1$-$C_6$-alkylthio, $C_1$-$C_6$-alkylcarbonylamino, $C_1$-$C_4$-alkylsulphonylamino, $C_3$-$C_8$-cycloalkylcarbonylamino, pyrrolyl, $C_1$-$C_6$-alkylaminocarbonylamino, morpholinyl, oxypiperidinyl, oxopyrrolidinyl, oxomorpholinyl, pyrrolidinyl, morpholinylcarbonyl, piperidinyl, pyridinyl, dihydropyrrolylcarbonyl, $C_1$-$C_4$-alkylpiperizinylcarbonyl, isoxazolecarbonylamino, tetrahydrofuranylcarbonylamino, furoylamino, piperidinylcarbonyl, or piperidinylcarbonyl, where $C_1$-$C_6$-alkyl may optionally be substituted by hydroxyl, amino, $C_1$-$C_6$-alkyl-aminocarbonylamino, $C_1$-$C_6$-alkylaminocarboxyl, morpholinyl or aryl, and $C_1$-$C_6$-alkylcarbonylamino may optionally be substituted by $C_1$-$C_6$-alkoxy, A is oxygen or sulphur, the ring B is benzo or pyrido, each of which are optionally substituted by radicals from the series halogen, cyano, formyl, trifluoromethyl, trifluoromethoxy, nitro, amino, $C_1$-$C_6$-alkyl and $C_1$-$C_6$-alkoxy, and E is C≡C, phenylene, thienylene, oxadizolylene, pyrrolylene, furanylene, pyrimidinylene, or pyridinylene wherein each ring system respectively is optionally substituted by radicals from the series halogen, cyano, trifluoromethyl, trifluoromethoxy, nitro, amino, $C_1$-$C_6$-alkoxy and $C_1$-$C_6$-alkyl or a salt thereof.

6. The method of claim 1, wherein:

$R^1$ is 1-azabicyclo[2.2.2]oct-3-yl, $R^2$ is hydrogen or $C_1$-$C_6$-alkyl, $R^3$ is hydrogen, halogen or $C_1$-$C_6$-alkyl, $R^4$ is hydrogen, halogen, cyano, trifluoromethyl, trifluoromethoxy, $C_1$-$C_6$-alkyl, $C_1$-$C_6$-alkoxy morpholinyl, piperidinyl or pyrrolidinyl, where alkyl is optionally substituted by a hydroxyl radical, A is oxygen or sulphur, the ring B is benzo or pyrido, each of which are optionally substituted by radicals from the series halogen, cyano, trifluoromethyl, trifluoromethoxy, nitro, amino, $C_1$-$C_6$-alkyl and $C_1$-$C_6$-alkoxy, and E is C≡C, phenylene, thienylene, oxadizolylene, pyrrolylene, furanylene, pyrimidinylene, or pyridinylene wherein each ring system respectively is optionally substituted by radicals from the series halogen, cyano, trifluoromethyl, trifluoromethoxy, nitro, amino, $C_1$-$C_6$-alkyl and $C_1$-$C_6$-alkoxy or a salt thereof.

7. The method of claim 1, wherein the compound of formula (I) is a compound represented by a compound of formula (Ia.):

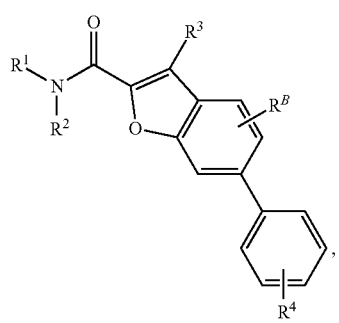

(Ia)

wherein:

$R^1$ is (3R)-1-azabicyclo[2.2.2]oct-3-yl, $R^2$ and $R^3$ are, independently of one another, hydrogen or methyl, $R^4$ is hydrogen, halogen, cyano, trifluoromethyl, trifluoromethoxy, $C_1$-$C_6$-alkyl, $C_1$-$C_6$-alkoxy or morpholinyl, piperidinyl or pyrrolidinyl, where alkyl is optionally substituted by a hydroxyl radical, and $R^B$ is hydrogen, halogen, cyano, trifluoromethyl, trifluoromethoxy, nitro, amino, $C_1$-$C_6$-alkyl or $C_1$-$C_6$-alkoxy, or a salt thereof.

8. The method of claim 1, wherein the compound of formula (I) is a compound represented by a compound of formula (Ib):

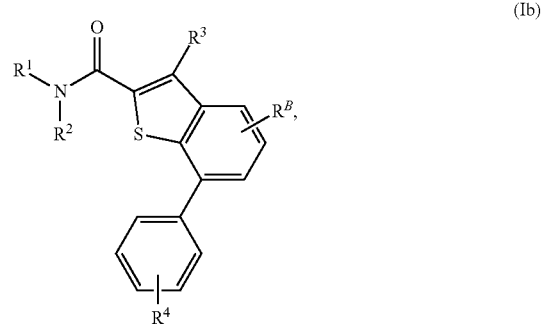

(Ib)

wherein:

$R^1$ is (3R)-1-azabicyclo[2.2.2]oct-3-yl, $R^2$ and $R^3$ are, independently of one another, hydrogen or methyl, $R^4$ is hydrogen, halogen, cyano, trifluoromethyl, trifluoromethoxy, $C_1$-$C_6$-alkyl, $C_1$-$C_6$-alkoxy morpholinyl, piperidinyl or pyrrolidinyl, where alkyl is optionally substituted by a hydroxyl radical, and $R^B$ is hydrogen, halogen, cyano, trifluoromethyl, trifluoromethoxy, nitro, amino, $C_1$-$C_6$-alkyl and $C_1$-$C_6$-alkoxy, or a salt thereof.

9. The method of claim 1, wherein:

$R^1$ is (3R)-1-azabicyclo[2.2.2]oct-3-yl, $R^2$ and $R^3$ are hydrogen, $R^4$ is hydrogen, fluorine, chlorine, bromine, trifluoromethoxy, hydroxymethyl, methoxy or morpholinyl or piperidinyl, and $R^B$ is hydrogen, halogen, cyano, trifluoromethyl, trifluoromethoxy or $C_1$-$C_4$-alkyl or a salt thereof.

10. The method of claim 1, wherein the compound of formula (I) is a compound represented by a compound of formula (Ic):

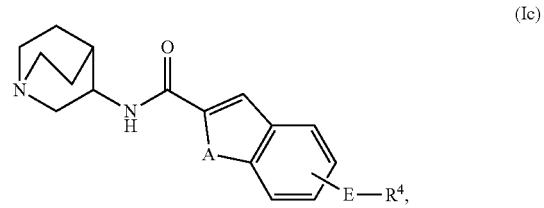

(Ic)

wherein:

E is phenylene, $R^4$ is $C_1$-$C_6$-alkoxy, aminomethyl, hydroxycarbonyl, $C_3$-$C_8$-cycloalkylcarbonylamino, a group of the formula

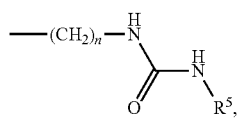

where
R⁵ is $C_1$-$C_6$-alkyl,
n is zero, 1, 2, 3 or 4,
or
morpholinyl, piperidinyl or pyrrolidinyl, which is optionally substituted by oxo,
A is sulphur or oxygen,
or a salt thereof.

11. The method of claim 10, wherein:
E is phenylene,
R⁴ is $C_1$-$C_4$-alkoxy, aminomethyl, hydroxycarbonyl, $C_3$-$C_6$-cycloalkylcarbonylamino, a group of the formula

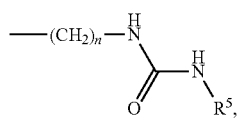

wherein:
R⁵ is $C_1$-$C_4$-alkyl,
n is zero, 1 or 2,
or
morpholinyl, piperidinyl or pyrrolidinyl, which is optionally substituted by oxo,
A is sulphur or oxygen,
or a salt thereof.

12. The method of claim 1, wherein the compound of formula (I) is a compound represented by:

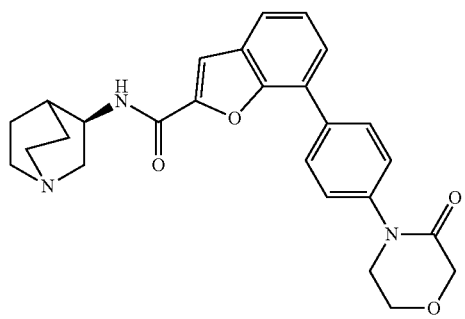

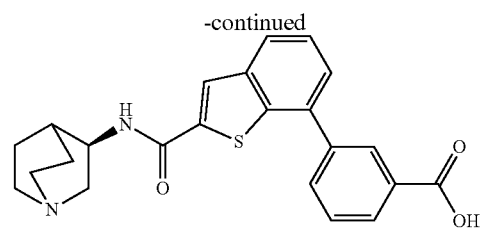

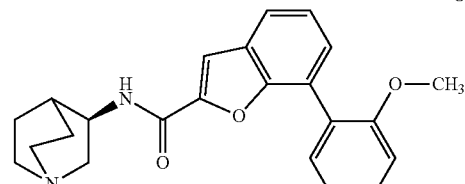

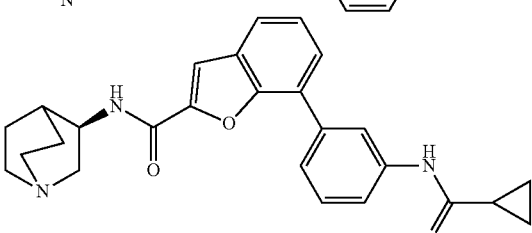

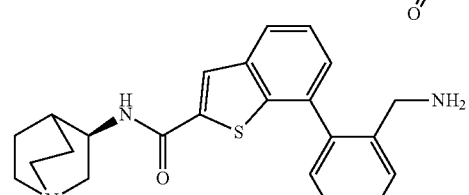

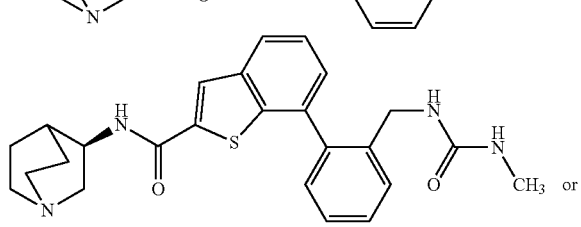 or

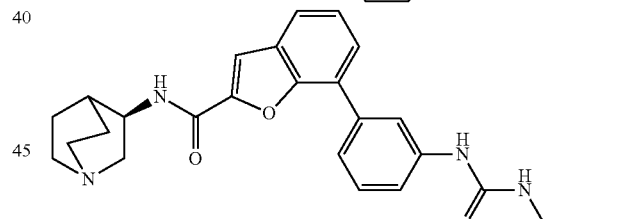

or a salt thereof.